(12) United States Patent
Lahser et al.

(10) Patent No.: US 8,841,302 B2
(45) Date of Patent: Sep. 23, 2014

(54) HCV INHIBITOR AND THERAPEUTIC AGENT COMBINATIONS

(75) Inventors: Frederick C. Lahser, Springfield, NJ (US); Zhengxian Gu, Princeton, NJ (US)

(73) Assignee: PTC Therapeutics, Inc., South Plainfield, NJ (US)

( * ) Notice: Subject to any disclaimer, the term of this patent is extended or adjusted under 35 U.S.C. 154(b) by 447 days.

(21) Appl. No.: 13/259,386

(22) PCT Filed: Apr. 5, 2010

(86) PCT No.: PCT/US2010/029933
§ 371 (c)(1),
(2), (4) Date: Nov. 30, 2011

(87) PCT Pub. No.: WO2010/117939
PCT Pub. Date: Oct. 14, 2010

(65) Prior Publication Data
US 2012/0070412 A1    Mar. 22, 2012

Related U.S. Application Data

(60) Provisional application No. 61/166,922, filed on Apr. 6, 2009.

(51) Int. Cl.
*A61K 31/50*    (2006.01)
*A61K 31/515*    (2006.01)
*A61K 31/44*    (2006.01)
*A61K 31/00*    (2006.01)
*A61K 31/404*    (2006.01)
*A61K 45/06*    (2006.01)

(52) U.S. Cl.
CPC ............... *A61K 45/06* (2013.01); *A61K 31/00* (2013.01); *A61K 31/404* (2013.01)
USPC ............ 514/252.06; 514/270; 514/339

(58) Field of Classification Search
USPC ............................. 514/252.06, 270, 339
See application file for complete search history.

(56) References Cited

FOREIGN PATENT DOCUMENTS

| WO | 2006019831 A1 | 2/2006 |
|---|---|---|
| WO | 2007084413 A2 | 7/2007 |
| WO | 2007092645 A2 | 8/2007 |

OTHER PUBLICATIONS

International Search Report for PCT/US2010/029933 mailed Jul. 1, 2010.
Written Opinion for PCT/US2010/029933 mailed Jul. 1, 2010.

*Primary Examiner* — Shengjun Wang
(74) *Attorney, Agent, or Firm* — Hoffmann & Baron, LLP

(57) ABSTRACT

The present invention is directed to a combination product for treating or ameliorating hepatitis C virus (HCV) infection or disorders or symptoms associated therewith in a subject in need thereof comprising, a HCV inhibitor and one or more therapeutic agents selected from either or both a HCV protease inhibitor and one or more different therapeutic agents administered in combination in an effective amount to the subject.

8 Claims, No Drawings

HCV INHIBITOR AND THERAPEUTIC AGENT COMBINATIONS

CROSS-REFERENCE TO RELATED APPLICATIONS

This application is the National Stage of International Application No. PCT/US2010/029933, filed Apr. 5, 2010 which claims benefit to provisional U.S. Ser. No. 61/166,922, filed Apr. 6, 2009, herein incorporated by reference.

This application is related to U.S. patent application Ser. No. 13/259,717, filed Sep. 23, 2011 (having 371(c) date Mar. 28, 2012), which is the National Stage of International Application No. PCT/US10/29923, filed Apr. 5, 2010, entitled "Compounds and Methods for Antiviral Treatment," which is incorporated herein by reference in its entirety and for all purposes.

GOVERNMENT SUPPORT

The present invention was not made with U.S. Government support.

STATEMENT OF JOINT RESEARCH AGREEMENT

The present invention was made by or on behalf of parties to a joint research agreement that was in effect on or before the date the invention was made, the present invention was made as a result of activities undertaken within the scope of the joint research agreement, and the application for patent of the present invention discloses the names of the parties to the joint research agreement.

FIELD OF THE INVENTION

The present invention is directed to a combination product for treating or ameliorating hepatitis C virus (HCV) infection or disorders or symptoms associated therewith in a subject in need thereof comprising, a HCV inhibitor and one or more therapeutic agents selected from either or both a HCV protease inhibitor and one or more different therapeutic agents administered in combination in an effective amount to the subject.

BACKGROUND OF THE INVENTION

Hepatitis C currently represents a major public health concern. The number of persons chronically infected with HCV in the world is estimated at 170 million to 200 million and hepatitis-C-related deaths at approximately 470,000 annually. Peak of incidence is expected to occur in 2025-2030 in developed countries. HCV is a virus that has been implicated in progressive liver diseases such as fibrosis and cirrhosis of the liver and in induction of hepatocellular carcinoma, which are the prime reasons for liver transplants. The prognosis for patients suffering from HCV infection is currently poor. HCV infection is more difficult to treat than other forms of hepatitis due to the lack of immunity or remission associated with HCV infection. Current data indicates a less than 50% survival rate at four years post cirrhosis diagnosis. Patients diagnosed with localized resectable hepatocellular carcinoma have a five-year survival rate of 10-30%, whereas those with localized unresectable hepatocellular carcinoma have a five-year survival rate of less than 1%.

The current standard of care for patients infected with the HCV genotype 1 is a combination of pegylated interferon alpha and ribavirin, a lengthy and often poorly tolerated therapy effective in 50% of patients that complete the therapy. In addition, a substantial number of patients never receive therapy.

Translation of the HCV RNA genome produces an approximately 3000 amino acid polyprotein that contains, from the amino terminus to the carboxy terminus, a nucleocapsid protein (C), envelope proteins (E1 and E2) and several non-structural proteins (P7, NS2, NS3, NS4a, NS4b, NS5a and NS5b).

The NS3 HCV protease necessary for polypeptide processing and viral replication has been identified, cloned and expressed. NS3 is an approximately 68 kda protein, encoded by approximately 1893 nucleotides of the HCV genome, and has two distinct domains: (a) a serine protease domain consisting of approximately 200 of the N-terminal amino acids; and (b) a RNA-dependent ATPase/helicase domain at the C-terminus of the protein.

The NS3 protease is considered a member of the chymotrypsin family because of similarities in protein sequence, overall three-dimensional structure and mechanism of catalysis. Other chymotrypsin-like enzymes are elastase, factor Xa, thrombin, trypsin, plasmin, urokinase, tPA and PSA.

The HCV NS3 protease is responsible for proteolysis of the polypeptide (polyprotein) at the NS3/NS4a, NS4a/NS4b, NS4b/NS5a and NS5a/NS5b junctions and is thus responsible for generating five viral proteins during viral replication. This has made the HCV NS3 protease an attractive target for antiviral chemotherapy. Additionally, the NS4a protein, an approximately 6 kda polypeptide, has been determined to be a co-factor for the protease activity of NS3. Autocleavage of the NS3/NS4a junction by the NS3/NS4a protease occurs intramolecularly (i.e., cis) while the other cleavage sites are processed intermolecularly (i.e., trans).

Analysis of the natural cleavage sites for HCV protease revealed the presence of cysteine at P1 and serine at P1' and that these residues are strictly conserved in the NS4a/NS4b, NS4b/NS5a and NS5a/NS5b junctions. The NS3/NS4a junction contains a threonine at P1 and a serine at P1'. The Cys-Thr substitution at NS3/NS4a is postulated to account for the requirement of cis rather than trans processing at this junction (see, e.g., Pizzi et al., Proc Natl Acad Sci (USA), 1994, 91(3): 888-892; Failla et al., Fold Des, 1996, 1(1):35-42; Wang et al., J Virol, 2004, 78(2):700-709). The NS3/NS4a cleavage site is also more tolerant of mutagenesis than the other sites (see, e.g., Kolykhalov et al., J Virol, 1994, 68(11):7525-7533). It has also been found that acidic residues in the region upstream of the cleavage site are required for efficient cleavage (see, e.g., Komoda et al., J Virol, 1994, 68(11):7351-7357).

Thus, the conserved portions of the HCV RNA genome are likely targets for effective therapeutic intervention (see, e.g., McCaffrey et al., Hepatology, 2003, 38(2):503-508) using one or more HCV inhibitors.

Inhibitors of HCV protease that have been reported include antioxidants (see, International Patent Publication WO1998/14181), certain peptides and peptide analogs (see, International Patent Publication WO1998/17679, Landro et al., Biochemistry, 1997, 36(31):9340-9348; Ingallinella et al., Biochemistry, 1997, 37(25):8906-89 14; Llinas-Brunet et al., Bioorg Med Chem Lett, 1998, 8(13):1713-1718), inhibitors based on the 70-amino acid polypeptide eglin c (see, Martin et al., Biochemistry, 1998, 37(33):11459-11468), human pancreatic secretory trypsin (hPST1-C3) and minibody repertoire (MBip) inhibitors (see, Dimasi et al., J Virol, 1997, 71(10):7461-7469), antibodies and fragments thereof (such as $cV_HE2$, a "camelized" variable domain antibody fragment)

(see, Martin et al., *Protein Eng*, 1997, 10(5):607-614) and α1-antichymotrypsin (ACT) (see, Elzouki et al., *J Hepat*, 1997, 27(1):42-48).

Combining various HCV protease inhibitors with an inhibitor of another target in the HCV life cycle including, but not limited to, HCV polymerase inhibitors, NS3 helicase or NS2/NS3 protease inhibitors as well as human immunodeficiency virus (HIV) and hepatitis B virus (HBV) inhibitors has been generally described.

U.S. patent application Ser. No. 12/281,022, filed Feb. 23, 2007 (having corresponding International Patent Application No. PCT/US2007/004721, filed Feb. 23, 2007) describes the use of certain indole and thienopyridine HCV inhibitor compounds and forms thereof in combination with at least one HCV protease inhibitor and, optionally at least one or more additional therapeutic agents, and is incorporated by reference herein in its entirety and for all purposes.

Additional HCV inhibitor compounds and forms thereof in combination with one or more anti-HCV agents have also been disclosed in U.S. patent application Ser. No. 11/653,450, filed Jan. 16, 2007 (having corresponding International Application No. PCT/US2007/00996, filed Jan. 16, 2007) and U.S. patent application Ser. No. 11/653,448, filed Jan. 16, 2007 (having corresponding International Application No. PCT/US2007/00923, filed Jan. 16, 2007), each of which are a continuation-in-part of U.S. patent application Ser. No. 11/331,180, filed Jan. 13, 2006, which is a continuation-in-part of U.S. patent application Ser. No. 11/180,961, filed Jul. 14, 2005 (having corresponding International Application No. PCT/US2005/024881, filed Jul. 14, 2005), each of which are incorporated herein by reference in their entirety and for all purposes.

United States Patent Publication 2006/0235028 discloses certain aryl and heteroaryl compounds as 11-beta-hydroxysteroid dehydrogenase type I inhibitors.

There continues to remain a strong need for new alternative approaches that work through multiple mechanisms of action, including combination products for use in treating or ameliorating HCV infection or disorders or symptoms associated therewith, and that modulate the processivity of viral replication and, in particular, the life cycle of the HCV polypeptide.

SUMMARY OF THE INVENTION

The present invention is directed to a combination product for treating or ameliorating HCV infection or disorders or symptoms associated therewith in a subject in need thereof comprising, a HCV inhibitor and one or more therapeutic agents selected from either or both a HCV protease inhibitor and one or more different therapeutic agents administered in combination in an effective amount to the subject.

An embodiment of the present invention includes a HCV inhibitor of Formula (I) or an enantiomer, stereoisomer, diastereomer, racemic, tautomeric, ester, prodrug, solvate, hydrate, isotopologue or salt form thereof:

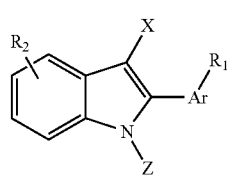

(I)

wherein $R_1$, $R_2$, X, Z and Ar are as defined herein.

Embodiments of the present invention include a HCV protease inhibitor selected from a NS2 protease inhibitor, a NS3 protease inhibitor, a peptide or dipeptide NS3 protease inhibitor or a NS4a protease cofactor inhibitor.

An embodiment of the present invention includes a HCV protease inhibitor selected from a HCV protease inhibitor of the present invention or an enantiomer, stereoisomer, diastereomer, racemic, tautomeric, ester, prodrug, solvate, hydrate, isotopologue or salt form thereof.

An embodiment of the present invention includes one or more different therapeutic agents selected from a HCV inhibitor, a HCV protease inhibitor, a nucleoside or non-nucleoside HCV polymerase inhibitor, a nonpegylated interferon, a pegylated interferon or another anti-HCV agent.

In one embodiment, one or more different HCV inhibitor therapeutic agents is selected from a HCV inhibitor of Formula (I) or a form thereof of the present invention.

In one embodiment, one or more different HCV inhibitor therapeutic agents is selected from a HCV inhibitor other than the HCV inhibitor compounds of Formula (I) or a form thereof of the present invention.

In one embodiment, one or more different HCV protease inhibitor therapeutic agents is selected from a NS2 protease inhibitor, a NS3 protease inhibitor, a peptide or dipeptide NS3 protease inhibitor or a NS4a protease cofactor inhibitor.

In one embodiment, one or more different HCV protease inhibitor therapeutic agents is selected from a HCV protease inhibitor or a form thereof of the present invention.

In one embodiment, one or more different HCV protease inhibitor therapeutic agents is selected from a HCV protease inhibitor or a form thereof other than the HCV protease inhibitor or forms thereof of the present invention.

In one embodiment, one or more different nucleoside or non-nucleoside HCV polymerase inhibitor therapeutic agents selected from a NS5b polymerase inhibitor.

An embodiment of the present invention includes one or more different therapeutic agents selected from a NS4b inhibitor, NS5a inhibitor, RES (internal ribosomal entry site) inhibitor, p7 inhibitor, entry inhibitor, fusion inhibitor, helicase inhibitor, ribavirin or a ribavirin analogue.

An embodiment of the present invention includes one or more different therapeutic agents selected from a Toll-like receptor (TLR) agonist, cyclophilin inhibitor, caspase or pan-caspase inhibitor, immunomodulator, immunomodulator/antiinflammatory, antiinflammatory, antiinflammatory/antifibrotic, broad spectrum immune stimulator, antifibrotic, antioxidant, hemopurifier, IMPDH (inosine monophosphate dehydrogenase) inhibitor, glycosidase inhibitor, glucosidase inhibitor, HCV therapeutic vaccine, A3 adenosine receptor (AR) agonist, polypeptide eglin c analog inhibitor, human pancreatic secretory trypsin and minibody repertoire inhibitor or a monoclonal antibody and fragment thereof.

Additional embodiments of the present invention include one or more different therapeutic agents selected from a HIV inhibitor, HBV inhibitor, RNA inhibitor, RNAi, anti-phospholipid therapy, protein therapeutic, botanical or non-specific pharmaceutical.

An embodiment of the present invention includes one or more different therapeutic agents selected from ribavirin and at least one or more of a nonpegylated interferon or a pegylated interferon.

The present invention is also directed to a method for treating or ameliorating HCV infection or disorders or symptoms associated therewith in a subject in need thereof comprising, administering an effective amount of a combination product to the subject, wherein the combination product is a HCV inhibitor and one or more therapeutic agents selected from either or both a HCV protease inhibitor and one or more different therapeutic agents administered in combination to the subject.

An embodiment of the present invention includes the use of a combination product comprising, a HCV inhibitor and one or more therapeutic agents selected from either or both a HCV protease inhibitor and one or more different therapeutic agents in the preparation of a medicament, pharmaceutical composition or pharmaceutical kit for treating or ameliorating HCV infection or disorders or symptoms associated therewith in a subject in need thereof.

DETAILED DESCRIPTION OF THE INVENTION

The present invention is directed to a combination product for treating or ameliorating HCV infection or disorders or symptoms associated therewith in a subject in need thereof comprising, a HCV inhibitor and one or more therapeutic agents selected from either or both a HCV protease inhibitor and one or more different therapeutic agents administered in combination in an effective amount to the subject.

An embodiment of the present invention includes a HCV inhibitor of Formula (I) or an enantiomer, stereoisomer, diastereomer, racemic, tautomeric, ester, prodrug, solvate, hydrate, isotopologue or salt form thereof:

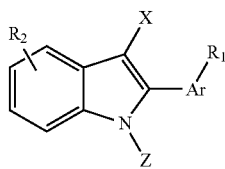

(I)

wherein
X is hydrogen, halogen, cyano, nitro, carboxyl, $C_{1-8}$alkyl-carbonyl, $C_{1-8}$alkoxy-carbonyl, formyl, amino, $C_{1-8}$alkyl-amino, amino-carbonyl, $C_{1-8}$alkyl-amino-carbonyl or $C_{1-8}$alkyl-sulfonyl;
Ar is heteroaryl or heterocyclyl, each optionally substituted with one or two substituents independently selected from halogen, $C_{1-8}$alkyl, halo-$C_{1-8}$alkyl, $C_{1-8}$alkoxy, halo-$C_{1-8}$ alkoxy, amino or $C_{1-8}$alkyl-amino;
Z is $C_{1-8}$alkyl, $C_{2-8}$alkenyl-$C_{1-8}$alkyl, $C_{2-8}$alkynyl-$C_{1-8}$alkyl, halo-$C_{1-8}$alkyl, $C_{1-8}$alkoxy-$C_{1-8}$alkyl, $C_{1-8}$alkoxy-carbonyl, carboxyl, $C_{3-14}$cycloalkyl, $C_{3-14}$cycloalkenyl, $C_{3-14}$cycloalkyl-$C_{1-8}$alkyl, aryl, aryl-$C_{1-8}$alkyl, heteroaryl, heteroaryl-$C_{1-8}$alkyl, heterocyclyl or heterocyclyl-$C_{1-8}$ alkyl, wherein each instance of aryl and heteroaryl is optionally substituted with one, two, three or four substituents each selected from hydroxy, cyano, nitro, halogen, $C_{1-8}$alkyl, $C_{2-8}$alkenyl, $C_{2-8}$alkynyl, hydroxy-$C_{1-8}$alkyl, halo-$C_{1-8}$alkyl, $C_{1-8}$alkoxy, halo-$C_{1-8}$alkoxy, amino, $C_{1-8}$alkyl-amino, $C_{1-8}$alkoxy-$C_{1-8}$alkyl, $C_{1-8}$alkylthio, $C_{1-8}$alkyl-carbonyl, $C_{1-8}$alkoxy-carbonyl, $C_{1-8}$alkyl-carbonyloxy or amino-sulfonyl;
$R_1$ is —N($R_3$)—SO$_2$—$R_4$, —N($R_3$)—SO$_2$—N($R_5$)—$R_8$, —SO$_2$—N($R_5$)—$R_6$ or —SO$_2$—$R_7$;
$R_2$ is one, two, three or four substituents each selected from hydrogen, halogen, hydroxy, cyano, nitro, $C_{1-8}$alkyl, hydroxy-$C_{1-8}$alkyl, halo-$C_{1-8}$alkyl, $C_{2-8}$alkenyl, halo-$C_{2-8}$ alkenyl, $C_{1-8}$alkoxy, halo-$C_{1-8}$alkoxy, $C_{1-8}$alkoxy-$C_{1-8}$ alkyl, $C_{1-8}$alkyl-carbonyl, $C_{1-8}$alkoxy-carbonyl, $C_{1-8}$alkyl-carbonyloxy, $C_{1-8}$alkyl-carbonyloxy-$C_{1-8}$alkyl, $C_{1-8}$alkyl-carbonyloxy-$C_{1-8}$alkoxy, amino, $C_{1-8}$alkyl-amino, amino-$C_{1-8}$alkyl, $C_{1-8}$alkyl-amino-$C_{1-8}$alkyl, amino-$C_{1-8}$alkoxy, $C_{1-8}$alkyl-amino-$C_{1-8}$alkoxy, $C_{1-8}$alkoxy-$C_{1-8}$alkyl-amino-$C_{1-8}$alkoxy, amino-$C_{1-8}$ alkyl-amino-$C_{1-8}$alkoxy, $C_{1-8}$alkyl-amino-$C_{1-8}$alkyl-amino-$C_{1-8}$alkoxy, $C_{1-8}$alkoxy-carbonyl-amino, carboxyl-amino, amino-carbonyl, amino-carbonyl-amino, $C_{1-8}$alkyl-amino-carbonyl-amino, $C_{1-8}$alkylthio, $C_{1-8}$alkyl-sulfinyl, $C_{1-8}$alkyl-sulfonyl, $C_{1-8}$alkyl-sulfonyl-amino, $C_{3-14}$cycloalkyl, $C_{3-14}$cycloalkyl-$C_{1-8}$alkyl, $C_{3-14}$cycloalkyl-$C_{1-8}$alkoxy, $C_{3-14}$cycloalkyloxy, aryl, aryl-$C_{1-8}$alkyl, aryl-$C_{1-8}$alkoxy, aryloxy, aryl-carbonyl-amino, heteroaryl, heteroaryl-$C_{1-8}$ alkyl, heteroaryl-$C_{1-8}$ alkoxy, heteroaryloxy, heterocyclyl, heterocyclyl-$C_{1-8}$ alkyl, heterocyclyl-$C_{1-8}$alkoxy, heterocyclyloxy or heterocyclyl-carbonyloxy, wherein each instance of $C_{3-14}$cycloalkyl, aryl, heteroaryl and heterocyclyl is optionally substituted with one, two, three or four substituents each selected from halogen, cyano, $C_{1-8}$alkyl, $C_{1-8}$alkoxy, $C_{1-8}$alkoxy-$C_{1-8}$alkyl, amino, $C_{1-8}$alkyl-amino, amino-$C_{1-8}$alkyl or $C_{1-8}$alkyl-amino-$C_{1-8}$alkyl;
$R_3$ is hydrogen or $C_{1-8}$alkyl, optionally substituted on $C_{1-8}$alkyl with one or more substituents each selected from halogen, hydroxy, cyano, $C_{1-8}$alkoxy, amino or $C_{1-8}$alkyl-amino;
$R_4$ is $C_{1-8}$alkyl, halo-$C_{1-8}$alkyl, $C_{1-8}$alkoxy, halo-$C_{1-8}$alkoxy, $C_{3-14}$cycloalkyl, $C_{3-14}$cycloalkyl-$C_{1-8}$alkyl, aryl, aryl-$C_{1-8}$ alkyl, heteroaryl, heteroaryl-$C_{1-8}$alkyl, heterocyclyl or heterocyclyl-$C_{1-8}$alkyl, wherein each instance of aryl, heteroaryl, heterocyclyl and $C_{3-14}$cycloalkyl is optionally substituted with one or two substituents each selected from halogen, $C_{1-8}$alkyl, halo-$C_{1-8}$alkyl, $C_{1-8}$alkoxy, halo-$C_{1-8}$ alkoxy, amino or $C_{1-8}$alkyl-amino;
$R_5$ is hydrogen or $C_{1-8}$alkyl, $C_{1-8}$alkyl-carbonyl- or $C_{3-14}$cycloalkyl, optionally substituted on $C_{1-8}$alkyl with one or more substituents each selected from halogen, hydroxy, cyano or $C_{1-8}$alkoxy;
$R_6$ is hydrogen, $C_{1-8}$alkyl, hydroxy-$C_{1-8}$alkyl, halo-$C_{1-8}$alkyl, cyano-$C_{1-8}$alkyl, $C_{1-8}$alkoxy-$C_{1-8}$alkyl, amino-$C_{1-8}$alkyl, $C_{1-8}$alkyl-amino-$C_{1-8}$alkyl, $C_{1-8}$alkyl-carbonyl, $C_{1-8}$alkoxy-carbonyl, $C_{3-14}$cycloalkyl, $C_{3-14}$cycloalkyl-$C_{1-8}$alkyl, aryl, aryl-$C_{1-8}$alkyl, heteroaryl, heteroaryl-$C_{1-8}$ lkyl, heterocyclyl or heterocyclyl-$C_{1-8}$alkyl, wherein each instance of aryl, heteroaryl, heterocyclyl and $C_{3-14}$cycloalkyl is optionally substituted with one or two substituents each selected from halogen, $C_{1-8}$alkyl, halo-$C_{1-8}$alkyl, $C_{1-8}$alkoxy, halo-$C_{1-8}$alkoxy, amino or $C_{1-8}$alkyl-amino; and
$R_7$ is $C_{1-8}$alkyl, $C_{3-14}$cycloalkyl, $C_{3-14}$cycloalkyl-$C_{1-8}$alkyl, aryl, aryl-$C_{1-8}$alkyl, heteroaryl, heteroaryl-$C_{1-8}$alkyl, heterocyclyl or heterocyclyl-$C_{1-8}$alkyl, wherein each instance of aryl, heteroaryl, $C_{3-14}$cycloalkyl and heterocyclyl is optionally substituted with one or two substituents each selected from halogen, $C_{1-8}$alkyl, halo-$C_{1-8}$alkyl, $C_{1-8}$alkoxy, halo-$C_{1-8}$alkoxy, amino or $C_{1-8}$alkyl-amino.

In another embodiment, the HCV inhibitor or an enantiomer, stereoisomer, diastereomer, racemic, tautomeric, ester, prodrug, solvate, hydrate, isotopologue or salt form thereof is selected from:

| Cpd | Name |
|---|---|
| 1 | 6-[3-cyano-6-(difluoromethoxy)-1-(propan-2-yl)-1H-indol-2-yl]-N-(propan-2-yl)pyridine-3-sulfonamide, |
| 2 | 6-[3-cyano-6-(difluoromethoxy)-1-(propan-2-yl)-1H-indol-2-yl]-N-cyclobutylpyridine-3-sulfonamide, |
| 3 | 6-[3-cyano-6-(difluoromethoxy)-1-propyl-1H-indol-2-yl]-N-(propan-2-yl)pyridine-3-sulfonamide, |
| 4 | 5-[3-cyano-1-cyclobutyl-6-(cyclobutyloxy)-1H-indol-2-yl]-N-(propan-2-yl)pyridine-2-sulfonamide, |
| 5 | 6-(3-cyano-1-cyclobutyl-5-fluoro-1H-indol-2-yl)-N-(propan-2-yl)pyridine-3-sulfonamide, |
| 6 | 6-[3-cyano-1-(cyclopropylmethyl)-5-fluoro-1H-indol-2-yl]-N-(propan-2-yl)pyridine-3-sulfonamide, |
| 7 | 6-(3-cyano-1-cyclobutyl-6-cyclopropyl-1H-indol-2-yl)-N-(propan-2-yl)pyridine-3-sulfonamide, |
| 8 | 6-(3-cyano-1-cyclobutyl-5-cyclopropyl-1H-indol-2-yl)-N-(propan-2-yl)pyridine-3-sulfonamide, |
| 9 | N-tert-butyl-6-(3-cyano-1-cyclobutyl-5-fluoro-1H-indol-2-yl)pyridine-3-sulfonamide, |
| 10 | 6-[3-cyano-1-cyclobutyl-6-(trifluoromethoxy)-1H-indol-2-yl]-N-(propan-2-yl)pyridine-3-sulfonamide, |
| 11 | 6-[3-cyano-1-(cyclopropylmethyl)-6-(trifluoromethoxy)-1H-indol-2-yl]-N-(propan-2-yl)pyridine-3-sulfonamide, |
| 12 | 6-[3-cyano-1-(propan-2-yl)-6-(trifluoromethoxy)-1H-indol-2-yl]-N-(propan-2-yl)pyridine-3-sulfonamide, |
| 13 | 6-[3-cyano-1-(cyclopropylmethyl)-6-(difluoromethoxy)-1H-indol-2-yl]-N-(propan-2-yl)pyridine-3-sulfonamide, |
| 14 | 6-(5-chloro-3-cyano-1-cyclobutyl-1H-indol-2-yl)-N-(propan-2-yl)pyridine-3-sulfonamide, |
| 15 | N-tert-butyl-6-(5-chloro-3-cyano-1-cyclobutyl-1H-indol-2-yl)pyridine-3-sulfonamide, |
| 16 | 6-[3-cyano-1-cyclobutyl-6-(propan-2-ylsulfanyl)-1H-indol-2-yl]-N-(propan-2-yl)pyridine-3-sulfonamide, |
| 17 | 6-[3-cyano-1-cyclopentyl-6-(trifluoromethoxy)-1H-indol-2-yl]-N-(propan-2-yl)pyridine-3-sulfonamide, |
| 18 | N-tert-butyl-6-[3-cyano-1-cyclopentyl-6-(trifluoromethoxy)-1H-indol-2-yl]pyridine-3-sulfonamide, |
| 19 | 6-[3-cyano-1-cyclobutyl-5-(difluoromethoxy)-1H-indol-2-yl]-N-(propan-2-yl)pyridine-3-sulfonamide, |
| 20 | N-tert-butyl-6-[3-cyano-1-cyclobutyl-5-(difluoromethoxy)-1H-indol-2-yl]pyridine-3-sulfonamide, |
| 21 | 6-[3-cyano-1-cyclopentyl-5-(difluoromethoxy)-1H-indol-2-yl]-N-(propan-2-yl)pyridine-3-sulfonamide, |
| 22 | 1-cyclobutyl-2-[5-(piperidin-1-ylsulfonyl)pyridin-2-yl]-6-(propan-2-ylsulfanyl)-1H-indole-3-carbonitrile, |
| 23 | 6-[3-cyano-1-cyclobutyl-5-(trifluoromethoxy)-1H-indol-2-yl]-N-(propan-2-yl)pyridine-3-sulfonamide, |
| 24 | 6-[3-cyano-1-cyclobutyl-6-(trifluoromethoxy)-1H-indol-2-yl]-N-(1,3-difluoropropan-2-yl)pyridine-3-sulfonamide, |
| 25 | 6-[3-cyano-1-cyclobutyl-5-(trifluoromethoxy)-1H-indol-2-yl]-N-(1,3-difluoropropan-2-yl)pyridine-3-sulfonamide, |
| 26 | 5-[3-cyano-1-cyclobutyl-6-(trifluoromethoxy)-1H-indol-2-yl]-N-(propan-2-yl)pyridine-2-sulfonamide, |
| 27 | 5-(3-cyano-1-cyclobutyl-6-cyclopropyl-1H-indol-2-yl)-N-(propan-2-yl)pyridine-2-sulfonamide, |
| 28 | 5-(5-chloro-3-cyano-1-cyclobutyl-1H-indol-2-yl)-N-(propan-2-yl)pyridine-2-sulfonamide, |
| 29 | 6-(3-cyano-1-cyclobutyl-5-fluoro-1H-indol-2-yl)-N-(1,3-difluoropropan-2-yl)pyridine-3-sulfonamide, |
| 30 | 6-(5-chloro-3-cyano-1-cyclobutyl-1H-indol-2-yl)-N-(1,3-difluoropropan-2-yl)pyridine-3-sulfonamide, |
| 31 | 6-[3-cyano-1-cyclobutyl-6-(difluoromethoxy)-1H-indol-2-yl]-N-(1,3-difluoropropan-2-yl)pyridine-3-sulfonamide, |
| 32 | 6-[3-cyano-1-cyclobutyl-5-(difluoromethoxy)-1H-indol-2-yl]-N-(1,3-difluoropropan-2-yl)pyridine-3-sulfonamide, |
| 33 | 6-[3-cyano-1-cyclopentyl-5-(difluoromethoxy)-1H-indol-2-yl]-N-(1,3-difluoropropan-2-yl)pyridine-3-sulfonamide, |
| 34 | 6-[3-cyano-1-cyclopentyl-5-(trifluoromethoxy)-1H-indol-2-yl]-N-(1,3-difluoropropan-2-yl)pyridine-3-sulfonamide, |
| 35 | 6-(3-cyano-1-cyclobutyl-6-cyclopropyl-1H-indol-2-yl)-N-(1,3-difluoropropan-2-yl)pyridine-3-sulfonamide, |
| 36 | 6-[3-cyano-6-(difluoromethoxy)-1-(propan-2-yl)-1H-indol-2-yl]-N-(1,3-difluoropropan-2-yl)pyridine-3-sulfonamide, |
| 37 | 6-(6-chloro-3-cyano-1-cyclobutyl-1H-indol-2-yl)-N-(1,3-difluoropropan-2-yl)pyridine-3-sulfonamide, |
| 38 | 6-(3-cyano-1-cyclopentyl-5-fluoro-1H-indol-2-yl)-N-(1,3-difluoropropan-2-yl)pyridine-3-sulfonamide, |
| 39 | 5-[3-cyano-1-cyclopropyl-6-(difluoromethoxy)-1H-indol-2-yl]-N-(propan-2-yl)pyridine-2-sulfonamide, |

-continued

| Cpd | Name |
|---|---|
| 40 | 5-[3-cyano-1-(cyclopropylmethyl)-6-(difluoromethoxy)-1H-indol-2-yl]-N-(propan-2-yl)pyridine-2-sulfonamide, |
| 41 | 6-[3-cyano-1-(cyclopropylmethyl)-6-(difluoromethoxy)-1H-indol-2-yl]-N-(1,3-difluoropropan-2-yl)pyridine-3-sulfonamide, |
| 42 | 6-[3-cyano-1-cyclopropyl-6-(difluoromethoxy)-1H-indol-2-yl]-N-(1,3-difluoropropan-2-yl)pyridine-3-sulfonamide, |
| 43 | 6-[3-cyano-1-cyclobutyl-6-(propan-2-yl)-1H-indol-2-yl]-N-(1,3-difluoropropan-2-yl)pyridine-3-sulfonamide, |
| 44 | 6-(3-cyano-1-cyclopentyl-6-methyl-1H-indol-2-yl)-N-(1,3-difluoropropan-2-yl)pyridine-3-sulfonamide, |
| 45 | 6-[3-cyano-6-(difluoromethoxy)-1-propyl-1H-indol-2-yl]-N-(1,3-difluoropropan-2-yl)pyridine-3-sulfonamide, |
| 46 | 6-[3-cyano-5-fluoro-1-(tetrahydrofuran-3-yl)-1H-indol-2-yl]-N-(1,3-difluoropropan-2-yl)pyridine-3-sulfonamide, |
| 47 | 6-[3-cyano-5-fluoro-1-(tetrahydrofuran-3-yl)-1H-indol-2-yl]-N-(propan-2-yl)pyridine-3-sulfonamide, |
| 48 | 6-(3-cyano-1-cyclobutyl-6-ethyl-1H-indol-2-yl)-N-(1,3-difluoropropan-2-yl)pyridine-3-sulfonamide, |
| 49 | 6-[3-cyano-1-cyclopentyl-6-(difluoromethoxy)-1H-indol-2-yl]-N-(1,3-difluoropropan-2-yl)pyridine-3-sulfonamide, |
| 50 | 6-(6-chloro-3-cyano-1-cyclobutyl-5-fluoro-1H-indol-2-yl)-N-(1,3-difluoropropan-2-yl)pyridine-3-sulfonamide, |
| 51 | 6-[3-cyano-1-cyclobutyl-6-(difluoromethoxy)-1H-indol-2-yl]-N-(propan-2-yl)pyridine-3-sulfonamide, |
| 52 | 6-[3-cyano-1-cyclopentyl-6-(difluoromethoxy)-1H-indol-2-yl]-N-(propan-2-yl)pyridine-3-sulfonamide, |
| 53 | 6-[3-cyano-1-cyclopentyl-6-(difluoromethoxy)-1H-indol-2-yl]-N-(1,1,1-trifluoropropan-2-yl)pyridine-3-sulfonamide, |
| 54 | 6-{3-cyano-6-methyl-1-[(3R)-tetrahydrofuran-3-yl]-1H-indol-2-yl}-N-(1,3-difluoropropan-2-yl)pyridine-3-sulfonamide, |
| 55 | 6-{3-cyano-6-methyl-1-[(3R)-tetrahydrofuran-3-yl]-1H-indol-2-yl}-N-(propan-2-yl)pyridine-3-sulfonamide, |
| 56 | 6-(3-cyano-1-cyclobutyl-6-fluoro-1H-indol-2-yl)-N-(1,3-difluoropropan-2-yl)pyridine-3-sulfonamide, |
| 57 | 6-[3-cyano-1-(cyclopropylmethyl)-6-fluoro-1H-indol-2-yl]-N-(1,3-difluoropropan-2-yl)pyridine-3-sulfonamide, |
| 58 | 6-[3-cyano-1-(cyclopropylmethyl)-5-fluoro-1H-indol-2-yl]-N-(1,3-difluoropropan-2-yl)pyridine-3-sulfonamide, |
| 59 | 6-[3-cyano-1-cyclobutyl-6-(2,2-difluoroethoxy)-1H-indol-2-yl]-N-(propan-2-yl)pyridine-3-sulfonamide, |
| 60 | 6-[3-cyano-5-fluoro-1-(propan-2-yl)-1H-indol-2-yl]-N-(1,3-difluoropropan-2-yl)pyridine-3-sulfonamide, |
| 61 | 6-[3-cyano-6-fluoro-1-(propan-2-yl)-1H-indol-2-yl]-N-(1,3-difluoropropan-2-yl)pyridine-3-sulfonamide, |
| 62 | 6-[6-chloro-3-cyano-1-(cyclopropylmethyl)-1H-indol-2-yl]-N-(1,3-difluoropropan-2-yl)pyridine-3-sulfonamide, |
| 63 | 6-[6-chloro-3-cyano-1-(propan-2-yl)-1H-indol-2-yl]-N-(1,3-difluoropropan-2-yl)pyridine-3-sulfonamide, |
| 64 | 6-(6-chloro-3-cyano-1-cyclopentyl-1H-indol-2-yl)-N-(1,3-difluoropropan-2-yl)pyridine-3-sulfonamide, |
| 65 | 6-[5-chloro-3-cyano-1-(propan-2-yl)-1H-indol-2-yl]-N-(1,3-difluoropropan-2-yl)pyridine-3-sulfonamide, |
| 66 | 6-(3-cyano-1-cyclopentyl-7-fluoro-1H-indol-2-yl)-N-(propan-2-yl)pyridine-3-sulfonamide, |
| 67 | 6-[3-cyano-1-cyclopentyl-6-(difluoromethoxy)-1H-indol-2-yl]-N-(1-fluoro-2-methylpropan-2-yl)pyridine-3-sulfonamide, |
| 68 | 6-[3-cyano-1-(cyclopropylmethyl)-6-(trifluoromethoxy)-1H-indol-2-yl]-N-(1,3-difluoropropan-2-yl)pyridine-3-sulfonamide, |
| 69 | 6-[3-cyano-1-(propan-2-yl)-6-(trifluoromethoxy)-1H-indol-2-yl]-N-(1,3-difluoropropan-2-yl)pyridine-3-sulfonamide, |
| 70 | 6-[3-cyano-1-cyclopentyl-6-(trifluoromethoxy)-1H-indol-2-yl]-N-(1,3-difluoropropan-2-yl)pyridine-3-sulfonamide, |
| 71 | 2-(3-cyano-1-cyclobutyl-6-cyclopropyl-1H-indol-2-yl)-N-(propan-2-yl)pyrimidine-5-sulfonamide, |
| 72 | 6-(5-chloro-3-cyano-1-cyclopentyl-1H-indol-2-yl)-N-(1,3-difluoropropan-2-yl)pyridine-3-sulfonamide, |
| 73 | 6-[5-chloro-3-cyano-1-(cyclopropylmethyl)-1H-indol-2-yl]-N-(1,3-difluoropropan-2-yl)pyridine-3-sulfonamide, |
| 74 | 2-(3-cyano-1-cyclopentyl-6-methyl-1H-indol-2-yl)-N-(propan-2-yl)pyrimidine-5-sulfonamide, |
| 75 | 6-[3-cyano-6-ethyl-1-(propan-2-yl)-1H-indol-2-yl]-N-(propan-2-yl)pyridine-3-sulfonamide, |
| 77 | 6-[3-cyano-1-cyclobutyl-6-(difluoromethoxy)-1H-indol-2-yl]-N-(1-fluoro-2-methylpropan-2-yl)pyridine-3-sulfonamide, |
| 78 | 6-[3-cyano-1-cyclobutyl-6-(difluoromethoxy)-1H-indol-2-yl]-N-(1,1,1-trifluoropropan-2-yl)pyridine-3-sulfonamide, |

-continued

| Cpd | Name |
|---|---|
| 79 | 6-(5-chloro-3-cyano-1-cyclohexyl-1H-indol-2-yl)-N-(1,3-difluoropropan-2-yl)pyridine-3-sulfonamide, |
| 80 | 6-[3-cyano-6-methyl-1-(propan-2-yl)-1H-indol-2-yl]-N-(1,3-difluoropropan-2-yl)pyridine-3-sulfonamide, |
| 81 | 6-[3-cyano-1-(cyclopropylmethyl)-6-methyl-1H-indol-2-yl]-N-(1,3-difluoropropan-2-yl)pyridine-3-sulfonamide, |
| 82 | 6-(3-cyano-1-cyclobutyl-6-methyl-1H-indol-2-yl)-N-(1,3-difluoropropan-2-yl)pyridine-3-sulfonamide, |
| 83 | 6-[3-cyano-6-cyclopropyl-1-(propan-2-yl)-1H-indol-2-yl]-N-(1,3-difluoropropan-2-yl)pyridine-3-sulfonamide, |
| 84 | 6-[3-cyano-6-cyclopropyl-1-(cyclopropylmethyl)-1H-indol-2-yl]-N-(1,3-difluoropropan-2-yl)pyridine-3-sulfonamide, |
| 85 | 6-(3-cyano-1-cyclopentyl-6-cyclopropyl-1H-indol-2-yl)-N-(1,3-difluoropropan-2-yl)pyridine-3-sulfonamide, |
| 86 | 6-(3-cyano-1-cyclopentyl-6-cyclopropyl-1H-indol-2-yl)-N-(1,1,1-trifluoropropan-2-yl)pyridine-3-sulfonamide, |
| 87 | 6-(3-cyano-1-cyclopentyl-7-fluoro-1H-indol-2-yl)-N-(1,3-difluoropropan-2-yl)pyridine-3-sulfonamide, |
| 88 | 6-(7-chloro-3-cyano-1-cyclopentyl-1H-indol-2-yl)-N-(1,3-difluoropropan-2-yl)pyridine-3-sulfonamide, |
| 89 | 6-(6-chloro-3-cyano-1-cyclohexyl-1H-indol-2-yl)-N-(1,3-difluoropropan-2-yl)pyridine-3-sulfonamide, |
| 90 | 6-(3-cyano-1-cyclobutyl-6-cyclopropyl-1H-indol-2-yl)pyridine-3-sulfonamide, |
| 92 | 6-(3-cyano-1-cyclohexyl-6-cyclopropyl-1H-indol-2-yl)-N-(1,3-difluoropropan-2-yl)pyridine-3-sulfonamide, |
| 93 | 6-[3-cyano-1-cyclobutyl-6-(difluoromethoxy)-1H-indol-2-yl]-N-[1-(trifluoromethyl)cyclopropyl]pyridine-3-sulfonamide, |
| 94 | 6-[3-cyano-1-cyclopentyl-6-(difluoromethoxy)-1H-indol-2-yl]-N-[1-(trifluoromethyl)cyclopropyl]pyridine-3-sulfonamide, |
| 95 | 6-(3-cyano-6-cyclopropyl-1-phenyl-1H-indol-2-yl)-N-(1,3-difluoropropan-2-yl)pyridine-3-sulfonamide, |
| 96 | 6-[3-cyano-5-fluoro-1-(pyridin-2-yl)-1H-indol-2-yl]-N-(1,3-difluoropropan-2-yl)pyridine-3-sulfonamide, |
| 97 | 2-(5-chloro-3-cyano-1-cyclohexyl-1H-indol-2-yl)-N-(propan-2-yl)pyrimidine-5-sulfonamide, |
| 98 | 2-(3-cyano-1-cyclohexyl-6-methyl-1H-indol-2-yl)-N-(propan-2-yl)pyrimidine-5-sulfonamide, |
| 99 | 6-[3-cyano-1-cyclohexyl-6-(difluoromethoxy)-1H-indol-2-yl]-N-(propan-2-yl)pyridine-3-sulfonamide, |
| 100 | 6-[3-cyano-1-cyclohexyl-6-(difluoromethoxy)-1H-indol-2-yl]-N-(1,3-difluoropropan-2-yl)pyridine-3-sulfonamide, |
| 101 | 6-(3-cyano-1-cyclobutyl-5-fluoro-6-methoxy-1H-indol-2-yl)-N-(propan-2-yl)pyridine-3-sulfonamide, |
| 102 | 6-(3-cyano-1-cyclobutyl-5-fluoro-6-methoxy-1H-indol-2-yl)-N-(1,3-difluoropropan-2-yl)pyridine-3-sulfonamide, |
| 103 | 6-[3-cyano-1-cyclobutyl-6-(2,2-difluoroethenyl)-1H-indol-2-yl]-N-(1,3-difluoropropan-2-yl)pyridine-3-sulfonamide, |
| 104 | 6-(3-cyano-1-cyclohexyl-5-fluoro-1H-indol-2-yl)-N-(1,3-difluoropropan-2-yl)pyridine-3-sulfonamide, |
| 105 | 6-[3-cyano-1-cyclohexyl-6-(trifluoromethoxy)-1H-indol-2-yl]-N-(1,3-difluoropropan-2-yl)pyridine-3-sulfonamide, |
| 106 | 6-[3-cyano-1-cyclobutyl-6-(difluoromethoxy)-1H-indol-2-yl]-N-[1-(trifluoromethyl)cyclobutyl]pyridine-3-sulfonamide, |
| 107 | 6-(3-cyano-1-cyclobutyl-6-cyclopropyl-5-fluoro-1H-indol-2-yl)-N-(1,3-difluoropropan-2-yl)pyridine-3-sulfonamide, |
| 108 | 6-(3-cyano-1-cyclobutyl-5-fluoro-6-methyl-1H-indol-2-yl)-N-(1,3-difluoropropan-2-yl)pyridine-3-sulfonamide, |
| 109 | 6-(3-cyano-1,6-dicyclopropyl-1H-indol-2-yl)-N-(propan-2-yl)pyridine-3-sulfonamide, |
| 110 | 6-[6-chloro-3-cyano-1-(cyclopropylmethyl)-5-fluoro-1H-indol-2-yl]-N-(1,3-difluoropropan-2-yl)pyridine-3-sulfonamide, |
| 111 | 6-(3-cyano-6-methyl-1-phenyl-1H-indol-2-yl)-N-(1,3-difluoropropan-2-yl)pyridine-3-sulfonamide, |
| 112 | 6-(5-chloro-3-cyano-1-phenyl-1H-indol-2-yl)-N-(1,3-difluoropropan-2-yl)pyridine-3-sulfonamide, |
| 113 | 6-(3-cyano-5-fluoro-1-phenyl-1H-indol-2-yl)-N-(1,3-difluoropropan-2-yl)pyridine-3-sulfonamide, |
| 114 | 2-(5-chloro-3-cyano-1-cyclobutyl-1H-indol-2-yl)-N-(propan-2-yl)pyrimidine-5-sulfonamide, |
| 115 | 2-(6-chloro-3-cyano-1-cyclobutyl-1H-indol-2-yl)-N-(propan-2-yl)pyrimidine-5-sulfonamide, |
| 116 | 2-[3-cyano-1-cyclobutyl-6-(trifluoromethoxy)-1H-indol-2-yl]-N-(propan-2-yl)pyrimidine-5-sulfonamide, |
| 117 | 2-[3-cyano-1-cyclopentyl-6-(trifluoromethoxy)-1H-indol-2-yl]-N-(propan-2-yl)pyrimidine-5-sulfonamide, |
| 118 | 6-(5-chloro-3-cyano-1-cyclopentyl-1H-indol-2-yl)-N-[(1S)-1-cyclopropylethyl]pyridine-3-sulfonamide, |

| Cpd | Name |
|---|---|
| 119 | 6-(5-chloro-3-cyano-1-cyclobutyl-1H-indol-2-yl)-N-[(1S)-1-cyclopropylethyl]pyridine-3-sulfonamide, |
| 120 | 2-[5-chloro-3-cyano-1-(propan-2-yl)-1H-indol-2-yl]-N-(propan-2-yl)pyrimidine-5-sulfonamide, |
| 121 | 2-(3-cyano-1-cyclobutyl-5-methyl-1H-indol-2-yl)-N-(propan-2-yl)pyrimidine-5-sulfonamide, |
| 122 | 2-(3-cyano-1-cyclobutyl-5-methyl-1H-indol-2-yl)-N-(1,3-difluoropropan-2-yl)pyrimidine-5-sulfonamide, |
| 123 | 2-[3-cyano-5-fluoro-1-(propan-2-yl)-1H-indol-2-yl]-N-(propan-2-yl)pyrimidine-5-sulfonamide, |
| 124 | 2-[3-cyano-6-cyclopropyl-1-(cyclopropylmethyl)-1H-indol-2-yl]-N-(propan-2-yl)pyrimidine-5-sulfonamide, |
| 125 | 2-(3-cyano-1-cyclopentyl-6-cyclopropyl-1H-indol-2-yl)-N-(propan-2-yl)pyrimidine-5-sulfonamide, |
| 126 | 2-(3-cyano-1-cyclobutyl-6-cyclopropyl-1H-indol-2-yl)-N-(1,3-difluoropropan-2-yl)pyrimidine-5-sulfonamide, |
| 127 | 2-[3-cyano-1-cyclobutyl-6-(difluoromethoxy)-1H-indol-2-yl]-N-(propan-2-yl)pyrimidine-5-sulfonamide, |
| 128 | 2-[3-cyano-1-cyclobutyl-6-(difluoromethoxy)-1H-indol-2-yl]-N-(1,1,1-trifluoropropan-2-yl)pyrimidine-5-sulfonamide, |
| 129 | 2-[3-cyano-1-cyclobutyl-6-(difluoromethoxy)-1H-indol-2-yl]-N-(1,3-difluoropropan-2-yl)pyrimidine-5-sulfonamide, |
| 130 | 2-[3-cyano-1-cyclobutyl-6-(difluoromethoxy)-1H-indol-2-yl]-N-[(1S)-1-cyclopropylethyl]pyrimidine-5-sulfonamide, |
| 131 | 2-(3-cyano-1-cyclobutyl-6-cyclopropyl-1H-indol-2-yl)-N-[(1S)-1-cyclopropylethyl]pyrimidine-5-sulfonamide, |
| 132 | 2-(3-cyano-1-cyclobutyl-6-methyl-1H-indol-2-yl)-N-(1,3-difluoropropan-2-yl)pyrimidine-5-sulfonamide, |
| 133 | 2-[3-cyano-1-(cyclopropylmethyl)-6-methyl-1H-indol-2-yl]-N-(1,3-difluoropropan-2-yl)pyrimidine-5-sulfonamide, |
| 134 | 2-[3-cyano-6-methyl-1-(propan-2-yl)-1H-indol-2-yl]-N-(1,3-difluoropropan-2-yl)pyrimidine-5-sulfonamide, |
| 135 | 2-(3-cyano-1-cyclopentyl-6-methyl-1H-indol-2-yl)-N-(1,3-difluoropropan-2-yl)pyrimidine-5-sulfonamide, |
| 136 | 2-[3-cyano-1-(cyclopropylmethyl)-6-(difluoromethoxy)-1H-indol-2-yl]-N-(1,3-difluoropropan-2-yl)pyrimidine-5-sulfonamide, |
| 137 | 2-[3-cyano-6-(difluoromethoxy)-1-(propan-2-yl)-1H-indol-2-yl]-N-(1,3-difluoropropan-2-yl)pyrimidine-5-sulfonamide, |
| 138 | 2-(3-cyano-1-cyclobutyl-6-fluoro-1H-indol-2-yl)-N-(propan-2-yl)pyrimidine-5-sulfonamide, |
| 139 | 2-[3-cyano-1-(cyclopropylmethyl)-6-fluoro-1H-indol-2-yl]-N-(propan-2-yl)pyrimidine-5-sulfonamide, |
| 140 | 2-[3-cyano-6-fluoro-1-(propan-2-yl)-1H-indol-2-yl]-N-(propan-2-yl)pyrimidine-5-sulfonamide, |
| 141 | 2-(3-cyano-1-cyclopentyl-6-fluoro-1H-indol-2-yl)-N-(propan-2-yl)pyrimidine-5-sulfonamide, |
| 142 | 6-(3-cyano-1-cyclobutyl-5-fluoro-1H-indol-2-yl)-N-[(1S)-1-cyclopropylethyl]pyridine-3-sulfonamide, |
| 143 | 6-(3-cyano-1-cyclopentyl-5-fluoro-1H-indol-2-yl)-N-[(1S)-1-cyclopropylethyl]pyridine-3-sulfonamide, |
| 144 | 6-(3-cyano-1-cyclobutyl-6-fluoro-1H-indol-2-yl)-N-[(1S)-1-cyclopropylethyl]pyridine-3-sulfonamide, |
| 145 | 2-(3-cyano-1-cyclobutyl-6-cyclopropyl-5-fluoro-1H-indol-2-yl)-N-(1,3-difluoropropan-2-yl)pyrimidine-5-sulfonamide, |
| 146 | 2-(3-cyano-1-cyclobutyl-5-fluoro-6-methyl-1H-indol-2-yl)-N-(1,3-difluoropropan-2-yl)pyrimidine-5-sulfonamide, |
| 147 | 6-(3-cyano-1,6-dicyclopropyl-1H-indol-2-yl)-N-(1,3-difluoropropan-2-yl)pyridine-3-sulfonamide, |
| 148 | 2-(3-cyano-1,6-dicyclopropyl-1H-indol-2-yl)-N-(1,3-difluoropropan-2-yl)pyrimidine-5-sulfonamide, |
| 149 | 2-(6-chloro-3-cyano-1-cyclobutyl-5-fluoro-1H-indol-2-yl)-N-(1,3-difluoropropan-2-yl)pyrimidine-5-sulfonamide, |
| 150 | 2-(3-cyano-1-cyclobutyl-5-fluoro-6-methoxy-1H-indol-2-yl)-N-(1,3-difluoropropan-2-yl)pyrimidine-5-sulfonamide, |
| 151 | 6-[3-cyano-1-cyclobutyl-6-(difluoromethoxy)-1H-indol-2-yl]-N-[(1S)-1-cyclopropylethyl]pyridine-3-sulfonamide, |
| 152 | 6-[3-cyano-1-cyclobutyl-6-(trifluoromethoxy)-1H-indol-2-yl]-N-[(1S)-1-cyclopropylethyl]pyridine-3-sulfonamide, |
| 153 | 6-(3-cyano-1-cyclobutyl-6-cyclopropyl-1H-indol-2-yl)-N-[1-(trifluoromethyl)cyclopropyl]pyridine-3-sulfonamide, |
| 154 | 6-(6-chloro-3-cyano-1-cyclobutyl-1H-indol-2-yl)-N-[(1S)-1-cyclopropylethyl]pyridine-3-sulfonamide, |
| 155 | 6-(6-chloro-3-cyano-1-cyclopentyl-1H-indol-2-yl)-N-[(1S)-1-cyclopropylethyl]pyridine-3-sulfonamide, |
| 156 | 2-[6-chloro-3-cyano-1-(propan-2-yl)-1H-indol-2-yl]-N-(propan-2-yl)pyrimidine-5-sulfonamide, |

| Cpd | Name |
| --- | --- |
| 157 | 2-(6-chloro-3-cyano-1-cyclopentyl-1H-indol-2-yl)-N-(1,3-difluoropropan-2-yl)pyrimidine-5-sulfonamide, |
| 158 | 6-(3-cyano-1-cyclopentyl-5-methyl-1H-indol-2-yl)-N-(1,3-difluoropropan-2-yl)pyridine-3-sulfonamide, |
| 159 | 2-(3-cyano-1-cyclopentyl-5-methyl-1H-indol-2-yl)-N-(propan-2-yl)pyrimidine-5-sulfonamide, |
| 160 | 2-(3-cyano-1-cyclopentyl-5-methyl-1H-indol-2-yl)-N-(1,3-difluoropropan-2-yl)pyrimidine-5-sulfonamide, |
| 161 | 6-[3-cyano-1-cyclobutyl-6-(methylsulfanyl)-1H-indol-2-yl]-N-(1,3-difluoropropan-2-yl)pyridine-3-sulfonamide, |
| 162 | 2-[3-cyano-1-cyclobutyl-6-(methylsulfanyl)-1H-indol-2-yl]-N-(1,3-difluoropropan-2-yl)pyrimidine-5-sulfonamide, |
| 163 | 2-(3-cyano-1-cyclobutyl-6-fluoro-1H-indol-2-yl)-N-(1,3-difluoropropan-2-yl)pyrimidine-5-sulfonamide, |
| 164 | 2-[3-cyano-1-(cyclopropylmethyl)-6-fluoro-1H-indol-2-yl]-N-(1,3-difluoropropan-2-yl)pyrimidine-5-sulfonamide, |
| 165 | 2-[3-cyano-6-fluoro-1-(propan-2-yl)-1H-indol-2-yl]-N-(1,3-difluoropropan-2-yl)pyrimidine-5-sulfonamide, |
| 166 | 2-(3-cyano-1-cyclopentyl-6-fluoro-1H-indol-2-yl)-N-(1,3-difluoropropan-2-yl)pyrimidine-5-sulfonamide, |
| 167 | 2-[3-cyano-6-methyl-1-(propan-2-yl)-1H-indol-2-yl]-N-(propan-2-yl)pyrimidine-5-sulfonamide, |
| 168 | 2-[3-cyano-1-(cyclopropylmethyl)-6-methyl-1H-indol-2-yl]-N-(propan-2-yl)pyrimidine-5-sulfonamide, |
| 169 | 2-(3-cyano-1-cyclobutyl-6-methyl-1H-indol-2-yl)-N-(propan-2-yl)pyrimidine-5-sulfonamide, |
| 170 | 2-[3-cyano-1-(cyclopropylmethyl)-6-(difluoromethoxy)-1H-indol-2-yl]-N-(propan-2-yl)pyrimidine-5-sulfonamide, |
| 171 | 2-[3-cyano-6-(difluoromethoxy)-1-(propan-2-yl)-1H-indol-2-yl]-N-(propan-2-yl)pyrimidine-5-sulfonamide, |
| 172 | 2-(3-cyano-1-cyclobutyl-6-methoxy-1H-indol-2-yl)-N-(propan-2-yl)pyrimidine-5-sulfonamide, |
| 173 | 2-(3-cyano-1-cyclopentyl-6-cyclopropyl-1H-indol-2-yl)-N-(1,3-difluoropropan-2-yl)pyrimidine-5-sulfonamide, |
| 174 | 6-[3-cyano-1-cyclopentyl-6-(difluoromethoxy)-1H-indol-2-yl]-N-[(1S)-1-cyclopropylethyl]pyridine-3-sulfonamide, |
| 175 | 2-(5-chloro-3-cyano-1-cyclobutyl-1H-indol-2-yl)-N-(1,3-difluoropropan-2-yl)pyrimidine-5-sulfonamide, |
| 176 | 2-(6-chloro-3-cyano-1-cyclobutyl-1H-indol-2-yl)-N-(1,3-difluoropropan-2-yl)pyrimidine-5-sulfonamide, |
| 177 | 2-[3-cyano-1-cyclobutyl-6-(trifluoromethoxy)-1H-indol-2-yl]-N-(1,3-difluoropropan-2-yl)pyrimidine-5-sulfonamide, |
| 178 | 2-[3-cyano-1-cyclopentyl-6-(trifluoromethoxy)-1H-indol-2-yl]-N-(1,3-difluoropropan-2-yl)pyrimidine-5-sulfonamide, |
| 179 | 2-[3-cyano-1-cyclohexyl-6-(difluoromethoxy)-1H-indol-2-yl]-N-(1,3-difluoropropan-2-yl)pyrimidine-5-sulfonamide, |
| 180 | 2-(3-cyano-1-cyclobutyl-6-cyclopropyl-1H-indol-2-yl)-N-[(2R)-1,1,1-trifluoropropan-2-yl]pyrimidine-5-sulfonamide, |
| 181 | 2-(3-cyano-1-cyclobutyl-6-methyl-1H-indol-2-yl)-N-[(2R)-1,1,1-trifluoropropan-2-yl]pyrimidine-5-sulfonamide, |
| 182 | 2-(3-cyano-1-cyclopentyl-6-methyl-1H-indol-2-yl)-N-[(2R)-1,1,1-trifluoropropan-2-yl]pyrimidine-5-sulfonamide, |
| 183 | 2-(3-cyano-1-cyclobutyl-6-methoxy-1H-indol-2-yl)-N-[(2R)-1,1,1-trifluoropropan-2-yl]pyrimidine-5-sulfonamide, |
| 184 | 2-[3-cyano-1-cyclobutyl-6-(difluoromethoxy)-1H-indol-2-yl]-N-[(2R)-1,1,1-trifluoropropan-2-yl]pyrimidine-5-sulfonamide, |
| 185 | 2-[3-cyano-1-cyclobutyl-6-(propan-2-yl)-1H-indol-2-yl]-N-(propan-2-yl)pyrimidine-5-sulfonamide, |
| 186 | 2-[3-cyano-1-cyclobutyl-6-(propan-2-yl)-1H-indol-2-yl]-N-(1,3-difluoropropan-2-yl)pyrimidine-5-sulfonamide, |
| 187 | 2-[5-chloro-3-cyano-1-(propan-2-yl)-1H-indol-2-yl]-N-(1,3-difluoropropan-2-yl)pyrimidine-5-sulfonamide, |
| 188 | 2-(5-chloro-3-cyano-1-cyclopentyl-1H-indol-2-yl)-N-(1,3-difluoropropan-2-yl)pyrimidine-5-sulfonamide, |
| 189 | 2-(6-chloro-3-cyano-1-cyclopentyl-1H-indol-2-yl)-N-(propan-2-yl)pyrimidine-5-sulfonamide, |
| 190 | 6-(3-cyano-1-cyclopentyl-6-methyl-1H-indol-2-yl)-N-[1-(trifluoromethyl)cyclopropyl]pyridine-3-sulfonamide, |
| 191 | 6-[3-cyano-1-cyclobutyl-6-(trifluoromethoxy)-1H-indol-2-yl]-N-[(2R)-1,1,1-trifluoropropan-2-yl]pyridine-3-sulfonamide, |
| 192 | 6-(3-cyano-1-cyclobutyl-6-methyl-1H-indol-2-yl)-N-[(2R)-1,1,1-trifluoropropan-2-yl]pyridine-3-sulfonamide, |
| 193 | 2-(3-cyano-1-cyclohexyl-6-cyclopropyl-1H-indol-2-yl)-N-(1,3-difluoropropan-2-yl)pyrimidine-5-sulfonamide, |
| 194 | 6-[3-cyano-6-(difluoromethoxy)-1-(propan-2-yl)-1H-indol-2-yl]-N-[(2R)-1,1,1-trifluoropropan-2-yl]pyridine-3-sulfonamide, |

-continued

| Cpd | Name |
|---|---|
| 195 | 6-[3-cyano-1-cyclohexyl-6-(difluoromethoxy)-1H-indol-2-yl]-N-[(2R)-1,1,1-trifluoropropan-2-yl]pyridine-3-sulfonamide, |
| 196 | 6-[3-cyano-1-cyclobutyl-6-(difluoromethoxy)-1H-indol-2-yl]-N-[(2R)-1,1,1-trifluoropropan-2-yl]pyridine-3-sulfonamide, |
| 197 | 6-[3-cyano-1-(cyclopropylmethyl)-6-methyl-1H-indol-2-yl]-N-[(2R)-1,1,1-trifluoropropan-2-yl]pyridine-3-sulfonamide, |
| 198 | 2-(3-cyano-1-cyclohexyl-5-methyl-1H-indol-2-yl)-N-(1,3-difluoropropan-2-yl)pyrimidine-5-sulfonamide, |
| 199 | 6-(3-cyano-1-cyclohexyl-5-methyl-1H-indol-2-yl)-N-(1,3-difluoropropan-2-yl)pyridine-3-sulfonamide, |
| 200 | 2-(3-cyano-1-cyclohexyl-5-methyl-1H-indol-2-yl)-N-(propan-2-yl)pyrimidine-5-sulfonamide, |
| 201 | 6-(3-cyano-1-cyclobutyl-5-methyl-1H-indol-2-yl)-N-[(1S)-1-cyclopropylethyl]pyridine-3-sulfonamide, |
| 202 | 2-(3-cyano-1-cyclobutyl-6-methyl-1H-indol-2-yl)-N-[(1S)-1-cyclopropylethyl]pyrimidine-5-sulfonamide, |
| 203 | 2-[3-cyano-1-(cyclopropylmethyl)-6-methyl-1H-indol-2-yl]-N-[(1S)-1-cyclopropylethyl]pyrimidine-5-sulfonamide, |
| 204 | 2-(3-cyano-1-cyclopentyl-6-methyl-1H-indol-2-yl)-N-[(1S)-1-cyclopropylethyl]pyrimidine-5-sulfonamide, |
| 205 | 2-(3-cyano-1-cyclobutyl-6-methoxy-1H-indol-2-yl)-N-[(1S)-1-cyclopropylethyl]pyrimidine-5-sulfonamide, |
| 206 | 2-(3-cyano-1-cyclopentyl-6-methoxy-1H-indol-2-yl)-N-[(1S)-1-cyclopropylethyl]pyrimidine-5-sulfonamide, |
| 207 | 2-[3-cyano-6-(difluoromethoxy)-1-(propan-2-yl)-1H-indol-2-yl]-N-[(1S)-1-cyclopropylethyl]pyrimidine-5-sulfonamide, |
| 208 | 2-[3-cyano-6-(difluoromethoxy)-1-propyl-1H-indol-2-yl]-N-[(1S)-1-cyclopropylethyl]pyrimidine-5-sulfonamide, |
| 209 | 2-[3-cyano-1-cyclopentyl-6-(difluoromethoxy)-1H-indol-2-yl]-N-[(1S)-1-cyclopropylethyl]pyrimidine-5-sulfonamide, |
| 210 | 6-[3-cyano-6-methyl-1-(propan-2-yl)-1H-indol-2-yl]-N-[(2R)-1,1,1-trifluoropropan-2-yl]pyridine-3-sulfonamide, |
| 211 | 6-(3-cyano-1-cyclopentyl-6-cyclopropyl-1H-indol-2-yl)-N-[(2R)-1,1,1-trifluoropropan-2-yl]pyridine-3-sulfonamide, |
| 212 | 6-(3-cyano-1-cyclobutyl-6-cyclopropyl-1H-indol-2-yl)-N-[(2R)-1,1,1-trifluoropropan-2-yl]pyridine-3-sulfonamide, |
| 213 | 6-(3-cyano-1-cyclohexyl-6-methyl-1H-indol-2-yl)-N-[(2R)-1,1,1-trifluoropropan-2-yl]pyridine-3-sulfonamide, |
| 214 | 6-(3-cyano-1-cyclopentyl-6-methyl-1H-indol-2-yl)-N-[(2R)-1,1,1-trifluoropropan-2-yl]pyridine-3-sulfonamide, |
| 215 | 6-(3-cyano-1-cyclobutyl-6-fluoro-1H-indol-2-yl)-N-[(2R)-1,1,1-trifluoropropan-2-yl]pyridine-3-sulfonamide, |
| 216 | 6-[3-cyano-1-(cyclopropylmethyl)-6-fluoro-1H-indol-2-yl]-N-[(2R)-1,1,1-trifluoropropan-2-yl]pyridine-3-sulfonamide, |
| 217 | 6-(3-cyano-6-fluoro-1-propyl-1H-indol-2-yl)-N-[(2R)-1,1,1-trifluoropropan-2-yl]pyridine-3-sulfonamide, |
| 218 | 6-(3-cyano-1-cyclopentyl-6-fluoro-1H-indol-2-yl)-N-[(2R)-1,1,1-trifluoropropan-2-yl]pyridine-3-sulfonamide, |
| 219 | 6-(3-cyano-1-cyclobutyl-5-fluoro-1H-indol-2-yl)-N-[(2R)-1,1,1-trifluoropropan-2-yl]pyridine-3-sulfonamide, |
| 220 | 6-(3-cyano-1-cyclopentyl-5-fluoro-1H-indol-2-yl)-N-[(2R)-1,1,1-trifluoropropan-2-yl]pyridine-3-sulfonamide, |
| 221 | 2-[5-chloro-3-cyano-1-(cyclopropylmethyl)-1H-indol-2-yl]-N-(1,3-difluoropropan-2-yl)pyrimidine-5-sulfonamide, |
| 222 | 6-(6-chloro-3-cyano-1-cyclobutyl-1H-indol-2-yl)-N-[(2R)-1,1,1-trifluoropropan-2-yl]pyridine-3-sulfonamide, |
| 223 | 6-(6-chloro-3-cyano-1-cyclopentyl-1H-indol-2-yl)-N-[(2R)-1,1,1-trifluoropropan-2-yl]pyridine-3-sulfonamide, |
| 224 | 6-(5-chloro-3-cyano-1-cyclopentyl-1H-indol-2-yl)-N-[(2R)-1,1,1-trifluoropropan-2-yl]pyridine-3-sulfonamide, |
| 225 | 6-[3-cyano-1-(cyclopropylmethyl)-5-fluoro-6-methoxy-1H-indol-2-yl]-N-(1,3-difluoropropan-2-yl)pyridine-3-sulfonamide, |
| 226 | 6-[3-cyano-6-(difluoromethoxy)-1-phenyl-1H-indol-2-yl]-N-(1,3-difluoropropan-2-yl)pyridine-3-sulfonamide, |
| 227 | 6-[3-cyano-6-(difluoromethoxy)-1-(2-fluorophenyl)-1H-indol-2-yl]-N-(1,3-difluoropropan-2-yl)pyridine-3-sulfonamide, |
| 228 | 6-[3-cyano-6-(difluoromethoxy)-1-(4-fluorophenyl)-1H-indol-2-yl]-N-(1,3-difluoropropan-2-yl)pyridine-3-sulfonamide, |
| 229 | 6-(3-cyano-1-cyclobutyl-6-methoxy-1H-indol-2-yl)-N-(1,3-difluoropropan-2-yl)pyridine-3-sulfonamide, |
| 230 | 2-(3-cyano-1-cyclobutyl-6-methoxy-1H-indol-2-yl)-N-(1,3-difluoropropan-2-yl)pyrimidine-5-sulfonamide, |
| 231 | 2-(3-cyano-1-cyclopentyl-6-methoxy-1H-indol-2-yl)-N-(1,3-difluoropropan-2-yl)pyrimidine-5-sulfonamide, |
| 232 | 2-[3-cyano-6-(difluoromethoxy)-1-propyl-1H-indol-2-yl]-N-(1,3-difluoropropan-2-yl)pyrimidine-5-sulfonamide, |

-continued

| Cpd | Name |
|---|---|
| 233 | 2-[3-cyano-1-cyclopentyl-6-(difluoromethoxy)-1H-indol-2-yl]-N-(1,3-difluoropropan-2-yl)pyrimidine-5-sulfonamide, |
| 234 | 6-(3-cyano-1-cyclohexyl-6-fluoro-1H-indol-2-yl)-N-(1,3-difluoropropan-2-yl)pyridine-3-sulfonamide, |
| 235 | 2-(3-cyano-1-cyclohexyl-6-fluoro-1H-indol-2-yl)-N-(1,3-difluoropropan-2-yl)pyrimidine-5-sulfonamide, |
| 236 | 6-(3-cyano-1-cyclobutyl-6-cyclopropyl-1H-indol-2-yl)-N-[(1S)-1-cyclopropylethyl]pyridine-3-sulfonamide, |
| 237 | 6-[3-cyano-1-(cyclopropylmethyl)-6-methyl-1H-indol-2-yl]-N-[(1S)-1-cyclopropylethyl]pyridine-3-sulfonamide, |
| 238 | 6-(3-cyano-1-cyclobutyl-6-methyl-1H-indol-2-yl)-N-[(1S)-1-cyclopropylethyl]pyridine-3-sulfonamide, |
| 239 | 6-[3-cyano-1-cyclobutyl-6-(difluoromethoxy)-1H-indol-2-yl]-N-(1,3-dihydroxypropan-2-yl)pyridine-3-sulfonamide, |
| 240 | 2-(3-cyano-1-cyclopentyl-5-fluoro-1H-indol-2-yl)-N-(1,3-difluoropropan-2-yl)pyrimidine-5-sulfonamide, |
| 241 | 2-(3-cyano-1-cyclohexyl-6-methyl-1H-indol-2-yl)-N-(1,3-difluoropropan-2-yl)pyrimidine-5-sulfonamide, |
| 242 | 2-[3-cyano-5-(difluoromethoxy)-1-ethyl-1H-indol-2-yl]-N-(propan-2-yl)pyrimidine-5-sulfonamide, |
| 243 | 6-(5-chloro-3-cyano-1-cyclobutyl-1H-indol-2-yl)-N-(3,3-difluorocyclobutyl)pyridine-3-sulfonamide, |
| 244 | 6-(6-chloro-3-cyano-1-cyclobutyl-1H-indol-2-yl)-N-(3,3-difluorocyclobutyl)pyridine-3-sulfonamide, |
| 245 | 6-(3-cyano-1-cyclobutyl-6-methyl-1H-indol-2-yl)-N-(3,3-difluorocyclobutyl)pyridine-3-sulfonamide, |
| 246 | 6-(3-cyano-1-cyclopentyl-6-methoxy-1H-indol-2-yl)-N-(3,3-difluorocyclobutyl)pyridine-3-sulfonamide, |
| 247 | 6-(3-cyano-1-cyclobutyl-6-cyclopropyl-1H-indol-2-yl)-N-(3,3-difluorocyclobutyl)pyridine-3-sulfonamide, |
| 248 | 6-[3-cyano-6-methyl-1-(pyridin-2-yl)-1H-indol-2-yl]-N-(1,3-difluoropropan-2-yl)pyridine-3-sulfonamide, |
| 249 | 6-[3-cyano-6-(difluoromethoxy)-1-(pyridin-2-yl)-1H-indol-2-yl]-N-(1,3-difluoropropan-2-yl)pyridine-3-sulfonamide, |
| 250 | 6-(3-cyano-1-cyclohexyl-5-fluoro-1H-indol-2-yl)-N-[(1S)-1-cyclopropylethyl]pyridine-3-sulfonamide, |
| 251 | 2-(3-cyano-1-cyclohexyl-6-fluoro-1H-indol-2-yl)-N-(propan-2-yl)pyrimidine-5-sulfonamide, |
| 252 | 6-(3-cyano-1-cyclohexyl-6-fluoro-1H-indol-2-yl)-N-[(2R)-1,1,1-trifluoropropan-2-yl]pyridine-3-sulfonamide, |
| 253 | 6-(3-cyano-1-cyclopentyl-6-methyl-1H-indol-2-yl)-N-[1-(trifluoromethyl)cyclobutyl]pyridine-3-sulfonamide, |
| 254 | 2-(3-cyano-1-cyclopentyl-6-cyclopropyl-1H-indol-2-yl)-N-[(1S)-1-cyclopropylethyl]pyrimidine-5-sulfonamide, |
| 255 | 6-[3-cyano-1-(cyclopropylmethyl)-6-methyl-1H-indol-2-yl]-N-[1-(trifluoromethyl)cyclopropyl]pyridine-3-sulfonamide, |
| 256 | 6-(3-cyano-1-cyclobutyl-6-methyl-1H-indol-2-yl)-N-[1-(trifluoromethyl)cyclopropyl]pyridine-3-sulfonamide, |
| 257 | 2-[6-chloro-3-cyano-1-(propan-2-yl)-1H-indol-2-yl]-N-(1,3-difluoropropan-2-yl)pyrimidine-5-sulfonamide, |
| 258 | 6-(3-cyano-1-cyclobutyl-5-ethyl-1H-indol-2-yl)-N-(1,3-difluoropropan-2-yl)pyridine-3-sulfonamide, |
| 259 | 6-[3-cyano-5-fluoro-1-(pyridin-4-yl)-1H-indol-2-yl]-N-(1,3-difluoropropan-2-yl)pyridine-3-sulfonamide, |
| 260 | 2-(3-cyano-6-methyl-1-phenyl-1H-indol-2-yl)-N-(1,3-difluoropropan-2-yl)pyrimidine-5-sulfonamide, |
| 261 | 6-(3-cyano-1-cyclohexyl-5-fluoro-1H-indol-2-yl)-N-[(2R)-1,1,1-trifluoropropan-2-yl]pyridine-3-sulfonamide, |
| 262 | 6-(3-cyano-1-cyclohexyl-6-fluoro-1H-indol-2-yl)-N-[(1S)-1-cyclopropylethyl]pyridine-3-sulfonamide, |
| 263 | 6-(3-cyano-1,6-dicyclobutyl-1H-indol-2-yl)-N-[(1S)-1-cyclopropylethyl]pyridine-3-sulfonamide, |
| 264 | 2-(3-cyano-1,6-dicyclobutyl-1H-indol-2-yl)-N-(1,3-difluoropropan-2-yl)pyrimidine-5-sulfonamide, |
| 265 | 2-(3-cyano-1,6-dicyclobutyl-1H-indol-2-yl)-N-(propan-2-yl)pyrimidine-5-sulfonamide, |
| 266 | 6-(3-cyano-1,6-dicyclobutyl-1H-indol-2-yl)-N-(propan-2-yl)pyridine-3-sulfonamide, |
| 267 | 6-[3-cyano-1-cyclobutyl-6-(2,2-difluoroethyl)-1H-indol-2-yl]-N-(1,3-difluoropropan-2-yl)pyridine-3-sulfonamide, |
| 268 | N-{5-[3-cyano-1-cyclobutyl-6-(pyrimidin-2-yloxy)-1H-indol-2-yl]pyridin-2-yl}-2-methylpropane-2-sulfonamide, |
| 269 | N-{5-[3-cyano-1-(cyclopropylmethyl)-6-(difluoromethoxy)-1H-indol-2-yl]pyridin-2-yl}-2-methylpropane-2-sulfonamide, |
| 270 | N-{6-[3-cyano-1-(cyclopropylmethyl)-6-(difluoromethoxy)-1H-indol-2-yl]pyridin-3-yl}cyclopropanesulfonamide, |

| Cpd | Name |
|---|---|
| 271 | N-{6-[3-cyano-1-cyclobutyl-6-(pyrimidin-2-yloxy)-1H-indol-2-yl]pyridin-3-yl}propane-1-sulfonamide, |
| 272 | N-(6-{3-cyano-6-[(3-cyanopyridin-2-yl)oxy]-1-cyclobutyl-1H-indol-2-yl}pyridin-3-yl)propane-1-sulfonamide, |
| 273 | N-(6-{3-cyano-6-[(3-cyanopyrazin-2-yl)oxy]-1-cyclobutyl-1H-indol-2-yl}pyridin-3-yl)propane-1-sulfonamide, |
| 274 | N-{6-[3-cyano-1-cyclobutyl-6-(propan-2-yloxy)-1H-indol-2-yl]pyridazin-3-yl}cyclopropanesulfonamide, |
| 275 | N-{6-[3-cyano-1-cyclobutyl-6-(propan-2-yloxy)-1H-indol-2-yl]pyridazin-3-yl}methanesulfonamide, |
| 276 | N-{6-[3-cyano-1-cyclobutyl-6-(propan-2-yloxy)-1H-indol-2-yl]pyridazin-3-yl}ethanesulfonamide, |
| 277 | N-[6-(3-cyano-1-cyclobutyl-6-methoxy-1H-indol-2-yl)pyridazin-3-yl]ethanesulfonamide, |
| 278 | N-[6-(3-cyano-1-cyclobutyl-6-methoxy-1H-indol-2-yl)pyridazin-3-yl]-2-methylpropane-2-sulfonamide, |
| 279 | N-{6-[3-cyano-1-(cyclopropylmethyl)-6-(propan-2-yloxy)-1H-indol-2-yl]pyridin-3-yl}ethanesulfonamide, |
| 280 | N-{6-[3-cyano-1-(cyclopropylmethyl)-6-(propan-2-yloxy)-1H-indol-2-yl]pyridin-3-yl}cyclopropanesulfonamide, |
| 281 | N-{6-[3-cyano-1-(cyclopropylmethyl)-6-(propan-2-yloxy)-1H-indol-2-yl]pyridin-3-yl}propane-2-sulfonamide, |
| 282 | N-{6-[3-cyano-1-ethyl-6-(propan-2-yloxy)-1H-indol-2-yl]pyridin-3-yl}-N-(propan-2-yl)ethanesulfonamide, |
| 283 | N-{6-[3-cyano-1-(cyclopropylmethyl)-6-(2,2,2-trifluoroethoxy)-1H-indol-2-yl]pyridin-3-yl}propane-2-sulfonamide, |
| 284 | N-{6-[3-cyano-1-(cyclopropylmethyl)-6-(2,2,2-trifluoroethoxy)-1H-indol-2-yl]pyridin-3-yl}ethanesulfonamide, |
| 285 | N-{6-[3-cyano-1-ethyl-6-(propan-2-yloxy)-1H-indol-2-yl]pyridin-3-yl}cyclopropanesulfonamide, |
| 286 | N-{6-[3-cyano-1-ethyl-6-(propan-2-yloxy)-1H-indol-2-yl]pyridin-3-yl}propane-2-sulfonamide, |
| 287 | N-[5-(3-cyano-1-cyclobutyl-6-cyclopropyl-1H-indol-2-yl)pyridin-2-yl]methanesulfonamide, |
| 288 | N-[5-(3-cyano-1-cyclobutyl-6-cyclopropyl-1H-indol-2-yl)pyridin-2-yl]ethanesulfonamide, |
| 289 | N-[5-(3-cyano-1-cyclobutyl-6-cyclopropyl-1H-indol-2-yl)pyridin-2-yl]propane-2-sulfonamide, |
| 290 | N-{5-[3-cyano-1-(cyclopropylmethyl)-6-(2,2,2-trifluoroethoxy)-1H-indol-2-yl]pyridin-2-yl}ethanesulfonamide, |
| 291 | N-{5-[3-cyano-1-(cyclopropylmethyl)-6-(2,2,2-trifluoroethoxy)-1H-indol-2-yl]pyridin-2-yl}propane-2-sulfonamide, |
| 292 | N-{5-[3-cyano-1-ethyl-6-(propan-2-yloxy)-1H-indol-2-yl]pyridin-2-yl}-N-(2,2-difluoroethyl)cyclopropanesulfonamide, |
| 293 | N-{5-[3-cyano-1-ethyl-6-(propan-2-yloxy)-1H-indol-2-yl]pyridin-2-yl}-N-(2-hydroxyethyl)cyclopropanesulfonamide, |
| 294 | N-{5-[3-cyano-1-ethyl-6-(propan-2-yloxy)-1H-indol-2-yl]pyridin-2-yl}-N-(cyanomethyl)cyclopropanesulfonamide, |
| 295 | N-{5-[3-cyano-1-cyclobutyl-6-(difluoromethoxy)-1H-indol-2-yl]pyridin-2-yl}-2-methylpropane-2-sulfonamide, |
| 296 | N-[6-(3-cyano-1-cyclopentyl-6-methyl-1H-indol-2-yl)pyridin-3-yl]cyclopropanesulfonamide, |
| 297 | N-[6-(3-cyano-1-cyclobutyl-6-methyl-1H-indol-2-yl)pyridin-3-yl]cyclopropanesulfonamide, |
| 298 | N-[6-(5-chloro-3-cyano-1-cyclohexyl-1H-indol-2-yl)pyridin-3-yl]cyclopropanesulfonamide, |
| 299 | N-{5-[3-cyano-6-(difluoromethoxy)-1-(propan-2-yl)-1H-indol-2-yl]pyridin-2-yl}-2-methylpropane-2-sulfonamide, |
| 300 | 6-[3-cyano-1-cyclobutyl-6-(difluoromethoxy)-1H-indol-2-yl]-N-[(2S)-1,1,1-trifluoropropan-2-yl]pyridine-3-sulfonamide, |
| 301 | 6-[3-cyano-1-cyclobutyl-6-(difluoromethoxy)-1H-indol-2-yl]-N-(1-cyanoethyl)pyridine-3-sulfonamide, |
| 302 | 2-[3-cyano-1-(cyclopropylmethyl)-5-fluoro-1H-indol-2-yl]-N-(1,3-difluoropropan-2-yl)pyrimidine-5-sulfonamide, |
| 303 | 2-[3-cyano-1-(cyclopropylmethyl)-5-fluoro-1H-indol-2-yl]-N-(propan-2-yl)pyrimidine-5-sulfonamide, |
| 304 | 6-[3-cyano-1-cyclohexyl-6-(trifluoromethoxy)-1H-indol-2-yl]-N-[(2R)-1,1,1-trifluoropropan-2-yl]pyridine-3-sulfonamide, |
| 305 | 6-[3-cyano-1-cyclohexyl-6-(trifluoromethoxy)-1H-indol-2-yl]-N-[(1S)-1-cyclopropylethyl]pyridine-3-sulfonamide, |
| 306 | 2-[3-cyano-1-cyclohexyl-6-(trifluoromethoxy)-1H-indol-2-yl]-N-(1,3-difluoropropan-2-yl)pyrimidine-5-sulfonamide, |
| 307 | 6-(3-cyano-1-cyclopentyl-6-fluoro-1H-indol-2-yl)-N-(1,3-difluoropropan-2-yl)pyridine-3-sulfonamide, |
| 308 | 6-[3-cyano-1-(propan-2-yl)-6-(trifluoromethoxy)-1H-indol-2-yl]-N-[(1S)-1-cyclopropylethyl]pyridine-3-sulfonamide, |

| Cpd | Name |
|---|---|
| 309 | 6-[3-cyano-1-(cyclopropylmethyl)-6-(trifluoromethoxy)-1H-indol-2-yl]-N-[(1S)-1-cyclopropylethyl]pyridine-3-sulfonamide, |
| 310 | 6-(3-cyano-1-cyclopentyl-6-ethyl-1H-indol-2-yl)-N-(1,3-difluoropropan-2-yl)pyridine-3-sulfonamide, |
| 311 | 6-(3-cyano-1-cyclopentyl-6-ethyl-1H-indol-2-yl)-N-[(2R)-1,1,1-trifluoropropan-2-yl]pyridine-3-sulfonamide, |
| 312 | 6-(3-cyano-1-cyclopentyl-6-ethyl-1H-indol-2-yl)-N-[(1S)-1-cyclopropylethyl]pyridine-3-sulfonamide, |
| 313 | 6-(3-cyano-1-cyclopentyl-5-methyl-1H-indol-2-yl)-N-[1-(trifluoromethyl)cyclopropyl]pyridine-3-sulfonamide, |
| 314 | 2-(5-chloro-3-cyano-1-cyclopentyl-1H-indol-2-yl)-N-(propan-2-yl)pyrimidine-5-sulfonamide, |
| 315 | 2-[3-cyano-1-cyclobutyl-6-(fluoromethyl)-1H-indol-2-yl]-N-(propan-2-yl)pyrimidine-5-sulfonamide, |
| 316 | 6-(5-chloro-3-cyano-1-cyclobutyl-1H-indol-2-yl)-N-[(2R)-1,1,1-trifluoropropan-2-yl]pyridine-3-sulfonamide, |
| 317 | 6-[3-cyano-1-cyclobutyl-6-(fluoromethyl)-1H-indol-2-yl]-N-[(1S)-1-cyclopropylethyl]pyridine-3-sulfonamide, |
| 318 | 6-[3-cyano-1-cyclobutyl-6-(fluoromethyl)-1H-indol-2-yl]-N-(1,3-difluoropropan-2-yl)pyridine-3-sulfonamide, |
| 319 | 6-[3-cyano-1-cyclobutyl-6-(fluoromethyl)-1H-indol-2-yl]-[(2R)-1,1,1-trifluoropropan-2-yl]pyridine-3-sulfonamide, |
| 320 | 6-[3-cyano-1-cyclopentyl-6-(trifluoromethoxy)-1H-indol-2-yl]-N-[(1S)-1-cyclopropylethyl]pyridine-3-sulfonamide, |
| 321 | 2-[3-cyano-1-cyclobutyl-6-(morpholin-4-yl)-1H-indol-2-yl]-(1,3-difluoropropan-2-yl)pyrimidine-5-sulfonamide, |
| 322 | 6-[3-cyano-1-cyclobutyl-6-(morpholin-4-yl)-1H-indol-2-yl]-N-(1,3-difluoropropan-2-yl)pyridine-3-sulfonamide, |
| 323 | 2-[3-cyano-1-cyclobutyl-6-(difluoromethoxy)-1H-indol-2-yl]-N-[(2S)-1,1,1-trifluoropropan-2-yl]pyrimidine-5-sulfonamide, |
| 324 | 2-(3-cyano-1-cyclobutyl-6-cyclopropyl-1H-indol-2-yl)-N-[(2S)-1,1,1-trifluoropropan-2-yl]pyrimidine-5-sulfonamide, |
| 325 | 2-(3-cyano-1-cyclobutyl-6-methyl-1H-indol-2-yl)-N-[(2S)-1,1,1-trifluoropropan-2-yl]pyrimidine-5-sulfonamide, |
| 326 | 2-[3-cyano-1-cyclopentyl-6-(difluoromethoxy)-1H-indol-2-yl]-N-[(2S)-1,1,1-trifluoropropan-2-yl]pyrimidine-5-sulfonamide, |
| 327 | 6-(3-cyano-1-cyclopentyl-5-fluoro-1H-indol-2-yl)-N-[1-(trifluoromethyl)cyclopropyl]pyridine-3-sulfonamide, |
| 328 | 6-(3-cyano-1-cyclobutyl-5-methyl-1H-indol-2-yl)-N-[1-(trifluoromethyl)cyclopropyl]pyridine-3-sulfonamide, |
| 329 | 6-(3-cyano-1-cyclobutyl-5-fluoro-1H-indol-2-yl)-N-[1-(trifluoromethyl)cyclopropyl]pyridine-3-sulfonamide, |
| 330 | 2-[3-cyano-1-cyclobutyl-6-(difluoromethyl)-1H-indol-2-yl]-N-(1,3-difluoropropan-2-yl)pyrimidine-5-sulfonamide, |
| 331 | 6-[3-cyano-1-cyclobutyl-6-(difluoromethyl)-1H-indol-2-yl]-N-(1,3-difluoropropan-2-yl)pyridine-3-sulfonamide, |
| 332 | 2-[3-cyano-1-cyclobutyl-6-(difluoromethyl)-1H-indol-2-yl]-N-(propan-2-yl)pyrimidine-5-sulfonamide, |
| 333 | 6-[3-cyano-1-cyclobutyl-6-(difluoromethyl)-1H-indol-2-yl]-N-(propan-2-yl)pyridine-3-sulfonamide, |
| 334 | 6-[3-cyano-1-cyclobutyl-6-(difluoromethyl)-1H-indol-2-yl]-N-[(2R)-1,1,1-trifluoropropan-2-yl]pyridine-3-sulfonamide, |
| 335 | 6-[3-cyano-1-cyclobutyl-6-(difluoromethyl)-1H-indol-2-yl]-N-[(1S)-1-cyclopropylethyl]pyridine-3-sulfonamide, |
| 336 | 6-[3-cyano-5-fluoro-1-(4-methoxyphenyl)-1H-indol-2-yl]-N-(1,3-difluoropropan-2-yl)pyridine-3-sulfonamide, |
| 337 | 2-[3-cyano-5-fluoro-1-(4-methoxyphenyl)-1H-indol-2-yl]-N-(1,3-difluoropropan-2-yl)pyrimidine-5-sulfonamide, |
| 338 | 6-(3-cyano-1-cyclobutyl-6-ethyl-1H-indol-2-yl)-N-[(2S)-1,1,1-trifluoropropan-2-yl]pyridine-3-sulfonamide, |
| 339 | 6-(3-cyano-1-cyclobutyl-5-ethyl-1H-indol-2-yl)-N-[(2S)-1,1,1-trifluoropropan-2-yl]pyridine-3-sulfonamide, |
| 340 | 6-(3-cyano-1-cyclobutyl-5-fluoro-6-methyl-1H-indol-2-yl)-N-[(2S)-1,1,1-trifluoropropan-2-yl]pyridine-3-sulfonamide, |
| 341 | 6-[3-cyano-1-cyclohexyl-6-(difluoromethoxy)-1H-indol-2-yl]-N-[(2S)-1,1,1-trifluoropropan-2-yl]pyridine-3-sulfonamide, |
| 342 | 6-(3-cyano-1,6-dicyclobutyl-1H-indol-2-yl)-N-(1,3-difluoropropan-2-yl)pyridine-3-sulfonamide, |
| 343 | 6-(3-cyano-6-cyclobutyl-1-cyclopentyl-1H-indol-2-yl)-N-[(2R)-1,1,1-trifluoropropan-2-yl]pyridine-3-sulfonamide, |
| 344 | 2-[3-cyano-6-cyclopropyl-1-(cyclopropylmethyl)-1H-indol-2-yl]-N-(1,3-difluoropropan-2-yl)pyrimidine-5-sulfonamide, |
| 345 | 6-(3-cyano-1-cyclopentyl-5-methyl-1H-indol-2-yl)-N-[(2S)-1,1,1-trifluoropropan-2-yl]pyridine-3-sulfonamide, |
| 346 | 6-(3,5-dicyano-1-cyclopentyl-1H-indol-2-yl)-N-[(2S)-1,1,1-trifluoropropan-2-yl]pyridine-3-sulfonamide, |

| Cpd | Name |
|---|---|
| 347 | 6-[3,6-dicyano-1-(cyclopropylmethyl)-1H-indol-2-yl]-N-(1,3-difluoropropan-2-yl)pyridine-3-sulfonamide, |
| 348 | 6[3,6-dicyano-1-(cyclopropylmethyl)-1H-indol-2-yl]-N-(propan-2-yl)pyridine-3-sulfonamide, |
| 349 | 6-[3,6-dicyano-1-(cyclopropylmethyl)-1H-indol-2-yl]-N-[(2S)-1,1,1-trifluoropropan-2-yl]pyridine-3-sulfonamide, |
| 350 | N-[(1S)-1-cyclopropylethyl]-6-[3,6-dicyano-1-(cyclopropylmethyl)-1H-indol-2-yl]pyridine-3-sulfonamide, |
| 351 | 6-(3-cyano-1-cyclobutyl-6-methyl-1H-indol-2-yl)-N-[(2S)-1,1,1-trifluoropropan-2-yl]pyridine-3-sulfonamide, |
| 352 | 6-(3-cyano-1-cyclopentyl-6-methyl-1H-indol-2-yl)-N-[(2S)-1,1,1-trifluoropropan-2-yl]pyridine-3-sulfonamide, |
| 353 | 6-[3-cyano-1-(cyclopropylmethyl)-6-methyl-1H-indol-2-yl]-N-[(2S)-1,1,1-trifluoropropan-2-yl]pyridine-3-sulfonamide, |
| 354 | 6-(3-cyano-1-cyclohexyl-6-methyl-1H-indol-2-yl)-N-[(2S)-1,1,1-trifluoropropan-2-yl]pyridine-3-sulfonamide, |
| 355 | 6-[3-cyano-6-methyl-1-(propan-2-yl)-1H-indol-2-yl]-N-[(2S)-1,1,1-trifluoropropan-2-yl]pyridine-3-sulfonamide, |
| 356 | 6-[3-cyano-5-fluoro-1-(4-methylphenyl)-1H-indol-2-yl]-N-(1,3-difluoropropan-2-yl)pyridine-3-sulfonamide, |
| 357 | 2-[3-cyano-5-fluoro-1-(4-methylphenyl)-1H-indol-2-yl]-N-(propan-2-yl)pyrimidine-5-sulfonamide, |
| 358 | 6-[3-cyano-1-cyclopentyl-6-(trifluoromethoxy)-1H-indol-2-yl]-N-[(2S)-1,1,1-trifluoropropan-2-yl]pyridine-3-sulfonamide, |
| 359 | 6-[3-cyano-6-(difluoromethoxy)-1-(propan-2-yl)-1H-indol-2-yl]-N-[(2S)-1,1,1-trifluoropropan-2-yl]pyridine-3-sulfonamide, |
| 360 | 6-(6-chloro-3-cyano-1-cyclobutyl-5-fluoro-1H-indol-2-yl)-N-[(2S)-1,1,1-trifluoropropan-2-yl]pyridine-3-sulfonamide, |
| 361 | 2-[3-cyano-1-cyclobutyl-6-(fluoromethyl)-1H-indol-2-yl]-N-(1,3-difluoropropan-2-yl)pyrimidine-5-sulfonamide, |
| 362 | 6-[3-cyano-1-cyclobutyl-6-(fluoromethyl)-1H-indol-2-yl]-N-[(2S)-1,1,1-trifluoropropan-2-yl]pyridine-3-sulfonamide, |
| 363 | 6-[3-cyano-1-cyclobutyl-6-(difluoromethyl)-1H-indol-2-yl]-N-[(2S)-1,1,1-trifluoropropan-2-yl]pyridine-3-sulfonamide, |
| 364 | 6-(6-chloro-3-cyano-1-cyclopentyl-1H-indol-2-yl)-N-[(2S)-1,1,1-trifluoropropan-2-yl]pyridine-3-sulfonamide, |
| 365 | 6-(5-chloro-3-cyano-1-cyclopentyl-1H-indol-2-yl)-N-[(2S)-1,1,1-trifluoropropan-2-yl]pyridine-3-sulfonamide, |
| 367 | N-[(1S)-1-cyclopropylethyl]-2-(3,5-dicyano-1-cyclopentyl-1H-indol-2-yl)pyrimidine-5-sulfonamide, |
| 368 | 6-[3-cyano-6-(difluoromethoxy)-1-(4-fluorophenyl)-1H-indol-2-yl]-N-[(2S)-1,1,1-trifluoropropan-2-yl]pyridine-3-sulfonamide, |
| 369 | 6-(3-cyano-1-cyclobutyl-6-cyclopropyl-1H-indol-2-yl)-N-[(2S)-1,1,1-trifluoropropan-2-yl]pyridine-3-sulfonamide, |
| 370 | 6-[3-cyano-1-cyclobutyl-6-(trifluoromethoxy)-1H-indol-2-yl]-N-[(2S)-1,1,1-trifluoropropan-2-yl]pyridine-3-sulfonamide, |
| 371 | 6-(3-cyano-1-cyclopentyl-6-methyl-1H-indol-2-yl)-N-(1,1,1-trifluoro-2-methylpropan-2-yl)pyridine-3-sulfonamide, |
| 372 | 6-[3-cyano-1-(cyclopropylmethyl)-5-methyl-1H-indol-2-yl]-N-[(2S)-1,1,1-trifluoropropan-2-yl]pyridine-3-sulfonamide, |
| 373 | 6-[3-cyano-1-(cyclopropylmethyl)-5-methyl-1H-indol-2-yl]-N-(1,3-difluoropropan-2-yl)pyridine-3-sulfonamide, |
| 374 | 6-(3-cyano-1-cyclopentyl-5-ethyl-1H-indol-2-yl)-N-[(2S)-1,1,1-trifluoropropan-2-yl]pyridine-3-sulfonamide, |
| 375 | 6-(6-chloro-3-cyano-1-cyclobutyl-1H-indol-2-yl)-N-[(2S)-1,1,1-trifluoropropan-2-yl]pyridine-3-sulfonamide, |
| 376 | 6-(5-chloro-3-cyano-1-cyclobutyl-1H-indol-2-yl)-N-[(2S)-1,1,1-trifluoropropan-2-yl]pyridine-3-sulfonamide, |
| 377 | 2-[3-cyano-1-cyclobutyl-5-(fluoromethyl)-1H-indol-2-yl]-N-(1,3-difluoropropan-2-yl)pyrimidine-5-sulfonamide, |
| 378 | 6[3-cyano-1-cyclobutyl-5-(difluoromethyl)-1H-indol-2-yl]-N-(1,3-difluoropropan-2-yl)pyridine-3-sulfonamide, |
| 379 | 2-[3-cyano-1-cyclobutyl-5-(difluoromethyl)-1H-indol-2-yl]-N-(1,3-difluoropropan-2-yl)pyrimidine-5-sulfonamide, |
| 380 | 2-[3-cyano-1-cyclobutyl-5-(difluoromethyl)-1H-indol-2-yl]-N-[(2S)-1,1,1-trifluoropropan-2-yl]pyrimidine-5-sulfonamide, |
| 381 | 6-(3-cyano-1-cyclopentyl-5-ethyl-1H-indol-2-yl)-N-(1,3-difluoropropan-2-yl)pyridine-3-sulfonamide, |
| 382 | 6-[3-cyano-1-cyclopentyl-6-(difluoromethoxy)-1H-indol-2-yl]-N-(1,1,1-trifluoro-2-methylpropan-2-yl)pyridine-3-sulfonamide, |
| 383 | 6-(3-cyano-1-cyclopentyl-6-cyclopropyl-1H-indol-2-yl)-N-[(2S)-1,1,1-trifluoropropan-2-yl]pyridine-3-sulfonamide, |
| 384 | 6-[3-cyano-1-cyclobutyl-6-(2,2-difluoroethyl)-1H-indol-2-yl]-N-[(2S)-1,1,1-trifluoropropan-2-yl]pyridine-3-sulfonamide, |
| 385 | 2-[3-cyano-1-cyclobutyl-6-(2,2-difluoroethyl)-1H-indol-2-yl]-N-[(2S)-1,1,1-trifluoropropan-2-yl]pyrimidine-5-sulfonamide, |

| Cpd | Name |
|---|---|
| 386 | 6-[3-cyano-5-fluoro-1-(pyridin-2-yl)-1H-indol-2-yl]-N-[(2S)-1,1,1-trifluoropropan-2-yl]pyridine-3-sulfonamide, |
| 387 | 6-[3-cyano-6-(difluoromethoxy)-1-(pyridin-2-yl)-1H-indol-2-yl]-N-[(2S)-1,1,1-trifluoropropan-2-yl]pyridine-3-sulfonamide, |
| 388 | 2-[3-cyano-1-(cyclopropylmethyl)-5-methyl-1H-indol-2-yl]-N-(propan-2-yl)pyrimidine-5-sulfonamide, |
| 389 | 2-[3-cyano-1-(cyclopropylmethyl)-5-methyl-1H-indol-2-yl]-N-[(2S)-1,1,1-trifluoropropan-2-yl]pyrimidine-5-sulfonamide, |
| 390 | 2-(3-cyano-1-cyclohexyl-5-methyl-1H-indol-2-yl)-N-[(2S)-1,1,1-trifluoropropan-2-yl]pyrimidine-5-sulfonamide, |
| 391 | 2-(3-cyano-1-cyclopentyl-5-methyl-1H-indol-2-yl)-N-[(2S)-1,1,1-trifluoropropan-2-yl]pyrimidine-5-sulfonamide, |
| 392 | 2-(3,5-dicyano-1-cyclopentyl-1H-indol-2-yl)-N-[(2S)-1,1,1-trifluoropropan-2-yl]pyrimidine-5-sulfonamide, |
| 393 | 2-(3-cyano-1-cyclohexyl-5-fluoro-1H-indol-2-yl)-N-[(2S)-1,1,1-trifluoropropan-2-yl]pyrimidine-5-sulfonamide, |
| 394 | 6-(3-cyano-1-cyclohexyl-6-fluoro-1H-indol-2-yl)-N-[(2S)-1,1,1-trifluoropropan-2-yl]pyridine-3-sulfonamide, |
| 395 | 6-(3-cyano-1-cyclobutyl-6-fluoro-1H-indol-2-yl)-N-[(2S)-1,1,1-trifluoropropan-2-yl]pyridine-3-sulfonamide, |
| 396 | 6-(3-cyano-1-cyclopentyl-6-fluoro-1H-indol-2-yl)-N-[(2S)-1,1,1-trifluoropropan-2-yl]pyridine-3-sulfonamide, |
| 397 | 6-[3-cyano-1-(cyclopropylmethyl)-6-fluoro-1H-indol-2-yl]-N-[(2S)-1,1,1-trifluoropropan-2-yl]pyridine-3-sulfonamide, |
| 398 | 2-[3-cyano-1-(cyclopropylmethyl)-6-(difluoromethoxy)-1H-indol-2-yl]-N-[(2S)-1,1,1-trifluoropropan-2-yl]pyrimidine-5-sulfonamide, |
| 399 | 2-[3-cyano-6-(difluoromethoxy)-1-(propan-2-yl)-1H-indol-2-yl]-N-[(2S)-1,1,1-trifluoropropan-2-yl]pyrimidine-5-sulfonamide, |
| 400 | 2-[3-cyano-6-(difluoromethoxy)-1-propyl-1H-indol-2-yl]-N-[(2S)-1,1,1-trifluoropropan-2-yl]pyrimidine-5-sulfonamide, |
| 401 | 2-(3-cyano-1-cyclopentyl-6-cyclopropyl-1H-indol-2-yl)-N-[(2S)-1,1,1-trifluoropropan-2-yl]pyrimidine-5-sulfonamide, |
| 402 | 2-[3-cyano-1-(cyclopropylmethyl)-6-methyl-1H-indol-2-yl]-N-[(2S)-1,1,1-trifluoropropan-2-yl]pyrimidine-5-sulfonamide, |
| 403 | 2-[3-cyano-6-methyl-1-(propan-2-yl)-1H-indol-2-yl]-N-[(2S)-1,1,1-trifluoropropan-2-yl]pyrimidine-5-sulfonamide, |
| 404 | 2-(3-cyano-1-cyclopentyl-6-methyl-1H-indol-2-yl)-N-[(2S)-1,1,1-trifluoropropan-2-yl]pyrimidine-5-sulfonamide, |
| 405 | 2-(3-cyano-1-cyclobutyl-6-methoxy-1H-indol-2-yl)-N-[(2S)-1,1,1-trifluoropropan-2-yl]pyrimidine-5-sulfonamide, |
| 406 | 2-(3-cyano-1-cyclopentyl-6-methoxy-1H-indol-2-yl)-N-[(2S)-1,1,1-trifluoropropan-2-yl]pyrimidine-5-sulfonamide, |
| 407 | 6-(3-cyano-1-cyclopentyl-5-fluoro-6-methyl-1H-indol-2-yl)-N-(1,3-difluoropropan-2-yl)pyridine-3-sulfonamide, |
| 408 | 6-(3-cyano-1-cyclopentyl-5-fluoro-6-methyl-1H-indol-2-yl)-N-[(2S)-1,1,1-trifluoropropan-2-yl]pyridine-3-sulfonamide, |
| 409 | 6-(3-cyano-1-cyclopentyl-5-fluoro-6-methyl-1H-indol-2-yl)-N-[(2R)-1,1,1-trifluoropropan-2-yl]pyridine-3-sulfonamide, |
| 410 | 6-(3-cyano-1-cyclohexyl-5-fluoro-1H-indol-2-yl)-N-[(2S)-1,1,1-trifluoropropan-2-yl]pyridine-3-sulfonamide, |
| 411 | 2-(3-cyano-1-cyclohexyl-6-fluoro-1H-indol-2-yl)-N-[(2S)-1,1,1-trifluoropropan-2-yl]pyrimidine-5-sulfonamide, |
| 412 | 6-[3-cyano-1-(cyclohex-2-en-1-yl)-5-fluoro-1H-indol-2-yl]-N-[(2R)-1,1,1-trifluoropropan-2-yl]pyridine-3-sulfonamide, |
| 413 | 6-[3-cyano-1-(cyclohex-2-en-1-yl)-5-fluoro-1H-indol-2-yl]-N-[(2S)-1,1,1-trifluoropropan-2-yl]pyridine-3-sulfonamide, |
| 414 | 2-(3-cyano-1-cyclobutyl-5-methyl-1H-indol-2-yl)-N-[(2S)-1,1,1-trifluoropropan-2-yl]pyrimidine-5-sulfonamide, |
| 415 | 2-[6-chloro-3-cyano-1-(cyclopropylmethyl)-1H-indol-2-yl]-N-[(2S)-1,1,1-trifluoropropan-2-yl]pyrimidine-5-sulfonamide, |
| 416 | 2-(3-cyano-1-cyclobutyl-5-fluoro-1H-indol-2-yl)-N-(propan-2-yl)pyrimidine-5-sulfonamide, |
| 417 | 2-(6-chloro-3-cyano-1-cyclopentyl-1H-indol-2-yl)-N-[(2S)-1,1,1-trifluoropropan-2-yl]pyrimidine-5-sulfonamide, |
| 418 | 2-[6-chloro-3-cyano-1-(propan-2-yl)-1H-indol-2-yl]-N-[(2S)-1,1,1-trifluoropropan-2-yl]pyrimidine-5-sulfonamide, |
| 419 | 2-(5-chloro-3-cyano-1-cyclopentyl-1H-indol-2-yl)-N-[(2S)-1,1,1-trifluoropropan-2-yl]pyrimidine-5-sulfonamide, |
| 420 | 2-[5-chloro-3-cyano-1-(propan-2-yl)-1H-indol-2-yl]-N-[(2S)-1,1,1-trifluoropropan-2-yl]pyrimidine-5-sulfonamide, |
| 421 | 6-(3-cyano-1-cyclobutyl-7-fluoro-6-methyl-1H-indol-2-yl)-N-[(2S)-1,1,1-trifluoropropan-2-yl]pyridine-3-sulfonamide, |
| 422 | 6-(3-cyano-1-cyclobutyl-7-fluoro-6-methyl-1H-indol-2-yl)-N-(1,3-difluoropropan-2-yl)pyridine-3-sulfonamide, |
| 423 | 6-(3-cyano-1-cyclopentyl-7-fluoro-6-methyl-1H-indol-2-yl)-N-(1,3-difluoropropan-2-yl)pyridine-3-sulfonamide, |

-continued

| Cpd | Name |
|---|---|
| 424 | 6-(3-cyano-1-cyclopentyl-7-fluoro-6-methyl-1H-indol-2-yl)-N-[(2S)-1,1,1-trifluoropropan-2-yl]pyridine-3-sulfonamide, |
| 425 | 6-[3-cyano-6-methyl-1-(propan-2-yl)-1H-indol-2-yl]-N-[(1S)-1-cyclopropylethyl]pyridine-3-sulfonamide, |
| 426 | 6-(3-cyano-1-cyclopentyl-6-methyl-1H-indol-2-yl)-N-[(1S)-1-cyclopropylethyl]pyridine-3-sulfonamide, |
| 427 | 6-(3-cyano-1-cyclobutyl-6-methoxy-1H-indol-2-yl)-N-[(2S)-1,1,1-trifluoropropan-2-yl]pyridine-3-sulfonamide, |
| 428 | 6-(3-cyano-1-cyclobutyl-6-methoxy-1H-indol-2-yl)-N-[(2R)-1,1,1-trifluoropropan-2-yl]pyridine-3-sulfonamide, |
| 429 | 6-(3-cyano-1-cyclobutyl-6-methoxy-1H-indol-2-yl)-N-[(1S)-1-cyclopropylethyl]pyridine-3-sulfonamide, |
| 430 | 6-(3-cyano-1-cyclopentyl-6-methoxy-1H-indol-2-yl)-N-[(2S)-1,1,1-trifluoropropan-2-yl]pyridine-3-sulfonamide, |
| 431 | 6-(3-cyano-1-cyclopentyl-6-methoxy-1H-indol-2-yl)-N-[(2R)-1,1,1-trifluoropropan-2-yl]pyridine-3-sulfonamide, |
| 432 | 6-(3-cyano-1-cyclopentyl-6-methoxy-1H-indol-2-yl)-N-[(1S)-1-cyclopropylethyl]pyridine-3-sulfonamide, |
| 433 | 6-(3-cyano-1-cyclopentyl-6-cyclopropyl-1H-indol-2-yl)-N-[(1S)-1-cyclopropylethyl]pyridine-3-sulfonamide, |
| 434 | 6-(3-cyano-1-cyclobutyl-5-fluoro-1H-indol-2-yl)-N-[(2S)-1,1,1-trifluoropropan-2-yl]pyridine-3-sulfonamide, |
| 435 | 6-(3-cyano-1-cyclopentyl-5-fluoro-1H-indol-2-yl)-N-[(2S)-1,1,1-trifluoropropan-2-yl]pyridine-3-sulfonamide, |
| 436 | 6-[3-cyano-1-(cyclopropylmethyl)-5-fluoro-1H-indol-2-yl]-N-[(2S)-1,1,1-trifluoropropan-2-yl]pyridine-3-sulfonamide, |
| 437 | 6-[6-chloro-3-cyano-1-(pyridin-2-yl)-1H-indol-2-yl]-N-[(2S)-1,1,1-trifluoropropan-2-yl]pyridine-3-sulfonamide, |
| 438 | 6-[6-chloro-3-cyano-1-(pyridin-2-yl)-1H-indol-2-yl]-N-(1,3-difluoropropan-2-yl)pyridine-3-sulfonamide, |
| 439 | 6-[3-cyano-5-fluoro-1-(pyridin-2-yl)-1H-indol-2-yl]-N-(propan-2-yl)pyridine-3-sulfonamide, |
| 440 | 6-(3-cyano-6-methyl-1-phenyl-1H-indol-2-yl)-N-[(2S)-1,1,1-trifluoropropan-2-yl]pyridine-3-sulfonamide, |
| 441 | 6-(5-chloro-3-cyano-1-phenyl-1H-indol-2-yl)-N-[(2S)-1,1,1-trifluoropropan-2-yl]pyridine-3-sulfonamide, |
| 442 | 6-[5-chloro-3-cyano-1-(pyridin-2-yl)-1H-indol-2-yl]-N-[(2S)-1,1,1-trifluoropropan-2-yl]pyridine-3-sulfonamide, |
| 443 | 6-[5-chloro-3-cyano-1-(pyridin-2-yl)-1H-indol-2-yl]-N-(1,3-difluoropropan-2-yl)pyridine-3-sulfonamide, |
| 444 | 6-(5-chloro-3-cyano-1-cyclobutyl-6-methyl-1H-indol-2-yl)-N-(1,3-difluoropropan-2-yl)pyridine-3-sulfonamide, |
| 445 | 6-(5-chloro-3-cyano-1-cyclobutyl-6-methyl-1H-indol-2-yl)-N-[(2R)-1,1,1-trifluoropropan-2-yl]pyridine-3-sulfonamide, |
| 446 | 6-(5-chloro-3-cyano-1-cyclobutyl-6-methyl-1H-indol-2-yl)-N-[(2S)-1,1,1-trifluoropropan-2-yl]pyridine-3-sulfonamide, |
| 447 | 2-(5-chloro-3-cyano-1-cyclobutyl-6-methyl-1H-indol-2-yl)-N-(1,3-difluoropropan-2-yl)pyrimidine-5-sulfonamide, |
| 448 | 2-(5-chloro-3-cyano-1-cyclobutyl-6-methyl-1H-indol-2-yl)-N-[(2S)-1,1,1-trifluoropropan-2-yl]pyrimidine-5-sulfonamide, |
| 449 | 2-[6-chloro-3-cyano-1-(pyridin-2-yl)-1H-indol-2-yl]-N-[(2S)-1,1,1-trifluoropropan-2-yl]pyrimidine-5-sulfonamide, |
| 450 | 2-[6-chloro-3-cyano-1-(pyridin-2-yl)-1H-indol-2-yl]-N-(1,3-difluoropropan-2-yl)pyrimidine-5-sulfonamide, |
| 451 | 2-(3-cyano-1-cyclobutyl-5-fluoro-1H-indol-2-yl)-N-[(2S)-1,1,1-trifluoropropan-2-yl]pyrimidine-5-sulfonamide, |
| 452 | 2-(3-cyano-1-cyclobutyl-5-fluoro-1H-indol-2-yl)-N-(1,3-difluoropropan-2-yl)pyrimidine-5-sulfonamide, |
| 453 | 6-(3-cyano-1-cyclobutyl-5-methoxy-1H-indol-2-yl)-N-[(2S)-1,1,1-trifluoropropan-2-yl]pyridine-3-sulfonamide, |
| 454 | 2-(5-chloro-3-cyano-1-cyclobutyl-1H-indol-2-yl)-N-[(2S)-1,1,1-trifluoropropan-2-yl]pyrimidine-5-sulfonamide, |
| 455 | 2-[3-cyano-1-cyclobutyl-6-(propan-2-yl)-1H-indol-2-yl]-N-[(2S)-1,1,1-trifluoropropan-2-yl]pyrimidine-5-sulfonamide, |
| 456 | 6-[3-cyano-1,6-di(propan-2-yl)-1H-indol-2-yl]-N-(1,3-difluoropropan-2-yl)pyridine-3-sulfonamide, |
| 457 | 6-[3-cyano-1-cyclopentyl-6-(propan-2-yl)-1H-indol-2-yl]-N-(1,3-difluoropropan-2-yl)pyridine-3-sulfonamide, |
| 458 | 6-[3-cyano-1-(cyclopropylmethyl)-5-methyl-1H-indol-2-yl]-N-[(2R)-1,1,1-trifluoropropan-2-yl]pyridine-3-sulfonamide, |
| 459 | 6-[3-cyano-1-cyclohexyl-6-(trifluoromethoxy)-1H-indol-2-yl]-N-[(2S)-1,1,1-trifluoropropan-2-yl]pyridine-3-sulfonamide, |
| 460 | 6-[3-cyano-1-(cyclopropylmethyl)-6-(propan-2-yl)-1H-indol-2-yl]-N-(1,3-difluoropropan-2-yl)pyridine-3-sulfonamide, |
| 461 | 6-(5-chloro-3-cyano-1-cyclohexyl-1H-indol-2-yl)-N-[(2R)-1,1,1-trifluoropropan-2-yl]pyridine-3-sulfonamide, |

-continued

| Cpd | Name |
|---|---|
| 462 | 6-(5-chloro-3-cyano-1-cyclohexyl-1H-indol-2-yl)-N-[(2S)-1,1,1-trifluoropropan-2-yl]pyridine-3-sulfonamide, |
| 463 | 2-(5-chloro-3-cyano-1-cyclohexyl-1H-indol-2-yl)-N-(1,3-difluoropropan-2-yl)pyrimidine-5-sulfonamide, |
| 464 | 2-(5-chloro-3-cyano-1-cyclohexyl-1H-indol-2-yl)-N-[(2S)-1,1,1-trifluoropropan-2-yl]pyrimidine-5-sulfonamide, |
| 465 | 6-(3,6-dicyano-1-cyclobutyl-1H-indol-2-yl)-N-(1,3-difluoropropan-2-yl)pyridine-3-sulfonamide, |
| 466 | 2-(3,6-dicyano-1-cyclobutyl-1H-indol-2-yl)-N-(1,3-difluoropropan-2-yl)pyrimidine-5-sulfonamide, |
| 467 | 6-(3,6-dicyano-1-cyclobutyl-1H-indol-2-yl)-N-[(2S)-1,1,1-trifluoropropan-2-yl]pyridine-3-sulfonamide, |
| 468 | 6-(3,6-dicyano-1-cyclopentyl-1H-indol-2-yl)-N-(1,3-difluoropropan-2-yl)pyridine-3-sulfonamide, |
| 469 | 2-(3,6-dicyano-1-cyclopentyl-1H-indol-2-yl)-N-(1,3-difluoropropan-2-yl)pyrimidine-5-sulfonamide, |
| 470 | 6-(3,6-dicyano-1-cyclopentyl-1H-indol-2-yl)-N-[(2S)-1,1,1-trifluoropropan-2-yl]pyridine-3-sulfonamide, |
| 471 | 2-[3-cyano-1-cyclohexyl-6-(difluoromethoxy)-1H-indol-2-yl]-N-[(1S)-1-cyclopropylethyl]pyrimidine-5-sulfonamide, |
| 472 | 2-[3-cyano-1-cyclohexyl-6-(difluoromethoxy)-1H-indol-2-yl]-N-[(2S)-1,1,1-trifluoropropan-2-yl]pyrimidine-5-sulfonamide, |
| 473 | 2-[3-cyano-1-cyclohexyl-6-(difluoromethoxy)-1H-indol-2-yl]-N-(propan-2-yl)pyrimidine-5-sulfonamide, |
| 474 | 2-[3-cyano-5-fluoro-1-(pyridin-2-yl)-1H-indol-2-yl]-N-[(2S)-1,1,1-trifluoropropan-2-yl]pyrimidine-5-sulfonamide, |
| 475 | 2-[3-cyano-6-methyl-1-(pyridin-2-yl)-1H-indol-2-yl]-N-[(2S)-1,1,1-trifluoropropan-2-yl]pyrimidine-5-sulfonamide, |
| 476 | 6-[3-cyano-6-methyl-1-(pyridin-2-yl)-1H-indol-2-yl]-N-[(2S)-1,1,1-trifluoropropan-2-yl]pyridine-3-sulfonamide, |
| 477 | 2-[3-cyano-6-(difluoromethoxy)-1-(4-fluorophenyl)-1H-indol-2-yl]-N-(1,3-difluoropropan-2-yl)pyrimidine-5-sulfonamide, |
| 478 | 6-(3-cyano-1-cyclobutyl-6-methyl-1H-indol-2-yl)-N-(1,1,1-trifluoro-2-methylpropan-2-yl)pyridine-3-sulfonamide, |
| 479 | 6-[3-cyano-1-cyclobutyl-6-(difluoromethoxy)-1H-indol-2-yl]-N-(1,1,1-trifluoro-2-methylpropan-2-yl)pyridine-3-sulfonamide, |
| 480 | 6-(3-cyano-1-cyclobutyl-5-methyl-1H-indol-2-yl)-N-(1,1,1-trifluoro-2-methylpropan-2-yl)pyridine-3-sulfonamide, |
| 481 | 6-(3-cyano-1-cyclobutyl-6-ethyl-1H-indol-2-yl)-N-(1,1,1-trifluoro-2-methylpropan-2-yl)pyridine-3-sulfonamide, |
| 482 | 6-(3-cyano-1-cyclopentyl-6-fluoro-5-methyl-1H-indol-2-yl)-N-(1,3-difluoropropan-2-yl)pyridine-3-sulfonamide, |
| 483 | 6-(3-cyano-1-cyclopentyl-6-fluoro-5-methyl-1H-indol-2-yl)-N-[(2S)-1,1,1-trifluoropropan-2-yl]pyridine-3-sulfonamide, |
| 484 | 6-(3-cyano-1-cyclobutyl-5-methyl-1H-indol-2-yl)-N-[(2R)-1,1,1-trifluoropropan-2-yl]pyridine-3-sulfonamide, |
| 485 | 6-[3-cyano-5-methyl-1-(propan-2-yl)-1H-indol-2-yl]-N-[(2R)-1,1,1-trifluoropropan-2-yl]pyridine-3-sulfonamide, |
| 486 | 6-(3-cyano-1-cyclopentyl-5-methyl-1H-indol-2-yl)-N-[(2R)-1,1,1-trifluoropropan-2-yl]pyridine-3-sulfonamide, |
| 487 | 6-(3-cyano-1-cyclohexyl-5-methyl-1H-indol-2-yl)-N-[(2R)-1,1,1-trifluoropropan-2-yl]pyridine-3-sulfonamide, |
| 488 | 6-[6-chloro-3-cyano-1-(pyridin-2-yl)-1H-indol-2-yl]-N-[(1S)-1-cyclopropylethyl]pyridine-3-sulfonamide, |
| 489 | 6-[6-chloro-3-cyano-1-(pyridin-2-yl)-1H-indol-2-yl]-N-[(2R)-1,1,1-trifluoropropan-2-yl]pyridine-3-sulfonamide, |
| 490 | 6-[5-chloro-3-cyano-1-(pyridin-2-yl)-1H-indol-2-yl]-N-[(1S)-1-cyclopropylethyl]pyridine-3-sulfonamide, |
| 491 | 6-[5-chloro-3-cyano-1-(pyridin-2-yl)-1H-indol-2-yl]-N-[(2R)-1,1,1-trifluoropropan-2-yl]pyridine-3-sulfonamide, |
| 492 | 6-(3-cyano-1-cyclobutyl-6-fluoro-5-methyl-1H-indol-2-yl)-N-[(2S)-1,1,1-trifluoropropan-2-yl]pyridine-3-sulfonamide, |
| 493 | 6-(3-cyano-1-cyclobutyl-6-fluoro-5-methyl-1H-indol-2-yl)-N-(1,3-difluoropropan-2-yl)pyridine-3-sulfonamide, |
| 494 | 2-(3-cyano-1-cyclobutyl-6-fluoro-1H-indol-2-yl)-N-[(2S)-1,1,1-trifluoropropan-2-yl]pyrimidine-5-sulfonamide, |
| 495 | 2-(3-cyano-1-cyclopentyl-6-fluoro-1H-indol-2-yl)-N-[(2S)-1,1,1-trifluoropropan-2-yl]pyrimidine-5-sulfonamide, |
| 496 | 2-(3-cyano-1-cyclobutyl-6-fluoro-1H-indol-2-yl)-N-[(1S)-1-cyclopropylethyl]pyrimidine-5-sulfonamide, |
| 497 | 2-(3-cyano-1-cyclopentyl-6-fluoro-1H-indol-2-yl)-N-[(1S)-1-cyclopropylethyl]pyrimidine-5-sulfonamide, |
| 498 | 2-[3-cyano-1-(cyclopropylmethyl)-6-fluoro-1H-indol-2-yl]-N-[(1S)-1-cyclopropylethyl]pyrimidine-5-sulfonamide, |
| 499 | 2-(3-cyano-1-cyclohexyl-6-fluoro-1H-indol-2-yl)-N-[(1S)-1-cyclopropylethyl]pyrimidine-5-sulfonamide, |

| Cpd | Name |
|---|---|
| 500 | 6-(3-cyano-1-cyclobutyl-5-methoxy-1H-indol-2-yl)-N-[(2R)-1,1,1-trifluoropropan-2-yl]pyridine-3-sulfonamide, |
| 501 | 6-[3-cyano-6-cyclopropyl-1-(pyridin-2-yl)-1H-indol-2-yl]-N-(1,3-difluoropropan-2-yl)pyridine-3-sulfonamide, |
| 502 | 6-[3-cyano-6-cyclopropyl-1-(pyridin-2-yl)-1H-indol-2-yl]-N-[(2S)-1,1,1-trifluoropropan-2-yl]pyridine-3-sulfonamide, |
| 503 | 6-[3-cyano-5-methyl-1-(pyridin-2-yl)-1H-indol-2-yl]-N-[(2S)-1,1,1-trifluoropropan-2-yl]pyridine-3-sulfonamide, |
| 504 | 6-[3-cyano-5-methyl-1-(pyridin-2-yl)-1H-indol-2-yl]-N-(1,3-difluoropropan-2-yl)pyridine-3-sulfonamide, |
| 505 | 6-(6-chloro-3-cyano-1-cyclobutyl-5-methyl-1H-indol-2-yl)-N-(1,3-difluoropropan-2-yl)pyridine-3-sulfonamide, |
| 506 | 6-(6-chloro-3-cyano-1-cyclobutyl-5-methyl-1H-indol-2-yl)-N-[(2S)-1,1,1-trifluoropropan-2-yl]pyridine-3-sulfonamide, |
| 507 | 2-(6-chloro-3-cyano-1-cyclobutyl-5-methyl-1H-indol-2-yl)-N-(propan-2-yl)pyrimidine-5-sulfonamide, |
| 508 | 6-(3-cyano-1-cyclopentyl-5,7-difluoro-6-methyl-1H-indol-2-yl)-N-[(2S)-1,1,1-trifluoropropan-2-yl]pyridine-3-sulfonamide, |
| 509 | 6-(3-cyano-1-cyclopentyl-5,7-difluoro-6-methyl-1H-indol-2-yl)-N-(1,3-difluoropropan-2-yl)pyridine-3-sulfonamide, |
| 510 | 6-(6-chloro-3-cyano-1-cyclobutyl-5-methyl-1H-indol-2-yl)-N-[(2R)-1,1,1-trifluoropropan-2-yl]pyridine-3-sulfonamide, |
| 511 | 6-(1-cyclobutyl-6-methyl-1H-indol-2-yl)-N-(1,3-difluoropropan-2-yl)pyridine-3-sulfonamide, |
| 512 | 6-[3-cyano-6-(difluoromethoxy)-1-(pyrimidin-2-yl)-1H-indol-2-yl]-N-[(2S)-1,1,1-trifluoropropan-2-yl]pyridine-3-sulfonamide, |
| 513 | 6-(3-cyano-1-cyclohexyl-6-methyl-1H-indol-2-yl)-N-(1,3-difluoropropan-2-yl)pyridine-3-sulfonamide, |
| 514 | 6-(6-chloro-3-cyano-1-cyclohexyl-1H-indol-2-yl)-N-[(2R)-1,1,1-trifluoropropan-2-yl]pyridine-3-sulfonamide, |
| 515 | 6-(6-chloro-3-cyano-1-cyclohexyl-1H-indol-2-yl)-N-[(2S)-1,1,1-trifluoropropan-2-yl]pyridine-3-sulfonamide, |
| 516 | 2-(6-chloro-3-cyano-1-cyclohexyl-1H-indol-2-yl)-N-[(2S)-1,1,1-trifluoropropan-2-yl]pyrimidine-5-sulfonamide, |
| 517 | 2-(6-chloro-3-cyano-1-cyclohexyl-1H-indol-2-yl)-N-(1,3-difluoropropan-2-yl)pyrimidine-5-sulfonamide, |
| 518 | 6-(3-cyano-1-cyclohexyl-6-methoxy-1H-indol-2-yl)-N-[(2R)-1,1,1-trifluoropropan-2-yl]pyridine-3-sulfonamide, |
| 519 | 6-(3-cyano-1-cyclohexyl-6-methoxy-1H-indol-2-yl)-N-[(2S)-1,1,1-trifluoropropan-2-yl]pyridine-3-sulfonamide, |
| 520 | 2-(3-cyano-1-cyclohexyl-6-methoxy-1H-indol-2-yl)-N-(1,3-difluoropropan-2-yl)pyrimidine-5-sulfonamide, |
| 521 | 6-(6-chloro-3-cyano-1-cyclopentyl-5-methyl-1H-indol-2-yl)-N-(1,3-difluoropropan-2-yl)pyridine-3-sulfonamide, |
| 522 | 6-(6-chloro-3-cyano-1-cyclopentyl-5-methyl-1H-indol-2-yl)-N-[(2S)-1,1,1-trifluoropropan-2-yl]pyridine-3-sulfonamide, |
| 523 | 2-(6-chloro-3-cyano-1-cyclopentyl-5-methyl-1H-indol-2-yl)-N-(propan-2-yl)pyrimidine-5-sulfonamide, |
| 524 | 2-[3-cyano-1-(cyclopropylmethyl)-5-methyl-1H-indol-2-yl]-N-(1,3-difluoropropan-2-yl)pyrimidine-5-sulfonamide, |
| 525 | 6-[3-cyano-1-(cyclopropylmethyl)-5-methyl-1H-indol-2-yl]-N-[(1S)-1-cyclopropylethyl]pyridine-3-sulfonamide, |
| 526 | 2-(3-cyano-1-cyclohexyl-5-fluoro-1H-indol-2-yl)-N-(propan-2-yl)pyrimidine-5-sulfonamide, |
| 527 | 2-(3-cyano-1-cyclohexyl-5-fluoro-1H-indol-2-yl)-N-(1,3-difluoropropan-2-yl)pyrimidine-5-sulfonamide, |
| 528 | 2-(3-cyano-1-cyclohexyl-5-fluoro-1H-indol-2-yl)-N-[(1S)-1-cyclopropylethyl]pyrimidine-5-sulfonamide, |
| 529 | 2-[3-cyano-5-fluoro-1-(propan-2-yl)-1H-indol-2-yl]-N-[(1S)-1-cyclopropylethyl]pyrimidine-5-sulfonamide, |
| 530 | 2-(3-cyano-1-cyclopentyl-5-fluoro-1H-indol-2-yl)-N-[(1S)-1-cyclopropylethyl]pyrimidine-5-sulfonamide, |
| 531 | 2-[3-cyano-1-(cyclopropylmethyl)-5-fluoro-1H-indol-2-yl]-N-[(1S)-1-cyclopropylethyl]pyrimidine-5-sulfonamide, |
| 532 | 6-(3-cyano-1-cyclobutyl-5,7-difluoro-6-methyl-1H-indol-2-yl)-N-[(2S)-1,1,1-trifluoropropan-2-yl]pyridine-3-sulfonamide, |
| 533 | 6-(3-cyano-1-cyclobutyl-5,7-difluoro-6-methyl-1H-indol-2-yl)-N-(1,3-difluoropropan-2-yl)pyridine-3-sulfonamide, |
| 534 | 6-[3-cyano-6-(difluoromethoxy)-1-(pyridin-2-yl)-1H-indol-2-yl]-N-[(2R)-1,1,1-trifluoropropan-2-yl]pyridine-3-sulfonamide, |
| 535 | 6-[3-cyano-1-cyclopentyl-5-(difluoromethyl)-1H-indol-2-yl]-N-(1,3-difluoropropan-2-yl)pyridine-3-sulfonamide, |
| 536 | 2-[3-cyano-1-cyclopentyl-5-(difluoromethyl)-1H-indol-2-yl]-N-(1,3-difluoropropan-2-yl)pyrimidine-5-sulfonamide, |
| 537 | 6-[3-cyano-1-cyclopentyl-5-(difluoromethyl)-1H-indol-2-yl]-N-[(2S)-1,1,1-trifluoropropan-2-yl]pyridine-3-sulfonamide, |

| Cpd | Name |
|---|---|
| 538 | 6-[3-cyano-1-cyclopentyl-5-(difluoromethyl)-1H-indol-2-yl]-N-[(2R)-1,1,1-trifluoropropan-2-yl]pyridine-3-sulfonamide, |
| 539 | 6-(3-cyano-1-cyclobutyl-5-fluoro-6-methyl-1H-indol-2-yl)-N-(1,1,1-trifluoro-2-methylpropan-2-yl)pyridine-3-sulfonamide, |
| 540 | 6-[3-cyano-5-fluoro-6-methyl-1-(pyridin-2-yl)-1H-indol-2-yl]-N-(1,3-difluoropropan-2-yl)pyridine-3-sulfonamide, |
| 541 | 6-[3-cyano-5-fluoro-6-methyl-1-(pyridin-2-yl)-1H-indol-2-yl]-N-[(2S)-1,1,1-trifluoropropan-2-yl]pyridine-3-sulfonamide, |
| 542 | 6-[3-cyano-1-cyclobutyl-6-(difluoromethoxy)-5-fluoro-1H-indol-2-yl]-N-(1,3-difluoropropan-2-yl)pyridine-3-sulfonamide, |
| 543 | N-tert-butyl-6-[3-cyano-1-cyclobutyl-6-(difluoromethoxy)-1H-indol-2-yl]pyridine-3-sulfonamide, |
| 544 | 2-(3-cyano-1-cyclobutyl-5-fluoro-1H-indol-2-yl)-N-[(1S)-1-cyclopropylethyl]pyrimidine-5-sulfonamide, |
| 545 | 2-(3-cyano-1-cyclobutyl-5-methyl-1H-indol-2-yl)-N-[(1S)-1-cyclopropylethyl]pyrimidine-5-sulfonamide, |
| 546 | 2-[3-cyano-5-fluoro-1-(propan-2-yl)-1H-indol-2-yl]-N-[(2S)-1,1,1-trifluoropropan-2-yl]pyrimidine-5-sulfonamide, |
| 547 | 2-(3-cyano-1-cyclopentyl-5-fluoro-1H-indol-2-yl)-N-[(2S)-1,1,1-trifluoropropan-2-yl]pyrimidine-5-sulfonamide, |
| 548 | 2-[3-cyano-1-(cyclopropylmethyl)-5-fluoro-1H-indol-2-yl]-N-[(2S)-1,1,1-trifluoropropan-2-yl]pyrimidine-5-sulfonamide, |
| 549 | 6-[3-cyano-1-cyclobutyl-6-(difluoromethoxy)-5-fluoro-1H-indol-2-yl]-N-[(2S)-1,1,1-trifluoropropan-2-yl]pyridine-3-sulfonamide, |
| 550 | 6-(3-cyano-1-cyclobutyl-5-methoxy-1H-indol-2-yl)-N-(1,3-difluoropropan-2-yl)pyridine-3-sulfonamide, |
| 551 | 2-(3-cyano-1-cyclobutyl-5-methoxy-1H-indol-2-yl)-N-(1,3-difluoropropan-2-yl)pyrimidine-5-sulfonamide, |
| 552 | 6-[3-cyano-1-cyclobutyl-6-(difluoromethoxy)-1H-indol-2-yl]pyridine-3-sulfonamide, |
| 553 | 6-[3-cyano-6-(difluoromethoxy)-1-phenyl-1H-indol-2-yl]-N-[(2S)-1,1,1-trifluoropropan-2-yl]pyridine-3-sulfonamide, |
| 554 | 6-[3-cyano-6-(difluoromethoxy)-1-phenyl-1H-indol-2-yl]-N-[(2R)-1,1,1-trifluoropropan-2-yl]pyridine-3-sulfonamide, |
| 555 | 6-(3-cyano-1-cyclobutyl-4,6-difluoro-5-methyl-1H-indol-2-yl)-N-[(2S)-1,1,1-trifluoropropan-2-yl]pyridine-3-sulfonamide, |
| 556 | 6-(3-cyano-1-cyclobutyl-4,6-difluoro-5-methyl-1H-indol-2-yl)-N-(1,3-difluoropropan-2-yl)pyridine-3-sulfonamide, |
| 557 | 2-(3-cyano-1-cyclobutyl-7-fluoro-6-methyl-1H-indol-2-yl)-N-(1,3-difluoropropan-2-yl)pyrimidine-5-sulfonamide, |
| 558 | 6-(3-cyano-1-cyclopentyl-4,6-difluoro-5-methyl-1H-indol-2-yl)-N-(1,3-difluoropropan-2-yl)pyridine-3-sulfonamide, |
| 559 | 6-(3-cyano-1-cyclopentyl-4,6-difluoro-5-methyl-1H-indol-2-yl)-N-[(2S)-1,1,1-trifluoropropan-2-yl]pyridine-3-sulfonamide, |
| 560 | 6-(3-cyano-1-cyclohexyl-5-methyl-1H-indol-2-yl)-N-[(2S)-1,1,1-trifluoropropan-2-yl]pyridine-3-sulfonamide, |
| 561 | 2-[3-cyano-1-(cyclopropylmethyl)-5-methyl-1H-indol-2-yl]-N-[(1S)-1-cyclopropylethyl]pyrimidine-5-sulfonamide, |
| 562 | 2-(3-cyano-1-cyclopentyl-5-methyl-1H-indol-2-yl)-N-[(1S)-1-cyclopropylethyl]pyrimidine-5-sulfonamide, |
| 563 | 2-[3-cyano-5-methyl-1-(propan-2-yl)-1H-indol-2-yl]-N-[(1S)-1-cyclopropylethyl]pyrimidine-5-sulfonamide, |
| 564 | 6-[3-cyano-5-methyl-1-(propan-2-yl)-1H-indol-2-yl]-N-[(1S)-1-cyclopropylethyl]pyridine-3-sulfonamide, |
| 565 | 2-[3-cyano-5-methyl-1-(propan-2-yl)-1H-indol-2-yl]-N-(propan-2-yl)pyrimidine-5-sulfonamide, |
| 566 | 2-[3-cyano-5-methyl-1-(propan-2-yl)-1H-indol-2-yl]-N-[(2S)-1,1,1-trifluoropropan-2-yl]pyrimidine-5-sulfonamide, |
| 567 | 2-[3-cyano-5-methyl-1-(propan-2-yl)-1H-indol-2-yl]-N-(1,3-difluoropropan-2-yl)pyrimidine-5-sulfonamide, |
| 568 | 1-cyclobutyl-6-(difluoromethoxy)-2-(5-sulfamoylpyridin-2-yl)-1H-indole-3-carboxamide, |
| 569 | 2-(3-cyano-1-cyclobutyl-5-methoxy-1H-indol-2-yl)-N-[(2S)-1,1,1-trifluoropropan-2-yl]pyrimidine-5-sulfonamide, |
| 570 | 2-(3-cyano-1-cyclobutyl-5-methoxy-1H-indol-2-yl)-N-[(1S)-1-cyclopropylethyl]pyrimidine-5-sulfonamide, |
| 571 | 6-(3-cyano-1-cyclopentyl-5-methoxy-1H-indol-2-yl)-N-(1,3-difluoropropan-2-yl)pyridine-3-sulfonamide, |
| 572 | 2-(3-cyano-1-cyclopentyl-5-methoxy-1H-indol-2-yl)-N-(1,3-difluoropropan-2-yl)pyrimidine-5-sulfonamide, |
| 573 | 6-[3-cyano-1-cyclopentyl-6-(difluoromethoxy)-5-fluoro-1H-indol-2-yl]-N-(1,3-difluoropropan-2-yl)pyridine-3-sulfonamide, |
| 574 | 6-[3-cyano-1-cyclopentyl-6-(difluoromethoxy)-5-fluoro-1H-indol-2-yl]-N-[(2S)-1,1,1-trifluoropropan-2-yl]pyridine-3-sulfonamide, |
| 575 | 6-(3-cyano-1-cyclopentyl-5-fluoro-6-hydroxy-1H-indol-2-yl)-N-(1,3-difluoropropan-2-yl)pyridine-3-sulfonamide, |

| Cpd | Name |
|---|---|
| 576 | 6-(3-cyano-1-cyclopentyl-5-fluoro-6-hydroxy-1H-indol-2-yl)-N-[(2S)-1,1,1-trifluoropropan-2-yl]pyridine-3-sulfonamide, |
| 577 | 6-(3-cyano-1-cyclobutyl-5,7-difluoro-6-methyl-1H-indol-2-yl)-N-(1,1,1-trifluoro-2-methylpropan-2-yl)pyridine-3-sulfonamide, |
| 578 | 6-(3-cyano-1-cyclobutyl-7-fluoro-6-methyl-1H-indol-2-yl)-N-(1,1,1-trifluoro-2-methylpropan-2-yl)pyridine-3-sulfonamide, |
| 579 | 6-(3-cyano-1-cyclopentyl-7-fluoro-6-methyl-1H-indol-2-yl)-N-(1,1,1-trifluoro-2-methylpropan-2-yl)pyridine-3-sulfonamide, |
| 580 | 6-(3-cyano-1-cyclopentyl-5,7-difluoro-6-methyl-1H-indol-2-yl)-N-(1,1,1-trifluoro-2-methylpropan-2-yl)pyridine-3-sulfonamide, |
| 581 | 1-cyclobutyl-6-(difluoromethoxy)-2-{5-[(1,3-difluoropropan-2-yl)sulfamoyl]pyridin-2-yl}-1H-indole-3-carboxamide, |
| 582 | 1-cyclobutyl-6-cyclopropyl-2-{5-[(1,3-difluoropropan-2-yl)sulfamoyl]pyridin-2-yl}-1H-indole-3-carboxamide, |
| 583 | 6-[3-cyano-6-(difluoromethoxy)-1-(pyridin-2-yl)-1H-indol-2-yl]-N-(1,1,1-trifluoro-2-methylpropan-2-yl)pyridine-3-sulfonamide, |
| 584 | 6-[3-cyano-6-cyclopropyl-1-(pyridin-2-yl)-1H-indol-2-yl]-N-(1,1,1-trifluoro-2-methylpropan-2-yl)pyridine-3-sulfonamide, |
| 585 | 6-(3-cyano-6-methyl-1-phenyl-1H-indol-2-yl)-N-(1,1,1-trifluoro-2-methylpropan-2-yl)pyridine-3-sulfonamide, |
| 586 | 2-(3-cyano-1-cyclopentyl-7-fluoro-6-methyl-1H-indol-2-yl)-N-(1,3-difluoropropan-2-yl)pyrimidine-5-sulfonamide, |
| 587 | 6-(3-cyano-1-cyclobutyl-6-methyl-1H-indol-2-yl)-N-[1-(trifluoromethyl)cyclobutyl]pyridine-3-sulfonamide, |
| 588 | 6-[3-cyano-1-cyclopentyl-6-(difluoromethoxy)-1H-indol-2-yl]-N-[1-(trifluoromethyl)cyclobutyl]pyridine-3-sulfonamide, |
| 589 | 6-[3-cyano-1-cyclopentyl-6-(difluoromethoxy)-1H-indol-2-yl]-N-[(2S)-1,1,1-trifluoropropan-2-yl]pyridine-3-sulfonamide, |
| 590 | 6-[3-cyano-1-cyclobutyl-6-(2,2-difluoroethyl)-1H-indol-2-yl]-N-[(1S)-1-cyclopropylethyl]pyridine-3-sulfonamide, |
| 591 | 2-[3-cyano-1-cyclobutyl-6-(2,2-difluoroethyl)-1H-indol-2-yl]-N-(1,3-difluoropropan-2-yl)pyrimidine-5-sulfonamide, |
| 592 | 2-[3-cyano-1-cyclobutyl-6-(2,2-difluoroethyl)-1H-indol-2-yl]-N-[(1S)-1-cyclopropylethyl]pyrimidine-5-sulfonamide, |
| 593 | 6-[3-cyano-1-cyclopentyl-6-(2,2-difluoroethyl)-1H-indol-2-yl]-N-(1,3-difluoropropan-2-yl)pyridine-3-sulfonamide, |
| 594 | 6-[3-cyano-1-cyclopentyl-6-(2,2-difluoroethyl)-1H-indol-2-yl]-N-[(1S)-1-cyclopropylethyl]pyridine-3-sulfonamide, |
| 595 | 6-[3-cyano-1-cyclopentyl-6-(2,2-difluoroethyl)-1H-indol-2-yl]-N-[(2S)-1,1,1-trifluoropropan-2-yl]pyridine-3-sulfonamide, |
| 596 | 6-[3-cyano-1-cyclopentyl-6-(2,2-difluoroethyl)-1H-indol-2-yl]-N-(1,1,1-trifluoro-2-methylpropan-2-yl)pyridine-3-sulfonamide, |
| 597 | 2-[3-cyano-1-cyclopentyl-6-(2,2-difluoroethyl)-1H-indol-2-yl]-N-[(1S)-1-cyclopropylethyl]pyrimidine-5-sulfonamide, |
| 598 | 2-[3-cyano-1-cyclopentyl-6-(2,2-difluoroethyl)-1H-indol-2-yl]-N-(propan-2-yl)pyrimidine-5-sulfonamide, |
| 599 | 2-[3-cyano-1-cyclopentyl-6-(2,2-difluoroethyl)-1H-indol-2-yl]-N-(1,3-difluoropropan-2-yl)pyrimidine-5-sulfonamide, |
| 600 | 2-[3-cyano-1-cyclopentyl-6-(2,2-difluoroethyl)-1H-indol-2-yl]-N-[(2S)-1,1,1-trifluoropropan-2-yl]pyrimidine-5-sulfonamide, |
| 601 | 6-[3-cyano-5-fluoro-1-(pyrimidin-2-yl)-1H-indol-2-yl]-N-[(2S)-1,1,1-trifluoropropan-2-yl]pyridine-3-sulfonamide, |
| 602 | 6-[3-cyano-5-fluoro-1-(pyrimidin-2-yl)-1H-indol-2-yl]-N-(1,1,1-trifluoro-2-methylpropan-2-yl)pyridine-3-sulfonamide, |
| 603 | 2-(3-cyano-1-cyclopentyl-5-fluoro-1H-indol-2-yl)-N-(propan-2-yl)pyrimidine-5-sulfonamide, |
| 604 | 6-[3-cyano-5-fluoro-1-(propan-2-yl)-1H-indol-2-yl]-N-[(1S)-1-cyclopropylethyl]pyridine-3-sulfonamide, |
| 605 | 2-(3-cyano-1-cyclohexyl-6-methyl-1H-indol-2-yl)-N-[(2S)-1,1,1-trifluoropropan-2-yl]pyrimidine-5-sulfonamide, |
| 606 | 6-(3-cyano-1-cyclohexyl-5-methyl-1H-indol-2-yl)-N-[(1S)-1-cyclopropylethyl]pyridine-3-sulfonamide, |
| 607 | 6-(3-cyano-1-cyclopentyl-5-methyl-1H-indol-2-yl)-N-(1,1,1-trifluoro-2-methylpropan-2-yl)pyridine-3-sulfonamide, |
| 608 | 6-[3-cyano-5-fluoro-1-(pyrimidin-2-yl)-1H-indol-2-yl]-N-(1,3-difluoropropan-2-yl)pyridine-3-sulfonamide, |
| 609 | 6-(3-cyano-1-cyclobutyl-5-fluoro-6-methyl-1H-indol-2-yl)-N-[(2R)-1,1,1-trifluoropropan-2-yl]pyridine-3-sulfonamide, |
| 610 | 2-[3-cyano-6-(difluoromethoxy)-1-phenyl-1H-indol-2-yl]-N-(1,3-difluoropropan-2-yl)pyrimidine-5-sulfonamide, |
| 611 | 2-[3-cyano-6-(difluoromethoxy)-1-phenyl-1H-indol-2-yl]-N-[(2S)-1,1,1-trifluoropropan-2-yl]pyrimidine-5-sulfonamide, |
| 612 | 6-[3-cyano-6-(difluoromethoxy)-1-phenyl-1H-indol-2-yl]-N-(1,1,1-trifluoro-2-methylpropan-2-yl)pyridine-3-sulfonamide, |
| 613 | 6-(3-cyano-1-cyclobutyl-5-fluoro-6-methyl-1H-indol-2-yl)-N-[1-(trifluoromethyl)cyclopropyl]pyridine-3-sulfonamide, |

| Cpd | Name |
|---|---|
| 614 | 6-(3-cyano-1-cyclopentyl-4-fluoro-5-methyl-1H-indol-2-yl)-N-(1,1,1-trifluoro-2-methylpropan-2-yl)pyridine-3-sulfonamide, |
| 615 | 6-(3-cyano-1-cyclopentyl-4-fluoro-5-methyl-1H-indol-2-yl)-N-[(2S)-1,1,1-trifluoropropan-2-yl]pyridine-3-sulfonamide, |
| 616 | 6-[3-cyano-1-(cyclopropylmethyl)-6-(2,2-difluoroethyl)-1H-indol-2-yl]-N-(1,3-difluoropropan-2-yl)pyridine-3-sulfonamide, |
| 617 | 6-[3-cyano-1-(cyclopropylmethyl)-6-(2,2-difluoroethyl)-1H-indol-2-yl]-N-[(1S)-1-cyclopropylethyl]pyridine-3-sulfonamide, |
| 618 | 6-[3-cyano-1-(cyclopropylmethyl)-6-(2,2-difluoroethyl)-1H-indol-2-yl]-N-[(2S)-1,1,1-trifluoropropan-2-yl]pyridine-3-sulfonamide, |
| 619 | 2-[3-cyano-1-(cyclopropylmethyl)-6-(2,2-difluoroethyl)-1H-indol-2-yl]-N-[(1S)-1-cyclopropylethyl]pyrimidine-5-sulfonamide, |
| 620 | 2-[3-cyano-1-(cyclopropylmethyl)-6-(2,2-difluoroethyl)-1H-indol-2-yl]-N-(propan-2-yl)pyrimidine-5-sulfonamide, |
| 621 | 2-[3-cyano-1-(cyclopropylmethyl)-6-(2,2-difluoroethyl)-1H-indol-2-yl]-N-(1,3-difluoropropan-2-yl)pyrimidine-5-sulfonamide, |
| 622 | 2-[3-cyano-1-(cyclopropylmethyl)-6-(2,2-difluoroethyl)-1H-indol-2-yl]-N-[(2S)-1,1,1-trifluoropropan-2-yl]pyrimidine-5-sulfonamide, |
| 623 | 6-[3-cyano-6-(difluoromethoxy)-1-(pyridin-2-yl)-1H-indol-2-yl]-N-[1-(trifluoromethyl)cyclopropyl]pyridine-3-sulfonamide, |
| 624 | N-tert-butyl-6-[3-cyano-6-(difluoromethoxy)-1-phenyl-1H-indol-2-yl]pyridine-3-sulfonamide, |
| 625 | 6-(3-cyano-1-cyclopentyl-4-fluoro-6-methyl-1H-indol-2-yl)-N-[(2S)-1,1,1-trifluoropropan-2-yl]pyridine-3-sulfonamide, |
| 626 | 6-(3-cyano-1-cyclopentyl-4-fluoro-6-methyl-1H-indol-2-yl)-N-(1,1,1-trifluoro-2-methylpropan-2-yl)pyridine-3-sulfonamide, |
| 627 | 6-(3-cyano-1-cyclobutyl-4-fluoro-6-methyl-1H-indol-2-yl)-N-[(2S)-1,1,1-trifluoropropan-2-yl]pyridine-3-sulfonamide, |
| 628 | 6-(3-cyano-1-cyclopentyl-4-fluoro-6-methyl-1H-indol-2-yl)-N-[1-(trifluoromethyl)cyclopropyl]pyridine-3-sulfonamide, |
| 629 | 6-(3-cyano-1-cyclobutyl-4-fluoro-6-methyl-1H-indol-2-yl)-N-[1-(trifluoromethyl)cyclopropyl]pyridine-3-sulfonamide, |
| 630 | 6-(3-cyano-1-cyclobutyl-6-cyclopropyl-5-fluoro-1H-indol-2-yl)-N-[(2S)-1,1,1-trifluoropropan-2-yl]pyridine-3-sulfonamide, |
| 631 | 6-(3-cyano-1-cyclobutyl-6-cyclopropyl-5-fluoro-1H-indol-2-yl)-N-[(2R)-1,1,1-trifluoropropan-2-yl]pyridine-3-sulfonamide, |
| 632 | 6-(3-cyano-1-cyclopentyl-6-ethyl-5-fluoro-1H-indol-2-yl)-N-[(2R)-1,1,1-trifluoropropan-2-yl]pyridine-3-sulfonamide, |
| 633 | 6-(3-cyano-1-cyclopentyl-6-ethyl-5-fluoro-1H-indol-2-yl)-N-[(2S)-1,1,1-trifluoropropan-2-yl]pyridine-3-sulfonamide, |
| 634 | 6-[3-cyano-5-fluoro-6-methyl-1-(pyrimidin-2-yl)-1H-indol-2-yl]-N-[(2S)-1,1,1-trifluoropropan-2-yl]pyridine-3-sulfonamide, |
| 635 | 6-[3-cyano-6-(difluoromethoxy)-1-(pyrimidin-2-yl)-1H-indol-2-yl]-N-(1,3-difluoropropan-2-yl)pyridine-3-sulfonamide, |
| 636 | 6-[5-chloro-3-cyano-1-cyclobutyl-6-(difluoromethoxy)-1H-indol-2-yl]-N-[(2S)-1,1,1-trifluoropropan-2-yl]pyridine-3-sulfonamide, |
| 637 | 6-(3-cyano-1-cyclopentyl-6-ethyl-5-fluoro-1H-indol-2-yl)-N-[1-(trifluoromethyl)cyclopropyl]pyridine-3-sulfonamide, |
| 638 | 2-(3-cyano-1-cyclopentyl-6-ethyl-5-fluoro-1H-indol-2-yl)-N-(1,3-difluoropropan-2-yl)pyrimidine-5-sulfonamide, |
| 639 | 6-(3-cyano-1-cyclopentyl-6-ethyl-5-fluoro-1H-indol-2-yl)-N-(1,3-difluoropropan-2-yl)pyridine-3-sulfonamide, |
| 640 | 6-(3-cyano-1-cyclobutyl-6-ethyl-5-fluoro-1H-indol-2-yl)-N-[(2S)-1,1,1-trifluoropropan-2-yl]pyridine-3-sulfonamide, |
| 641 | 6-(3-cyano-1-cyclobutyl-6-ethyl-5-fluoro-1H-indol-2-yl)-N-[(2R)-1,1,1-trifluoropropan-2-yl]pyridine-3-sulfonamide, |
| 642 | 6-(3-cyano-1-cyclobutyl-6-ethyl-5-fluoro-1H-indol-2-yl)-N-[1-(trifluoromethyl)cyclopropyl]pyridine-3-sulfonamide, |
| 643 | N-tert-butyl-6-(3-cyano-1-cyclopentyl-5-fluoro-6-methyl-1H-indol-2-yl)pyridine-3-sulfonamide, |
| 644 | 6-(3-cyano-1-cyclopentyl-5-fluoro-6-methyl-1H-indol-2-yl)-N-[1-(trifluoromethyl)cyclopropyl]pyridine-3-sulfonamide, |
| 645 | 6-(3-cyano-1-cyclopentyl-5-fluoro-6-methyl-1H-indol-2-yl)-N-(1-methylcyclopropyl)pyridine-3-sulfonamide, |
| 646 | 6-[1-cyclobutyl-6-(difluoromethoxy)-5-methyl-1H-indol-2-yl]-N-[(2S)-1,1,1-trifluoropropan-2-yl]pyridine-3-sulfonamide, |
| 647 | 6-[3-cyano-1-cyclobutyl-6-(difluoromethoxy)-5-ethyl-1H-indol-2-yl]-N-[(2S)-1,1,1-trifluoropropan-2-yl]pyridine-3-sulfonamide, |
| 648 | 6-[3-cyano-1-cyclobutyl-6-(difluoromethoxy)-5-fluoro-1H-indol-2-yl]-N-[(2R)-1,1,1-trifluoropropan-2-yl]pyridine-3-sulfonamide, |
| 649 | 6-[3-cyano-6-(difluoromethoxy)-1-(4-fluorophenyl)-1H-indol-2-yl]-N-[(2R)-1,1,1-trifluoropropan-2-yl]pyridine-3-sulfonamide, |
| 650 | 6-[3-cyano-6-cyclopropyl-1-(pyrimidin-2-yl)-1H-indol-2-yl]-N-[(2S)-1,1,1-trifluoropropan-2-yl]pyridine-3-sulfonamide, |
| 651 | N-tert-butyl-6-(3-cyano-1-cyclobutyl-5-fluoro-6-methyl-1H-indol-2-yl)pyridine-3-sulfonamide, |

-continued

| Cpd | Name |
|---|---|
| 652 | 6-(3-cyano-1-cyclobutyl-5-fluoro-6-methyl-1H-indol-2-yl)-N-cyclopropylpyridine-3-sulfonamide, |
| 653 | 6-(3-cyano-1-cyclopentyl-5,7-difluoro-6-methyl-1H-indol-2-yl)-N-[(2R)-1,1,1-trifluoropropan-2-yl]pyridine-3-sulfonamide, |
| 654 | 6-(3-cyano-1-cyclopentyl-5,7-difluoro-6-methyl-1H-indol-2-yl)-N-[1-(trifluoromethyl)cyclopropyl]pyridine-3-sulfonamide, |
| 655 | 6-(3-cyano-1-cyclobutyl-5-fluoro-6-methyl-1H-indol-2-yl)-N-(propan-2-yl)pyridine-3-sulfonamide, |
| 656 | 2-(3-cyano-1-cyclopentyl-5,7-difluoro-6-methyl-1H-indol-2-yl)-N-(1,3-difluoropropan-2-yl)pyrimidine-5-sulfonamide, |
| 657 | 6-[3-cyano-6-(difluoromethoxy)-5-fluoro-1-(pyridine-2-yl)-1H-indol-2-yl]-N-[(2S)-1,1,1-trifluoropropan-2-yl]pyridine-3-sulfonamide, |
| 658 | 6-[5-chloro-3-cyano-1-cyclobutyl-6-(difluoromethoxy)-1H-indol-2-yl]-N-(1-methylcyclopropyl)pyridine-3-sulfonamide, |
| 659 | 2-[5-chloro-3-cyano-1-cyclobutyl-6-(difluoromethoxy)-1H-indol-2-yl]-N-(1,3-difluoropropan-2-yl)pyrimidine-5-sulfonamide, |
| 660 | 6-[3-cyano-1-cyclobutyl-6-(difluoromethoxy)-5-methyl-1H-indol-2-yl]-N-[(2S)-1,1,1-trifluoropropan-2-yl]pyridine-3-sulfonamide, |
| 661 | 6-(3-cyano-1-cyclopentyl-6-cyclopropyl-5-fluoro-1H-indol-2-yl)-N-[(2S)-1,1,1-trifluoropropan-2-yl]pyridine-3-sulfonamide, |
| 662 | 6-(3-cyano-1-cyclopentyl-6-cyclopropyl-5-fluoro-1H-indol-2-yl)-N-[(2R)-1,1,1-trifluoropropan-2-yl]pyridine-3-sulfonamide, |
| 663 | 6-[3-cyano-6-(difluoromethoxy)-1-(pyrimidin-2-yl)-1H-indol-2-yl]-N-(1,1,1-trifluoro-2-methylpropan-2-yl)pyridine-3-sulfonamide, |
| 664 | 6-[3-cyano-6-(difluoromethoxy)-1-(4-fluorophenyl)-1H-indol-2-yl]-N-[1-(trifluoromethyl)cyclopropyl]pyridine-3-sulfonamide, |
| 665 | 6-[3-cyano-1-cyclobutyl-6-(difluoromethoxy)-5-methyl-1H-indol-2-yl]-N-[(2R)-1,1,1-trifluoropropan-2-yl]pyridine-3-sulfonamide, |
| 666 | 6-(3-cyano-1-cyclobutyl-5,7-difluoro-6-methyl-1H-indol-2-yl)-N-[(2R)-1,1,1-trifluoropropan-2-yl]pyridine-3-sulfonamide, |
| 667 | 6-(3-cyano-1-cyclobutyl-5,7-difluoro-6-methyl-1H-indol-2-yl)-N-[1-(trifluoromethyl)cyclopropyl]pyridine-3-sulfonamide, |
| 668 | 2-(3-cyano-1-cyclobutyl-5,7-difluoro-6-methyl-1H-indol-2-yl)-N-(1,3-difluoropropan-2-yl)pyrimidine-5-sulfonamide, |
| 669 | 6-(3-cyano-1-cyclopentyl-5-methoxy-6-methyl-1H-indol-2-yl)-N-[(2S)-1,1,1-trifluoropropan-2-yl]pyridine-3-sulfonamide, |
| 670 | 6-[3-cyano-6-(difluoromethoxy)-5-fluoro-1-(pyridin-2-yl)-1H-indol-2-yl]-N-[(2R)-1,1,1-trifluoropropan-2-yl]pyridine-3-sulfonamide, |
| 671 | 6-[3-cyano-6-methyl-1-(pyridin-2-yl)-1H-indol-2-yl]-N-[(2R)-1,1,1-trifluoropropan-2-yl]pyridine-3-sulfonamide, |
| 672 | 6-(3-cyano-1-cyclopentyl-6-ethyl-5-fluoro-1H-indol-2-yl)-N-(1,1,1-trifluoro-2-methylpropan-2-yl)pyridine-3-sulfonamide, |
| 673 | 6-[3-cyano-5-fluoro-1-(pyrimidin-2-yl)-1H-indol-2-yl]-N-[(2R)-1,1,1-trifluoropropan-2-yl]pyridine-3-sulfonamide, |
| 674 | 6-[3-cyano-1-cyclobutyl-6-(difluoromethoxy)-5-hydroxy-1H-indol-2-yl]-N-[(2S)-1,1,1-trifluoropropan-2-yl]pyridine-3-sulfonamide, |
| 675 | 6-(5-bromo-3-cyano-1-cyclopentyl-6-methyl-1H-indol-2-yl)-N-[(2S)-1,1,1-trifluoropropan-2-yl]pyridine-3-sulfonamide, |
| 676 | 6-[3-cyano-1-cyclobutyl-6-(difluoromethoxy)-5-fluoro-1H-indol-2-yl]-N-(1,1,1-trifluoro-2-methylpropan-2-yl)pyridine-3-sulfonamide, |
| 677 | 6-[3-cyano-6-methyl-1-(pyrimidin-2-yl)-1H-indol-2-yl]-N-[(2S)-1,1,1-trifluoropropan-2-yl]pyridine-3-sulfonamide, |
| 678 | 6-(3-cyano-1-cyclohexyl-5-fluoro-6-methyl-1H-indol-2-yl)-N-[(2S)-1,1,1-trifluoropropan-2-yl]pyridine-3-sulfonamide, |
| 679 | 2-(3-cyano-1-cyclohexyl-5-fluoro-6-methyl-1H-indol-2-yl)-N-[(2S)-1,1,1-trifluoropropan-2-yl]pyrimidine-5-sulfonamide, |
| 680 | 6-(3-cyano-1-cyclohexyl-5-fluoro-6-methyl-1H-indol-2-yl)-N-[(2R)-1,1,1-trifluoropropan-2-yl]pyridine-3-sulfonamide, |
| 681 | 6-(3-cyano-1-cyclopentyl-5-fluoro-6-methyl-1H-indol-2-yl)-N-(1,1,1-trifluoro-2-methylpropan-2-yl)pyridine-3-sulfonamide, |
| 682 | 6-[3-cyano-6-(difluoromethoxy)-5-fluoro-1-(pyrimidin-2-yl)-1H-indol-2-yl]-N-[(2S)-1,1,1-trifluoropropan-2-yl]pyridine-3-sulfonamide, |
| 683 | 2-[5-(tert-butylsulfamoyl)pyridin-2-yl]-1-cyclopentyl-5-fluoro-6-methyl-1H-indole-3-carboxamide, |
| 684 | 6-(5-bromo-3-cyano-1-cyclobutyl-6-hydroxy-1H-indol-2-yl)-N-[(2S)-1,1,1-trifluoropropan-2-yl]pyridine-3-sulfonamide, |
| 685 | 6-[3-cyano-1-cyclobutyl-6-(difluoromethoxy)-5-(methylsulfanyl)-1H-indol-2-yl]-N-[(2S)-1,1,1-trifluoropropan-2-yl]pyridine-3-sulfonamide, |
| 686 | 6-[3-cyano-6-methyl-1-(pyridin-2-yl)-1H-indol-2-yl]-N-(1,1,1-trifluoro-2-methylpropan-2-yl)pyridine-3-sulfonamide, |
| 687 | 6-[3-cyano-6-(difluoromethoxy)-1-(4-fluorophenyl)-1H-indol-2-yl]-N-(1,1,1-trifluoro-2-methylpropan-2-yl)pyridine-3-sulfonamide, |
| 688 | 6-[3-cyano-6-methyl-1-(pyrimidin-2-yl)-1H-indol-2-yl]-N-[(2R)-1,1,1-trifluoropropan-2-yl]pyridine-3-sulfonamide, |
| 689 | 6-[3-cyano-6-methyl-1-(pyrimidin-2-yl)-1H-indol-2-yl]-N-(1,1,1-trifluoro-2-methylpropan-2-yl)pyridine-3-sulfonamide, |

| Cpd | Name |
|---|---|
| 690 | 6-[3-cyano-6-(difluoromethoxy)-1-(pyrimidin-2-yl)-1H-indol-2-yl]-N-[1-(trifluoromethyl)cyclopropyl]pyridine-3-sulfonamide, |
| 691 | 6-(3-cyano-1-cyclopentyl-5-hydroxy-6-methyl-1H-indol-2-yl)-N-[(2S)-1,1,1-trifluoropropan-2-yl]pyridine-3-sulfonamide, |
| 692 | 6-(5-bromo-3-cyano-1-cyclopentyl-6-methyl-1H-indol-2-yl)-N-[(2R)-1,1,1-trifluoropropan-2-yl]pyridine-3-sulfonamide, |
| 693 | 6-(3-cyano-1-cyclopentyl-5-hydroxy-6-methyl-1H-indol-2-yl)-N-[(2R)-1,1,1-trifluoropropan-2-yl]pyridine-3-sulfonamide, |
| 694 | 6-(3-cyano-1-cyclopentyl-5-methoxy-6-methyl-1H-indol-2-yl)-N-[(2R)-1,1,1-trifluoropropan-2-yl]pyridine-3-sulfonamide, |
| 695 | 6-[3-cyano-5-fluoro-6-methyl-1-(pyrimidin-2-yl)-1H-indol-2-yl]-N-[(2R)-1,1,1-trifluoropropan-2-yl]pyridine-3-sulfonamide, |
| 696 | 6-[3-cyano-1-cyclobutyl-5-(2,2-difluoroethyl)-1H-indol-2-yl]-N-(1-methylcyclopropyl)pyridine-3-sulfonamide, |
| 697 | 6-[3-cyano-1-cyclobutyl-6-(2,2-difluoroethyl)-5-fluoro-1H-indol-2-yl]-N-[(2S)-1,1,1-trifluoropropan-2-yl]pyridine-3-sulfonamide, |
| 698 | 6-[3-cyano-5-fluoro-6-methyl-1-(pyridin-2-yl)-1H-indol-2-yl]-N-[(2R)-1,1,1-trifluoropropan-2-yl]pyridine-3-sulfonamide, |
| 699 | 1-cyclopentyl-5-fluoro-6-methyl-2-(5-{[(2R)-1,1,1-trifluoropropan-2-yl]sulfamoyl}pyridin-2-yl)-1H-indole-3-carboxamide, |
| 700 | 1-cyclopentyl-5-fluoro-6-methyl-2-(5-{[(2S)-1,1,1-trifluoropropan-2-yl]sulfamoyl}pyridin-2-yl)-1H-indole-3-carboxamide, |
| 701 | 1-cyclopentyl-5-fluoro-6-methyl-2-{5-[(1,1,1-trifluoro-2-methylpropan-2-yl)sulfamoyl]pyridin-2-yl}-1H-indole-3-carboxamide, |
| 702 | 6-[3-cyano-1-cyclobutyl-5-(2,2-difluoroethyl)-1H-indol-2-yl]-N-[(2S)-1,1,1-trifluoropropan-2-yl]pyridine-3-sulfonamide, |
| 703 | 1-cyclobutyl-6-(difluoromethoxy)-5-fluoro-2-(5-{[(2S)-1,1,1-trifluoropropan-2-yl]sulfamoyl}pyridin-2-yl)-1H-indole-3-carboxamide, |
| 704 | 6-[3-cyano-6-ethyl-5-fluoro-1-(pyrimidin-2-yl)-1H-indol-2-yl]-N-[(2S)-1,1,1-trifluoropropan-2-yl]pyridine-3-sulfonamide, |
| 705 | 6-(3-cyano-1-cyclohexyl-5-fluoro-6-methyl-1H-indol-2-yl)-N-(1,1,1-trifluoro-2-methylpropan-2-yl)pyridine-3-sulfonamide, |
| 706 | 1-cyclohexyl-5-fluoro-6-methyl-2-(5-{[(2S)-1,1,1-trifluoropropan-2-yl]sulfamoyl}pyridin-2-yl)-1H-indole-3-carboxamide, |
| 707 | 1-cyclohexyl-5-fluoro-6-methyl-2-(5-{[(2S)-1,1,1-trifluoropropan-2-yl]sulfamoyl}pyrimidin-2-yl)-1H-indole-3-carboxamide, |
| 708 | 6-[5-chloro-3-cyano-1-(pyrimidin-2-yl)-1H-indol-2-yl]-N-[(2S)-1,1,1-trifluoropropan-2-yl]pyridine-3-sulfonamide, |
| 709 | N-{[6-(3-cyano-1-cyclopentyl-5-fluoro-6-methyl-1H-indol-2-yl)pyridin-3-yl]sulfonyl}-N-[(2R)-1,1,1-trifluoropropan-2-yl]acetamide, |
| 710 | N-tert-butyl-6-(3-cyano-1-cyclohexyl-5-fluoro-6-methyl-1H-indol-2-yl)pyridine-3-sulfonamide, |
| 711 | 6-(3-cyano-1-cyclobutyl-5-fluoro-6-hydroxy-1H-indol-2-yl)-N-[(2S)-1,1,1-trifluoropropan-2-yl]pyridine-3-sulfonamide, |
| 712 | 6-[3-cyano-1-cyclobutyl-6-(difluoromethoxy)-5-fluoro-1H-indol-2-yl]-N-(difluoromethyl)-N-[(2S)-1,1,1-trifluoropropan-2-yl]pyridine-3-sulfonamide, |
| 713 | 6-[3-cyano-1-cyclopentyl-6-(difluoromethoxy)-5-fluoro-1H-indol-2-yl]-N-[(2R)-1,1,1-trifluoropropan-2-yl]pyridine-3-sulfonamide, |
| 714 | 1-cyclohexyl-5-fluoro-6-methyl-2-{5-[(1,1,1-trifluoro-2-methylpropan-2-yl)sulfamoyl]pyridin-2-yl}-1H-indole-3-carboxamide, |
| 715 | 1-cyclohexyl-5-fluoro-6-methyl-2-(5-sulfamoylpyridin-2-yl)-1H-indole-3-carboxamide, |
| 716 | 1-cyclohexyl-5-fluoro-6-methyl-2-(5-{[(2R)-1,1,1-trifluoropropan-2-yl]sulfamoyl}pyridin-2-yl)-1H-indole-3-carboxamide, |
| 717 | methyl 1-cyclohexyl-5-fluoro-2-(5-{[(2S)-1,1,1-trifluoropropan-2-yl]sulfamoyl}pyridin-2-yl)-1H-indole-3-carboxylate, |
| 718 | 1-cyclopentyl-6-(difluoromethoxy)-5-fluoro-2-(5-{[(2R)-1,1,1-trifluoropropan-2-yl]sulfamoyl}pyridin-2-yl)-1H-indole-3-carboxamide, |
| 719 | N-tert-butyl-6-(3-cyano-1-cyclobutyl-5-fluoro-6-hydroxy-1H-indol-2-yl)pyridine-3-sulfonamide, |
| 720 | N-tert-butyl-6-[3-cyano-1-cyclobutyl-6-(difluoromethoxy)-5-fluoro-1H-indol-2-yl]pyridine-3-sulfonamide, |
| 721 | N-tert-butyl-6-[3-cyano-1-cyclobutyl-6-(difluoromethoxy)-5-fluoro-1H-indol-2-yl]-N-(difluoromethyl)pyridine-3-sulfonamide, |
| 722 | 6-[3-cyano-1-cyclobutyl-6-(difluoromethoxy)-5-fluoro-1H-indol-2-yl]pyridine-3-sulfonamide, |
| 723 | 2-[5-(tert-butylsulfamoyl)pyridin-2-yl]-1-cyclobutyl-6-(difluoromethoxy)-5-fluoro-1H-indole-3-carboxamide, |
| 724 | 6-{3-cyano-5-fluoro-1-[5-(trifluoromethyl)pyridin-2-yl]-1H-indol-2-yl}-N-[(2S)-1,1,1-trifluoropropan-2-yl]pyridine-3-sulfonamide, |
| 725 | 6-(3-cyano-1-cyclobutyl-5-fluoro-6-methoxy-1H-indol-2-yl)-N-[(2S)-1,1,1-trifluoropropan-2-yl]pyridine-3-sulfonamide, |
| 726 | 6-(3-cyano-1-cyclobutyl-6-ethoxy-5-fluoro-1H-indol-2-yl)-N-[(2S)-1,1,1-trifluoropropan-2-yl]pyridine-3-sulfonamide, |
| 727 | 6-[1-cyclobutyl-6-(difluoromethoxy)-5-fluoro-1H-indol-2-yl]-N-[(2S)-1,1,1-trifluoropropan-2-yl]pyridine-3-sulfonamide, |

-continued

| Cpd | Name |
|---|---|
| 728 | 6-(1-cyclobutyl-5-fluoro-6-hydroxy-1H-indol-2-yl)-N-[(2S)-1,1,1-trifluoropropan-2-yl]pyridine-3-sulfonamide, |
| 729 | 1-cyclobutyl-6-(difluoromethoxy)-5-fluoro-2-{5-[(1,1,1-trifluoro-2-methylpropan-2-yl)sulfamoyl]pyridin-2-yl}-1H-indole-3-carboxamide, |
| 730 | 1-cyclopentyl-5-fluoro-6-methyl-2-(5-{[1-(trifluoromethyl)cyclopropyl]sulfamoyl}pyridin-2-yl)-1H-indole-3-carboxamide, |
| 731 | 1-cyclobutyl-6-cyclopropyl-5-fluoro-2-(5-{[(2S)-1,1,1-trifluoropropan-2-yl]sulfamoyl}pyridin-2-yl)-1H-indole-3-carboxamide, |
| 732 | 1-cyclobutyl-5-fluoro-6-methyl-2-(5-{[(2R)-1,1,1-trifluoropropan-2-yl]sulfamoyl}pyridin-2-yl)-1H-indole-3-carboxamide, |
| 733 | 5-chloro-1-cyclobutyl-6-methyl-2-(5-{[(2S)-1,1,1-trifluoropropan-2-yl]sulfamoyl}pyrimidin-2-yl)-1H-indole-3-carboxamide, |
| 734 | 5-chloro-1-cyclobutyl-6-methyl-2-(5-{[(2S)-1,1,1-trifluoropropan-2-yl]sulfamoyl}pyridin-2-yl)-1H-indole-3-carboxamide, |
| 735 | 5-chloro-1-cyclobutyl-6-methyl-2-(5-{[(2R)-1,1,1-trifluoropropan-2-yl]sulfamoyl}pyridin-2-yl)-1H-indole-3-carboxamide, |
| 736 | 6-chloro-1-cyclobutyl-5-fluoro-2-(5-{[(2S)-1,1,1-trifluoropropan-2-yl]sulfamoyl}pyridin-2-yl)-1H-indole-3-carboxamide, |
| 737 | 1-cyclobutyl-5-fluoro-6-methyl-2-(5-{[(2S)-1,1,1-trifluoropropan-2-yl]sulfamoyl}pyridin-2-yl)-1H-indole-3-carboxamide, |
| 738 | 6-[3-cyano-1-cyclobutyl-6-(difluoromethoxy)-5-fluoro-1H-indol-2-yl]-N-[(2S)-1,1,1-trifluorobutan-2-yl]pyridine-3-sulfonamide, |
| 739 | 6-[3-cyano-5-fluoro-6-methyl-1-(3-methylpyridin-2-yl)-1H-indol-2-yl]-N-[(2S)-1,1,1-trifluoropropan-2-yl]pyridine-3-sulfonamide, |
| 740 | 6-{3-cyano-5-fluoro-6-methyl-1-[5-(trifluoromethyl)pyridin-2-yl]-1H-indol-2-yl}-N-[(2S)-1,1,1-trifluoropropan-2-yl]pyridine-3-sulfonamide, |
| 741 | 1-cyclohexyl-5-fluoro-2-(5-{[(2S)-1,1,1-trifluoropropan-2-yl]sulfamoyl}pyridin-2-yl)-1H-indole-3-carboxylic acid, |
| 742 | 6-[3-cyano-5-fluoro-1-(5-fluoropyridin-2-yl)-6-methyl-1H-indol-2-yl]-N-[(2S)-1,1,1-trifluoropropan-2-yl]pyridine-3-sulfonamide, |
| 743 | 6-[3-cyano-1-(5-cyanopyridin-2-yl)-5-fluoro-6-methyl-1H-indol-2-yl]-N-[(2S)-1,1,1-trifluoropropan-2-yl]pyridine-3-sulfonamide, |
| 744 | 6-[3-cyano-5-fluoro-6-methyl-1-(5-nitropyridin-2-yl)-1H-indol-2-yl]-N-[(2S)-1,1,1-trifluoropropan-2-yl]pyridine-3-sulfonamide, |
| 745 | 5-chloro-1-cyclobutyl-2-[5-(propan-2-ylsulfamoyl)pyrimidin-2-yl]-1H-indole-3-carboxamide, |
| 746 | 1-cyclohexyl-6-(difluoromethoxy)-2-(5-{[(2S)-1,1,1-trifluoropropan-2-yl]sulfamoyl}pyrimidin-2-yl)-1H-indole-3-carboxamide, |
| 747 | 1-cyclohexyl-6-(difluoromethoxy)-2-[5-(propan-2-ylsulfamoyl)pyrimidin-2-yl]-1H-indole-3-carboxamide, |
| 748 | 5-fluoro-1-(pyridin-2-yl)-2-(5-{[(2S)-1,1,1-trifluoropropan-2-yl]sulfamoyl}pyridin-2-yl)-1H-indole-3-carboxamide, |
| 749 | 6-[3-cyano-5-fluoro-6-methyl-1-(tetrahydro-2H-pyran-4-yl)-1H-indol-2-yl]-N-[(2R)-1,1,1-trifluoropropan-2-yl]pyridine-3-sulfonamide, |
| 750 | 6-[3-cyano-5-fluoro-6-methyl-1-(tetrahydro-2H-pyran-4-yl)-1H-indol-2-yl]-N-(1,1,1-trifluoro-2-methylpropan-2-yl)pyridine-3-sulfonamide, |
| 751 | 6-[3-cyano-5-fluoro-6-methyl-1-(tetrahydro-2H-pyran-4-yl)-1H-indol-2-yl]-N-[(2S)-1,1,1-trifluoropropan-2-yl]pyridine-3-sulfonamide, |
| 752 | N-tert-butyl-6-[3-cyano-5-fluoro-6-methyl-1-(tetrahydro-2H-pyran-4-yl)-1H-indol-2-yl]pyridine-3-sulfonamide, |
| 753 | 2-[3-cyano-5-fluoro-6-methyl-1-(tetrahydro-2H-pyran-4-yl)-1H-indol-2-yl]-N-[(2S)-1,1,1-trifluoropropan-2-yl]pyrimidine-5-sulfonamide, |
| 754 | methyl 1-cyclopentyl-5-fluoro-6-methyl-2-{5-[(1,1,1-trifluoro-2-methylpropan-2-yl)sulfamoyl]pyridin-2-yl}-1H-indole-3-carboxylate, |
| 755 | methyl 2-[5-(tert-butylsulfamoyl)pyridin-2-yl]-1-cyclopentyl-5-fluoro-6-methyl-1H-indole-3-carboxylate, |
| 756 | methyl 1-cyclopentyl-5-fluoro-6-methyl-2-(5-{[(2S)-1,1,1-trifluoropropan-2-yl]sulfamoyl}pyridin-2-yl)-1H-indole-3-carboxylate, |
| 757 | 6-(3-cyano-1-cyclobutyl-5-methoxy-6-methyl-1H-indol-2-yl)-N-[(2S)-1,1,1-trifluoropropan-2-yl]pyridine-3-sulfonamide, |
| 758 | 1-cyclopentyl-5-fluoro-6-methyl-2-(5-{[(2S)-1,1,1-trifluoropropan-2-yl]sulfamoyl}pyridin-2-yl)-1H-indole-3-carboxylic acid, |
| 760 | 6-(1-cyclopentyl-5-fluoro-6-methyl-1H-indol-2-yl)-N-[(2S)-1,1,1-trifluoropropan-2-yl]pyridine-3-sulfonamide, |
| 761 | 1-cyclopentyl-5-fluoro-N,6-dimethyl-2-(5-{[(2S)-1,1,1-trifluoropropan-2-yl]sulfamoyl}pyridin-2-yl)-1H-indole-3-carboxamide, |
| 762 | 1-cyclopentyl-N-ethyl-5-fluoro-6-methyl-2-(5-{[(2S)-1,1,1-trifluoropropan-2-yl]sulfamoyl}pyridin-2-yl)-1H-indole-3-carboxamide, |
| 763 | 1-cyclopentyl-5-fluoro-6-methyl-N-(propan-2-yl)-2-(5-{[(2S)-1,1,1-trifluoropropan-2-yl]sulfamoyl}pyridin-2-yl)-1H-indole-3-carboxamide, |
| 764 | N-tert-butyl-6-(3-cyano-1-cyclobutyl-6-ethyl-5-fluoro-1H-indol-2-yl)pyridine-3-sulfonamide, |
| 765 | 1-cyclopentyl-5-fluoro-6-methyl-2-{5-[(1,1,1-trifluoro-2-methylpropan-2-yl)sulfamoyl]pyridin-2-yl}-1H-indole-3-carboxylic acid, |
| 766 | 2-[5-(tert-butylsulfamoyl)pyridin-2-yl]-1-cyclopentyl-5-fluoro-6-methyl-1H-indole-3-carboxylic acid, |

-continued

| Cpd | Name |
|---|---|
| 767 | 5-fluoro-6-methyl-1-(tetrahydro-2H-pyran-4-yl)-2-(5-{[(2R)-1,1,1-trifluoropropan-2-yl]sulfamoyl}pyridin-2-yl)-1H-indole-3-carboxamide, |
| 768 | 5-fluoro-6-methyl-1-(tetrahydro-2H-pyran-4-yl)-2-{5-[(1,1,1-trifluoro-2-methylpropan-2-yl)sulfamoyl]pyridin-2-yl}-1H-indole-3-carboxamide, |
| 769 | 5-fluoro-6-methyl-1-(tetrahydro-2H-pyran-4-yl)-2-(5-{[(2S)-1,1,1-trifluoropropan-2-yl]sulfamoyl}pyridin-2-yl)-1H-indole-3-carboxamide, |
| 770 | methyl 2-[5-(tert-butylsulfamoyl)pyridin-2-yl]-1-cyclobutyl-5-fluoro-6-methyl-1H-indole-3-carboxylate, |
| 771 | methyl 1-cyclobutyl-5-fluoro-6-methyl-2-(5-{[(2S)-1,1,1-trifluoropropa-2-yl]sulfamoyl}pyridin-2-yl)-1H-indole-3-carboxylate, |
| 772 | 6-[3-cyano-1-cyclobutyl-5-fluoro-6-(methylsulfanyl)-1H-indol-2-yl]-N-[(2S)-1,1,1-trifluoropropan-2-yl]pyridine-3-sulfonamide, |
| 773 | 6-[3-cyano-1-(cyclopropylmethyl)-6-(difluoromethoxy)-4-fluoro-1H-indol-2-yl]-N-[(2S)-1,1,1-trifluoropropan-2-yl]pyridine-3-sulfonamide, |
| 774 | methyl 1-cyclobutyl-5-fluoro-6-methyl-2-(5-{[(2S)-1,1,1-trifluoropropan-2-yl]sulfamoyl}pyrimidin-2-yl)-1H-indole-3-carboxamide, |
| 775 | 1-cyclobutyl-5-fluoro-6-methyl-2-(5-{[(2S)-1,1,1-trifluoropropan-2-yl]sulfamoyl}pyrimidin-2-yl)-1H-indole-3-carboxylic acid, |
| 776 | 2-[5-(tert-butylsulfamoyl)pyridin-2-yl]-1-cyclobutyl-5-fluoro-6-methyl-1H-indole-3-carboxylic acid, |
| 777 | 6-[3-cyano-6-ethyl-5-fluoro-1-(5-fluoropyridin-2-yl)-1H-indol-2-yl]-N-[(2S)-1,1,1-trifluoropropan-2-yl]pyridine-3-sulfonamide, |
| 778 | 6-[3-cyano-6-ethyl-5-fluoro-1-(pyridin-2-yl)-1H-indol-2-yl]-N-[(2S)-1,1,1-trifluoropropan-2-yl]pyridine-3-sulfonamide, |
| 780 | 6-chloro-1-cyclobutyl-2-[5-(propan-2-ylsulfamoyl)pyrimidin-2-yl]-1H-indole-3-carboxamide, |
| 781 | 1-cyclobutyl-2-[5-(propan-2-ylsulfamoyl)pyrimidin-2-yl]-6-(trifluoromethoxy)-1H-indole-3-carboxamide, |
| 782 | 1-cyclopentyl-2-[5-(propan-2-ylsulfamoyl)pyrimidin-2-yl]-6-(trifluoromethoxy)-1H-indole-3-carboxamide, |
| 783 | 1-cyclopentyl-5-fluoro-N,N,6-trimethyl-2-(5-{[(2S)-1,1,1-trifluoropropan-2-yl]sulfamoyl}pyridin-2-yl)-1H-indole-3-carboxamide, |
| 784 | 6-[3-cyano-6-(difluoromethoxy)-4-fluoro-1-(propan-2-yl)-1H-indol-2-yl]-N-[(2S)-1,1,1-trifluoropropan-2-yl]pyridine-3-sulfonamide, |
| 785 | 6-[5-chloro-3-cyano-6-methyl-1-(pyrimidin-2-yl)-1H-indol-2-yl]-N-[(2S)-1,1,1-trifluoropropan-2-yl]pyridine-3-sulfonamide, |
| 786 | 6-[3-cyano-6-(difluoromethoxy)-5-fluoro-1-propyl-1H-indol-2-yl]-N-[(2S)-1,1,1-trifluoropropan-2-yl]pyridine-3-sulfonamide, |
| 787 | 6-[3-cyano-1-(cyclopropylmethyl)-6-(difluoromethoxy)-5-fluoro-1H-indol-2-yl]-N-[(2S)-1,1,1-trifluoropropan-2-yl]pyridine-3-sulfonamide, |
| 788 | 6-[3-cyano-6-(difluoromethoxy)-5-fluoro-1-propyl-1H-indol-2-yl]-N-[(2R)-1,1,1-trifluoropropan-2-yl]pyridine-3-sulfonamide, |
| 789 | 6-[3-cyano-1-(cyclopropylmethyl)-6-(difluoromethoxy)-5-fluoro-1H-indol-2-yl]-N-[(2R)-1,1,1-trifluoropropan-2-yl]pyridine-3-sulfonamide, |
| 790 | 6-[3-cyano-1-cyclobutyl-6-(difluoromethoxy)-5-fluoro-1H-indol-2-yl]-N-(1,1,1-trifluorobutan-2-yl)pyridine-3-sulfonamide, |
| 791 | 6-[3-cyano-1-cyclobutyl-6-(difluoromethoxy)-5-fluoro-1H-indol-2-yl]-N-phenylpyridine-3-sulfonamide, |
| 793 | 1-cyclobutyl-5-fluoro-6-methyl-2-(5-{[(2S)-1,1,1-trifluoropropan-2-yl]sulfamoyl}pyridin-2-yl)-1H-indole-3-carboxylic acid, |
| 794 | 2-[5-(tert-butylsulfamoyl)pyrimidin-2-yl]-1-cyclobutyl-5-fluoro-6-methyl-1H-indole-3-carboxylic acid, |
| 795 | 2-[5-(tert-butylsulfamoyl)pyridin-2-yl]-1-cyclobutyl-5-fluoro-N,6-dimethyl-1H-indole-3-carboxamide, |
| 796 | 6-(3-cyano-1-cyclobutyl-5-hydroxy-6-methyl-1H-indol-2-yl)-N-[(2S)-1,1,1-trifluoropropan-2-yl]pyridine-3-sulfonamide, |
| 797 | 6-[3-cyano-1-cyclobutyl-6-(difluoromethoxy)-4-fluoro-1H-indol-2-yl]-N-[(2S)-1,1,1-trifluoropropan-2-yl]pyridine-3-sulfonamide, |
| 798 | 1-cyclobutyl-6-(difluoromethoxy)-5-fluoro-2-[5-(phenylsulfamoyl)pyridin-2-yl]-1H-indole-3-carboxamide, |
| 799 | 2-[5-(tert-butylsulfamoyl)pyridin-2-yl]-1-cyclopentyl-5-fluoro-N,6-dimethyl-1H-indole-3-carboxamide, |
| 800 | 2-[5-(tert-butylsulfamoyl)pyridin-2-yl]-1-cyclobutyl-5-fluoro-6-methyl-1H-indole-3-carboxamide, |
| 801 | 1-cyclobutyl-5-fluoro-N,6-dimethyl-2-(5-{[(2S)-1,1,1-trifluoropropan-2-yl]sulfamoyl}pyridin-2-yl)-1H-indole-3-carboxamide, |
| 802 | 2-[5-(tert-butylsulfamoyl)pyrimidin-2-yl]-1-cyclobutyl-5-fluoro-N,6-dimethyl-1H-indole-3-carboxamide, |
| 803 | 6-[5-chloro-3-cyano-6-methyl-1-(pyridin-2-yl)-1H-indol-2-yl]-N-[(2S)-1,1,1-trifluoropropan-2-yl]pyridine-3-sulfonamide, |
| 804 | 6-[5-chloro-3-cyano-1-(5-fluoropyridin-2-yl)-6-methyl-1H-indol-2-yl]-N-[(2S)-1,1,1-trifluoropropan-2-yl]pyridine-3-sulfonamide, |
| 805 | N-tert-butyl-6-(3-cyano-1-cyclobutyl-5-hydroxy-6-methyl-1H-indol-2-yl)pyridine-3-sulfonamide, |
| 806 | 1-cyclopentyl-6-(difluoromethoxy)-5-fluoro-2-(5-{[(2S)-1,1,1-trifluoropropan-2-yl]sulfamoyl}pyridin-2-yl)-1H-indole-3-carboxamide, |

-continued

| Cpd | Name |
|---|---|
| 807 | 6-(3-cyano-1-cyclobutyl-5-hydroxy-6-methyl-1H-indol-2-yl)-N-[(2R)-1,1,1-trifluoropropan-2-yl]pyridine-3-sulfonamide, |
| 808 | 6-[3-cyano-1-cyclobutyl-6-(difluoromethoxy)-5-fluoro-1H-indol-2-yl]-N-[1-(trifluoromethyl)cyclopropyl]pyridine-3-sulfonamide, |
| 809 | 1-cyclobutyl-6-(difluoromethoxy)-5-fluoro-2-(5-{[1-(trifluoromethyl)cyclopropyl]sulfamoyl}pyridin-2-yl)-1H-indole-3-carboxamide, |
| 810 | 6-[3-cyano-1-cyclobutyl-6-(difluoromethoxy)-5-fluoro-4-methyl-1H-indol-2-yl]-N-[(2S)-1,1,1-trifluoropropan-2-yl]pyridine-3-sulfonamide, |
| 811 | 6-[3-cyano-1-cyclobutyl-6-(difluoromethoxy)-5-fluoro-7-methyl-1H-indol-2-yl]-N-[(2S)-1,1,1-trifluoropropan-2-yl]pyridine-3-sulfonamide, |
| 812 | 6-[3-cyano-1-(cyclopropylmethyl)-6-(difluoromethoxy)-5-fluoro-1H-indol-2-yl]pyridine-3-sulfonamide, |
| 813 | 6-(3-cyano-1-cyclobutyl-5-fluoro-6-hydroxy-1H-indol-2-yl)-N-[1-(trifluoromethyl)cyclopropyl]pyridine-3-sulfonamide, |
| 814 | 6-[3-cyano-5-fluoro-1-(3-fluoropyridin-2-yl)-6-methyl-1H-indol-2-yl]-N-[(2S)-1,1,1-trifluoropropan-2-yl]pyridine-3-sulfonamide, |
| 815 | 6-[3-cyano-5-fluoro-1-(6-fluoropyridin-2-yl)-6-methyl-1H-indol-2-yl]-N-[(2S)-1,1,1-trifluoropropan-2-yl]pyridine-3-sulfonamide, |
| 816 | 6-[3-cyano-5-fluoro-1-(4-methoxypyridin-2-yl)-6-methyl-1H-indol-2-yl]-N-[(2S)-1,1,1-trifluoropropan-2-yl]pyridine-3-sulfonamide, |
| 817 | 6-[3-cyano-5-fluoro-6-methyl-1-(pyrazin-2-yl)-1H-indol-2-yl]-N-[(2S)-1,1,1-trifluoropropan-2-yl]pyridine-3-sulfonamide, |
| 818 | 6-[3-cyano-6-cyclopropyl-5-fluoro-1-(5-fluoropyridin-2-yl)-1H-indol-2-yl]-N-[(2S)-1,1,1-trifluoropropan-2-yl]pyridine-3-sulfonamide, |
| 819 | 6-[3-cyano-6-cyclopropyl-5-fluoro-1-(pyridin-2-yl)-1H-indol-2-yl]-N-[(2S)-1,1,1-trifluoropropan-2-yl]pyridine-3-sulfonamide, |
| 820 | 6-[3-cyano-6-cyclopropyl-5-fluoro-1-(pyrimidin-2-yl)-1H-indol-2-yl]-N-[(2S)-1,1,1-trifluoropropan-2-yl]pyridine-3-sulfonamide, |
| 821 | 6-(3-cyano-1-cyclopentyl-5-fluoro-6-methyl-1H-indol-2-yl)-N-[(2S)-1,1,1-trifluorobutan-2-yl]pyridine-3-sulfonamide, |
| 822 | 6-[3-cyano-1-cyclobutyl-6-(difluoromethoxy)-5-fluoro-1H-indol-2-yl]-4-methyl-N-[(2S)-1,1,1-trifluoropropan-2-yl]pyridine-3-sulfonamide, |
| 823 | N-tert-butyl-6-[3-cyano-5-fluoro-1-(pyrimidin-2-yl)-1H-indol-2-yl]pyridine-3-sulfonamide, |
| 824 | N-tert-butyl-6-[3-cyano-5-fluoro-6-methyl-1-(pyrimidin-2-yl)-1H-indol-2-yl]pyridine-3-sulfonamide, |
| 825 | 1-cyclobutyl-6-(difluoromethoxy)-4-fluoro-2-(5-{[(2S)-1,1,1-trifluoropropan-2-yl]sulfamoyl}pyridin-2-yl)-1H-indole-3-carboxamide, |
| 826 | 6-(3-cyano-1-cyclobutyl-5-fluoro-6-methyl-1H-indol-2-yl)-N-[(2S)-1,1,1-trifluorobutan-2-yl]pyridine-3-sulfonamide, |
| 827 | 6-[3-cyano-1-cyclobutyl-6-(difluoromethoxy)-5-fluoro-1H-indol-2-yl]-5-methyl-N-[(2S)-1,1,1-trifluoropropan-2-yl]pyridine-3-sulfonamide, |
| 828 | 2-[5-(tert-butylsulfamoyl)pyridin-2-yl]-1-cyclobutyl-5-hydroxy-6-methyl-1H-indole-3-carboxamide, |
| 829 | 1-cyclopentyl-6-cyclopropyl-5-fluoro-2-(5-{[(2R)-1,1,1-trifluoropropan-2-yl]sulfamoyl}pyridin-2-yl)-1H-indole-3-carboxamide, |
| 830 | 1-cyclopentyl-6-ethyl-5-fluoro-2-(5-{[(2S)-1,1,1-trifluoropropan-2-yl]sulfamoyl}pyridin-2-yl)-1H-indole-3-carboxamide, |
| 831 | 6-(3-cyano-1-cyclopentyl-6-cyclopropyl-5-fluoro-1H-indol-2-yl)-N-(1,1,1-trifluoro-2-methylpropan-2-yl)pyridine-3-sulfonamide, |
| 832 | N-tert-butyl-6-(3-cyano-1-cyclopentyl-6-cyclopropyl-5-fluoro-1H-indol-2-yl)pyridine-3-sulfonamide, |
| 833 | 1-cyclobutyl-5-hydroxy-6-methyl-2-(5-{[(2S)-1,1,1-trifluoropropan-2-yl]sulfamoyl}pyridin-2-yl)-1H-indole-3-carboxamide, |
| 834 | 1-cyclopentyl-5-methoxy-6-methyl-2-(5-{[(2R)-1,1,1-trifluoropropan-2-yl]sulfamoyl}pyridin-2-yl)-1H-indole-3-carboxamide, |
| 835 | 1-cyclohexyl-5-fluoro-6-methyl-2-(5-{[1-(trifluoromethyl)cyclopropyl]sulfamoyl}pyridin-2-yl)-1H-indole-3-carboxylic acid, |
| 836 | N-[6-(3-cyano-1-cyclopentyl-5-fluoro-6-methyl-1H-indol-2-yl)pyridin-3-yl]N'-[(2S)-1,1,1-trifluoropropan-2-yl]sulfuric diamide, |
| 837 | 6-(3-cyano-1-cyclopentyl-5-fluoro-6-methyl-1H-indol-2-yl)-5-methyl-N-[(2S)-1,1,1-trifluoropropan-2-yl]pyridine-3-sulfonamide, |
| 838 | 1-cyclopentyl-6-cyclopropyl-5-fluoro-2-(5-{[(2S)-1,1,1-trifluoropropan-2-yl]sulfamoyl}pyridin-2-yl)-1H-indole-3-carboxamide, |
| 839 | 6-(difluoromethoxy)-4-fluoro-1-(propan-2-yl)-2-(5-{[(2S)-1,1,1-trifluoropropan-2-yl]sulfamoyl}pyridin-2-yl)-1H-indole-3-carboxamide, |
| 840 | 1-(cyclopropylmethyl)-6-(difluoromethoxy)-4-fluoro-2-(5-{[(2S)-1,1,1-trifluoropropan-2-yl]sulfamoyl}pyridin-2-yl)-1H-indole-3-carboxamide, |
| 841 | 1-cyclopentyl-5-hydroxy-6-methyl-2-(5-{[(2S)-1,1,1-trifluoropropan-2-yl]sulfamoyl}pyridin-2-yl)-1H-indole-3-carboxamide, |
| 842 | 6-(3-cyano-1-cyclopentyl-5-fluoro-6-methyl-1H-indol-2-yl)-4-methyl-N-[(2S)-1,1,1-trifluoropropan-2-yl]pyridine-3-sulfonamide, |
| 843 | 6-[3-cyano-5-methyl-1-(pyrimidin-2-yl)-1H-indol-2-yl]-N-[(2S)-1,1,1-trifluoropropan-2-yl]pyridine-3-sulfonamide, |
| 844 | 6-[3-cyano-1-(3-fluoropyridin-2-yl)-5-methyl-1H-indol-2-yl]N-[(2S)-1,1,1-trifluoropropan-2-yl]pyridine-3-sulfonamide, |

| Cpd | Name |
|---|---|
| 845 | 6-[3-cyano-5-methyl-1-(pyrazin-2-yl)-1H-indol-2-yl]-N-[(2S)-1,1,1-trifluoropropan-2-yl]pyridine-3-sulfonamide, |
| 846 | 5-methyl-1-(pyrimidin-2-yl)-2-(5-{[(2S)-1,1,1-trifluoropropan-2-yl]sulfamoyl}pyridin-2-yl)-1H-indole-3-carboxamide, |
| 847 | 6-[3-cyano-5-fluoro-1-(pyridin-2-yl)-1H-indol-2-yl]-4-methyl-N-[(2S)-1,1,1-trifluoropropan-2-yl]pyridine-3-sulfonamide, |
| 848 | 6-[3-cyano-5-fluoro-1-(pyrimidin-2-yl)-1H-indol-2-yl]-4-methyl-N-[(2S)-1,1,1-trifluoropropan-2-yl]pyridine-3-sulfonamide, |
| 849 | 6-ethyl-5-fluoro-1-(pyrimidin-2-yl)-2-(5-{[(2S)-1,1,1-trifluoropropan-2-yl]sulfamoyl}pyridin-2-yl)-1H-indole-3-carboxamide, |
| 850 | 1-cyclopentyl-6-cyclopropyl-5-fluoro-2-{5-[(1,1,1-trifluoro-2-methylpropan-2-yl)sulfamoyl]pyridin-2-yl}-1H-indole-3-carboxamide, |
| 851 | 6-[3-cyano-6-ethyl-5-fluoro-1-(pyrimidin-2-yl)-1H-indol-2-yl]-4-methyl-N-[(2S)-1,1,1-trifluoropropan-2-yl]pyridine-3-sulfonamide, |
| 852 | 6-[3-cyano-6-ethyl-5-fluoro-1-(pyridin-2-yl)-1H-indol-2-yl]-4-methyl-N-[(2S)-1,1,1-trifluoropropan-2-yl]pyridine-3-sulfonamide, |
| 853 | 6-[3-cyano-5-fluoro-6-methyl-1-(pyrimidin-2-yl)-1H-indol-2-yl]-4-methyl-N-[(2S)-1,1,1-trifluoropropan-2-yl]pyridine-3-sulfonamide, |
| 854 | 6-[3-cyano-5-fluoro-6-methyl-1-(pyridin-2-yl)-1H-indol-2-yl]-4-methyl-N-[(2S)-1,1,1-trifluoropropan-2-yl]pyridine-3-sulfonamide, |
| 855 | N-tert-butyl-6-[3-cyano-6-ethyl-5-fluoro-1-(pyrimidin-2-yl)-1H-indol-2-yl]pyridine-3-sulfonamide, |
| 856 | 6-(3-cyano-1-cyclohexyl-5-fluoro-6-methyl-1H-indol-2-yl)-N-[1-(trifluoromethyl)cyclopropyl]pyridine-3-sulfonamide, |
| 857 | 1-cyclohexyl-5-fluoro-6-methyl-2-(5-{[1-(trifluoromethyl)cyclopropyl]sulfamoyl}pyridin-2-yl)-1H-indole-3-carboxamide, |
| 858 | 6-(3-cyano-1-cyclobutyl-6-ethyl-4-methoxy-1H-indol-2-yl)-N-[(2S)-1,1,1-trifluoropropan-2-yl]pyridine-3-sulfonamide, |
| 859 | 6-[3-cyano-6-ethyl-5-fluoro-1-(pyrimidin-2-yl)-1H-indol-2-yl]-N-(1,1,1-trifluoro-2-methylpropan-2-yl)pyridine-3-sulfonamide, |
| 860 | 6-[3-cyano-6-ethyl-5-fluoro-1-(pyrimidin-2-yl)-1H-indol-2-yl]-N-(1-methylcyclopropyl)pyridine-3-sulfonamide, |
| 861 | 6-[3-cyano-6-ethyl-5-fluoro-1-(pyrimidin-2-yl)-1H-indol-2-yl]-N-(1-methylcyclopropyl)-N-(pyrimidin-2-yl)pyridine-3-sulfonamide, |
| 862 | 6-[3-cyano-1-cyclopentyl-6-(difluoromethoxy)-5-fluoro-1H-indol-2-yl]-N-(1,1,1-trifluoro-2-methylpropan-2-yl)pyridine-3-sulfonamide, |
| 863 | 1-cyclopentyl-6-(difluoromethoxy)-5-fluoro-2-{5-[(1,1,1-trifluoro-2-methylpropan-2-yl)sulfamoyl]pyridin-2-yl}-1H-indole-3-carboxamide, |
| 864 | 6-[3-cyano-6-ethyl-5-fluoro-1-(pyrimidin-2-yl)-1H-indol-2-yl]-N-[1-(trifluoromethyl)cyclopropyl]pyridine-3-sulfonamide, |
| 865 | 6-[3-cyano-5-fluoro-6-methyl-1-(5-methylpyrazin-2-yl)-1H-indol-2-yl]-N-[(2S)-1,1,1-trifluoropropan-2-yl]pyridine-3-sulfonamide, |
| 866 | 6-[3-cyano-5-fluoro-1-(4-methoxypyrimidin-2-yl)-6-methyl-1H-indol-2-yl]-N-[(2S)-1,1,1-trifluoropropan-2-yl]pyridine-3-sulfonamide, |
| 867 | 6-[3-cyano-6-ethyl-5-fluoro-1-(pyrimidin-2-yl)-1H-indol-2-yl]-5-methyl-N-[(2S)-1,1,1-trifluoropropan-2-yl]pyridine-3-sulfonamide, |
| 868 | 6-(3-cyano-1-cyclopentyl-5-fluoro-6-methyl-1H-indol-2-yl)-2-methyl-N-[(2S)-1,1,1-trifluoropropan-2-yl]pyridine-3-sulfonamide, |
| 869 | N-tert-butyl-6-[6-ethyl-5-fluoro-3-(methylsulfonyl)-1-(pyrimidin-2-yl)-1H-indol-2-yl]pyridine-3-sulfonamide, |
| 870 | 6-[3-cyano-6-ethyl-5-fluoro-1-(pyridin-2-yl)-1H-indol-2-yl]-5-methyl-N-[(2S)-1,1,1-trifluoropropan-2-yl]pyridine-3-sulfonamide, |
| 871 | 1-cyclopentyl-6-ethyl-5-fluoro-2-{5-[(1,1,1-trifluoro-2-methylpropan-2-yl)sulfamoyl]pyridin-2-yl}-1H-indole-3-carboxamide, |
| 872 | 1-cyclopentyl-6-ethyl-5-fluoro-2-(5-{[1-(trifluoromethyl)cyclopropyl]sulfamoyl}pyridin-2-yl)-1H-indole-3-carboxamide, |
| 873 | 6-[3-cyano-5-fluoro-6-methyl-1-(4-methylpyrimidin-2-yl)-1H-indol-2-yl]-N-[(2S)-1,1,1-trifluoropropan-2-yl]pyridine-3-sulfonamide, |
| 874 | 5-fluoro-6-methyl-1-(pyridin-2-yl)-2-(5-{[(2S)-1,1,1-trifluoropropan-2-yl]sulfamoyl}pyridin-2-yl)-1H-indole-3-carboxamide, |
| 875 | 5-fluoro-6-methyl-1-(pyrazin-2-yl)-2-(5-{[(2S)-1,1,1-trifluoropropan-2-yl]sulfamoyl}pyridin-2-yl)-1H-indole-3-carboxamide, |
| 876 | 5-fluoro-1-(5-fluoropyridin-2-yl)-6-methyl-2-(5-{[(2S)-1,1,1-trifluoropropan-2-yl]sulfamoyl}pyridin-2-yl)-1H-indole-3-carboxamide, |
| 877 | 5-fluoro-1-(6-fluoropyridin-2-yl)-6-methyl-2-(5-{[(2S)-1,1,1-trifluoropropan-2-yl]sulfamoyl}pyridin-2-yl)-1H-indole-3-carboxamide, |
| 878 | 6-[3-cyano-6-ethyl-5-fluoro-1-(pyrimidin-2-yl)-1H-indol-2-yl]-N-[(2R)-1,1,1-trifluoropropan-2-yl]pyridine-3-sulfonamide, |
| 879 | 6-[3-cyano-6-ethyl-5-fluoro-1-(pyridin-2-yl)-1H-indol-2-yl]-N-[(2R)-1,1,1-trifluoropropan-2-yl]pyridine-3-sulfonamide, |
| 880 | 6-[3-cyano-6-ethyl-5-fluoro-1-(5-fluoropyridin-2-yl)-1H-indol-2-yl]-N-[(2R)-1,1,1-trifluoropropan-2-yl]pyridine-3-sulfonamide, |
| 881 | 6-[3-cyano-6-ethyl-5-fluoro-1-(pyrimidin-2-yl)-1H-indol-2-yl]-2-methyl-N-[(2S)-1,1,1-trifluoropropan-2-yl]pyridine-3-sulfonamide, |
| 882 | N-tert-butyl-6-[3-cyano-6-ethyl-5-fluoro-1-(pyridin-2-yl)-1H-indol-2-yl]pyridine-3-sulfonamide, |

| Cpd | Name |
|---|---|
| 883 | 2-[5-(tert-butylsulfamoyl)pyridin-2-yl]-6-ethyl-5-fluoro-1-(pyridin-2-yl)-1H-indole-3-carboxamide, |
| 884 | N-tert-butyl-6-(3-cyano-6-ethyl-5-fluoro-1-phenyl-1H-indol-2-yl)pyridine-3-sulfonamide, |
| 885 | 6-[3-cyano-5-fluoro-6-methyl-1-(5-methylpyridin-2-yl)-1H-indol-2-yl]-N-[(2S)-1,1,1-trifluoropropan-2-yl]pyridine-3-sulfonamide, |
| 886 | 6-[3-cyano-5-fluoro-6-methyl-1-(4-methylpyridin-2-yl)-1H-indol-2-yl]-N-[(2S)-1,1,1-trifluoropropan-2-yl]pyridine-3-sulfonamide, |
| 887 | 6-[3-cyano-6-ethyl-5-fluoro-1-(pyridin-2-yl)-1H-indol-2-yl]-2-methyl-N-[(2S)-1,1,1-trifluoropropan-2-yl]pyridine-3-sulfonamide, |
| 888 | 6-[3-cyano-5-fluoro-6-methyl-1-(pyrimidin-2-yl)-1H-indol-2-yl]-5-methyl-N-[(2S)-1,1,1-trifluoropropan-2-yl]pyridine-3-sulfonamide, |
| 889 | 6-[3-cyano-5-fluoro-6-methyl-1-(pyridin-2-yl)-1H-indol-2-yl]-5-methyl-N-[(2S)-1,1,1-trifluoropropan-2-yl]pyridine-3-sulfonamide, |
| 890 | 6-[3-cyano-6-ethyl-5-fluoro-1-(pyrimidin-2-yl)-1H-indol-2-yl]-4-methyl-N-[(2R)-1,1,1-trifluoropropan-2-yl]pyridine-3-sulfonamide, |
| 891 | 6-[3-cyano-6-ethyl-5-fluoro-1-(pyridin-2-yl)-1H-indol-2-yl]-4-methyl-N-[(2R)-1,1,1-trifluoropropan-2-yl]pyridine-3-sulfonamide, |
| 892 | 6-[3-cyano-5-fluoro-6-methyl-1-(pyridazin-3-yl)-1H-indol-2-yl]-N-[(2S)-1,1,1-trifluoropropan-2-yl]pyridine-3-sulfonamide, |
| 893 | 6-[3-cyano-5-fluoro-6-methyl-1-(pyridin-3-yl)-1H-indol-2-yl]-N-[(2S)-1,1,1-trifluoropropan-2-yl]pyridine-3-sulfonamide, |
| 894 | 6-[3-cyano-5-fluoro-6-methyl-1-(pyrimidin-5-yl)-1H-indol-2-yl]-N-[(2S)-1,1,1-trifluoropropan-2-yl]pyridine-3-sulfonamide, |
| 895 | 6-[6-bromo-3-cyano-5-fluoro-1-(pyrimidin-2-yl)-1H-indol-2-yl]-N-[(2S)-1,1,1-trifluoropropan-2-yl]pyridine-3-sulfonamide, |
| 896 | 6-[3-cyano-5-fluoro-6-methyl-1-(pyrimidin-4-yl)-1H-indol-2-yl]-N-[(2S)-1,1,1-trifluoropropan-2-yl]pyridine-3-sulfonamide, |
| 897 | 6-[3-cyano-1-(pyrazin-2-yl)-5-(trifluoromethyl)-1H-indol-2-yl]-N-[(2S)-1,1,1-trifluoropropan-2-yl]pyridine-3-sulfonamide, |
| 898 | 6-[3-cyano-1-(pyrazin-2-yl)-5-(trifluoromethoxy)-1H-indol-2-yl]-N-[(2S)-1,1,1-trifluoropropan-2-yl]pyridine-3-sulfonamide, |
| 899 | N-tert-butyl-6-[3-cyano-6-ethyl-5-fluoro-1-(pyrazin-2-yl)-1H-indol-2-yl]pyridine-3-sulfonamide, |
| 900 | N-tert-butyl-6-[3-cyano-6-ethyl-5-fluoro-1-(3-fluoropyridin-2-yl)-1H-indol-2-yl]pyridine-3-sulfonamide, |
| 901 | 6-[3-cyano-6-fluoro-5-methyl-1-(pyrimidin-2-yl)-1H-indol-2-yl]-N-[(2S)-1,1,1-trifluoropropan-2-yl]pyridine-3-sulfonamide, |
| 902 | 5-fluoro-1-(3-fluoropyridin-2-yl)-6-methyl-2-(5-{[(2S)-1,1,1-trifluoropropan-2-yl]sulfamoyl}pyridin-2-yl)-1H-indole-3-carboxamide, |
| 903 | 6-[5-fluoro-6-methyl-1-(1,3-thiazol-2-yl)-1H-indol-2-yl]-N-[(2S)-1,1,1-trifluoropropan-2-yl]pyridine-3-sulfonamide, |
| 904 | 5-fluoro-6-methyl-1-(5-methylpyrazin-2-yl)-2-(5-{[(2S)-1,1,1-trifluoropropan-2-yl]sulfamoyl}pyridin-2-yl)-1H-indole-3-carboxamide, |
| 905 | 5-fluoro-6-methyl-1-(4-methylpyrimidin-2-yl)-2-(5-{[(2S)-1,1,1-trifluoropropan-2-yl]sulfamoyl}pyridin-2-yl)-1H-indole-3-carboxamide, |
| 906 | 5-fluoro-1-(4-methoxypyrimidin-2-yl)-6-methyl-2-(5-{[(2S)-1,1,1-trifluoropropan-2-yl]sulfamoyl}pyridin-2-yl)-1H-indole-3-carboxamide, |
| 907 | 6-[6-acetyl-3-cyano-5-fluoro-1-(pyrimidin-2-yl)-1H-indol-2-yl]-N-[(2S)-1,1,1-trifluoropropan-2-yl]pyridine-3-sulfonamide, |
| 908 | 6-[3-cyano-6-ethenyl-5-fluoro-1-(pyrimidin-2-yl)-1H-indol-2-yl]-N-[(2S)-1,1,1-trifluoropropan-2-yl]pyridine-3-sulfonamide, |
| 909 | 6-ethyl-5-fluoro-1-(pyridin-2-yl)-2-(5-{[(2S)-1,1,1-trifluoropropan-2-yl]sulfamoyl}pyridin-2-yl)-1H-indole-3-carboxamide, |
| 910 | 6-(3-cyano-1-cyclopropyl-6-ethyl-5-fluoro-1H-indol-2-yl)-N-[(2S)-1,1,1-trifluoropropan-2-yl]pyridine-3-sulfonamide, |
| 911 | 6-[3-cyano-5-fluoro-6-(1-hydroxyethyl)-1-(pyrimidin-2-yl)-1H-indol-2-yl]-N-[(2S)-1,1,1-trifluoropropan-2-yl]pyridine-3-sulfonamide, |
| 912 | 5-fluoro-6-methyl-1-(pyridazin-3-yl)-2-(5-{[(2S)-1,1,1-trifluoropropan-2-yl]sulfamoyl}pyridin-2-yl)-1H-indole-3-carboxamide, |
| 913 | 5-fluoro-6-methyl-1-(pyridin-3-yl)-2-(5-{[(2S)-1,1,1-trifluoropropan-2-yl]sulfamoyl}pyridin-2-yl)-1H-indole-3-carboxamide, |
| 914 | 6-[1-(5-chloropyrimidin-2-yl)-3-cyano-5-fluoro-6-methyl-1H-indol-2-yl]-N-[(2S)-1,1,1-trifluoropropan-2-yl]pyridine-3-sulfonamide, |
| 915 | 6-[3-cyano-5-fluoro-6-methyl-1-(6-methylpyrazin-2-yl)-1H-indol-2-yl]-N-[(2S)-1,1,1-trifluoropropan-2-yl]pyridine-3-sulfonamide, |
| 916 | 5-methyl-1-(pyrazin-2-yl)-2-(5-{[(2S)-1,1,1-trifluoropropan-2-yl]sulfamoyl}pyridin-2-yl)-1H-indole-3-carboxamide, |
| 917 | 6-[3-cyano-6-fluoro-5-methyl-1-(pyridin-2-yl)-1H-indol-2-yl]-N-[(2S)-1,1,1-trifluoropropan-2-yl]pyridine-3-sulfonamide, |
| 918 | 6-fluoro-5-methyl-1-(pyrimidin-2-yl)-2-(5-{[(2S)-1,1,1-trifluoropropan-2-yl]sulfamoyl}pyridin-2-yl)-1H-indole-3-carboxamide, |
| 919 | 6-[3-cyano-6-fluoro-5-methyl-1-(pyrazin-2-yl)-1H-indol-2-yl]-N-[(2S)-1,1,1-trifluoropropan-2-yl]pyridine-3-sulfonamide, |
| 920 | 6-[3-cyano-1-(4-fluorophenyl)-5-methyl-1H-indol-2-yl]-N-[(2S)-1,1,1-trifluoropropan-2-yl]pyridine-3-sulfonamide, |

| Cpd | Name |
|---|---|
| 921 | 6-(3-cyano-5-methyl-1-phenyl-1H-indol-2-yl)-N-[(2S)-1,1,1-trifluoropropan-2-yl]pyridine-3-sulfonamide, |
| 922 | 6-[3-cyano-1-(pyrimidin-2-yl)-5-(trifluoromethyl)-1H-indol-2-yl]-N-[(2S)-1,1,1-trifluoropropan-2-yl]pyridine-3-sulfonamide, |
| 923 | 6-[3-cyano-5-fluoro-6-methyl-1-(6-methylpyridin-2-yl)-1H-indol-2-yl]-N-[(2S)-1,1,1-trifluoropropan-2-yl]pyridine-3-sulfonamide, |
| 924 | 6-[3-cyano-5-fluoro-1-(5-fluoropyrimidin-2-yl)-6-methyl-1H-indol-2-yl]-N-[(2S)-1,1,1-trifluoropropan-2-yl]pyridine-3-sulfonamide, |
| 925 | 6-[3-cyano-5-fluoro-6-methyl-1-(5-methylpyrimidin-2-yl)-1H-indol-2-yl]-N-[(2S)-1,1,1-trifluoropropan-2-yl]pyridine-3-sulfonamide, |
| 926 | 6-[3-cyano-5-fluoro-1-(4-fluoropyridin-2-yl)-6-methyl-1H-indol-2-yl]-N-[(2S)-1,1,1-trifluoropropan-2-yl]pyridine-3-sulfonamide, |
| 927 | 6-[3-cyano-5-fluoro-6-(2-methyl-1,3-dioxolan-2-yl)-1-(pyrimidin-2-yl)-1H-indol-2-yl]-N-[(2S)-1,1,1-trifluoropropan-2-yl]pyridine-3-sulfonamide, |
| 928 | 1-cyclohexyl-6-(difluoromethoxy)-5-fluoro-2-{5-[(1,1,1-trifluoro-2-methylpropan-2-yl)sulfamoyl]pyridin-2-yl}-1H-indole-3-carboxylic acid, |
| 929 | 6-[3-cyano-6-ethyl-5-fluoro-1-(pyrazin-2-yl)-1H-indol-2-yl]-N-[(2S)-1,1,1-trifluoropropan-2-yl]pyridine-3-sulfonamide, |
| 930 | 6-[3-cyano-6-ethyl-5-fluoro-1-(6-fluoropyridin-2-yl)-1H-indol-2-yl]-N-[(2S)-1,1,1-trifluoropropan-2-yl]pyridine-3-sulfonamide, |
| 931 | 6-[3-cyano-6-ethyl-5-fluoro-1-(5-methylpyridin-2-yl)-1H-indol-2-yl]-N-[(2S)-1,1,1-trifluoropropan-2-yl]pyridine-3-sulfonamide, |
| 932 | 6-[3-cyano-6-ethyl-5-fluoro-1-(4-methylpyridin-2-yl)-1H-indol-2-yl]-N-[(2S)-1,1,1-trifluoropropan-2-yl]pyridine-3-sulfonamide, |
| 933 | 6-[3-cyano-5-fluoro-6-methyl-1-(pyridin-4-yl)-1H-indol-2-yl]-N-[(2S)-1,1,1-trifluoropropan-2-yl]pyridine-3-sulfonamide, |
| 934 | 6-[3-cyano-5-fluoro-6-methyl-1-(1,3-thiazol-2-yl)-1H-indol-2-yl]-N-[(2S)-1,1,1-trifluoropropan-2-yl]pyridine-3-sulfonamide, |
| 935 | 6-[3-cyano-6-ethyl-5-fluoro-1-(1,3-thiazol-2-yl)-1H-indol-2-yl]-N-[(2S)-1,1,1-trifluoropropan-2-yl]pyridine-3-sulfonamide, |
| 936 | 6-[3-cyano-6-(difluoromethoxy)-5-fluoro-1-(propan-2-yl)-1H-indol-2-yl]-N-[(2S)-1,1,1-trifluoropropan-2-yl]pyridine-3-sulfonamide, |
| 937 | 6-[3-cyano-6-(difluoromethoxy)-5-fluoro-1-(2-methylpropyl)-1H-indol-2-yl]-N-[(2S)-1,1,1-trifluoropropan-2-yl]pyridine-3-sulfonamide, |
| 938 | 6-[6-bromo-3-cyano-5-fluoro-1-(pyrimidin-2-yl)-1H-indol-2-yl]-N-tert-butylpyridine-3-sulfonamide, |
| 939 | N-tert-butyl-6-[3,6-diacetyl-5-fluoro-1-(pyrimidin-2-yl)-1H-indol-2-yl]pyridine-3-sulfonamide, |
| 940 | 6-[3-cyano-6-(difluoromethoxy)-5-fluoro-1-(2-hydroxyethyl)-1H-indol-2-yl]-N-[(2S)-1,1,1-trifluoropropan-2-yl]pyridine-3-sulfonamide, |
| 941 | 6-[3-cyano-1-(1,6-dihydropyrimidin-2-yl)-6-ethyl-5-fluoro-1H-indol-2-yl]-N-[(2S)-1,1,1-trifluoropropan-2-yl]pyridine-3-sulfonamide, |
| 942 | 6-[1-(5-chloropyrimidin-2-yl)-3-cyano-6-ethyl-5-fluoro-1H-indol-2-yl]-N-[(2S)-1,1,1-trifluoropropan-2-yl]pyridine-3-sulfonamide, |
| 943 | 6-[3-cyano-6-ethyl-5-fluoro-1-(2-methylpyrimidin-4-yl)-1H-indol-2-yl]-N-[(2S)-1,1,1-trifluoropropan-2-yl]pyridine-3-sulfonamide, |
| 944 | 6-[5-fluoro-1-(2-fluoropyridin-4-yl)-6-methyl-1H-indol-2-yl]-N-[(2S)-1,1,1-trifluoropropan-2-yl]pyridine-3-sulfonamide, |
| 945 | 6-[3-cyano-5-fluoro-1-(5-fluoropyridin-3-yl)-6-methyl-1H-indol-2-yl]-N-[(2S)-1,1,1-trifluoropropan-2-yl]pyridine-3-sulfonamide, |
| 946 | 6-[3-cyano-6-ethyl-5-fluoro-1-(5-fluoropyrimidin-2-yl)-1H-indol-2-yl]-N-[(2S)-1,1,1-trifluoropropan-2-yl]pyridine-3-sulfonamide, |
| 947 | 6-[3-chloro-6-cyclopropyl-5-fluoro-1-(pyrimidin-2-yl)-1H-indol-2-yl]-N-[(2S)-1,1,1-trifluoropropan-2-yl]pyridine-3-sulfonamide, |
| 948 | 6-[3-cyano-1-(5-fluoropyrimidin-2-yl)-5-methyl-1H-indol-2-yl]-N-[(2S)-1,1,1-trifluoropropan-2-yl]pyridine-3-sulfonamide, |
| 949 | 6-[3-cyano-6-fluoro-1-(5-fluoropyrimidin-2-yl)-5-methyl-1H-indol-2-yl]-N-[(2S)-1,1,1-trifluoropropan-2-yl]pyridine-3-sulfonamide, |
| 950 | 6-[3-cyano-1-(pyrimidin-2-yl)-6-(trifluoromethyl)-1H-indol-2-yl]-N-[(2S)-1,1,1-trifluoropropan-2-yl]pyridine-3-sulfonamide, |
| 951 | 6-[3-cyano-1-(pyrazin-2-yl)-6-(trifluoromethyl)-1H-indol-2-yl]-N-[(2S)-1,1,1-trifluoropropan-2-yl]pyridine-3-sulfonamide, |
| 952 | 6-[3-cyano-1-(pyridin-2-yl)-6-(trifluoromethyl)-1H-indol-2-yl]-N-[(2S)-1,1,1-trifluoropropan-2-yl]pyridine-3-sulfonamide, |
| 953 | 6-[3-cyano-6-ethyl-5-fluoro-1-(pyrimidin-2-yl)-1H-indol-2-yl]-N-(cyclobutylmethyl)pyridine-3-sulfonamide, |
| 954 | 6-[3-cyano-6-ethyl-5-fluoro-1-(pyridin-3-yl)-1H-indol-2-yl]-N-[(2S)-1,1,1-trifluoropropan-2-yl]pyridine-3-sulfonamide, |
| 955 | 6-[3-cyano-6-ethyl-5-fluoro-1-(4-methoxypyridin-2-yl)-1H-indol-2-yl]-N-[(2S)-1,1,1-trifluoropropan-2-yl]pyridine-3-sulfonamide, |
| 956 | 6-[3-cyano-6-ethyl-5-fluoro-1-(pyrimidin-2-yl)-1H-indol-2-yl]-N-[(2S)-1,1,1-trifluoro(2-deuterium)propan-2-yl]pyridine-3-sulfonamide, |
| 957 | 6-[5-fluoro-6-methyl-1-(1,3-thiazol-4-yl)-1H-indol-2-yl]-N-[(2S)-1,1,1-trifluoropropan-2-yl]pyridine-3-sulfonamide, |
| 958 | 6-[5-fluoro-6-methyl-1-(1,3,4-thiadiazol-2-yl)-1H-indol-2-yl]-N-[(2S)-1,1,1-trifluoropropan-2-yl]pyridine-3-sulfonamide, |

-continued

| Cpd | Name |
|---|---|
| 959 | 6-[5-fluoro-6-methyl-1-(1,3-thiazol-5-yl)-1H-indol-2-yl]-N-[(2S)-1,1,1-trifluoropropan-2-yl]pyridine-3-sulfonamide, |
| 960 | 6-[3-cyano-5-fluoro-6-methyl-1-(1,3-thiazol-4-yl)-1H-indol-2-yl]-N-[(2S)-1,1,1-trifluoropropan-2-yl]pyridine-3-sulfonamide, |
| 961 | 6-[3-cyano-5-fluoro-1-(5-fluoro-6-methylpyridin-2-yl)-6-methyl-1H-indol-2-yl]-N-[(2S)-1,1,1-trifluoropropan-2-yl]pyridine-3-sulfonamide, |
| 962 | 6-[1-(6-chloropyridin-2-yl)-3-cyano-5-fluoro-6-methyl-1H-indol-2-yl]-N-[(2S)-1,1,1-trifluoropropan-2-yl]pyridine-3-sulfonamide, |
| 963 | 6-[3-cyano-6-ethyl-5-fluoro-1-(pyrimidin-5-yl)-1H-indol-2-yl]-N-[(2S)-1,1,1-trifluoropropan-2-yl]pyridine-3-sulfonamide, |
| 964 | 6-[3-cyano-6-ethyl-5-fluoro-1-(pyrimidin-4-yl)-1H-indol-2-yl]-N-[(2S)-1,1,1-trifluoropropan-2-yl]pyridine-3-sulfonamide, |
| 965 | 6-[1-(3-chloropyridin-2-yl)-3-cyano-6-ethyl-5-fluoro-1H-indol-2-yl]-N-[(2S)-1,1,1-trifluoropropan-2-yl]pyridine-3-sulfonamide, |
| 966 | 6-[1-(5-chloropyridin-2-yl)-3-cyano-6-ethyl-5-fluoro-1H-indol-2-yl]-N-[(2S)-1,1,1-trifluoropropan-2-yl]pyridine-3-sulfonamide, |
| 967 | 6-[3-cyano-5-fluoro-6-(prop-2-en-1-yl)-1-(pyrimidin-2-yl)-1H-indol-2-yl]-N-[(2S)-1,1,1-trifluoropropan-2-yl]pyridine-3-sulfonamide, |
| 968 | 6-[3-chloro-5-fluoro-6-(prop-2-en-1-yl)-1-(pyrimidin-2-yl)-1H-indol-2-yl]-N-[(2S)-1,1,1-trifluoropropan-2-yl]pyridine-3-sulfonamide, |
| 969 | 6-[5-fluoro-6-(prop-2-en-1-yl)-1-(pyrimidin-2-yl)-1H-indol-2-yl]-N-[(2S)-1,1,1-trifluoropropan-2-yl]pyridine-3-sulfonamide, |
| 970 | 6-[3-cyano-5-fluoro-6-(2-hydroxyethyl)-1-(pyrimidin-2-yl)-1H-indol-2-yl]-N-[(2S)-1,1,1-trifluoropropan-2-yl]pyridine-3-sulfonamide, |
| 971 | 6-[1-(3-chloropyridin-2-yl)-3-cyano-5-fluoro-6-methyl-1H-indol-2-yl]-N-[(2S)-1,1,1-trifluoropropan-2-yl]pyridine-3-sulfonamide, |
| 972 | 6-[3-chloro-5-fluoro-6-methyl-1-(1,3,4-thiadiazol-2-yl)-1H-indol-2-yl]-N-[(2S)-1,1,1-trifluoropropan-2-yl]pyridine-3-sulfonamide, |
| 973 | 6-[3-cyano-5-fluoro-6-methyl-1-(1,3-thiazol-5-yl)-1H-indol-2-yl]-N-[(2S)-1,1,1-trifluoropropan-2-yl]pyridine-3-sulfonamide, |
| 974 | 6-[3-cyano-6-ethyl-5-fluoro-1-(pyridin-4-yl)-1H-indol-2-yl]-N-[(2S)-1,1,1-trifluoropropan-2-yl]pyridine-3-sulfonamide, |
| 975 | 6-[3-cyano-6-ethyl-5-fluoro-1-(pyridazin-3-yl)-1H-indol-2-yl]-N-[(2S)-1,1,1-trifluoropropan-2-yl]pyridine-3-sulfonamide, |
| 976 | 6-[3-cyano-6-ethyl-5-fluoro-1-(5-methylpyrimidin-2-yl)-1H-indol-2-yl]-N-[(2S)-1,1,1-trifluoropropan-2-yl]pyridine-3-sulfonamide, |
| 977 | 6-[3-cyano-5-fluoro-6-methyl-1-(1,3,4-thiadiazol-2-yl)-1H-indol-2-yl]-N-[(2S)-1,1,1-trifluoropropan-2-yl]pyridine-3-sulfonamide, |
| 978 | 6-ethyl-5-fluoro-1-(pyrimidin-2-yl)-2-{5-[(1,1,1-trifluoro-2-methylpropan-2-yl)sulfamoyl]pyridin-2-yl}-1H-indole-3-carboxamide, |
| 979 | 6-ethyl-5-fluoro-1-(pyrimidin-2-yl)-2-(5-{[1-(trifluoromethyl)cyclopropyl]sulfamoyl}pyridin-2-yl)-1H-indole-3-carboxamide, |
| 980 | 6-ethyl-5-fluoro-1-(4-methylpyridin-2-yl)-2-(5-{[(2S)-1,1,1-trifluoropropan-2-yl]sulfamoyl}pyridin-2-yl)-1H-indole-3-carboxamide, |
| 981 | 6-ethyl-5-fluoro-1-(5-fluoropyridin-2-yl)-2-(5-{[(2S)-1,1,1-trifluoropropan-2-yl]sulfamoyl}pyridin-2-yl)-1H-indole-3-carboxamide, |
| 982 | 6-ethyl-5-fluoro-1-(2-methylpyrimidin-4-yl)-2-(5-{[(2S)-1,1,1-trifluoropropan-2-yl]sulfamoyl}pyridin-2-yl)-1H-indole-3-carboxamide, |
| 983 | 6-[1-(5-chloropyridin-3-yl)-3-cyano-6-ethyl-5-fluoro-1H-indol-2-yl]-N-[(2S)-1,1,1-trifluoropropan-2-yl]pyridine-3-sulfonamide, |
| 984 | 6-{3-cyano-5-fluoro-1-[5-(hydroxymethyl)-1,3-thiazol-2-yl]-6-methyl-1H-indol-2-yl}-N-[(2S)-1,1,1-trifluoropropan-2-yl]pyridine-3-sulfonamide, |
| 985 | methyl 2-[3-cyano-5-fluoro-6-methyl-2-(5-{[(2S)-1,1,1-trifluoropropan-2-yl]sulfamoyl}pyridin-2-yl)-1H-indol-1-yl]-1,3-thiazole-5-carboxylate, |
| 986 | methyl 2-[3-cyano-5-fluoro-6-methyl-2-(5-{[(2S)-1,1,1-trifluoropropan-2-yl]sulfamoyl}pyridin-2-yl)-1H-indol-1-yl]-1,3-thiazole-4-carboxylate, |
| 987 | 6-[5-fluoro-6-methyl-1-(thiophen-3-yl)-1H-indol-2-yl]-N-[(2S)-1,1,1-trifluoropropan-2-yl]pyridine-3-sulfonamide, |
| 988 | 6-[5-fluoro-1-(furan-3-yl)-6-methyl-1H-indol-2-yl]-N-[(2S)-1,1,1-trifluoropropan-2-yl]pyridine-3-sulfonamide, |
| 989 | 6-[5-fluoro-6-methyl-1-(thiophen-2-yl)-1H-indol-2-yl]-N-[(2S)-1,1,1-trifluoropropan-2-yl]pyridine-3-sulfonamide, |
| 990 | 6-[3-cyano-5-fluoro-6-methyl-1-(thiophen-2-yl)-1H-indol-2-yl]-N-[(2S)-1,1,1-trifluoropropan-2-yl]pyridine-3-sulfonamide, |
| 991 | 6-[3-cyano-5-fluoro-1-(furan-3-yl)-6-methyl-1H-indol-2-yl]-N-[(2S)-1,1,1-trifluoropropan-2-yl]pyridine-3-sulfonamide, |
| 992 | 6-[3-cyano-5-fluoro-6-methyl-1-(thiophen-3-yl)-1H-indol-2-yl]-N-[(2S)-1,1,1-trifluoropropan-2-yl]pyridine-3-sulfonamide, |
| 993 | 6-[1-(4-chloropyridin-2-yl)-3-cyano-6-ethyl-5-fluoro-1H-indol-2-yl]-N-[(2S)-1,1,1-trifluoropropan-2-yl]pyridine-3-sulfonamide, |
| 994 | 6-ethyl-5-fluoro-1-(pyrazin-2-yl)-2-(5-{[(2S)-1,1,1-trifluoropropan-2-yl]sulfamoyl}pyridin-2-yl)-1H-indole-3-carboxamide |
| 995 | 6-ethyl-5-fluoro-1-(6-fluoropyridin-2-yl)-2-(5-{[(2S)-1,1,1-trifluoropropan-2-yl]sulfamoyl}pyridin-2-yl)-1H-indole-3-carboxamide, |
| 996 | 5-chloro-1-cyclobutyl-2-(5-{[(2S)-1,1,1-trifluoropropan-2-yl]sulfamoyl}pyridin-2-yl)-1H-indole-3-carboxamide, |

| Cpd | Name |
|---|---|
| 997 | 1-cyclobutyl-5-fluoro-2-(5-{[(2S)-1,1,1-trifluoropropan-2-yl]sulfamoyl}pyridin-2-yl)-1H-indole-3-carboxamide, |
| 998 | 2-{5-[(tert-butylsulfonyl)amino]pyridin-2-yl}-1-cyclohexyl-6-ethyl-5-fluoro-1H-indole-3-carboxylic, |
| 999 | 2-{5-[(tert-butylsulfonyl)amino]pyridin-2-yl}-1-cyclohexyl-6-ethyl-5-fluoro-1H-indole-3-carboxamide, |
| 1000 | 6-[3-cyano-5-fluoro-6-methyl-1-(3-methylthiophen-2-yl)-1H-indol-2-yl]-N-[(2S)-1,1,1-trifluoropropan-2-yl]pyridine-3-sulfonamide, |
| 1001 | 6-[3-cyano-1-(4,6-difluoropyridin-2-yl)-5-fluoro-6-methyl-1H-indol-2-yl]-N-[(2S)-1,1,1-trifluoropropan-2-yl]pyridine-3-sulfonamide, |
| 1002 | 6-[3-cyano-6-ethyl-5-fluoro-1-(4-fluorophenyl)-1H-indol-2-yl]-N-[(2S)-1,1,1-trifluoropropan-2-yl]pyridine-3-sulfonamide, |
| 1003 | 6-[1-(4-chlorophenyl)-3-cyano-6-ethyl-5-fluoro-1H-indol-2-yl]-N-[(2S)-1,1,1-trifluoropropan-2-yl]pyridine-3-sulfonamide, |
| 1004 | 6-[3-cyano-6-ethyl-5-fluoro-1-(4-methylphenyl)-1H-indol-2-yl]-N-[(2S)-1,1,1-trifluoropropan-2-yl]pyridine-3-sulfonamide, |
| 1005 | 6-[3-cyano-6-ethyl-5-fluoro-1-(4-methoxyphenyl)-1H-indol-2-yl]-N-[(2S)-1,1,1-trifluoropropan-2-yl]pyridine-3-sulfonamide, |
| 1006 | 6-{3-cyano-6-ethyl-5-fluoro-1-[4-(trifluoromethyl)phenyl]-1H-indol-2-yl}-N-[(2S)-1,1,1-trifluoropropan-2-yl]pyridine-3-sulfonamide, |
| 1007 | 6-[3-cyano-1-(4-cyanophenyl)-6-ethyl-5-fluoro-1H-indol-2-yl]-N-[(2S)-1,1,1-trifluoropropan-2-yl]pyridine-3-sulfonamide, |
| 1008 | 6-[3-cyano-6-ethyl-5-fluoro-1-(3-fluorophenyl)-1H-indol-2-yl]-N-[(2S)-1,1,1-trifluoropropan-2-yl]pyridine-3-sulfonamide, |
| 1009 | 6-[3-cyano-6-ethyl-5-fluoro-1-(3-methylphenyl)-1H-indol-2-yl]-N-[(2S)-1,1,1-trifluoropropan-2-yl]pyridine-3-sulfonamide, |
| 1010 | 6-[3-cyano-6-ethyl-5-fluoro-1-(3-methoxyphenyl)-1H-indol-2-yl]-N-[(2S)-1,1,1-trifluoropropan-2-yl]pyridine-3-sulfonamide, |
| 1011 | 6-{3-cyano-6-ethyl-5-fluoro-1-[3-(trifluoromethyl)phenyl]-1H-indol-2-yl}-N-[(2S)-1,1,1-trifluoropropan-2-yl]pyridine-3-sulfonamide, |
| 1012 | 6-[3-cyano-1-(3-cyanophenyl)-6-ethyl-5-fluoro-1H-indol-2-yl]-N-[(2S)-1,1,1-trifluoropropan-2-yl]pyridine-3-sulfonamide, |
| 1013 | 6-[3-cyano-5-fluoro-1-(2-fluoropyridin-4-yl)-6-methyl-1H-indol-2-yl]-N-[(2S)-1,1,1-trifluoropropan-2-yl]pyridine-3-sulfonamide, |
| 1014 | 6-[3-cyano-5-fluoro-1-(3-fluoropyridin-4-yl)-6-methyl-1H-indol-2-yl]-N-[(2S)-1,1,1-trifluoropropan-2-yl]pyridine-3-sulfonamide, |
| 1015 | 6-[3-cyano-5-fluoro-1-(6-fluoropyridin-3-yl)-6-methyl-1H-indol-2-yl]-N-[(2S)-1,1,1-trifluoropropan-2-yl]pyridine-3-sulfonamide, |
| 1016 | 6-[3-cyano-5-fluoro-6-methyl-1-(1-methyl-1H-pyrazol-4-yl)-1H-indol-2-yl]-N-[(2S)-1,1,1-trifluoropropan-2-yl]pyridine-3-sulfonamide, |
| 1017 | 6-[3-cyano-5-fluoro-6-methyl-1-(5-methyl-1,3-thiazol-2-yl)-1H-indol-2-yl]-N-[(2S)-1,1,1-trifluoropropan-2-yl]pyridine-3-sulfonamide, |
| 1018 | 6-[1-(3-chlorophenyl)-3-cyano-6-ethyl-5-fluoro-1H-indol-2-yl]-N-[(2S)-1,1,1-trifluoropropan-2-yl]pyridine-3-sulfonamide, |
| 1019 | 6-ethyl-5-fluoro-1-(4-fluorophenyl)-2-(5-{[(2S)-1,1,1-trifluoropropan-2-yl]sulfamoyl}pyridin-2-yl)-1H-indole-3-carboxamide, |
| 1020 | 1-(4-chlorophenyl)-6-ethyl-5-fluoro-2-(5-{[(2S)-1,1,1-trifluoropropan-2-yl]sulfamoyl}pyridin-2-yl)-1H-indole-3-carboxamide, |
| 1021 | 6-ethyl-5-fluoro-1-(4-methylphenyl)-2-(5-{[(2S)-1,1,1-trifluoropropan-2-yl]sulfamoyl}pyridin-2-yl)-1H-indole-3-carboxamide, |
| 1022 | 6-ethyl-5-fluoro-1-[4-(trifluoromethyl)phenyl]-2-(5-{[(2S)-1,1,1-trifluoropropan-2-yl]sulfamoyl}pyridin-2-yl)-1H-indole-3-carboxamide, |
| 1023 | 6-ethyl-5-fluoro-1-(3-fluorophenyl)-2-(5-{[(2S)-1,1,1-trifluoropropan-2-yl]sulfamoyl}pyridin-2-yl)-1H-indole-3-carboxamide, |
| 1024 | 6-ethyl-5-fluoro-1-(3-methylphenyl)-2-(5-{[(2S)-1,1,1-trifluoropropan-2-yl]sulfamoyl}pyridin-2-yl)-1H-indole-3-carboxamide, |
| 1025 | 6-ethyl-5-fluoro-1-(3-methoxyphenyl)-2-(5-{[(2S)-1,1,1-trifluoropropan-2-yl]sulfamoyl}pyridin-2-yl)-1H-indole-3-carboxamide, |
| 1026 | 6-ethyl-5-fluoro-1-[3-(trifluoromethyl)phenyl]-2-(5-{[(2S)-1,1,1-trifluoropropan-2-yl]sulfamoyl}pyridin-2-yl)-1H-indole-3-carboxamide, |
| 1027 | 1-(3-chlorophenyl)-6-ethyl-5-fluoro-2-(5-{[(2S)-1,1,1-trifluoropropan-2-yl]sulfamoyl}pyridin-2-yl)-1H-indole-3-carboxamide, |
| 1028 | 2-{5-[(tert-butylsulfonyl)amino]pyrimidin-2-yl}-1-cyclohexyl-6-ethyl-5-fluoro-1H-indole-3-carboxylic acid, |
| 1029 | 2-{2-[(tert-butylsulfonyl)amino]pyrimidin-5-yl}-1-cyclohexyl-6-ethyl-5-fluoro-1H-indole-3-carboxylic acid, |
| 1030 | 6-[3-cyano-5-fluoro-6-methyl-1-(3-methyl-1H-pyrazol-4-yl)-1H-indol-2-yl]-N-[(2S)-1,1,1-trifluoropropan-2-yl]pyridine-3-sulfonamide, |
| 1031 | 6-[3-cyano-5-fluoro-6-methyl-1-(5-methylthiophen-2-yl)-1H-indol-2-yl]-N-[(2S)-1,1,1-trifluoropropan-2-yl]pyridine-3-sulfonamide, |
| 1032 | 6-[1-(5-chlorothiophen-2-yl)-3-cyano-5-fluoro-6-methyl-1H-indol-2-yl]-N-[(2S)-1,1,1-trifluoropropan-2-yl]pyridine-3-sulfonamide, |
| 1033 | 6-[3-cyano-1-(5-cyanothiophen-2-yl)-5-fluoro-6-methyl-1H-indol-2-yl]-N-[(2S)-1,1,1-trifluoropropan-2-yl]pyridine-3-sulfonamide, |
| 1034 | 6-[3-cyano-5-fluoro-6-methyl-1-(5-sulfamoylthiophen-2-yl)-1H-indol-2-yl]-N-[(2S)-1,1,1-trifluoropropan-2-yl]pyridine-3-sulfonamide, |

| Cpd | Name |
|---|---|
| 1035 | 6-[1-(5-acetylthiophen-2-yl)-3-cyano-5-fluoro-6-methyl-1H-indol-2-yl]-N-[(2S)-1,1,1-trifluoropropan-2-yl]pyridine-3-sulfonamide, |
| 1036 | 2-{2-[(tert-butylsulfonyl)amino]pyrimidin-5-yl}-1-cyclohexyl-6-ethyl-5-fluoro-1H-indole-3-carboxamide, |
| 1037 | 2-{6-[(tert-butylsulfonyl)amino]pyridin-3-yl}-1-cyclohexyl-6-ethyl-5-fluoro-1H-indole-3-carboxamide, |
| 1038 | 6-[3-cyano-5-fluoro-6-methyl-1-(4-methyl-1,3-thiazol-2-yl)-1H-indol-2-yl]-N-[(2S)-1,1,1-trifluoropropan-2-yl]pyridine-3-sulfonamide, |
| 1039 | 6-ethyl-5-fluoro-1-(5-methylpyridin-2-yl)-2-(5-{[(2S)-1,1,1-trifluoropropan-2-yl]sulfamoyl}pyridin-2-yl)-1H-indole-3-carboxamide, |
| 1040 | 6-ethyl-5-fluoro-1-(pyridin-3-yl)-2-(5-{[(2S)-1,1,1-trifluoropropan-2-yl]sulfamoyl}pyridin-2-yl)-1H-indole-3-carboxamide, |
| 1041 | 6-ethyl-5-fluoro-1-(pyrimidin-4-yl)-2-(5-{[(2S)-1,1,1-trifluoropropan-2-yl]sulfamoyl}pyridin-2-yl)-1H-indole-3-carboxamide, |
| 1042 | 1-(3-chloropyridin-2-yl)-6-ethyl-5-fluoro-2-(5-{[(2S)-1,1,1-trifluoropropan-2-yl]sulfamoyl}pyridin-2-yl)-1H-indole-3-carboxamide, |
| 1043 | 1-(5-chloropyridin-2-yl)-6-ethyl-5-fluoro-2-(5-{[(2S)-1,1,1-trifluoropropan-2-yl]sulfamoyl}pyridin-2-yl)-1H-indole-3-carboxamide, |
| 1044 | 1-(5-chloropyridin-3-yl)-6-ethyl-5-fluoro-2-(5-{[(2S)-1,1,1-trifluoropropan-2-yl]sulfamoyl}pyridin-2-yl)-1H-indole-3-carboxamide, |
| 1045 | 6-ethyl-5-fluoro-1-(pyridin-4-yl)-2-(5-{[(2S)-1,1,1-trifluoropropan-2-yl]sulfamoyl}pyridin-2-yl)-1H-indole-3-carboxamide, |
| 1046 | 6-ethyl-5-fluoro-1-(pyridazin-3-yl)-2-(5-{[(2S)-1,1,1-trifluoropropan-2-yl]sulfamoyl}pyridin-2-yl)-1H-indole-3-carboxamide, |
| 1047 | 6-ethyl-5-fluoro-1-(5-methylpyrimidin-2-yl)-2-(5-{[(2S)-1,1,1-trifluoropropan-2-yl]sulfamoyl}pyridin-2-yl)-1H-indole-3-carboxamide, |
| 1048 | 1-(4-chloropyridin-2-yl)-6-ethyl-5-fluoro-2-(5-{[(2S)-1,1,1-trifluoropropan-2-yl]sulfamoyl}pyridin-2-yl)-1H-indole-3-carboxamide, |
| 1055 | 6-[1-(2-acetylthiophen-3-yl)-3-cyano-5-fluoro-6-methyl-1H-indol-2-yl]-N-[(2S)-1,1,1-trifluoropropan-2-yl]pyridine-3-sulfonamide, |
| 1056 | 6-[3-cyano-5-fluoro-6-methyl-1-(4-methylthiophen-3-yl)-1H-indol-2-yl]-N-[(2S)-1,1,1-trifluoropropan-2-yl]pyridine-3-sulfonamide, |
| 1057 | 6-[1-(2-chlorothiophen-3-yl)-3-cyano-5-fluoro-6-methyl-1H-indol-2-yl]-N-[(2S)-1,1,1-trifluoropropan-2-yl]pyridine-3-sulfonamide, |
| 1058 | 6-[3-cyano-5-fluoro-6-methyl-1-(5-methylthiophen-3-yl)-1H-indol-2-yl]-N-[(2S)-1,1,1-trifluoropropan-2-yl]pyridine-3-sulfonamide, |
| 1059 | 6-[5-fluoro-6-methyl-1-(1,3-oxazol-2-yl)-1H-indol-2-yl]-N-[(2S)-1,1,1-trifluoropropan-2-yl]pyridine-3-sulfonamide, |
| 1060 | 6-[1-(5-cyanofuran-2-yl)-5-fluoro-6-methyl-1H-indol-2-yl]-N-[(2S)-1,1,1-trifluoropropan-2-yl]pyridine-3-sulfonamide, |
| 1061 | 6-[3-cyano-1-(3,4-difluorophenyl)-6-ethyl-5-fluoro-1H-indol-2-yl]-N-[(2S)-1,1,1-trifluoropropan-2-yl]pyridine-3-sulfonamide, |
| 1062 | 6-[1-(3-chloro-4-fluorophenyl)-3-cyano-6-ethyl-5-fluoro-1H-indol-2-yl]-N-[(2S)-1,1,1-trifluoropropan-2-yl]pyridine-3-sulfonamide, |
| 1063 | 2-{6-[(tert-butylsulfonyl)amino]pyridin-3-yl}-1-cyclohexyl-6-(difluoromethoxy)-5-fluoro-1H-indole-3-carboxamide, |
| 1064 | 2-{6-[(tert-butylsulfonyl)amino]pyridin-3-yl}-1-cyclohexyl-6-(difluoromethoxy)-5-fluoro-1H-indole-3-carboxylic acid, |
| 1065 | N-{5-[3-cyano-1-cyclohexyl-6-(difluoromethoxy)-5-fluoro-1H-indol-2-yl]pyridin-2-yl}-2-methylpropane-2-sulfonamide, |
| 1072 | 6-[3-cyano-1-(3-cyanofuran-2-yl)-5-fluoro-6-methyl-1H-indol-2-yl]-N-[(2S)-1,1,1-trifluoropropan-2-yl]pyridine-3-sulfonamide, |
| 1073 | 6-[3-cyano-5-fluoro-6-methyl-1-(1,3-oxazol-2-yl)-1H-indol-2-yl]-N-[(2S)-1,1,1-trifluoropropan-2-yl]pyridine-3-sulfonamide, |
| 1074 | 6-[3-cyano-1-(4-cyano-1,3-oxazol-2-yl)-5-fluoro-6-methyl-1H-indol-2-yl]-N-[(2S)-1,1,1-trifluoropropan-2-yl]pyridine-3-sulfonamide, |
| 1075 | 6-[3-cyano-6-ethyl-5-fluoro-1-(2-fluorophenyl)-1H-indol-2-yl]-N-[(2S)-1,1,1-trifluoropropan-2-yl]pyridine-3-sulfonamide, |
| 1078 | 6-{3-cyano-6-[(1,1-dideuterium)ethyl]-5-fluoro-1-(pyrimidin-2-yl)-1H-indol-2-yl}-N-[(2S)-1,1,1-trifluoropropan-2-yl]pyridine-3-sulfonamide, |
| 1079 | 6-{3-cyano-6-[(1,1-dideuterium)ethyl]-5-fluoro-1-(pyrimidin-2-yl)-1H-indol-2-yl}-N-[(2S)-1,1,1-trifluoro(2-deuterium)propan-2-yl]pyridine-3-sulfonamide, |
| 1080 | 2-{6-[(tert-butylsulfonyl)amino]pyridin-3-yl}-1-[(1S)-1-cyclopropylethyl]-6-(difluoromethoxy)-5-fluoro-1H-indole-3-carboxylic acid, |
| 1081 | 2-{6-[(tert-butylsulfonyl)amino]pyridin-3-yl}-1-[(1S)-1-cyclopropylethyl]-6-(difluoromethoxy)-5-fluoro-1H-indole-3-carboxamide, |
| 1082 | N-(5-{3-cyano-1-[(1S)-1-cyclopropylethyl]-6-ethyl-5-fluoro-1H-indol-2-yl}pyridin-2-yl)-2-methylpropane-2-sulfonamide, |
| 1083 | 2-{6-[(tert-butylsulfonyl)amino]pyridin-3-yl}-1-[(1S)-1-cyclopropylethyl]-6-ethyl-5-fluoro-1H-indole-3-carboxamide, |
| 1084 | 2-{6-[(tert-butylsulfonyl)amino]pyridin-3-yl}-1-[(1R)-1-cyclopropylethyl]-6-(difluoromethoxy)-5-fluoro-1H-indole-3-carboxylic acid, |
| 1085 | 2-{6-[(tert-butylsulfonyl)amino]pyridin-3-yl}-1-[(1R)-1-cyclopropylethyl]-6-(difluoromethoxy)-5-fluoro-1H-indole-3-carboxamide, |
| 1086 | 2-{6-[(tert-butylsulfonyl)amino]-4-methylpyridin-3-yl}-1-[(1R)-1-cyclopropylethyl]-6-(difluoromethoxy)-5-fluoro-1H-indole-3-carboxylic acid, |

| Cpd | Name |
|---|---|
| 1087 | 2-{6-[(tert-butylsulfonyl)amino]-4-methylpyridin-3-yl}-1-[(1R)-1-cyclopropylethyl]-6-(difluoromethoxy)-5-fluoro-1H-indole-3-carboxamide, |
| 1088 | 2-{6-[(tert-butylsulfonyl)amino]pyridin-3-yl}-1-cyclohexyl-6-cyclopropyl-4-fluoro-1H-indole-3-carboxamide, |
| 1092 | N-[6-(3-cyano-1-cyclohexyl-6-cyclopropyl-4-fluoro-1H-indol-2-yl)pyridin-3-yl]-2-methylpropane-2-sulfonamide, |
| 1093 | 2-{6-[(tert-butylsulfonyl)amino]-2-methylpyridin-3-yl}-6-(difluoromethoxy)-5-fluoro-1-(propan-2-yl)-1H-indole-3-carboxylic acid, |
| 1094 | 2-{6-[(tert-butylsulfonyl)amino]-2-methylpyridin-3-yl}-1-[(1R)-1-cyclopropylethyl]-6-(difluoromethoxy)-5-fluoro-1H-indole-3-carboxylic acid, |
| 1095 | 2-{6-[(tert-butylsulfonyl)amino]-2-methylpyridin-3-yl}-6-(difluoromethoxy)-5-fluoro-1-(propan-2-yl)-1H-indole-3-carboxamide, |
| 1096 | 2-{6-[(tert-butylsulfonyl)amino]-2-methylpyridin-3-yl}-1-[(1S)-1-cyclopropylethyl]-6-(difluoromethoxy)-5-fluoro-1H-indole-3-carboxamide, |
| 1097 | 2-{5-[(tert-butylsulfonyl)amino]pyridin-2-yl}-1-cyclohexyl-6-cyclopropyl-4-fluoro-1H-indole-3-carboxamide, |
| 1098 | 6-[3-cyano-6-cyclopropyl-4-fluoro-1-(pyrimidin-2-yl)-1H-indol-2-yl]-N-(1,1,1-trifluoro-2-methylpropan-2-yl)pyridine-3-sulfonamide, |
| 1099 | methyl 2-{6-[(tert-butylsulfonyl)amino]pyridin-3-yl}-1-cyclohexyl-5-fluoro-6-(fluoromethoxy)-1H-indole-3-carboxylate, |
| 1100 | 2-{6-[(tert-butylsulfonyl)amino]pyridin-3-yl}-6-cyclopropyl-5-fluoro-1-phenyl-1H-indole-3-carboxamide, |
| 1101 | N-[5-(3-cyano-6-cyclopropyl-5-fluoro-1-phenyl-1H-indol-2-yl)pyridin-2-yl]-2-methylpropane-2-sulfonamide, |
| 1102 | 2-{6-[(tert-butylsulfonyl)amino]pyridin-3-yl}-1-cyclohexyl-5-fluoro-6-(fluoromethoxy)-1H-indole-3-carboxamide, |
| 1103 | 2-{6-[(tert-butylsulfonyl)amino]pyridin-3-yl}-1-[(1R)-1-cyclopropylethyl]-6-ethyl-5-fluoro-1H-indole-3-carboxylic acid, |
| 1104 | 2-{6-[(tert-butylsulfonyl)amino]pyridin-3-yl}-1-[(1R)-1-cyclopropylethyl]-6-ethyl-5-fluoro-1H-indole-3-carboxamide, |
| 1105 | 2-{6-[(tert-butylsulfonyl)amino]pyridin-3-yl}-6-cyclopropyl-4-fluoro-1-(4-fluorophenyl)-1H-indole-3-carboxamide, |
| 1106 | 2-{6-[(tert-butylsulfonyl)amino]pyridin-3-yl}-6-ethyl-4-fluoro-1-(4-fluorophenyl)-1H-indole-3-carboxamide, |
| 1107 | 6-[3-cyano-5-fluoro-6-(1,1,1-trideuterium)methyl-1-(pyrimidin-2-yl)-1H-indol-2-yl]-N-[(2S)-1,1,1-trifluoro(2-deuterium)propan-2-yl]pyridine-3-sulfonamide, |
| 1108 | N-tert-butyl-6-(3-cyano-5-fluoro-6-methyl-1-phenyl-1H-indol-2-yl)pyridine-3-sulfonamide, |
| 1109 | 2-[5-(tert-butylsulfamoyl)pyridin-2-yl]-6-ethyl-5-fluoro-1-phenyl-1H-indole-3-carboxamide, |
| 1110 | 2-{5-[(tert-butylsulfonyl)amino]pyridin-2-yl}-1-cyclobutyl-6-ethyl-4-fluoro-1H-indole-3-carboxamide, |
| 1111 | 2-{6-[(tert-butylsulfonyl)amino]pyridin-3-yl}-6-ethyl-4-fluoro-1-phenyl-1H-indole-3-carboxamide, |
| 1112 | 6-(3-cyano-1-cyclobutyl-5-fluoro-6-methyl-1H-indol-2-yl)-N-[(2-deuterium)propan-2-yl]pyridine-3-sulfonamide, |
| 1113 | 6-(3-cyano-1-cyclobutyl-5-fluoro-6-methyl-1H-indol-2-yl)-N-[(2S)-1,1,1-trifluoro(2-deuterium)propan-2-yl]pyridine-3-sulfonamide, |
| 1114 | 6-[3-cyano-1-cyclobutyl-5-fluoro-6-(1,1,1-trideuterium)methyl-1H-indol-2-yl]-N-[(2S)-1,1,1-trifluoro(2-deuterium)propan-2-yl]pyridine-3-sulfonamide, |
| 1115 | 2-[5-(tert-butylsulfamoyl)pyridin-2-yl]-1-cyclohexyl-5-fluoro-6-methyl-1H-indole-3-carboxamide, |
| 1116 | 2-[5-(tert-butylsulfamoyl)pyridin-2-yl]-5-fluoro-6-methyl-1-phenyl-1H-indole-3-carboxamide, |
| 1117 | N-tert-butyl-6-(3-cyano-6-cyclopropyl-5-fluoro-1-phenyl-1H-indol-2-yl)pyridine-3-sulfonamide, |
| 1118 | 2-{6-[(tert-butylsulfonyl)amino]pyridin-3-yl}-1-cyclobutyl-6-ethyl-4-fluoro-1H-indole-3-carboxamide or |
| 1119 | 6-[3-cyano-1-(cyclopropylmethyl)-5-fluoro-6-(1,1,1-trideuterium)methyl-1H-indol-2-yl]-N-[(2-deuterium)propan-2-yl]pyridine-3-sulfonamide. |

In another embodiment, the HCV inhibitor or an enantiomer, stereoisomer, diastereomer, racemic, tautomeric, ester, prodrug, solvate, hydrate, isotopologue or salt form thereof is selected from:

| Cpd | Name |
|---|---|
| 7 | 6-(3-cyano-1-cyclobutyl-6-cyclopropyl-1H-indol-2-yl)-N-(propan-2-yl)pyridine-3-sulfonamide, |
| 31 | 6-[3-cyano-1-cyclobutyl-6-(difluoromethoxy)-1H-indol-2-yl]-N-(1,3-difluoropropan-2-yl)pyridine-3-sulfonamide, |
| 35 | 6-(3-cyano-1-cyclobutyl-6-cyclopropyl-1H-indol-2-yl)-N-(1,3-difluoropropan-2-yl)pyridine-3-sulfonamide, |

-continued

| Cpd | Name |
|---|---|
| 44 | 6-(3-cyano-1-cyclopentyl-6-methyl-1H-indol-2-yl)-N-(1,3-difluoropropan-2-yl)pyridine-3-sulfonamide, |
| 51 | 6-[3-cyano-1-cyclobutyl-6-(difluoromethoxy)-1H-indol-2-yl]-N-(propan-2-yl)pyridine-3-sulfonamide, |
| 107 | 6-(3-cyano-1-cyclobutyl-6-cyclopropyl-5-fluoro-1H-indol-2-yl)-N-(1,3-difluoropropan-2-yl)pyridine-3-sulfonamide, |
| 108 | 6-(3-cyano-1-cyclobutyl-5-fluoro-6-methyl-1H-indol-2-yl)-N-(1,3-difluoropropan-2-yl)pyridine-3-sulfonamide, |
| 190 | 6-(3-cyano-1-cyclopentyl-6-methyl-1H-indol-2-yl)-N-[1-(trifluoromethyl)cyclopropyl]pyridine-3-sulfonamide, |
| 277 | N-[6-(3-cyano-1-cyclobutyl-6-methoxy-1H-indol-2-yl)pyridazin-3-yl]ethanesulfonamide, |
| 300 | 6-[3-cyano-1-cyclobutyl-6-(difluoromethoxy)-1H-indol-2-yl]-N-[(2S)-1,1,1-trifluoropropan-2-yl]pyridine-3-sulfonamide, |
| 371 | 6-(3-cyano-1-cyclopentyl-6-methyl-1H-indol-2-yl)-N-(1,1,1-trifluoro-2-methylpropan-2-yl)pyridine-3-sulfonamide, |
| 387 | 6-[3-cyano-6-(difluoromethoxy)-1-(pyridin-2-yl)-1H-indol-2-yl]-N-[(2S)-1,1,1-trifluoropropan-2-yl]pyridine-3-sulfonamide, |
| 407 | 6-(3-cyano-1-cyclopentyl-5-fluoro-6-methyl-1H-indol-2-yl)-N-(1,3-difluoropropan-2-yl)pyridine-3-sulfonamide, |
| 408 | 6-(3-cyano-1-cyclopentyl-5-fluoro-6-methyl-1H-indol-2-yl)-N-[(2S)-1,1,1-trifluoropropan-2-yl]pyridine-3-sulfonamide, |
| 409 | 6-(3-cyano-1-cyclopentyl-5-fluoro-6-methyl-1H-indol-2-yl)-N-[(2R)-1,1,1-trifluoropropan-2-yl]pyridine-3-sulfonamide, |
| 421 | 6-(3-cyano-1-cyclobutyl-7-fluoro-6-methyl-1H-indol-2-yl)-N-[(2S)-1,1,1-trifluoropropan-2-yl]pyridine-3-sulfonamide, |
| 512 | 6-[3-cyano-6-(difluoromethoxy)-1-(pyrimidin-2-yl)-1H-indol-2-yl]-N-[(2S)-1,1,1-trifluoropropan-2-yl]pyridine-3-sulfonamide, |
| 532 | 6-(3-cyano-1-cyclobutyl-5,7-difluoro-6-methyl-1H-indol-2-yl)-N-[(2S)-1,1,1-trifluoropropan-2-yl]pyridine-3-sulfonamide, |
| 541 | 6-[3-cyano-5-fluoro-6-methyl-1-(pyridin-2-yl)-1H-indol-2-yl]-N-[(2S)-1,1,1-trifluoropropan-2-yl]pyridine-3-sulfonamide, |
| 549 | 6-[3-cyano-1-cyclobutyl-6-(difluoromethoxy)-5-fluoro-1H-indol-2-yl]-N-[(2S)-1,1,1-trifluoropropan-2-yl]pyridine-3-sulfonamide, |
| 601 | 6-[3-cyano-5-fluoro-1-(pyrimidin-2-yl)-1H-indol-2-yl]-N-[(2S)-1,1,1-trifluoropropan-2-yl]pyridine-3-sulfonamide, |
| 634 | 6-[3-cyano-5-fluoro-6-methyl-1-(pyrimidin-2-yl)-1H-indol-2-yl]-N-[(2S)-1,1,1-trifluoropropan-2-yl]pyridine-3-sulfonamide, |
| 640 | 6-(3-cyano-1-cyclobutyl-6-ethyl-5-fluoro-1H-indol-2-yl)-N-[(2S)-1,1,1-trifluoropropan-2-yl]pyridine-3-sulfonamide, |
| 650 | 6-[3-cyano-6-cyclopropyl-1-(pyrimidin-2-yl)-1H-indol-2-yl]-N-[(2S)-1,1,1-trifluoropropan-2-yl]pyridine-3-sulfonamide, |
| 657 | 6-[3-cyano-6-(difluoromethoxy)-5-fluoro-1-(pyridine-2-yl)-1H-indol-2-yl]-N-[(2S)-1,1,1-trifluoropropan-2-yl]pyridine-3-sulfonamide, |
| 682 | 6-[3-cyano-6-(difluoromethoxy)-5-fluoro-1-(pyrimidin-2-yl)-1H-indol-2-yl]-N-[(2S)-1,1,1-trifluoropropan-2-yl]pyridine-3-sulfonamide, |
| 683 | 2-[5-(tert-butylsulfamoyl)pyridin-2-yl]-1-cyclopentyl-5-fluoro-6-methyl-1H-indole-3-carboxamide, |
| 704 | 6-[3-cyano-6-ethyl-5-fluoro-1-(pyrimidin-2-yl)-1H-indol-2-yl]-N-[(2S)-1,1,1-trifluoropropan-2-yl]pyridine-3-sulfonamide, |
| 716 | 1-cyclohexyl-5-fluoro-6-methyl-2-(5-{[(2R)-1,1,1-trifluoropropan-2-yl]sulfamoyl}pyridin-2-yl)-1H-indole-3-carboxamide, |
| 749 | 6-[3-cyano-5-fluoro-6-methyl-1-(tetrahydro-2H-pyran-4-yl)-1H-indol-2-yl]-N-[(2R)-1,1,1-trifluoropropan-2-yl]pyridine-3-sulfonamide, |
| 810 | 6-[3-cyano-1-cyclobutyl-6-(difluoromethoxy)-5-fluoro-4-methyl-1H-indol-2-yl]-N-[(2S)-1,1,1-trifluoropropan-2-yl]pyridine-3-sulfonamide, |
| 820 | 6-[3-cyano-6-cyclopropyl-5-fluoro-1-(pyrimidin-2-yl)-1H-indol-2-yl]-N-[(2S)-1,1,1-trifluoropropan-2-yl]pyridine-3-sulfonamide, |
| 821 | 6-(3-cyano-1-cyclopentyl-5-fluoro-6-methyl-1H-indol-2-yl)-N-[(2S)-1,1,1-trifluorobutan-2-yl]pyridine-3-sulfonamide, |
| 849 | 6-ethyl-5-fluoro-1-(pyrimidin-2-yl)-2-(5-{[(2S)-1,1,1-trifluoropropan-2-yl]sulfamoyl}pyridin-2-yl)-1H-indole-3-carboxamide, |
| 937 | 6-[3-cyano-6-(difluoromethoxy)-5-fluoro-1-(2-methylpropyl)-1H-indol-2-yl]-N-[(2S)-1,1,1-trifluoropropan-2-yl]pyridine-3-sulfonamide, |
| 960 | 6-[3-cyano-5-fluoro-6-methyl-1-(1,3-thiazol-4-yl)-1H-indol-2-yl]-N-[(2S)-1,1,1-trifluoropropan-2-yl]pyridine-3-sulfonamide, |
| 977 | 6-[3-cyano-5-fluoro-6-methyl-1-(1,3,4-thiadiazol-2-yl)-1H-indol-2-yl]-N-[(2S)-1,1,1-trifluoropropan-2-yl]pyridine-3-sulfonamide, |
| 1037 | 2-{6-[(tert-butylsulfonyl)amino]pyridin-3-yl}-1-cyclohexyl-6-ethyl-5-fluoro-1H-indole-3-carboxamide, |
| 1064 | 2-{6-[(tert-butylsulfonyl)amino]pyridin-3-yl}-1-cyclohexyl-6-(difluoromethoxy)-5-fluoro-1H-indole-3-carboxylic acid, |
| 1065 | N-{5-[3-cyano-1-cyclohexyl-6-(difluoromethoxy)-5-fluoro-1H-indol-2-yl]pyridin-2-yl}-2-methylpropane-2-sulfonamide, |
| 1085 | 2-{6-[(tert-butylsulfonyl)amino]pyridin-3-yl}-1-[(1R)-1-cyclopropylethyl]-6-(difluoromethoxy)-5-fluoro-1H-indole-3-carboxamide, |

-continued

| Cpd | Name |
|---|---|
| 1088 | 2-{6-[(tert-butylsulfonyl)amino]pyridin-3-yl}-1-cyclohexyl-6-cyclopropyl-4-fluoro-1H-indole-3-carboxamide, |
| 1092 | N-[6-(3-cyano-1-cyclohexyl-6-cyclopropyl-4-fluoro-1H-indol-2-yl)pyridin-3-yl]-2-methylpropane-2-sulfonamide, |
| 1100 | 2-{6-[(tert-butylsulfonyl)amino]pyridin-3-yl}-6-cyclopropyl-5-fluoro-1-phenyl-1H-indole-3-carboxamide, |
| 1110 | 2-{5-[(tert-butylsulfonyl)amino]pyridin-2-yl}-1-cyclobutyl-6-ethyl-4-fluoro-1H-indole-3-carboxamide or |
| 1111 | 2-{6-[(tert-butylsulfonyl)amino]pyridin-3-yl}-6-ethyl-4-fluoro-1-phenyl-1H-indole-3-carboxamide. |

In another embodiment, the HCV inhibitor or an enantiomer, stereoisomer, diastereomer, racemic, tautomeric, ester, prodrug, solvate, hydrate, isotopologue or salt form thereof is selected from:

| Cpd | Name |
|---|---|
| 300 | 6-[3-cyano-1-cyclobutyl-6-(difluoromethoxy)-1H-indol-2-yl]-N-[(2S)-1,1,1-trifluoropropan-2-yl]pyridine-3-sulfonamide, |
| 387 | 6-[3-cyano-6-(difluoromethoxy)-1-(pyridin-2-yl)-1H-indol-2-yl]-N-[(2S)-1,1,1-trifluoropropan-2-yl]pyridine-3-sulfonamide, |
| 409 | 6-(3-cyano-1-cyclopentyl-5-fluoro-6-methyl-1H-indol-2-yl)-N-[(2R)-1,1,1-trifluoropropan-2-yl]pyridine-3-sulfonamide, |
| 512 | 6-[3-cyano-6-(difluoromethoxy)-1-(pyrimidin-2-yl)-1H-indol-2-yl]-N-[(2S)-1,1,1-trifluoropropan-2-yl]pyridine-3-sulfonamide, |
| 541 | 6-[3-cyano-5-fluoro-6-methyl-1-(pyridin-2-yl)-1H-indol-2-yl]-N-[(2S)-1,1,1-trifluoropropan-2-yl]pyridine-3-sulfonamide, |
| 549 | 6-[3-cyano-1-cyclobutyl-6-(difluoromethoxy)-5-fluoro-1H-indol-2-yl]-N-[(2S)-1,1,1-trifluoropropan-2-yl]pyridine-3-sulfonamide, |
| 601 | 6-[3-cyano-5-fluoro-1-(pyrimidin-2-yl)-1H-indol-2-yl]-N-[(2S)-1,1,1-trifluoropropan-2-yl]pyridine-3-sulfonamide, |
| 634 | 6-[3-cyano-5-fluoro-6-methyl-1-(pyrimidin-2-yl)-1H-indol-2-yl]-N-[(2S)-1,1,1-trifluoropropan-2-yl]pyridine-3-sulfonamide, |
| 650 | 6-[3-cyano-6-cyclopropyl-1-(pyrimidin-2-yl)-1H-indol-2-yl]-N-[(2S)-1,1,1-trifluoropropan-2-yl]pyridine-3-sulfonamide, |
| 682 | 6-[3-cyano-6-(difluoromethoxy)-5-fluoro-1-(pyrimidin-2-yl)-1H-indol-2-yl]-N-[(2S)-1,1,1-trifluoropropan-2-yl]pyridine-3-sulfonamide, |
| 704 | 6-[3-cyano-6-ethyl-5-fluoro-1-(pyrimidin-2-yl)-1H-indol-2-yl]-N-[(2S)-1,1,1-trifluoropropan-2-yl]pyridine-3-sulfonamide, |
| 820 | 6-[3-cyano-6-cyclopropyl-5-fluoro-1-(pyrimidin-2-yl)-1H-indol-2-yl]-N-[(2S)-1,1,1-trifluoropropan-2-yl]pyridine-3-sulfonamide, |
| 849 | 6-ethyl-5-fluoro-1-(pyrimidin-2-yl)-2-(5-{[(2S)-1,1,1-trifluoropropan-2-yl]sulfamoyl}pyridin-2-yl)-1H-indole-3-carboxamide, |
| 960 | 6-[3-cyano-5-fluoro-6-methyl-1-(1,3-thiazol-4-yl)-1H-indol-2-yl]-N-[(2S)-1,1,1-trifluoropropan-2-yl]pyridine-3-sulfonamide, |
| 1037 | 2-{6-[(tert-butylsulfonyl)amino]pyridin-3-yl}-1-cyclohexyl-6-ethyl-5-fluoro-1H-indole-3-carboxamide, |
| 1064 | 2-{6-[(tert-butylsulfonyl)amino]pyridin-3-yl}-1-cyclohexyl-6-(difluoromethoxy)-5-fluoro-1H-indole-3-carboxylic acid, |
| 1065 | N-{5-[3-cyano-1-cyclohexyl-6-(difluoromethoxy)-5-fluoro-1H-indol-2-yl]pyridin-2-yl}-2-methylpropane-2-sulfonamide, |
| 1088 | 2-{6-[(tert-butylsulfonyl)amino]pyridin-3-yl}-1-cyclohexyl-6-cyclopropyl-4-fluoro-1H-indole-3-carboxamide or |
| 1100 | 2-{6-[(tert-butylsulfonyl)amino]pyridin-3-yl}-6-cyclopropyl-5-fluoro-1-phenyl-1H-indole-3-carboxamide. |

An embodiment of the present invention includes a HCV protease inhibitor or an enantiomer, stereoisomer, diastereomer, racemic, tautomeric, ester, prodrug, solvate, hydrate, isotopologue or salt form thereof selected from:

Cpd 1p
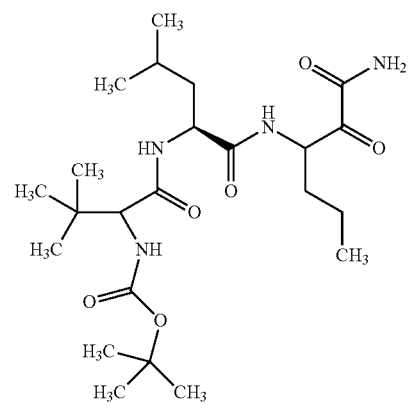
Cpd 2p
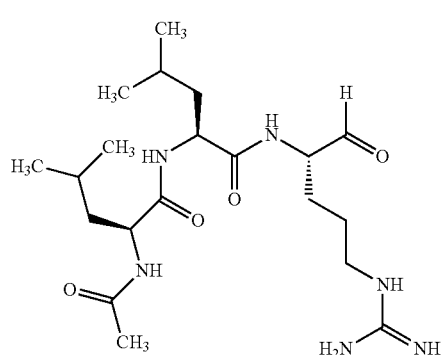
Cpd 3p
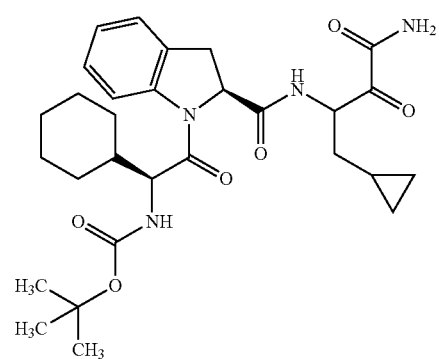
Cpd 4p
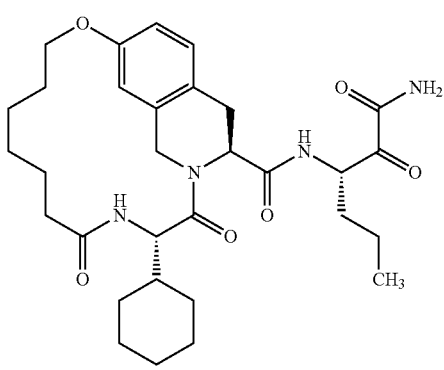
-continued
Cpd 5p
Cpd 6p
Cpd 7p
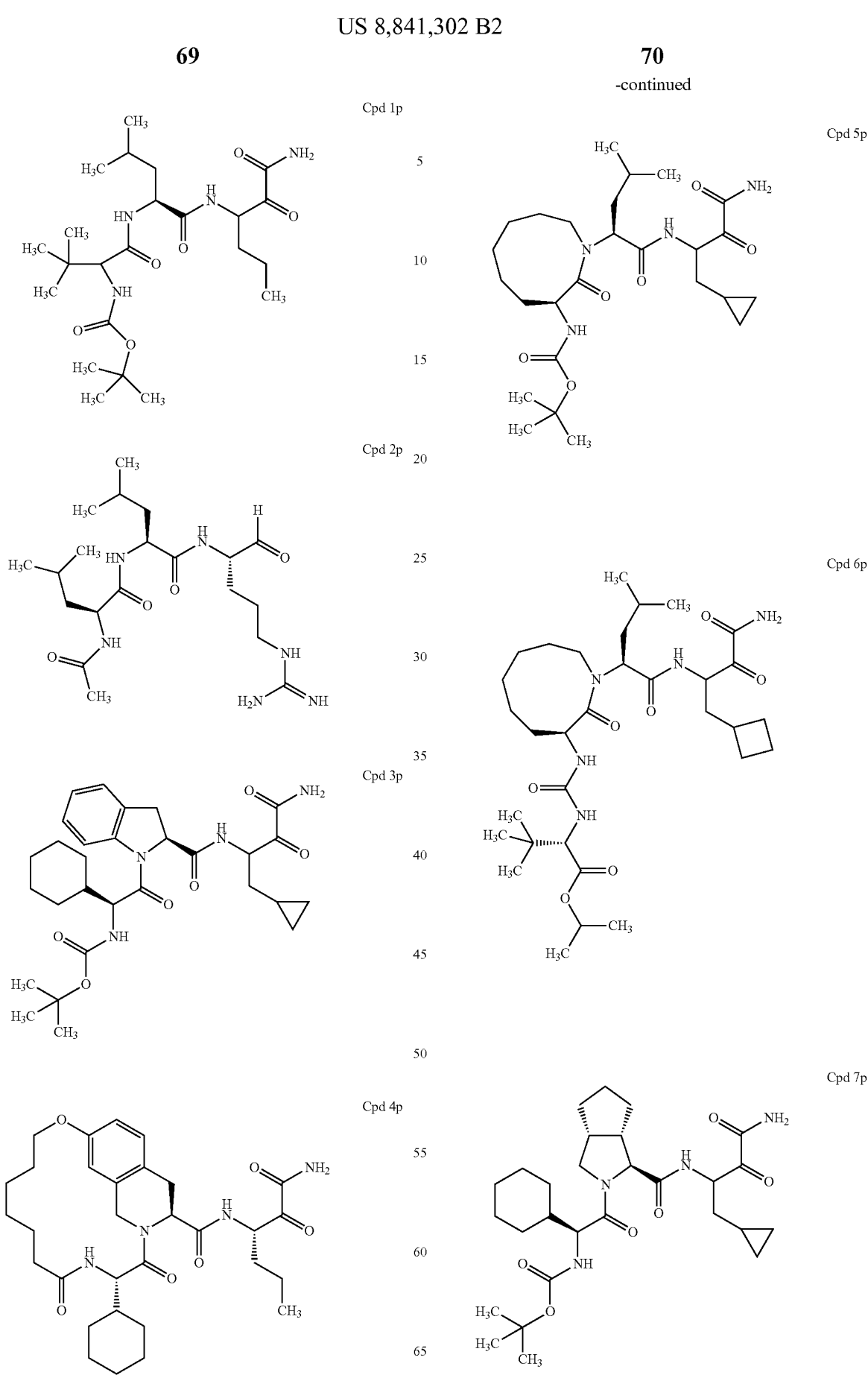

-continued
Cpd 8p
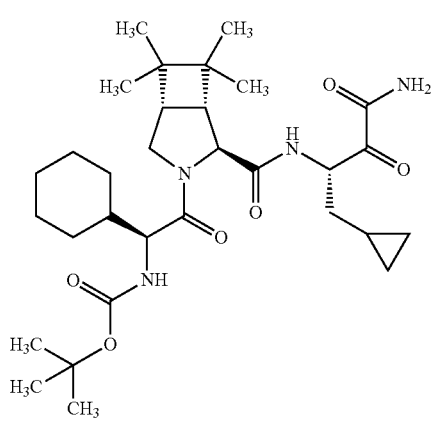
Cpd 9p
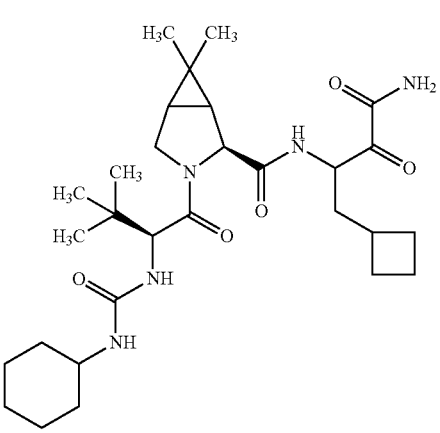
Cpd 10p
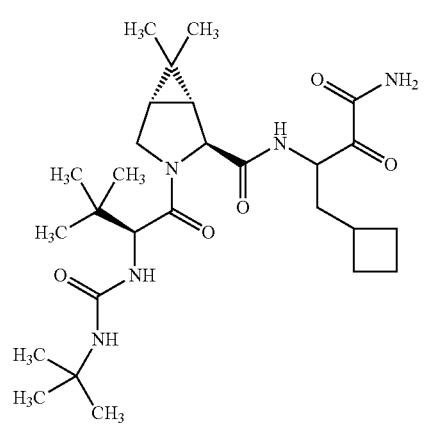
Cpd 11p
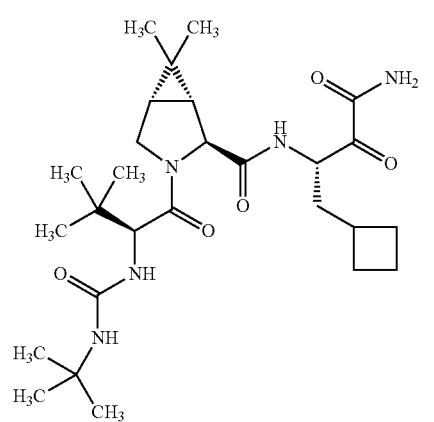
-continued
Cpd 12p
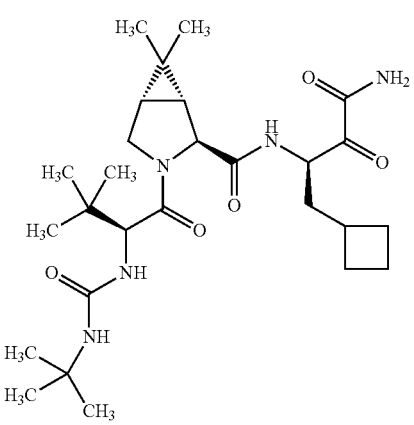
Cpd 13p
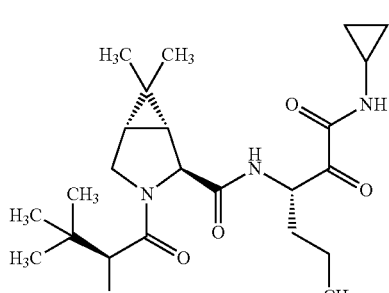
Cpd 14p
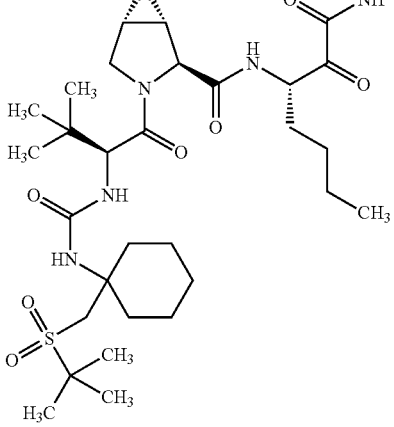

Cpd 15p
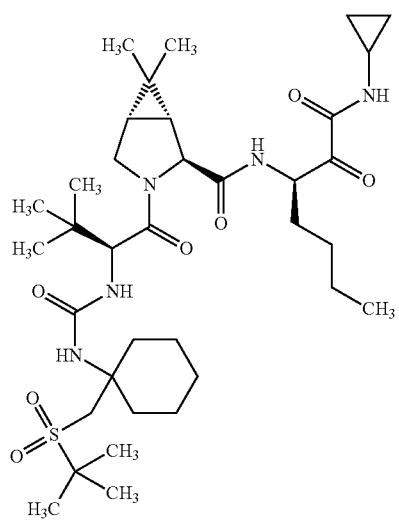
Cpd 16p
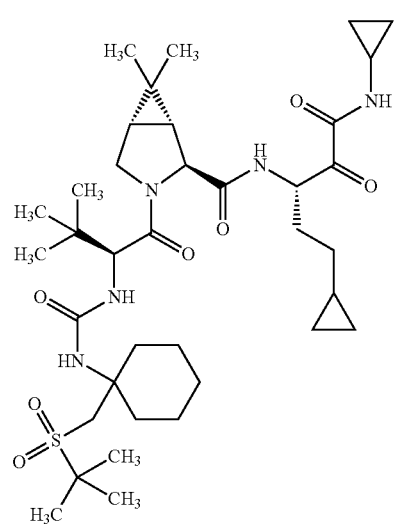
Cpd 17p
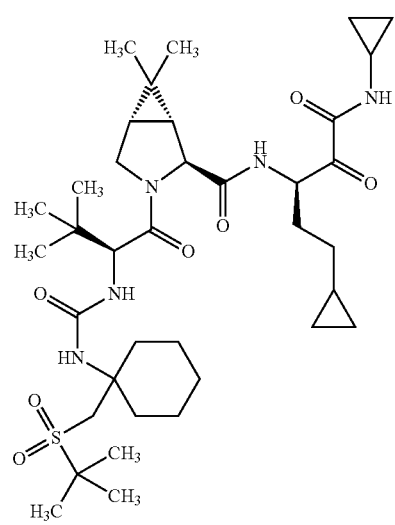
Cpd 18p
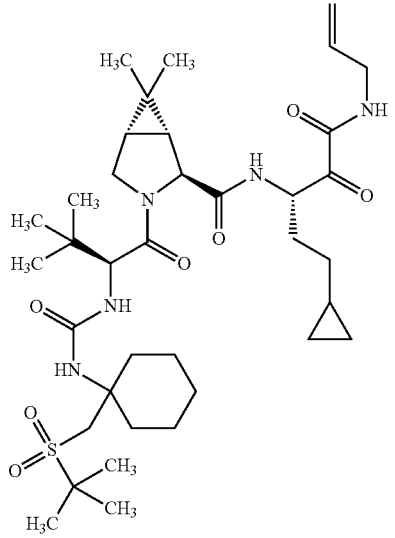
Cpd 19p
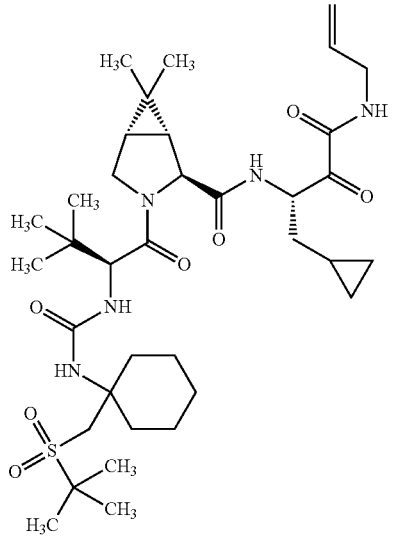
Cpd 20p
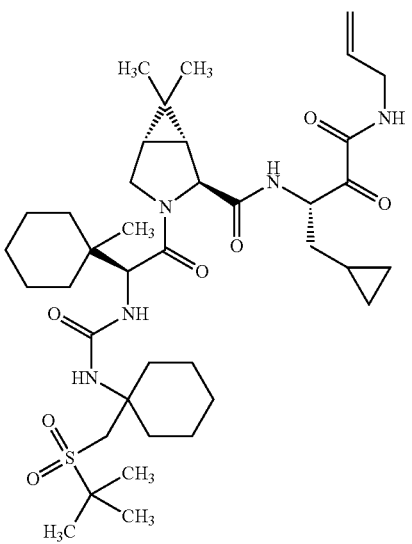

Cpd 21p
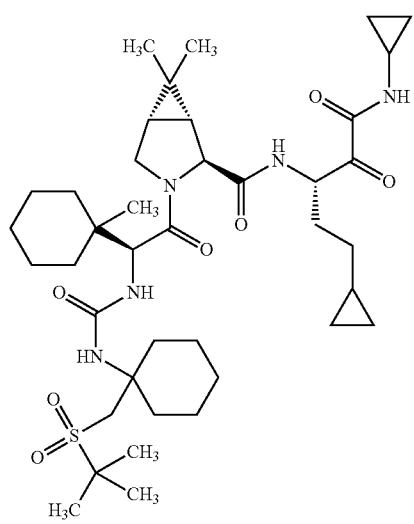
Cpd 22p
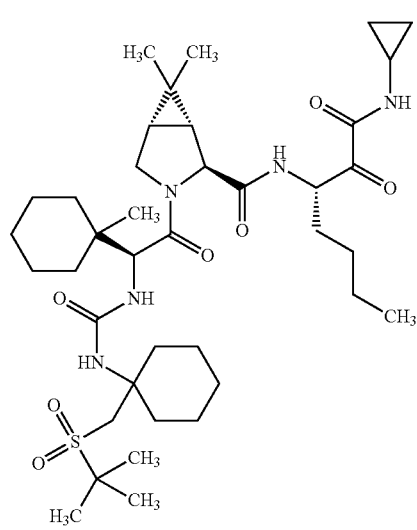
Cpd 23p
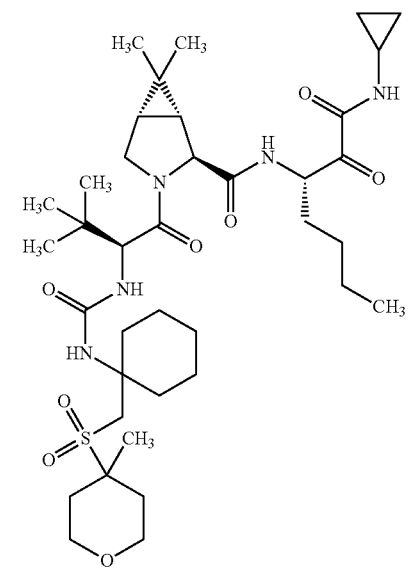
Cpd 24p
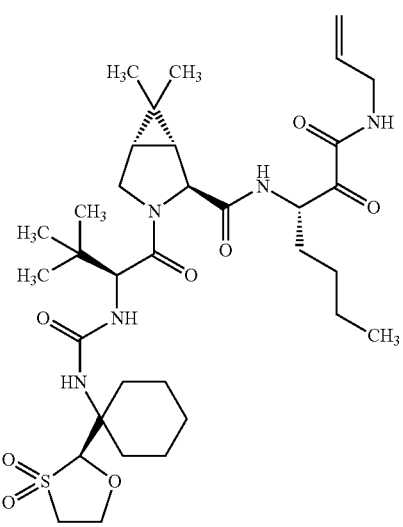
Cpd 25p
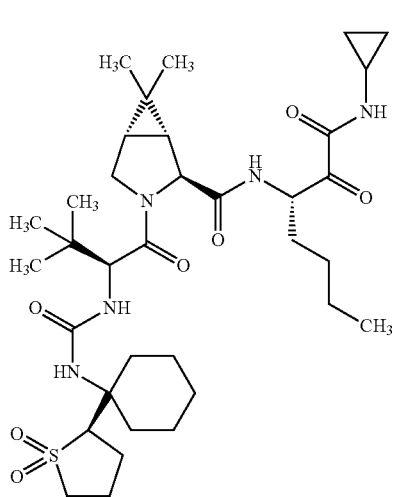
Cpd 26p
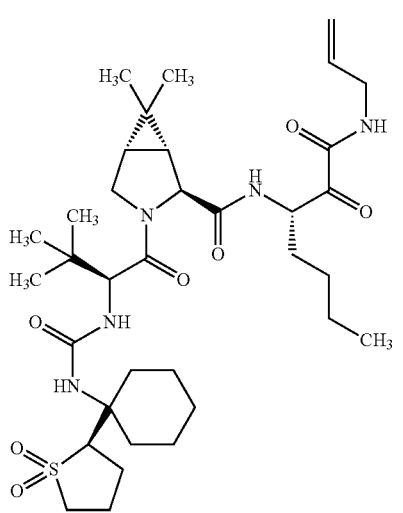

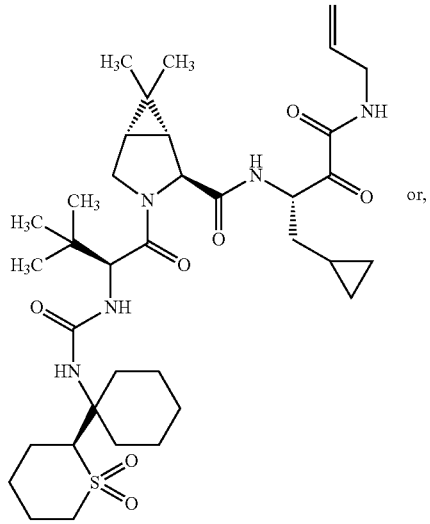

Cpd 27p

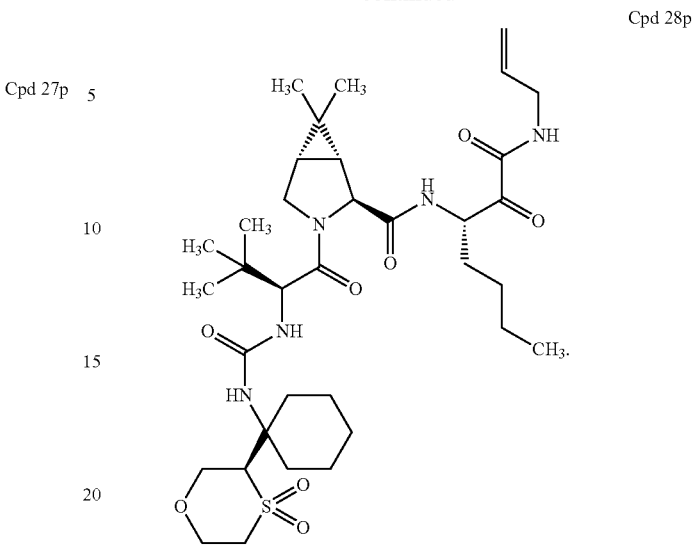

Cpd 28p

In another embodiment, the HCV protease inhibitor or an enantiomer, stereoisomer, diastereomer, racemic, tautomeric, ester, prodrug, solvate, hydrate, isotopologue or salt form thereof is selected from:

| Cpd | Name |
|---|---|
| 1p | tert-butyl 1-((2S)-1-(1-amino-1,2-dioxohexan-3-ylamino)-4-methyl-1-oxopentan-2-ylamino)-3,3-dimethyl-1-oxobutan-2-ylcarbamate, |
| 2p | (S)-2-acetamido-N-((S)-1-((S)-5-guanidino-1-oxopentan-2-ylamino)-4-methyl-1-oxopentan-2-yl)-4-methylpentanamide, |
| 3p | tert-butyl(1S)-2-((2S)-2-(4-amino-1-cyclopropyl-3,4-dioxobutan-2-ylcarbamoyl)indolin-1-yl)-1-cyclohexyl-2-oxoethylcarbamate, |
| 4p | (3S,18S)-N-[(3S)-1-amino-1,2-dioxohexan-3-yl]-18-cyclohexyl-16,19-dioxo-3,4-dihydro-1H-7,2-(epoxyheptanoiminoethano)isoquinoline-3-carboxamide, |
| 5p | tert-butyl(3S)-1-((2S)-1-(4-amino-1-cyclopropyl-3,4-dioxobutan-2-ylamino)-4-methyl-1-oxopentan-2-yl)-2-oxoazonan-3-ylcarbamate, |
| 6p | (2S)-isopropyl 2-(3-((3S)-1-((2S)-1-(4-amino-1-cyclobutyl-3,4-dioxobutan-2-ylamino)-4-methyl-1-oxopentan-2-yl)-2-oxoazonan-3-yl)ureido)-3,3-dimethylbutanoate, |
| 7p | tert-butyl(1S)-2-((1S,3aR,6aS)-1-(4-amino-1-cyclopropyl-3,4-dioxobutan-2-ylcarbamoyl)hexahydrocyclopenta[c]pyrrol-2(1H)-yl)-1-cyclohexyl-2-oxoethylcarbamate, |
| 8p | tert-butyl(S)-2-((1R,2S,5S)-2-((S)-4-amino-1-cyclopropyl-3,4-dioxobutan-2-ylcarbamoyl)-6,6,7,7-tetramethyl-3-azabicyclo[3.2.0]heptan-3-yl)-1-cyclohexyl-2-oxoethylcarbamate, |
| 9p | (2S)-N-(4-amino-1-cyclobutyl-3,4-dioxobutan-2-yl)-3-((S)-2-(3-cyclohexylureido)-3,3-dimethylbutanoyl)-6,6-dimethyl-3-azabicyclo[3.1.0]hexane-2-carboxamide, |
| 10p | (1R,2S,5S)-N-(4-amino-1-cyclobutyl-3,4-dioxobutan-2-yl)-3-((S)-2-(3-tert-butylureido)-3,3-dimethylbutanoyl)-6,6-dimethyl-3-azabicyclo[3.1.0]hexane-2-carboxamide, |
| 11p | (1R,2S,5S)-N-((S)-4-amino-1-cyclobutyl-3,4-dioxobutan-2-yl)-3-((S)-2-(3-tert-butylureido)-3,3-dimethylbutanoyl)-6,6-dimethyl-3-azabicyclo[3.1.0]hexane-2-carboxamide, |
| 12p | (1R,2S,5S)-N-((R)-4-amino-1-cyclobutyl-3,4-dioxobutan-2-yl)-3-((S)-2-(3-tert-butylureido)-3,3-dimethylbutanoyl)-6,6-dimethyl-3-azabicyclo[3.1.0]hexane-2-carboxamide, |
| 13p | (1R,2S,5S)-3-((S)-2-(3-(1-(tert-butylsulfonylmethyl)cyclohexyl)ureido)-3,3-dimethylbutanoyl)-N-((S)-1-(cyclopropylamino)-1,2-dioxohexan-3-yl)-6,6-dimethyl-3-azabicyclo[3.1.0]hexane-2-carboxamide, |
| 14p | (1R,2S,5S)-3-((S)-2-(3-(1-(tert-butylsulfonylmethyl)cyclohexyl)ureido)-3,3-dimethylbutanoyl)-N-((S)-1-(cyclopropylamino)-1,2-dioxoheptan-3-yl)-6,6-dimethyl-3-azabicyclo[3.1.0]hexane-2-carboxamide, |
| 15p | (1R,2S,5S)-3-((S)-2-(3-(1-(tert-butylsulfonylmethyl)cyclohexyl)ureido)-3,3-dimethylbutanoyl)-N-((R)-1-(cyclopropylamino)-1,2-dioxoheptan-3-yl)-6,6-dimethyl-3-azabicyclo[3.1.0]hexane-2-carboxamide, |
| 16p | (1R,2S,5S)-3-((S)-2-(3-(1-(tert-butylsulfonylmethyl)cyclohexyl)ureido)-3,3-dimethylbutanoyl)-N-((S)-5-cyclopropyl-1-(cyclopropylamino)-1,2-dioxopentan-3-yl)-6,6-dimethyl-3-azabicyclo[3.1.0]hexane-2-carboxamide, |

| Cpd | Name |
|---|---|
| 17p | (1R,2S,5S)-3-((S)-2-(3-(1-(tert-butylsulfonylmethyl)cyclohexyl)ureido)-3,3-dimethylbutanoyl)-N-((R)-5-cyclopropyl-1-(cyclopropylamino)-1,2-dioxopentan-3-yl)-6,6-dimethyl-3-azabicyclo[3.1.0]hexane-2-carboxamide, |
| 18p | (1R,2S,5S)-N-((S)-1-(allylamino)-5-cyclopropyl-1,2-dioxopentan-3-yl)-3-((S)-2-(3-(1-(tert-butylsulfonylmethyl)cyclohexyl)ureido)-3,3-dimethylbutanoyl)-6,6-dimethyl-3-azabicyclo[3.1.0]hexane-2-carboxamide, |
| 19p | (1R,2S,5S)-N-((S)-4-(allylamino)-1-cyclopropyl-3,4-dioxobutan-2-yl)-3-((S)-2-(3-(1-(tert-butylsulfonylmethyl)cyclohexyl)ureido)-3,3-dimethylbutanoyl)-6,6-dimethyl-3-azabicyclo[3.1.0]hexane-2-carboxamide, |
| 20p | (1R,2S,5S)-N-((S)-4-(allylamino)-1-cyclopropyl-3,4-dioxobutan-2-yl)-3-((S)-2-(3-(1-(tert-butylsulfonylmethyl)cyclohexyl)ureido)-2-(1-methylcyclohexyl)acetyl)-6,6-dimethyl-3-azabicyclo[3.1.0]hexane-2-carboxamide, |
| 21p | (1R,2S,5S)-3-((S)-2-(3-(1-(tert-butylsulfonylmethyl)cyclohexyl)ureido)-2-(1-methylcyclohexyl)acetyl)-N-((S)-5-cyclopropyl-1-(cyclopropylamino)-1,2-dioxopentan-3-yl)-6,6-dimethyl-3-azabicyclo[3.1.0]hexane-2-carboxamide, |
| 22p | (1R,2S,5S)-3-((S)-2-(3-(1-(tert-butylsulfonylmethyl)cyclohexyl)ureido)-2-(1-methylcyclohexyl)acetyl)-N-((S)-1-(cyclopropylamino)-1,2-dioxoheptan-3-yl)-6,6-dimethyl-3-azabicyclo[3.1.0]hexane-2-carboxamide, |
| 23p | (1R,2S,5S)-N-((S)-1-(cyclopropylamino)-1,2-dioxoheptan-3-yl)-3-((S)-3,3-dimethyl-2-(3-(1-((4-methyltetrahydro-2H-pyran-4-yl)sulfonyl)methyl)cyclohexyl)ureido)butanoyl)-6,6-dimethyl-3-azabicyclo[3.1.0]hexane-2-carboxamide, |
| 24p | (1R,2S,5S)-3-[N-({1-[(2S)-3,3-dioxido-1,3-oxathiolan-2-yl]cyclohexyl}carbamoyl)-3-methyl-L-valyl]-N-[(3S)-1,2-dioxo-1-(prop-2-en-1-ylamino)heptan-3-yl]-6,6-dimethyl-3-azabicyclo[3.1.0]hexane-2-carboxamide, |
| 25p | (1R,2S,5S)-N-[(3S)-1-(cyclopropylamino)-1,2-dioxoheptan-3-yl]-3-[N-({1-[(2R)-1,1-dioxidotetrahydrothiophen-2-yl]cyclohexyl}carbamoyl)-3-methyl-L-valyl]-6,6-dimethyl-3-azabicyclo[3.1.0]hexane-2-carboxamide, |
| 26p | (1R,2S,5S)-3-[N-({1-[(2R)-1,1-dioxidotetrahydrothiophen-2-yl]cyclohexyl}carbamoyl)-3-methyl-L-valyl]-N-[(3S)-1,2-dioxo-1-(prop-2-en-1-ylamino)heptan-3-yl]-6,6-dimethyl-3-azabicyclo[3.1.0]hexane-2-carboxamide, |
| 27p | (1R,2S,5S)-N-[(2S)-1-cyclopropyl-3,4-dioxo-4-(prop-2-en-1-ylamino)butan-2-yl]-3-[N-({1-[(2S)-1,1-dioxidotetrahydro-2H-thiopyran-2-yl]cyclohexyl}carbamoyl)-3-methyl-L-valyl]-6,6-dimethyl-3-azabicyclo[3.1.0]hexane-2-carboxamide, or |
| 28p | (1R,2S,5S)-3-[N-({1-[(3R)-4,4-dioxido-1,4-oxathian-3-yl]cyclohexyl}carbamoyl)-3-methyl-L-valyl]-N-[(3S)-1,2-dioxo-1-(prop-2-en-1-ylamino)heptan-3-yl]-6,6-dimethyl-3-azabicyclo[3.1.0]hexane-2-carboxamide. |

In another embodiment, the HCV protease inhibitor or an enantiomer, stereoisomer, diastereomer, racemic, tautomeric, ester, prodrug, solvate, hydrate, isotopologue or salt form thereof is selected from:

Chemical Definitions

Compound names used herein were obtained using ACD Labs Index Name software Version 10.0, provided by ACD Labs; and/or, the Autonom function of ChemDraw Ultra

| Cpd | Name |
|---|---|
| 10p | (1R,2S,5S)-N-(4-amino-1-cyclobutyl-3,4-dioxobutan-2-yl)-3-((S)-2-(3-tert-butylureido)-3,3-dimethylbutanoyl)-6,6-dimethyl-3-azabicyclo[3.1.0]hexane-2-carboxamide, |
| 11p | (1R,2S,5S)-N-((S)-4-amino-1-cyclobutyl-3,4-dioxobutan-2-yl)-3-((S)-2-(3-tert-butylureido)-3,3-dimethylbutanoyl)-6,6-dimethyl-3-azabicyclo[3.1.0]hexane-2-carboxamide, |
| 12p | (1R,2S,5S)-N-((R)-4-amino-1-cyclobutyl-3,4-dioxobutan-2-yl)-3-((S)-2-(3-tert-butylureido)-3,3-dimethylbutanoyl)-6,6-dimethyl-3-azabicyclo[3.1.0]hexane-2-carboxamide, |
| 13p | (1R,2S,5S)-3-((S)-2-(3-(1-(tert-butylsulfonylmethyl)cyclohexyl)ureido)-3,3-dimethylbutanoyl)-N-((S)-1-(cyclopropylamino)-1,2-dioxohexan-3-yl)-6,6-dimethyl-3-azabicyclo[3.1.0]hexane-2-carboxamide, |
| 14p | (1R,2S,5S)-3-((S)-2-(3-(1-(tert-butylsulfonylmethyl)cyclohexyl)ureido)-3,3-dimethylbutanoyl)-N-((S)-1-(cyclopropylamino)-1,2-dioxoheptan-3-yl)-6,6-dimethyl-3-azabicyclo[3.1.0]hexane-2-carboxamide, |
| 16p | (1R,2S,5S)-3-((S)-2-(3-(1-(tert-butylsulfonylmethyl)cyclohexyl)ureido)-3,3-dimethylbutanoyl)-N-((S)-5-cyclopropyl-1-(cyclopropylamino)-1,2-dioxopentan-3-yl)-6,6-dimethyl-3-azabicyclo[3.1.0]hexane-2-carboxamide, |
| 21p | (1R,2S,5S)-3-((S)-2-(3-(1-(tert-butylsulfonylmethyl)cyclohexyl)ureido)-2-(1-methylcyclohexyl)acetyl)-N-((S)-5-cyclopropyl-1-(cyclopropylamino)-1,2-dioxopentan-3-yl)-6,6-dimethyl-3-azabicyclo[3.1.0]hexane-2-carboxamide, or |
| 28p | (1R,2S,5S)-3-[N-({1-[(3R)-4,4-dioxido-1,4-oxathian-3-yl]cyclohexyl}carbamoyl)-3-methyl-L-valyl]-N-[(3S)-1,2-dioxo-1-(prop-2-en-1-ylamino)heptan-3-yl]-6,6-dimethyl-3-azabicyclo[3.1.0]hexane-2-carboxamide. |

10.0.4, provided by CambridgeSoft. When the compound name disclosed herein conflicts with the structure depicted, the structure shown will supercede the use of the name to define the compound intended.

The chemical terms used above and throughout the description of the invention, unless specifically defined otherwise, shall be understood by one of ordinary skill in the art to have the following indicated meanings.

As used herein, the term "$C_{1-8}$alkyl" generally refers to saturated hydrocarbon radicals having from one to eight carbon atoms in a straight or branched chain configuration, including methyl, ethyl, n-propyl, isopropyl, n-butyl, isobutyl, sec-butyl, tert-butyl, n-pentyl, n-hexyl, n-heptyl, n-octyl and the like. In some embodiments, $C_{1-8}$alkyl includes $C_{1-8}$alkyl, $C_{1-4}$alkyl and the like. A $C_{1-8}$alkyl radical may be optionally substituted where allowed by available valences.

As used herein, the term "$C_{2-8}$alkenyl" generally refers to partially unsaturated hydrocarbon radicals having from two to eight carbon atoms in a straight or branched chain configuration and one or more carbon-carbon double bonds therein, including ethenyl, allyl, propenyl and the like. In some embodiments, $C_{2-8}$alkenyl includes $C_{2-6}$alkenyl, $C_{2-4}$alkenyl and the like. A $C_{2-8}$alkenyl radical may be optionally substituted where allowed by available valences.

As used herein, the term "$C_{1-8}$alkoxy" generally refers to saturated hydrocarbon radicals having from one to eight carbon atoms in a straight or branched chain configuration of the formula: —O—$C_{1-8}$alkyl, including methoxy, ethoxy, n-propoxy, isopropoxy, n-butoxy, isobutoxy, sec-butoxy, tert-butoxy, n-pentoxy, n-hexoxy and the like. In some embodiments, $C_{1-8}$alkoxy includes $C_{1-6}$alkoxy, $C_{1-4}$alkoxy and the like. A $C_{1-8}$alkoxy radical may be optionally substituted where allowed by available valences.

As used herein, the term "$C_{3-14}$cycloalkyl" generally refers to a saturated monocyclic, bicyclic or polycyclic hydrocarbon radical, including cyclopropyl, cyclobutyl, cyclopentyl, cyclohexyl, cycloheptyl, cyclooctyl, 1H-indanyl, indenyl, tetrahydro-naphthalenyl and the like. In some embodiments, $C_{3-14}$cycloalkyl includes $C_{3-8}$cycloalkyl, $C_{5-8}$cycloalkyl, $C_{3-10}$cycloalkyl and the like. A $C_{3-14}$cycloalkyl radical may be optionally substituted where allowed by available valences.

As used herein, the term "$C_{3-14}$cycloalkenyl" generally refers to a partially unsaturated monocyclic, bicyclic or polycyclic hydrocarbon radical having one or more chemically stable carbon-carbon double bonds therein, including cyclopropenyl, cyclobutenyl, cyclopentenyl, cyclohexenyl, cycloheptenyl, cyclooctenyl and the like. In some embodiments, $C_{3-14}$cycloalkenyl includes $C_{3-8}$cycloalkenyl, $C_{5-8}$cycloalkenyl, $C_{3-10}$cycloalkenyl and the like. A $C_{3-14}$cycloalkenyl radical may be optionally substituted where allowed by available valences.

As used herein, the term "aryl" generally refers to a monocyclic, bicyclic or polycyclic aromatic carbon atom ring structure radical, including phenyl, naphthyl, anthracenyl, fluorenyl, azulenyl, phenanthrenyl and the like. An aryl radical may be optionally substituted where allowed by available valences.

As used herein, the term "heteroaryl" generally refers to a monocyclic, bicyclic or polycyclic aromatic carbon atom ring structure radical in which one or more carbon atom ring members have been replaced, where allowed by structural stability, with one or more heteroatoms, such as an O, S or N atom, including furanyl, thienyl (or thiophenyl), 2H-pyrrolyl, 3H-pyrrolyl, pyrazolyl, imidazolyl, isoxazolyl, isothiazolyl, oxazolyl, thiazolyl, triazolyl, oxadiazolyl, thiadiazolyl, tetrazolyl, pyranyl, thiopyranyl, pyridinyl, pyrimidinyl, pyrazinyl, pyridazinyl, triazinyl, indole, indazolyl, isoindolyl, benzofuranyl, benzothienyl, benzimidazolyl, benzoxazolyl, purinyl, quinolinyl, isoquinolinyl, quinazolinyl, quinoxalinyl, 1,3-diazinyl, 1,2-diazinyl, 1,2-diazolyl, 1,4-diazanaphthalenyl, acridinyl and the like. A heteroaryl radical may be optionally substituted on a carbon or nitrogen atom ring member where allowed by available valences.

As used herein, the term "heterocyclyl" generally refers to a saturated or partially unsaturated monocyclic, bicyclic or polycyclic carbon atom ring structure radical in which one or more carbon atom ring members have been replaced, where allowed by structural stability, with a heteroatom, such as an O, S or N atom, including oxiranyl, oxetanyl, azetidinyl, dihydrofuranyl, tetrahydrofuranyl, dihydrothienyl, tetrahydrothienyl, pyrrolinyl, pyrrolidinyl, dihydropyrazolyl, pyrazolinyl, pyrazolidinyl, dihydroimidazolyl, imidazolinyl, imidazolidinyl, isoxazolinyl, isoxazolidinyl, isothiazolinyl, isothiazolidinyl, oxazolinyl, oxazolidinyl, thiazolinyl, thiazolidinyl, triazolinyl, triazolidinyl, oxadiazolinyl, oxadiazolidinyl, thiadiazolinyl, thiadiazolidinyl, tetrazolinyl, tetrazolidinyl, dihydro-2H-pyranyl, tetrahydro-2H-pyranyl, tetrahydro-thiopyranyl, dihydro-pyridinyl, tetrahydro-pyridinyl, hexahydro-pyridinyl, dihydro-pyrimidinyl, tetrahydro-pyrimidinyl, dihydro-pyrazinyl, tetrahydro-pyrazinyl, dihydro-pyridazinyl, tetrahydro-pyridazinyl, piperazinyl, piperidinyl, morpholinyl, thiomorpholinyl, dihydro-triazinyl, tetrahydro-triazinyl, hexahydro-triazinyl, dihydro-indole, tetrahydro-indole, dihydro-indazolyl, tetrahydro-indazolyl, dihydro-isoindolyl, tetrahydro-isoindolyl, dihydro-benzofuranyl, tetrahydro-benzofuranyl, dihydro-benzothienyl, tetrahydro-benzothienyl, dihydro-benzimidazolyl, tetrahydro-benzimidazolyl, dihydro-benzoxazolyl, tetrahydro-benzoxazolyl, benzo[1,3]dioxolyl, benzo[1,4]dioxanyl, dihydro-purinyl, tetrahydro-purinyl, dihydro-quinolinyl, tetrahydro-quinolinyl, dihydro-isoquinolinyl, tetrahydro-isoquinolinyl, dihydro-quinazolinyl, tetrahydro-quinazolinyl, dihydro-quinoxalinyl, tetrahydro-quinoxalinyl and the like. A heterocyclyl radical may be optionally substituted on a carbon or nitrogen atom ring member where allowed by available valences.

As used herein, the term "$C_{2-8}$alkenyl-$C_{1-8}$alkyl" refers to a radical of the formula: —$C_{1-8}$alkyl-$C_{2-8}$alkenyl.

As used herein, the term "$C_{1-8}$alkoxy-$C_{1-8}$alkyl" refers to a radical of the formula: —$C_{1-8}$alkyl-O—$C_{1-8}$alkyl.

As used herein, the term "$C_{1-8}$alkoxy-$C_{1-8}$alkyl-amino-$C_{1-8}$ alkoxy" refers to a radical of the formula: —O—$C_{1-8}$alkyl-NH—$C_{1-8}$alkyl-O—$C_{1-8}$alkyl or —O—$C_{1-8}$alkyl-N($C_{1-8}$ alkyl-O—$C_{1-8}$alkyl)$_2$.

As used herein, the term "$C_{1-8}$alkoxy-carbonyl" refers to a radical of the formula: —C(O)—O—$C_{1-8}$alkyl.

As used herein, the term "$C_{1-8}$alkoxy-carbonyl-$C_{1-8}$alkyl" refers to a radical of the formula: —$C_{1-8}$alkyl-C(O)—O—$C_{1-8}$ alkyl.

As used herein, the term "$C_{1-8}$alkoxy-carbonyl-amino" refers to a radical of the formula: —NH—C(O)—O—$C_{1-8}$alkyl.

As used herein, the term "$C_{1-8}$alkyl-amino" refers to a radical of the formula: —NH—$C_{1-8}$alkyl or —N($C_{1-8}$alkyl)$_2$.

As used herein, the term "$C_{1-8}$alkyl-amino-$C_{1-8}$alkoxy" refers to a radical of the formula: —O—$C_{1-8}$alkyl-NH—$C_{1-8}$ alkyl or —$C_{1-8}$alkyl-N($C_{1-8}$alkyl)$_2$.

As used herein, the term "$C_{1-8}$alkyl-amino-$C_{1-8}$alkyl" refers to a radical of the formula: —$C_{1-8}$alkyl-NH—$C_{1-8}$alkyl or —$C_{1-8}$alkyl-N($C_{1-8}$alkyl)$_2$.

As used herein, the term "$C_{1-8}$alkyl-amino-$C_{1-8}$alkyl-amino-$C_{1-8}$alkoxy" refers to a radical of the formula:

—O—$C_{1-8}$alkyl-NH—$C_{1-8}$alkyl-NH—$C_{1-8}$alkyl or —O—$C_{1-8}$alkyl-N($C_{1-8}$alkyl-NH—$C_{1-8}$alkyl)$_2$.

As used herein, the term "$C_{1-8}$alkyl-amino-carbonyl" refers to a radical of the formula: —C(O)—NH—$C_{1-8}$alkyl or —C(O)—N($C_{1-8}$alkyl)$_2$.

As used herein, the term "$C_{1-8}$alkyl-amino-carbonyl-amino" refers to a radical of the formula: —NH—C(O)—NH—$C_{1-8}$alkyl or —NH—C(O)—N($C_{1-8}$alkyl)$_2$.

As used herein, the term "$C_{1-8}$alkyl-carbonyl" refers to a radical of the formula: —C(O)—$C_{1-8}$alkyl.

As used herein, the term "$C_{1-8}$alkyl-carbonyloxy" refers to a radical of the formula: —O—C(O)—$C_{1-8}$alkyl.

As used herein, the term "$C_{1-8}$alkyl-carbonyloxy-$C_{1-8}$alkoxy" refers to a radical of the formula: —O—$C_{1-8}$alkyl-O—C(O)—$C_{1-8}$alkyl.

As used herein, the term "$C_{1-8}$alkyl-carbonyloxy-$C_{1-8}$alkyl" refers to a radical of the formula: —$C_{1-8}$alkyl-O—C(O)—$C_{1-8}$alkyl.

As used herein, the term "$C_{1-8}$alkyl-sulfinyl" refers to a radical of the formula: —SO—$C_{1-8}$alkyl.

As used herein, the term "$C_{1-8}$alkyl-sulfonyl" refers to a radical of the formula: —SO$_2$—$C_{1-8}$alkyl.

As used herein, the term "amino-sulfonyl" refers to a radical of the formula: —SO$_2$—NH$_2$.

As used herein, the term "$C_{1-8}$alkyl-sulfonyl-amino" refers to a radical of the formula: —NH—SO$_2$—$C_{1-8}$alkyl.

As used herein, the term "$C_{1-8}$alkylthio" refers to a radical of the formula: —S—$C_{1-8}$alkyl.

As used herein, the term "$C_{2-8}$alkynyl-$C_{1-8}$alkyl" refers to a radical of the formula: —$C_{1-8}$alkyl-$C_{2-8}$alkynyl.

As used herein, the term "amino" refers to a radical of the formula: —NH$_2$.

As used herein, the term "amino-$C_{1-8}$alkoxy" refers to a radical of the formula: —O—$C_{1-8}$alkyl-NH$_2$.

As used herein, the term "amino-$C_{1-8}$alkyl" refers to a radical of the formula: —$C_{1-8}$alkyl-NH$_2$.

As used herein, the term "amino-$C_{1-8}$alkyl-amino-$C_{1-8}$alkoxy" refers to a radical of the formula: —O—$C_{1-8}$alkyl-NH—$C_{1-8}$alkyl-NH$_2$ or —O—$C_{1-8}$alkyl-N($C_{1-8}$alkyl-NH$_2$)$_2$.

As used herein, the term "amino-carbonyl" refers to a radical of the formula: —C(O)—NH$_2$.

As used herein, the term "amino-carbonyl-amino" refers to a radical of the formula: —NH—C(O)—NH$_2$.

As used herein, the term "aryl-$C_{1-8}$alkoxy" refers to a radical of the formula:

As used herein, the term "aryl-$C_{1-8}$alkyl" refers to a radical of the formula:

As used herein, the term "aryl-carbonyl-amino" refers to a radical of the formula: —NH—C(O)-aryl.

As used herein, the term "aryloxy" refers to a radical of the formula: —O-aryl.

As used herein, the term "carboxyl" refers to a radical of the formula: —COON, —C(O)OH or —CO$_2$H.

As used herein, the term "carboxyl-amino" refers to a radical of the formula: —NH—COOH, —NH—C(O)OH or —NH—CO$_2$H.

As used herein, the term "cyano-$C_{1-8}$alkyl" refers to a radical of the formula:

As used herein, the term "1-cyano-ethyl" refers to a radical of the formula: —CH(CN)—CH$_3$.

As used herein, the term "$C_{3-14}$cycloalkyl-$C_{1-8}$alkoxy" refers to a radical of the formula: —O—$C_{1-8}$alkyl-$C_{3-14}$cycloalkyl.

As used herein, the term "$C_{3-14}$cycloalkyl-$C_{1-8}$alkyl" refers to a radical of the formula: —$C_{1-8}$alkyl-$C_{3-14}$cycloalkyl.

As used herein, the term "$C_{3-14}$cycloalkyloxy" refers to a radical of the formula: —O—$C_{3-14}$cycloalkyl.

As used herein, the term "1-cyclopropyl-ethyl" refers to a radical of the formula: —CH(cyclopropyl)-CH$_3$.

As used herein, the term "cyclopropyl-methyl" refers to a radical of the formula: —CH$_2$-cyclopropyl.

As used herein, the term "formyl" refers to a radical of the formula: —C(O)—H

As used herein, the term "halo" or "halogen" generally refers to a halogen atom radical, including fluoro, chloro, bromo and iodo.

As used herein, the term "halo-$C_{2-8}$alkenyl" refers to a radical of the formula: —$C_{2-8}$alkenyl-halo, wherein $C_{2-8}$alkenyl may be partially or completely substituted where allowed by available valences with one or more halogen atoms, including fluoroethenyl, difluoroethenyl or difluoroallyl and the like. In some embodiments, difluoroethenyl includes 2,2-difluorovinyl or 1,2-difluorovinyl and the like; difluoroallyl includes 1,1-difluoroallyl and the like. In some embodiments, halo-$C_{2-8}$alkenyl includes halo-$C_{2-6}$alkenyl, halo-$C_{2-4}$alkenyl and the like.

As used herein, the term "halo-$C_{1-8}$alkoxy" refers to a radical of the formula: —O—$C_{1-8}$alkyl-halo, wherein $C_{1-8}$alkyl may be partially or completely substituted where allowed by available valences with one or more halogen atoms, including fluoromethoxy, difluoromethoxy, trifluoromethoxy, fluoroethoxy, difluoroethoxy or trifluoroethoxy and the like. In some embodiments, difluoroethoxy includes 2,2-difluoroethoxy, 1,2-difluoroethoxy or 1,1-difluoroethoxy and the like. In some embodiments, halo-$C_{1-8}$alkoxy includes halo-$C_{1-8}$alkoxy, halo-$C_{1-4}$alkoxy and the like.

As used herein, the term "halo-$C_{1-8}$alkyl" refers to a radical of the formula: —$C_{1-8}$alkyl-halo, wherein $C_{1-8}$alkyl may be partially or completely substituted where allowed by available valences with one or more halogen atoms, including fluoromethyl, difluoromethyl, trifluoromethyl, fluoroethyl, difluoroethyl, trifluoroethyl, fluoroisopropyl, difluoroisopropyl, trifluoroisopropyl, fluoro-tert-butyl, difluoro-tert-butyl, trifluoro-tert-butyl and the like. In some embodiments, difluoroethyl includes 2,2-difluoroethyl, 1,2-difluoroethyl or 1,1-difluoroethyl and the like; difluoroisopropyl includes 1,3-difluoropropan-2-yl and the like; trifluoroisopropyl includes 1,1,1-trifluoropropan-2-yl and the like; trifluoro-tert-butyl includes 1,1,1-trifluoro-2-methylpropan-2-yl and the like. In some embodiments, halo-$C_{1-8}$alkyl includes halo-$C_{1-8}$alkyl, halo-$C_{1-4}$alkyl and the like.

As used herein, the term "heteroaryl-$C_{1-8}$alkoxy" refers to a radical of the formula: —O—$C_{1-8}$alkyl-heteroaryl.

As used herein, the term "heteroaryl-$C_{1-8}$alkyl" refers to a radical of the formula: —$C_{1-8}$alkyl-heteroaryl.

As used herein, the term "heteroaryloxy" refers to a radical of the formula: —O-heteroaryl.

As used herein, the term "heterocyclyl-$C_{1-8}$alkoxy" refers to a radical of the formula: —O—$C_{1-8}$alkyl-heterocyclyl.

As used herein, the term "heterocyclyl-$C_{1-8}$alkyl" refers to a radical of the formula: —$C_{1-8}$alkyl-heterocyclyl.

As used herein, the term "heterocyclyl-carbonyloxy" refers to a radical of the formula: —O—C(O)-heterocyclyl.

As used herein, the term "heterocyclyloxy" refers to a radical of the formula: —O-heterocyclyl.

As used herein, the term "hydroxy-$C_{1-8}$alkyl" refers to a radical of the formula: —$C_{1-8}$alkyl-OH, wherein $C_{1-8}$alkyl may be partially or completely substituted where allowed by available valences with one or more hydroxy radicals.

As used herein, the term "substituent" means positional variables on the atoms of a core molecule that are substituted at a designated atom position, replacing one or more hydrogens on the designated atom, provided that the designated atom's normal valency is not exceeded, and that the substitution results in a stable compound. Combinations of substituents and/or variables are permissible only if such combinations result in stable compounds. It should also be noted that any carbon as well as heteroatom with valences that appear to be unsatisfied as described or shown herein is assumed to have a sufficient number of hydrogen atom(s) to satisfy the valences described or shown.

For the purposes of this invention, where one or more substituent variables for a compound of Formula (I) encompass functionalities incorporated into a compound of Formula (I), each functionality appearing at any location within the disclosed compound may be independently selected, and as appropriate, independently and/or optionally substituted.

As used herein, the terms "independently selected," or "each selected" refer to functional variables in a substituent list that may occur more than once on the structure of Formula (I) or Formula (Ia), the pattern of substitution at each occurrence is independent of the pattern at any other occurrence. Further, the use of a generic substituent variable on any formula or structure for a compound of the present invention is understood to include the replacement of the generic substituent with species substituents that are included within the particular genus, e.g., aryl may be replaced with phenyl or naphthalenyl and the like, and that the resulting compound is to be included within the scope of the compounds representative of the present invention.

As used herein, the term "each instance of" when used in a phrase such as " . . . aryl, aryl-$C_{1-8}$alkyl, heterocyclyl and heterocyclyl-$C_{1-8}$alkyl, wherein each instance of aryl and heterocyclyl is optionally substituted with one or two substituents." is intended to include optional, independent substitution on each of the aryl and heterocyclyl rings and on the aryl and heterocyclyl portions of aryl-$C_{1-8}$alkyl and heterocyclyl-$C_{1-8}$alkyl.

As used herein, the term "optionally substituted" means optional substitution with the specified substituent variables, groups, radicals or moieties.

As used herein, the terms "stable compound" or "stable structure" mean a compound that is sufficiently robust to survive isolation to a useful degree of purity from a reaction mixture and formulations thereof into an efficacious therapeutic agent.

Compound names used herein were obtained using ACD Labs Index Name software Version 10.0, provided by ACD Labs; and/or, were provided using the Autonom function of ChemDraw Ultra 10.0.4, provided by CambridgeSoft. When the compound name disclosed herein conflicts with the structure depicted, the structure shown will supercede the use of the name to define the compound intended.

Compound Forms

As used herein, the term "form" means a compound of Formula (I), or Formula (Ia) isolated for use selected from a free acid, free base, salt, hydrate, solvate, clathrate, isotopologue, racemate, enantiomer, diastereomer, stereoisomer, polymorph or tautomer form thereof.

As used herein, the term "isolated" means the physical state of a compound of Formula (I), or Formula (Ia) after being isolated and/or purified from a synthetic process (e.g., from a reaction mixture) or natural source or combination thereof according to an isolation or purification process or processes described herein or which are well known to the skilled artisan (e.g., chromatography, recrystallization and the like) in sufficient purity to be characterizable by standard analytical techniques described herein or well known to the skilled artisan.

As used herein, the term "protected" means that a functional group in a compound of Formula (I) is in a form modified to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

Prodrugs and solvates of the compounds of the invention are also contemplated herein.

As used herein, the term "prodrug" means a form of an instant compound (e.g., a drug precursor) that is transformed in vivo to yield an active compound of Formula (I) or a form thereof. The transformation may occur by various mechanisms (e.g., by metabolic and/or non-metabolic chemical processes), such as, for example, through hydrolysis and/or metabolism in blood, liver and/or other organs and tissues. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

In one example, when a compound of Formula (I) or a form thereof contains a carboxylic acid functional group, a prodrug can comprise an ester formed by the replacement of the hydrogen atom of the acid group with a functional group such as alkyl and the like. In another example, when a compound of Formula (I) or a form thereof contains an alcohol functional group, a prodrug can be formed by the replacement of the hydrogen atom of the alcohol group with a functional group such as alkyl or carbonyloxy and the like. In another example, when a compound of Formula (I) or a form thereof contains an amine functional group, a prodrug can be formed by the replacement of one or more amine hydrogen atoms with a functional group such as alkyl or substituted carbonyl.

One or more compounds of the invention may exist in unsolvated as well as solvated forms with pharmaceutically acceptable solvents such as water, ethanol, and the like, and it is intended that the invention embrace both solvated and unsolvated forms.

As used herein, the term "solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. As used herein, "solvate" encompasses both solution-phase and isolatable solvates. Non-limiting examples of suitable solvates include ethanolates, methanolates, and the like.

One or more compounds of the invention may optionally be converted to a solvate. Preparation of solvates is generally known. The preparation of solvates of the antifungal fluconazole in ethyl acetate as well as from water has been described (see, M. Caira et al, *J. Pharmaceutical Sci.*, 93(3), 601-611 (2004)). Similar preparations of solvates, hemisolvate, hydrates and the like have also been described (see, E. C. van Tonder et al, *AAPS PharmSciTech.*, 5(1), article 12 (2004); and A. L. Bingham et al, *Chem. Commun.*, 603-604 (2001)). A typical, non-limiting process involves dissolving a compound in a desired amount of the desired solvent (organic or water or mixtures thereof) at a higher than ambient temperature, and cooling the solution at a rate sufficient to form crystals which are then isolated by standard methods. Analytical techniques such as, for example infrared spectroscopy, show the presence of the solvent (or water) in the crystals as a solvate (or hydrate).

As used herein, the term "hydrate" means a solvate wherein the solvent molecule is water.

The compounds of Formula (I) can form salts which are also within the scope of this invention. Reference to a compound of Formula (I) herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula (I) contains both a basic moiety, such as, but not limited to a pyridine or imidazole, and an acidic moiety, such as, but not limited to a carboxylic acid, zwitterions ("inner salts") may be formed and are included within the term "salt(s)" as used herein.

Pharmaceutically acceptable (i.e., non-toxic, physiologically acceptable) salts are preferred, although other salts are also useful. Salts of the compounds of the Formula (I) may be formed, for example, by reacting a compound of Formula (I) with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like.

Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66(1) 1-19; P. Gould, *International J. of Pharmaceutics* (1986) 33, 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quaternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: carboxylic acid esters, sulfonate esters, amino acid esters phosphonate esters and mono-, di- or triphosphate esters.

Compounds of Formula (I), and salts, solvates, esters and prodrugs thereof, may further exist in their tautomeric form (for example, as an amide or imino ether).

All such tautomeric forms are contemplated herein as part of the present invention.

The compounds of Formula (I) may contain asymmetric or chiral centers, and, therefore, exist in different stereoisomeric forms. It is intended that all stereoisomeric forms of the compounds of Formula (I) as well as mixtures thereof, including racemic mixtures, form part of the present invention.

The compounds of the invention may include one or more chiral centers, and as such may exist as racemic mixtures (R/S) or as substantially pure enantiomers and diastereomers. The compounds may also exist as substantially pure (R) or (S) enantiomers (when one chiral center is present). In one embodiment, the compounds of the invention are (S) isomers and may exist as enantiomerically pure compositions substantially comprising only the (S) isomer. In another embodiment, the compounds of the invention are (R) isomers and may exist as enantiomerically pure compositions substantially comprising only the (R) isomer. As one of skill in the art will recognize, when more than one chiral center is present, the compounds of the invention may also exist as a (R,R), (R,S), (S,R) or (S,S) isomer, as defined by IUPAC Nomenclature Recommendations.

As used herein, the term "substantially pure" refers to compounds consisting substantially of a single isomer in an amount greater than or equal to 90%, in an amount greater than or equal to 92%, in an amount greater than or equal to 95%, in an amount greater than or equal to 98%, in an amount greater than or equal to 99%, or in an amount equal to 100% of the single isomer.

In one aspect of the invention, a compound of Formula (I) is a substantially pure (S) enantiomer present in an amount greater than or equal to 90%, in an amount greater than or equal to 92%, in an amount greater than or equal to 95%, in an amount greater than or equal to 98%, in an amount greater than or equal to 99%, or in an amount equal to 100%.

In one aspect of the invention, a compound of Formula (I) is a substantially pure (R) enantiomer present in an amount greater than or equal to 90%, in an amount greater than or equal to 92%, in an amount greater than or equal to 95%, in an amount greater than or equal to 98%, in an amount greater than or equal to 99%, or in an amount equal to 100%.

As used herein, a "racemate" is any mixture of isometric forms that are not "enantiomerically pure", including mixtures such as, without limitation, in a ratio of about 50/50, about 60/40, about 70/30, or about 80/20.

In addition, the present invention embraces all geometric and positional isomers. For example, if a compound of Formula (I) incorporates a double bond or a fused ring, both the cis- and trans-forms, as well as mixtures, are embraced within the scope of the invention. Diastereomeric mixtures can be separated into their individual diastereomers on the basis of their physical chemical differences by methods well known to those skilled in the art, such as, for example, by chromatography and/or fractional crystallization. Enantiomers can be separated by use of chiral HPLC column or other chromatographic methods known to those skilled in the art. Enantiomers can also be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this invention.

It is also possible that the compounds of Formula (I) may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). For example, if a compound of Formula (I) incorporates a double bond or a fused ring, both the cis- and trans-forms, as well as mixtures thereof, are embraced within the scope of the invention. Also, for example, all keto-enol and imine-enamine forms of the compounds are included in the invention. Individual stereoisomers of the compounds of the invention may, for example, be substantially free of other isomers, or may be present in a racemic mixture, as described supra.

The use of the terms "salt", "solvate", "ester", "prodrug" and the like, is intended to equally apply to the salt, solvate, ester and prodrug of enantiomers, stereoisomers, rotamers, tautomers, positional isomers, racemates, isotopologues or prodrugs of the instant compounds.

The term "isotopologue" refers to isotopically-enriched compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $H^2$, $H^3$, $C^{13}$, $C^{14}$, $N^{15}$, $O^{18}$, $O^{17}$, $P^{31}$, $P^{32}$, $S^{35}$, $F^{18}$, $Cl^{35}$ and $Cl^{36}$, respectively, each of which are also within the scope of this invention.

Certain isotopically-enriched compounds of the present invention (e.g., those labeled with $H^3$ and $C^{14}$) are useful in compound and/or substrate tissue distribution assays. Tritiated (i.e., $H^3$) and carbon-14 (i.e., $C^{14}$) isotopes are particularly preferred for their ease of preparation and detectability. Further, substitution with heavier isotopes such as deuterium (i.e., $H^2$) may afford certain therapeutic advantages resulting from greater metabolic stability (e.g., increased in vivo half-life or reduced dosage requirements) and hence may be preferred in some circumstances. Isotopically-enriched compounds of Formula (I) can generally be prepared by following procedures analogous to those disclosed in the Schemes and/or in the Examples hereinbelow, by substituting an appropriate isotopically-enriched reagent for a non-isotopically-enriched reagent.

Polymorphic crystalline and amorphous forms of the compounds of Formula (I), and of the salts, solvates, esters and prodrugs of the compounds of Formula (I), are further intended to be included in the present invention.

Methods of Use

The combination product of the present invention comprising a HCV inhibitor and one or more therapeutic agents selected from either or both a HCV protease inhibitor and one or more different therapeutic agents administered in combination in an effective amount to the subject has demonstrated activity to inhibit viral replication.

Accordingly, the combination product of the present invention is useful for treating or ameliorating HCV infection or disorders or symptoms associated therewith in a subject in need thereof comprising, a HCV inhibitor and one or more therapeutic agents selected from either or both a HCV protease inhibitor and one or more different therapeutic agents administered in combination in an effective amount to the subject.

An embodiment of the present invention includes a HCV inhibitor selected from a compound of Formula (I) or an enantiomer, stereoisomer, diastereomer, racemic, tautomeric, ester, prodrug, solvate, hydrate, isotopologue or salt form thereof.

Embodiments of the present invention include a HCV protease inhibitor selected from a NS2 protease inhibitor, a NS3 protease inhibitor, a peptide or dipeptide NS3 protease inhibitor or a NS4a protease cofactor inhibitor.

An embodiment of the present invention includes a HCV protease inhibitor selected from a HCV protease inhibitor of the present invention or an enantiomer, stereoisomer, diastereomer, racemic, tautomeric, ester, prodrug, solvate, hydrate, isotopologue or salt form thereof.

An embodiment of the present invention includes one or more different therapeutic agents selected from a HCV inhibitor, a HCV protease inhibitor, a nucleoside or non-nucleoside HCV polymerase inhibitor, a nonpegylated interferon, a pegylated interferon or another anti-HCV agent.

In one embodiment, one or more different HCV inhibitor therapeutic agents is selected from a HCV inhibitor of Formula (I) or a form thereof of the present invention.

In one embodiment, one or more different HCV inhibitor therapeutic agents is selected from a HCV inhibitor other than the HCV inhibitor compounds of Formula (I) or a form thereof of the present invention.

In one embodiment, one or more different HCV protease inhibitor therapeutic agents is selected from a NS2 protease inhibitor, a NS3 protease inhibitor, a peptide or dipeptide NS3 protease inhibitor or a NS4a protease cofactor inhibitor.

In one embodiment, one or more different HCV protease inhibitor therapeutic agents is selected from a HCV protease inhibitor or a form thereof of the present invention.

In one embodiment, one or more different HCV protease inhibitor therapeutic agents is selected from a HCV protease inhibitor or a form thereof other than the HCV protease inhibitor or forms thereof of the present invention.

In one embodiment, one or more different therapeutic agents other than the HCV inhibitor compounds of Formula (I) and forms thereof of the present invention is selected from HCV inhibitor compounds and forms thereof disclosed in U.S. patent application Ser. No. 11/653,450 (referenced above), U.S. patent application Ser. No. 11/653,448 (referenced above), U.S. patent application Ser. No. 11/331,180 (referenced above) and U.S. patent application Ser. No. 11/180,961 (referenced above), each of which is incorporated herein by reference in their entirety and for all purposes.

In one embodiment, one or more different nucleoside or non-nucleoside HCV polymerase inhibitor therapeutic agents is selected from a NS5b polymerase inhibitor.

In one embodiment, one or more different therapeutic agents is selected from a NS4b inhibitor, NS5a inhibitor, IRES inhibitor, p7 inhibitor, entry inhibitor, fusion inhibitor, helicase inhibitor, ribavirin or a ribavirin analogue.

An embodiment of the present invention includes one or more different therapeutic agents selected from a TLR agonist, cyclophilin inhibitor, caspase or pancaspase inhibitor, immunomodulator, immunomodulator/antiinflammatory, antiinflammatory, antiinflammatory/antifibrotic, broad spectrum immune stimulator, antifibrotic, antioxidant, hemopurifier, IMPDH inhibitor, glycosidase inhibitor, glucosidase inhibitor, HCV therapeutic vaccine, A3 adenosine receptor (AR) agonist, polypeptide eglin c analog inhibitor, human pancreatic secretory trypsin and minibody repertoire inhibitor or a monoclonal antibody and fragment thereof.

An embodiment of the present invention includes one or more different therapeutic agents selected from a HIV inhibitor, HBV inhibitor, RNA inhibitor, RNAi, anti-phospholipid therapy, protein therapeutic, interferon replacement agent, botanical or non-specific pharmaceutical.

In one embodiment, the NS3 HCV protease inhibitor or one or more different NS3 HCV protease inhibitor therapeutic agents is selected from ACH-1625 (Achillion), BI 201335 (Boehringer Ingelheim Pharma), boceprevir (also referred to as SCH-503034 and shown as Compound 10p herein, Schering-Plough Corporation), ciluprevir (also referred to as BILN-2061, Boehringer Ingelheim Pharma), IDX136 (Idenix Pharmaceuticals, Inc.), IDX316 (Idenix Pharmaceuticals, Inc.), ITMN-191 (also referred to as R-7227, InterMune/Roche Pharmaceuticals), MK-7009 (Merck), PHX1766 (Phenomix), SCH-6 (Schering-Plough Corporation), SCH-900518 (also referred to as SCH-518, Schering-Plough Corporation), telaprevir (also referred to as VX 950, Vertex Pharmaceuticals, Inc.), TMC435350 (also referred to as TMC435, Medivir/Tibotec), VBY-376 and VBY-106 (Virobay), VP50406 (ViroPharma, Inc.), VX-500 (Vertex Pharmaceuticals, Inc.), VX 550 (Vertex Pharmaceuticals, Inc.) or VX-813 (Vertex Pharmaceuticals, Inc.).

In one embodiment, the HCV NS4a protease cofactor inhibitor or one or more different HCV NS4a protease cofactor inhibitor therapeutic agents is selected from ACH-806 (also referred to as GS-9132, Achillion/Gilead) or ACH-1095 (also known as GS-9525, Gilead/Achillion.

In one embodiment, the one or more different nucleoside or non-nucleoside NS5b polymerase inhibitor therapeutic agents is selected from A-837093 (Abbott Laboratories), A-848837 (Abbott Laboratories), ABT-333 (Abbott Laboratories), AG-021541 (Pfizer Pharmaceuticals), ANA598 (Anadys Pharmaceuticals, Inc.), BILN-1941 (Boehringer Ingelheim Pharma), GL-59728 (Genelabs), GL-60667 (Genelabs), GS-9190 (Gilead), GSK-625433 (GlaxoSmithKline), HCV-796 (WyethNiropharma, Inc.), HCV-896 (ViroPharma, Inc.), IDX102 (Idenix Pharmaceuticals, Inc.), IDX184 (Idenix Pharmaceuticals, Inc.), IDX375 (Idenix Pharmaceuticals, Inc.), JDK-003 (Akros Pharmaceuticals), MK-0608 (Merck), MK-3281 (Merck), NM107 (active moiety of valopicitabine, Idenix/Novartis), PF-00868554 (also referred to as PF-868554 or PF-868,554, Pfizer Pharmaceuticals), PSI-6130 (Pharmasset), PSI-7851 (Pharmasset), R1626 (a prodrug of R1479, Roche Pharmaceuticals), R7128 (a prodrug of PSI-6130, Pharmasset/Roche Pharmaceuticals), valopicitabine (also referred to as NM-283, Idenix/Novartis), VBY-708 (Virobay), VCH-222 (Virochem), VCH-759 (Virochem), VCH-916 (Virochem) or XTL-2125 (also referred to as BC2125, XTL Biopharmaceuticals, Ltd.).

In one embodiment, the one or more different NS4b inhibitor therapeutic agents is selected from anguizole (Genelabs/GSKNiropharma, Inc.), clemizole (Stanford University/Eiger Biopharmaceuticals) or Compound A (BMS).

In one embodiment, the one or more different NS5a inhibitor therapeutic agents is selected from A-689 (also referred to as AZD7295, Arrow Therapeutics, Ltd./AstraZeneca), A-831 (also referred to as AZD2836, Arrow Therapeutics, Ltd./AstraZeneca), BMS-790052 (Bristol-Myers Squibb).

In one embodiment, the one or more different IRES inhibitor therapeutic agents is selected from a steroid, a ribozyme, miRNA, siRNA or an antisense RNA.

In one embodiment, the one or more different IRES inhibitor steroid therapeutic agents is mifepristone (also referred to as VGX-410C, VGX Pharmaceuticals).

In one embodiment, the one or more different IRES inhibitor ribozyme, miRNA, siRNA or antisense RNA therapeutic agents is selected from an antisense oligonucleotide ISIS-14803 (Isis Pharmaceuticals), a ribozyme such as HEPTAZYME®, (a synthetic ribozyme, Ribozyme Pharmaceuticals, Inc.), a RNAi such as TT033 (Benitec/Tacere Bio/Pfizer) or SIRNA-034 (Sirna Therapeutics), a miRNA such as SPC3649 (LNA-antimiR™-122 brand, Santaris Pharma) or an anti-miR-122 miRNA (Regulus Therapeutics), siRNA.

In one embodiment, one or more different p7 inhibitor therapeutic agents is selected from BIT225 (Biotron Limited), and one or more different viral entry inhibitor therapeutic agents is selected from ITX5061 (iTherX Pharmaceuticals, Inc.), PRO206 (Progenics), an SP-30 entry inhibitor (Samaritan Pharmaceuticals) or a broad spectrum entry inhibitor therapeutic agent selected from REP 9AC (an amphipathic DNA polymer, REPLICor, Inc.).

In one embodiment, one or more different ribavirin therapeutic agents is selected from ribavirin (VIRAZOLE® and VILONA® brands, ICN Pharmaceuticals), ribavirin for oral administration (REBETOL® brand, Schering-Plough Corporation), ribavirin tablets (COPEGUS® brand, Roche Pharmaceuticals), ribavirin capsules (RIBASPHERE® brand, Three Rivers Pharmaceuticals, LLC).

In one embodiment, one or more different ribavirin analogue therapeutic agents is selected from levovirin (L-isomer of ribavirin, Valeant Pharmaceuticals), R1518 (a prodrug of levovirin, also referred to as levovirin valinate, Roche Pharmaceuticals) or taribavirin (an oral prodrug of ribavirin, also referred to as viramidine, Valeant Pharmaceuticals).

An embodiment of the present invention includes one or more different therapeutic agents selected from ribavirin and at least one or more of a nonpegylated interferon or a pegylated interferon.

In one embodiment, the one or more different non-pegylated interferon therapeutic agent optionally adiministered with ribavirin is selected from interferon alfa-2a (ROFERON®-A brand, Roche Pharmaceuticals), interferon alfa-2b (INTRON® A brand, Schering-Plough Corporation), interferon alfa-2c (BEROFOR® brand, Boehringer Ingelheim), interferon-alpha variant GEA007.1 (GenOdyssee SA), interferon-alpha for low dose oral administration (Amarillo Biosciences, Inc./CytoPharm, Inc.), interferon-alpha for oral administration (BELEROFON® brand, Nautilus Biotech), long-acting interferon-alpha (LOCTERON® brand, also referred to as BLX-883, Biolex Therapeutics/OctoPlus), long-acting albuminfusion interferon alfa-2b (ALBUFERON® brand, also referred to as albinterferon alfa-2b, Human Genome Sciences), purified multi-subtype human leukocyte interferon-alpha (MULTIFERON® brand, Swedish Orphan International), interferon beta-1a (REBIF® brand, Merck Serono), interferon omega (also referred to as leukocycle (II) interferon, Intarcia Therapeutics), interferon omega (VIRBAGEN OMEGA® brand, Virbac), interferon omega (OMEGA INTERFERON® brand, Biomedicines), consensus interferon (INFERGEN® brand, also referred to as interferon alfacon-1, Three Rivers Pharma), medusa interferon (MEDUSA INTERFERON® brand, Flamel Technologies).

In one embodiment, the one or more different pegylated interferon therapeutic agent optionally adiministered with ribavirin is selected from Peginterferon alfa-2a (PEGASYS® brand, Roche Pharmaceuticals), Peginterferon alfa-2b (PEGINTRON® brand, Schering-Plough Corporation), Peginterferon alfacon-1 (pegylated form of interferon alfacon-1, also referred to as PEG-Alfacon, InterMune), Peg-Interferon Lambda IL-29 (Zymogenetics/Bristol-Myers Squibb).

In one embodiment, the one or more different therapeutic agents are a TLR agonist selected from ANA773 (Anadys Pharmaceuticals, Inc.), a TLR-7 agonist selected from isatoribine (also referred to as ANA245, Anadys Pharmaceuticals, Inc.), ANA-971 (a prodrug of TLR-7 agonist isatoribine, Anadys Pharmaceuticals, Inc.), ANA975 (a prodrug of TLR-7 agonist isatoribine, Anadys Pharmaceuticals, Inc.), a TLR9 agonist selected from IMO-2125 (Idera Pharmaceuticals), a TLR9 agonist (Actilon brand, Coley), a cyclophilin B inhibitor selected from Debio 025 (Debiopharm Group) or SCY-635 (Scynexis) or a cyclosporin A analog selected from NIM811 (Novartis), a pancaspase inhibitor selected from PF-03491390 (also referred to as IDN-6556, Pfizer Pharmaceuticals), an interleukin-7 immunomodulator selected from CYT107 (Cytheris SA), NOV-205 (Novelos Therapeutics), oglufanide disodium (Implicit Bioscience) or thymosin alpha 1 (also referred to as thymalfasin, ZADAXIN® brand, SciClone Pharmaceuticals), a immunomodulator/antiinflammatory selected from NOV205 (Navelos Therapeutics, Inc.), an antiinflammatory selected from CTS-1027, a matrix metalloproteinase selected from a (MMP) inhibitor (Conatus) or CF102, an A3AR agonist (Can-Fite BioPharma, Ltd.), an antiinflammatory/antifibrotic selected from mitoquinone (MitoQ® brand, Antipodean Pharmaceuticals) or PYN17 (Phynova), a broad spectrum immune stimulator selected from SCV-07 (SciClone), W an immune regulator selected from ECH18 (Enzo BioChem/Therapeutics), an antifibrotic selected from JKB-122 (Jenken Biosciences), a tumor necrosis factor α inhibitor antifibrotic selected from ENBREL® brand (Wyeth), a phospholipid antifibrotic for oral administration selected from IP-501 (Indevus Pharmaceuticals), a hemopurifier (Aethlon Medical), an IMPDH inhibitor selected from merimepodib (also referred to as VX-497, Vertex Pharmaceuticals, Inc.), a glucosidase inhibitor selected from celgosivir, an alpha-glucosidase I inhibitor selected from MX-3253 (Migenix), a HCV therapeutic vaccine selected from a DNA vaccine (ChronVac-C® brand, Inovio/Tripep AB), a MVA virus vaccine carrying and expressing HCV non-structural proteins (NS3, NS4 and NS5b) selected from TG4040 (Transgene) or (Inovio/Tripep AB), an antiviral vaccine selected from GNI-103 (GENimmune), a virosome-based combination vaccine of synthetic HCV peptide antigens (Pevion Biotect), an E1 vaccine (Innogenetics), a HCV E1/E2/MF59 vaccine (Chiron/Novartis), a vaccine selected from CSL123 (Chiron/CSL), a targeted molecular immunogen vaccine selected from GI-5005 (Globelmmune), a vaccine having a combination of five synthetic peptides selected from IC-41 (Intercell AG/Novartis), an antiviral vaccine (AMANTADINE® brand, Endo Labs), a monoclonal antibody selected from I70® (also referred to as HCV-AB$^{XTL}$68 or HCV-AB, Biochem Therapeutics/OSI Pharmaceuticals), an immune globulin polyclonal antibody selected from intravenous human immune globulin (CIVACIR® brand, NABI), a humanized Y-90 labeled antibody (Immunomedics, Inc.) an anti-PD1 antibody selected from MDX-1106 (also referred to as ONO-4538, Medarex, Inc./Ono Pharmaceutical), an anti-CD20 monoclonal antibody (RITUXIMAB® brand, Genentech), a monoclonal antibody selected from XTL-6865 or XTL-002 (XTL Biopharmaceuticals, Ltd.), a HIV fusion inhibitor selected from enfuvirtide (FUZEON® brand, Trimeris/Roche Pharmaceuticals), an anti-phospholipid therapy selected from bavituximab (formerly TARVACIN® brand, Peregrine Pharmaceuticals, Inc.), a protein therapeutic or interferon replacement agent selected from oligoadenylate synthetase stimulant CB-183,872 (Cubist Pharmaceuticals, also referred to as IB657 from Illumigen Biosciences), a botanical selected from an antiviral botanical extract PYN18 (Phynova) or a non-specific pharmaceutical selected from the cholesterol-lowering agent fluvastatin (Oklahoma University Health Sciences Center), atorvastatin (Okayama University, Japan), lovastatin (Okayama University, Japan) or simvastatin (Okayama University, Japan), a thiazolide analog selected from nitazoxanide (ALINIA™ brand, Romark Pharmaceuticals), photo-sensitized methylene blue (SUVUS® brand, Bioenvision), a synthetic phytochemical selected from KPE02003002 (Kemin Pharma) or KPE00001133 (Kemin Pharma), an antiviral agent selected from CB5300 (Canopus BioPharma, Inc.) or a tyrosine phosphatase inhibitor selected from sodium stibogluconate (LENOCTA™ brand, VioQuest Pharmaceuticals).

In one embodiment, one or more different therapeutic agents is selected from histamine dihydrochloride (CEPLENE® and MAXAMINE® brands, Maxim Pharmaceuticals), an immunosuppressive agent selected from mycophenolate mofetil (Roche Pharmaceuticals), mycophenolic acid (Roche Pharmaceuticals), or α1-antichymotrypsin.

The present invention is also directed to a method for treating or ameliorating HCV infection or disorders or symptoms associated therewith in a subject in need thereof comprising, administering an effective amount of a combination product to the subject, wherein the combination product is a HCV inhibitor and one or more therapeutic agents selected from either or both a HCV protease inhibitor and one or more different therapeutic agents administered in combination to the subject.

An embodiment of the present invention includes the use of a combination product comprising, a HCV inhibitor and one or more therapeutic agents selected from either or both a HCV protease inhibitor and one or more different therapeutic agents in the preparation of a medicament, pharmaceutical composition or pharmaceutical kit for treating or ameliorating HCV infection or disorders or symptoms associated therewith in a subject in need thereof.

An effective amount of the combination product used in the method of the present invention includes an amount of a HCV inhibitor, an amount of a HCV protease inhibitor and an amount of one or more different therapeutic agents that, when administered in combination to the subject is effective to inhibit viral replication.

An embodiment of the method of the present invention includes one or more different therapeutic agents selected from ribavirin and at least one or more of a nonpegylated interferon or a pegylated interferon.

Similarly, a therapeutically effective amount of the combination product used in the method of the present invention is an amount effective against HCV infection to produce the desired therapeutic effect in a suitable human subject.

As used herein, the term "treating or ameliorating" refers to: (i) preventing a disease, disorder or condition from occurring in a subject that may be predisposed to the disease, disorder and/or condition but has not yet been diagnosed as having it; (ii) inhibiting a disease, disorder or condition, i.e., arresting its development; and/or (iii) relieving a disease, disorder or condition, i.e., causing regression of the disease, disorder and/or condition.

As used herein, the term "subject" refers to an animal or any living organism having sensation and the power of voluntary movement, and which requires for its existence oxygen and organic food. Nonlimiting examples include members of the human, equine, porcine, bovine, murine, canine and feline species. In some embodiments, the subject is a mammal or a warm-blooded vertebrate animal. In other embodiments, the subject is a human. As used herein, the term "patient" may be used interchangeably with "subject" and "human".

The term "effective amount" or "therapeutically effective amount" is meant to describe an amount of the combination product of the present invention, wherein the combination product includes an amount of a HCV inhibitor, an amount of a HCV protease inhibitor and an amount of one or more different therapeutic agents that, when administered in combination to the subject is effective to inhibit viral replication and produce the desired therapeutic or ameliorative effect in a suitable human subject.

The therapeutic effect of the combination product used in the method of the present invention can be determined by analyzing (1) the presence of HCV RNA; (2) the presence of anti-HCV antibodies; (3) the level of serum alanine aminotransferase (ALT) and aspartate aminotransferase (AST) (ALT and AST are elevated in patients chronically infected with HCV); or (4) hepatocellular damage or any combination thereof. The precise effective amount for a subject will depend upon the subject's body weight, size and health. Therapeutically effective amounts for a given patient can be determined by routine experimentation that is within the skill and judgment of the clinician.

For a HCV inhibitor and one or more therapeutic agents selected from either or both a HCV protease inhibitor and one or more different therapeutic agents administered in combination to the subject, as used in the method described herein, the therapeutically effective amount can be estimated initially either in cell culture assays, including the HCV replicon and HCV infectious system (HCVcc), or in relevant animal models, such as the chimeric SCID-beige/Alb-uPA mouse model or in chimpanzees, marmosets and tamarins. The animal model may also be used to determine the appropriate concentration range and route of administration. Such information can then be used to determine useful doses and routes for administration in humans.

Therapeutic efficacy and toxicity may be determined by standard pharmaceutical procedures in cell cultures or experimental animals, e.g. $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $LD_{50}/ED_{50}$. A combination product as used in the method described herein that exhibits a large therapeutic index is preferred. The dosage contained in such a combination product is preferably within a range of circulating concentrations that include an $ED_{50}$ with little or no toxicity. The dosage may vary within this range depending upon the dosage form employed, therapeutic sensitivity of the patient, use of prior anti-viral therapies and the route of administration.

More specifically, the concentration-biological effect relationships observed with regard to use of a combination product indicates an initial target plasma concentration ranging from approximately 0.1 pg/mL to approximately 500 µg/mL, or from approximately 0.1 ng/mL to approximately 250 µg/mL, or from approximately 0.1 µg/mL to approximately 50 µg/mL, or from approximately 0.5 µg/mL to approximately 50 µg/mL, or from approximately 1.0 µg/mL to approximately 25 µg/mL.

To achieve such plasma concentrations, the effective amount of the combination product comprising a HCV inhibitor and one or more therapeutic agents selected from either or both a HCV protease inhibitor and one or more different therapeutic agents administered in combination to the subject, as used in the method described herein, may each be administered at doses that vary from about 0.1 µg to about 3,600 mg, depending upon the route of administration. Guidance as to particular dosages and methods of delivery is provided in the literature and is generally available to practitioners in the art. In general, the dose for each may be in the range of from about 1 mg/day to about 3 g/day, or from about 0.1 g/day to about 3 g/day, or from about 0.3 g/day to about 3 g/day, or from about 0.5 g/day to about 2 g/day, in single, divided, or continuous doses for a patient weighing between about 40 to about 100 kg (which dose may be adjusted for patients above or below this weight range, particularly for children under 40 kg).

The exact dosage will be determined by the practitioner, in light of factors related to the subject that requires treatment. Dosage and administration are adjusted to provide sufficient levels of the active agent(s) or to maintain the desired effect. Factors which may be taken into account include the severity of the disease state, general health of the subject, age, weight, and gender of the subject, diet, time, and frequency of administration, drug combination(s), reaction sensitivities, and tolerance/response to therapy. Long-acting medicaments or pharmaceutical compositions may be administered every 3 to 4 days, every week, or once every two weeks depending on half-life and clearance rate of the particular formulation.

In one embodiment, the combination product comprising a HCV inhibitor and one or more therapeutic agents selected from either or both a HCV protease inhibitor and one or more different therapeutic agents administered in combination to the subject, as used in the method described herein, may each be administered at a dosage range of from about 0.1 µg to about 3600 mg per day (e.g., at a dose selected from 0.1 mg, 1 mg, 5 mg, 10 mg, 25 mg, 50 mg, 75 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, 1900 mg, 1950 mg, 2000 mg, 2050 mg, 2100 mg, 2150 mg, 2200 mg, 2250 mg, 2300 mg, 2350 mg, 2400 mg, 2450 mg, 2500 mg, 2550 mg, 2600 mg, 2650 mg, 2700 mg, 2750 mg, 2800 mg, 2850 mg, 2900 mg, 2950 mg, 3000 mg, 3050 mg, 3100 mg, 3150 mg, 3200 mg, 3250 mg, 3300 mg, 3350 mg, 3400 mg, 3450 mg, 3500 mg, 3550 mg or 3600 mg per day).

In one embodiment, a HCV inhibitor and one or more therapeutic agents selected from either or both a HCV protease inhibitor and one or more different therapeutic agents administered in combination to the subject, as used in the method described herein, may each be administered at a dosage range of from about 0.1 mg to about 2500 mg per day.

In another embodiment, a HCV inhibitor and one or more therapeutic agents selected from either or both a HCV protease inhibitor and one or more different therapeutic agents administered in combination to the subject, as used in the method described herein, may each be administered as a single dose (i.e., QD) or divided over 2-4 doses (i.e., BID, TID, or QID) per day. In another embodiment, a HCV inhibitor and one or more therapeutic agents selected from either or both a HCV protease inhibitor and one or more different therapeutic agents may each be administered in combination either concurrently or consecutively to the subject, as used in the method described herein.

In one embodiment, a HCV inhibitor and one or more therapeutic agents selected from either or both a HCV protease inhibitor and one or more different therapeutic agents administered in combination to the subject, as used in the method described herein, may each be administered orally.

In one embodiment, a HCV inhibitor and one or more therapeutic agents selected from either or both a HCV protease inhibitor and one or more different therapeutic agents administered in combination to the subject, as used in the method described herein, may each be administered at a dosage range of from about 1.0 mg to about 2400 mg per day.

In another embodiment, the HCV protease inhibitor may be administered at a dosage of about 1200 mg per day, administered as a dosage of about 400 mg TID.

In another embodiment, the HCV protease inhibitor may be administered at a dosage of about 800 mg, 1600 mg, or 2400 mg per day administered as a dosage of about 800 mg QD, BID or TID, respectively.

In one embodiment, the present invention includes a combination product comprising, a HCV inhibitor and one or more therapeutic agents selected from either or both a HCV protease inhibitor and one or more different therapeutic agents for use in the preparation of a medicament for treating or ameliorating HCV infection or disorders or symptoms associated therewith in a subject in need thereof.

In one embodiment, the present invention includes a combination product comprising, a HCV inhibitor and one or more therapeutic agents selected from either or both a HCV protease inhibitor and one or more different therapeutic agents for use in the preparation of a pharmaceutical composition comprising the combination product in admixture with a pharmaceutically acceptable carrier.

In one embodiment, the present invention includes a combination product comprising, a HCV inhibitor and one or more therapeutic agents selected from either or both a HCV protease inhibitor and one or more different therapeutic agents for use in the preparation of a pharmaceutical kit comprising the combination product and instructions for administering the combination product for treating or ameliorating HCV infection or disorders or symptoms associated therewith in a subject in need thereof.

In one embodiment, the subject is treatment naive. In another embodiment, the subject is not treatment naive.

Pharmaceutical Compositions

Embodiments of the present invention include pharmaceutical compositions and combinations of the present invention useful for treating subjects having any HCV genotype. HCV genotypes and subtypes may differ in their antigenicity, level of viremia, severity of disease produced, and response to interferon therapy (see, Holland, J, et al., HCV genotyping by direct sequencing of the product from the Roche Amplicor Test: methodology and application to a South Australian population, *Pathology*, 1998, 30:192-195). The nomenclature of HCV classification (see, Simmonds, P. et al., Classification of HCV into six major genotypes and a series of subtypes by phylogenetic analysis of the NS5 region, *J. Gen. Virol.*, 1993, 74:2391-9) is widely used and classifies HCV isolates into six major genotypes, 1 through 6, with two or more related subtypes, e.g., 1a, 1b. Additional genotypes 7-11 have been proposed, however the phylogenetic basis on which this classification is based has been questioned, and thus types 7, 8, 9 and 11 isolates have been reassigned as type 6, and type 10 isolates as type 3 (see, Lamballerie, et al., Classification of hepatitis C variants in six major types based on analysis of the envelope 1 and nonstructural 5B genome regions and complete polyprotein sequences, *J. Gen. Virol.*, 1997, 78:45-51). The major genotypes have been defined as having sequence similarities of between 55 and 72% (mean 64.5%), and subtypes within types as having 75%-86% similarity (mean 80%) when sequenced in the NS5 region (see, P Simmonds, et al., Identification of genotypes of hepatitis C by sequence comparisons in the core, E1 and NS5 regions, *J. Gen, Viral.*, 1994, 75:1053-61).

In one embodiment, a dosage for the administration of a combination product, medicament, pharmaceutical composition or pharmaceutical kit of the present invention is from about 0.001 to about 500 mg/kg of body weight/day; or, from about 0.01 to about 25 mg/kg of body weight/day.

As used herein, the term "composition" means a product comprising the specified ingredients in the specified amounts, as well as any product which results, directly or indirectly, from combination of the specified ingredients in the specified amounts.

For administration of pharmaceutically acceptable salts of the compounds, the weights indicated above refer to the weight of the acid equivalent or the base equivalent of the therapeutic compound derived from the salt.

When administering an effective amount of a combination product to the subject in need thereof, wherein the combination product is a HCV inhibitor and one or more therapeutic agents selected from either or both a HCV protease inhibitor and one or more different therapeutic agents administered in combination either concurrently or consecutively to the subject, the term "either concurrently or consecutively" refers to administering the HCV inhibitor and one or more therapeutic agents selected from either or both the HCV protease inhibitor and one or more different therapeutic agents in any order such as, for example, simultaneously, sequentially, in alternation, concurrently, in parallel, or by any other combination therapy regimen known in the art.

When delivered in alternation therapy, the methods of the invention may comprise administering or delivering the active ingredients sequentially, e.g., in separate solution, emulsion, suspension, tablets, pills or capsules, or by different injections in separate syringes. In general, during alternation therapy, an effective dosage of each active ingredient is administered sequentially, i.e., serially, whereas in simultaneous therapy, effective dosages of two or more active ingredients are administered together. Various sequences of intermittent combination therapy may also be used.

The amounts of the various active ingredients in a combination therapy may be administered in different amounts (i.e., different dosage amounts) or in the same amount (i.e., the same dosage amount). Thus, for illustration purposes, a HCV inhibitor compound of the present invention and one or more therapeutic agents selected from either or both a HCV protease inhibitor and one or more different therapeutic agents may each be present in fixed amounts (dosage amounts) in a single dosage unit (e.g., a capsule, a tablet and the like). If formulated as a fixed dose, such a combination product may employ the HCV inhibitor compounds of the present invention within the dosage range described herein and one or more therapeutic agents selected from either or both a HCV protease inhibitor and one or more different therapeutic agents within the dosage range recommended for each HCV inhibitor and/or HCV protease inhibitor and/or different therapeutic agent. HCV inhibitor compounds of the present invention may also be administered sequentially with one or more known therapeutic agents selected from either or both a HCV protease inhibitor and one or more different therapeutic agents when a combination formulation is inappropriate. The invention is not limited in the sequence of administration; the HCV inhibitor compounds of the present invention may also be administered either prior to or after administration of one or more of the known therapeutic agent selected from either or both a HCV protease inhibitor and one or more different therapeutic agents. Such techniques are within the skills of persons skilled in the art as well as attending physicians and clinicians.

The pharmacological properties of the active ingredients in the combination product comprising a HCV inhibitor and one or more therapeutic agents selected from either or both a HCV protease inhibitor and one or more different therapeutic agents used in the preparation of a medicament, pharmaceutical composition or pharmaceutical kit for treating or ameliorating HCV infection or disorders or symptoms associated therewith in a subject in need thereof may be confirmed by any number of pharmacological assays for measuring inhibition of viral replication such as are well known to those skilled in the art.

While it is possible for each of the active ingredients of the present invention to be administered alone, it is preferable to administer the active ingredients as a combination product. The combination product comprising a HCV inhibitor and one or more therapeutic agents selected from either or both a HCV protease inhibitor and one or more different therapeutic agents may also comprise at least the HCV inhibitor and one or more therapeutic agents selected from either or both a HCV protease inhibitor and one or more different therapeutic agents, as defined above, together with one or more acceptable carriers, adjuvants or vehicles thereof and optionally other adjuvant therapeutic agents. Each carrier, adjuvant or vehicle must be acceptable in the sense of being compatible with the other ingredients of the composition and pharmaceutically acceptable for use in a combination product for use in a subject in need of such treatment.

Accordingly, the invention also relates to pharmaceutical compositions of the active ingredients in the combination product comprising at least one HCV inhibitor compound and one or more therapeutic agents selected from either or both a HCV protease inhibitor and one or more different therapeutic agents as utilized in the presently claimed methods, and at least one pharmaceutically acceptable carrier, adjuvant or vehicle.

In yet another embodiment, the present invention discloses methods for preparing pharmaceutical compositions of the combination product comprising the HCV inhibitor compounds and one or more therapeutic agents selected from either or both a HCV protease inhibitor and one or more different therapeutic agents as active ingredients. In the combination product and methods of the present invention, the active ingredients may typically be administered in admixture with suitable carrier materials suitably selected with respect to the intended form of administration, i.e. oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active HCV inhibitor compounds and one or more therapeutic agents selected from either or both a HCV protease inhibitor and one or more different therapeutic agents may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Moreover, when desired or needed, suitable binders, lubricants, disintegrating agents and coloring agents may also be incorporated in the mixture.

Powders and tablets of the active ingredients in the combination product may be comprised of from about 5 to about 95 percent of said active ingredients. Surfactants may be present in the pharmaceutical compositions of the combination product of the present invention in an amount of from about 0.1 to about 10% by weight or from about 1 to about 5% by weight. Acidifying agents may be present in the pharmaceutical formulations of the present invention in a total amount of from about 0.1 to about 10% by weight or from about 1 to about 5% by weight.

Suitable binders may be included where appropriate and include starch, gelatin, natural sugars, corn sweeteners, or natural and synthetic gums such as acacia, sodium alginate, carboxymethylcellulose, polyethylene glycol and waxes.

Suitable lubricants may be included where appropriate and include boric acid, sodium benzoate, sodium acetate, sodium chloride, and the like. Disintegrants may be included where appropriate and include starch, methylcellulose, guar gum and the like.

Sweetening and flavoring agents and preservatives may also be included where appropriate. Some of the terms noted above, namely disintegrants, diluents, lubricants, binders and the like, are discussed in more detail below.

Additionally, the active ingredients in the combination product of the present invention may be formulated in sustained release form to provide a controlled release rate of any one or more of the components or active ingredients to optimize the therapeutic effects, i.e. HCV inhibitory activity. Suitable dosage forms for sustained release include layered tablets containing layers of varying disintegration rates or controlled release polymeric matrices impregnated with the active ingredients in the combination product and shaped in tablet form or capsules containing such impregnated or encapsulated porous polymeric matrices.

Liquid form preparations for active ingredients in the combination product include solutions, suspensions and emulsions. As an example, such forms include those in a water or water-propylene glycol solution for use as a parenteral injection. The liquid form preparation may also include the addition of sweeteners and pacifiers for oral solutions, suspensions and emulsions. Liquid form preparations may also include solutions for intranasal administration.

Aerosol preparations for active ingredients in the combination product suitable for inhalation may include solutions and solids in powder form, which may be in combination with a pharmaceutically acceptable carrier such as inert compressed gas, e.g. nitrogen.

For preparing suppositories of active ingredients in the combination product, a low melting wax such as a mixture of fatty acid glycerides such as cocoa butter is first melted, and the active ingredient is dispersed homogeneously therein by stirring or similar mixing. The molten homogeneous mixture is then poured into convenient sized molds, allowed to cool and thereby solidify.

Also included are solid form preparations for active ingredients in the combination product which are intended to be converted, shortly before use, to liquid form preparations for either oral or parenteral administration. Such resulting liquid forms include solutions, suspensions and emulsions.

The active ingredients in a combination product of the present invention may also be deliverable transdermally. The transdermal compositions may take the form of creams, lotions, aerosols and/or emulsions and can be included in a transdermal patch of the matrix or reservoir type as are conventional in the art for this purpose.

Preferably the active ingredients in a combination product are administered orally, intravenously, intrathecally or subcutaneously, parenteraly, transdermally or by any combination of such methods.

Preferably, the combination product is in a unit dosage form. In such form, the product is subdivided into suitably sized unit doses containing appropriate quantities of the active components, e.g., an effective amount to achieve the desired purpose. Other useful dosage forms include solid tablets, lyophilized wafers, capsules, powder, oral gels and the like.

Tablets for active ingredients in the combination product include compressed or molded solid dosage forms containing the active ingredients in admixture with suitable excipients. The tablet can be prepared by compression of mixtures or granulations obtained by wet granulation, dry granulation or by compaction.

Lyophilized wafers for active ingredients in the combination product include mouth-soluble, freeze-dried, taste-masked solid dosage forms containing the active ingredients in admixture with suitable excipients. The wafer can be prepared by freeze drying suspensions or solutions containing the active ingredients and optional excipients.

Capsule forms of active ingredients in the combination product may include capsules made of methyl cellulose, polyvinyl alcohol, or denatured gelatins or starch for holding or containing compositions comprising the active ingredients. Hard shell capsules are typically made of blends of relatively high gel strength bone and pork skin gelatins. The capsule itself may contain small amounts of dyes, opaquing agents, plasticizers and preservatives.

Powders for active ingredients in the combination product may include powder blends containing the active ingredients and suitable diluents for reconstitution or suspension in water or juices.

Oral gels for active ingredients in the combination product include active ingredients dispersed or solubilized in a hydrophilic semi-solid matrix.

Suitable excipients for use in the combination product are those substances that usually make up the major portion of the composition or dosage form, including sugars such as lactose, sucrose, mannitol and sorbitol; starches derived from wheat, corn, rice and potato; and celluloses such as microcrystalline cellulose. The amount of excipient in the pharmaceutical composition of the combination product can range from about 10 to about 90% by weight of the total composition, or from about 25 to about 75%, or from about 30 to about 60% by weight, or from about 12 to about 60%.

Suitable disintegrants are those materials added to the pharmaceutical composition of the combination product to help the composition to break apart (disintegrate) and release the active ingredients, including "cold water soluble" modified starches such as sodium carboxymethyl starch; natural and synthetic gums such as locust bean, karaya, guar, tragacanth and agar; cellulose derivatives such as methylcellulose and sodium carboxymethylcellulose; microcrystalline celluloses and cross-linked microcrystalline celluloses such as sodium croscarmellose; alginates such as alginic acid and sodium alginate; clays such as bentonites; and effervescent mixtures. The amount of disintegrant in the pharmaceutical composition of the combination product can range from about 2 to about 15% by weight of the composition, or from about 4 to about 10% by weight.

Suitable binders are those substances that bind or "glue" powders together and make them cohesive by forming granules, thus serving as the "adhesive" in the pharmaceutical composition and further adding cohesive strength already available in the diluent or bulking agent, including sugars such as sucrose; starches derived from wheat, corn rice and potato; natural gums such as acacia, gelatin and tragacanth; derivatives of seaweed such as alginic acid, sodium alginate and ammonium calcium alginate; cellulosic materials such as methylcellulose and sodium carboxymethylcellulose and hydroxypropylmethylcellulose; polyvinylpyrrolidone; and inorganics such as magnesium aluminum silicate. The amount of binder in the pharmaceutical composition can range from about 2 to about 20% by weight of the composition, or from about 3 to about 10% by weight, or from about 3 to about 6% by weight.

Suitable lubricants are those substances added to the pharmaceutical composition to enable the tablet, granules, etc., after they have been compressed, to release from the mold or die by reducing friction or wear, including metallic stearates such as magnesium stearate, calcium stearate or potassium stearate; stearic acid; high melting point waxes; and water soluble lubricants such as sodium chloride, sodium benzoate, sodium acetate, sodium oleate, polyethylene glycols and D-leucine or L-leucine. Lubricants are usually added at the very last step before compression, since they must be present on the surfaces of the granules and in between them and the parts of the tablet press. The amount of lubricant in the pharmaceutical composition can range from about 0.2 to about 5% by weight of the composition, or from about 0.5 to about 2%, or from about 0.3 to about 1.5% by weight.

Suitable glidents are those materials that prevent caking and improve the flow characteristics of granulations, so that flow is smooth and uniform, including silicon dioxide and talc. The amount of glident in the pharmaceutical composition can range from about 0.1% to about 5% by weight of the total composition, or from about 0.5 to about 2% by weight.

Suitable coloring agents are those excipients that provide coloration to the composition or the dosage form, including food grade dyes and food grade dyes adsorbed onto a suitable adsorbent such as clay or aluminum oxide. The amount of the coloring agent can vary from about 0.1 to about 5% by weight of the composition, or from about 0.1 to about 1%.

The term "bioavailability" refers to the rate at and extent to which the active ingredient of the combination product is absorbed into the systemic circulation from an administered dose as compared to a standard or control.

Conventional methods for preparing tablet forms of the active ingredients are known. Such methods include dry methods such as direct compression and compression of granulation produced by compaction, or wet methods or other special procedures. Conventional methods for making other forms of the active ingredients for administration such as, for example, capsules, suppositories and the like are also well known.

For preparing pharmaceutical compositions of the combination product comprising, a HCV inhibitor and one or more therapeutic agents selected from either or both a HCV protease inhibitor and one or more different therapeutic agents described herein, the combination product active ingredients are intimately admixed with inert, pharmaceutically acceptable carriers that can be either solid or liquid. Solid form preparations include powders (including sachets or packets thereof), dispersible granules (including sachets or packets thereof), tablets, capsules and suppositories. The powders and tablets may be comprised of from about 5 to about 95 percent of the active ingredient. Suitable solid carriers are known in the art, e.g., magnesium carbonate, magnesium stearate, talc, sugar or lactose.

Tablets, powders (including sachets or packets thereof), dispersible granules (including sachets or packets thereof) and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

The term "pharmaceutical composition" is also intended to encompass both the bulk composition and individual dosage units comprised of more than one (e.g., two) pharmaceutically active agents such as, for example, a HCV inhibitor and one or more therapeutic agents selected from either or both a HCV protease inhibitor and one or more different therapeutic agents, as described herein, along with any pharmaceutically inactive excipients. The bulk composition and each individual dosage unit can contain fixed amounts of the aforesaid "more than one pharmaceutically active agents". The bulk composition is material that has not yet been formed into individual dosage units. An illustrative dosage unit is an oral dosage unit such as tablets, pills and the like. Similarly, the herein-described method of treating a subject by administering a pharmaceutical composition of the active ingredients in the combination product of the present invention is also intended to encompass the administration of the afore-said bulk composition and individual dosage units.

In one embodiment, the pharmaceutical composition of the active ingredients in the combination product is administered orally, intravenously or subcutaneously as a unit dosage form subdivided into suitably sized unit doses containing appropriate quantities of the active ingredients, e.g., an effective amount to achieve the desired therapeutic purpose. The actual dosage employed may be varied depending upon the requirements of the patient and the severity of the condition being treated.

Determination of the proper dosage regimen for a particular situation is within the skill of the art. For convenience, the total daily dosage of the active ingredients in the combination product may be divided and administered in portions during the day as required.

The pharmaceutical composition(s) of the active ingredients in the combination product of the present invention may be administered in an amount effective to reduce the concentration of HCV RNA per milliliter of plasma to a level of less than about 29 IU/mL. The term "concentration of less than 29 International Units of HCV RNA per milliliter of plasma (29 IU/mL)" in the context of the present invention means that there are fewer than 29 IU/mL of HCV RNA, which translates into fewer than 100 copies of HCV-RNA per mL of plasma of the patient as measured by quantitative, multi-cycle reverse transcriptase PCR methodology. HCV-RNA is preferably measured in the present invention by research-based RT-PCR methodology well known to the skilled clinician. This methodology is referred to herein as HCV-RNA/qPCR. The lower limit of detection of HCV-RNA is 29 IU/mL or 100 copies/mL. Serum HCV-RNA/qPCR testing and HCV genotype testing will be performed by a central laboratory (see, JG McHutchinson, et al., N. Engl. J. Med., 1998, 339:1485-1492; and, GL Davis, et al., N. Engl. J. Med., 1998, 339:1493-1499).

BIOLOGICAL EXAMPLES

Among other assays known to those skilled in the art for determining inhibition of viral replication, the following example demonstrates the effect on HCV replicon RNA response after treatment with an embodiment of the combination product of the present invention.

Example 1

Combination of HCV Protease Inhibitor and HCV Inhibitor Replicon RNA Response to Antiviral Agent(s)

Replicon cells were seeded at ~5000 cells/well in 96-well collagen I-coated Biocoat plates (Becton Dickinson). At 24 hrs post-seeding, a series of replicon cells were treated with a HCV protease inhibitor and a HCV inhibitor. The final concentration of DMSO was 0.5%, fetal bovine serum was 10%, and G418 (an aminoglycoside used as a selective agent) was 500 μg/mL.

The HCV protease inhibitor Compound 10p was serially diluted to the concentrations indicated in Table 1. To each concentration of Compound 10p, HCV inhibitor Compound 31 was titrated. After 3 days, the cells were washed with PBS and lysed in 1× Cell Lysis Buffer (Ambion cat #8721).

The replicon RNA level was measured using real time PCR (Taqman assay). The ampicon was located in NS5b. The PCR primers used were: 5B.2F, ATGGACAGGCGCCCTGA (SEQ ID NO: 1); 5B.2R, TTGATGGGCAGCTTGGTTTC (SEQ ID NO: 2); the probe sequence was FAM-labeled CACGCCATGCGCTGCGG (SEQ ID NO: 3). GAPDH RNA was used as endogenous control and was amplified in the same reaction as NS5b (multiplex PCR) using primers and VIC-labeled probe recommended by the manufacturer (PE Applied Biosystem). The real-time RT-PCR reactions were run on ABI PRISM 7900HT Sequence Detection System using the following program: 48° C. for 30 min, 95° C. for 10 min, 40 cycles of 95° C. for 15 sec, 60° C. for 1 min. The ΔCT values ($CT_{5B}$-$CT_{GAPDH}$) were plotted against test compound concentration and fitted to the sigmoid dose response model using Graphpad PRISM software (Graphpad Software Inc.). The half maximal inhibitory concentration ($IC_{50}$) is the concentration necessary to achieve ΔCT=1 over the projected baseline. The 90% maximal inhibitory concentration ($IC_{90}$) is the concentration necessary to achieve ΔCT=3.2 over the baseline. Alternatively, to quantitate the absolute amount of replicon RNA, a standard curve was established by including serially diluted T7 transcripts of replicon RNA in the Taqman assay. All Taqman reagents were from PE Applied Biosystem.

The relative inhibition results (logarithmic scale) for various concentrations of a representative embodiment of the combination product of the present invention shown in Table 1 demonstrate the inhibition of replicon replication after treatment, wherein the embodiment of the combination product comprises HCV inhibitor Compound 31, representative of compounds described herein, in combination with HCV protease inhibitor Compound 10p.

TABLE 1

| Compound 31 | Cpd 10p | |
|---|---|---|
| Conc (μM) | 1.5 | 0.19 |
| 0 | −1.52 | −0.11 |
| 0.045 | −1.72 | −1.16 |
| 0.405 | −2.02 | −1.73 |

The summary of results for the combination product in Table 1 shows reduced replicon RNA levels after replicon cells were treated for three days with an embodiment of the combination product of the present invention.

The results of Example 1 demonstrate that the combination of a HCV protease inhibitor and a HCV inhibitor is more efficacious in inhibiting HCV RNA replication in replicon cells than either the HCV inhibitor or HCV protease inhibitor alone.

It will be appreciated by those skilled in the art that changes could be made to the embodiments described above without departing from the broad inventive concept thereof. It is understood, therefore, that this invention is not limited to the particular embodiments disclosed herein, but it is intended to cover modifications that are within the spirit and scope of the invention, as defined by the appended claims.

Each document (including granted patents, published patent applications, and nonpatent publications such as journal articles) referred to in this application is incorporated herein in its entirety by reference for all purposes. Citation of or reference to any application or publication herein is not an admission that such document is available as prior art to the present invention.

What is claimed:

1. A combination product for treating or ameliorating HCV (hepatitis C virus) infection or disorders or symptoms associated therewith in a subject in need thereof comprising, a HCV inhibitor compound of Formula (I) or a free acid, free base, salt, isotopologue, racemate, enantiomer, diastereomer or stereoisomer form thereof:

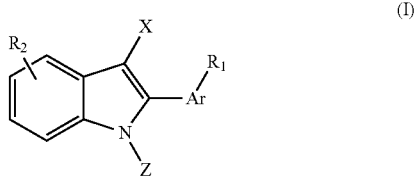

wherein

X is hydrogen, halogen, cyano, nitro, carboxyl, $C_{1-8}$alkyl-carbonyl, $C_{1-8}$alkoxy-carbonyl, formyl, amino, $C_{1-8}$alkyl-amino, amino-carbonyl, $C_{1-8}$alkyl-amino-carbonyl or $C_{1-8}$alkyl-sulfonyl;

Ar is pyridinyl, pyrimidinyl or pyridazinyl;

Z is $C_{1-8}$alkyl, $C_{2-8}$alkenyl-$C_{1-8}$alkyl, $C_{2-8}$alkynyl-$C_{1-8}$alkyl, halo-$C_{1-8}$alkyl, $C_{1-8}$alkoxy-$C_{1-8}$alkyl, $C_{1-8}$alkoxy-carbonyl, carboxyl, $C_{3-14}$cycloalkyl, $C_{3-14}$cycloalkenyl, $C_{3-14}$cycloalkyl-$C_{1-8}$alkyl, aryl, aryl-$C_{1-8}$alkyl, heteroaryl, heteroaryl-$C_{1-8}$alkyl, heterocyclyl or heterocyclyl-$C_{1-8}$alkyl, wherein each instance of aryl and heteroaryl is optionally substituted with one, two, three or four substituents each selected from hydroxy, cyano, nitro, halogen, $C_{1-8}$alkyl, $C_{2-8}$alkenyl, $C_{2-8}$alkynyl, hydroxy-$C_{1-8}$alkyl, halo-$C_{1-8}$alkyl, $C_{1-8}$alkoxy, halo-$C_{1-8}$alkoxy, amino, $C_{1-8}$alkyl-amino, $C_{1-8}$alkoxy-$C_{1-8}$alkyl, $C_{1-8}$alkylthio, $C_{1-8}$alkyl-carbonyl, $C_{1-8}$alkoxy-carbonyl, $C_{1-8}$alkyl-carbonyloxy or amino-sulfonyl;

$R_1$ is —$SO_2$—$N(R_5)$—$R_6$;

$R_2$ is one, two, three or four substituents each selected from hydrogen, halogen, hydroxy, cyano, nitro, $C_{1-8}$alkyl, hydroxy-$C_{1-8}$alkyl, halo-$C_{1-8}$alkyl, $C_{2-8}$alkenyl, halo-$C_{2-8}$alkenyl, $C_{1-8}$alkoxy, halo-$C_{1-8}$alkoxy, $C_{1-8}$alkoxy-$C_{1-8}$alkyl, $C_{1-8}$alkyl-carbonyl, $C_{1-8}$alkoxy-carbonyl, $C_{1-8}$alkyl-carbonyloxy, $C_{1-8}$alkyl-carbonyloxy-$C_{1-8}$alkyl, $C_{1-8}$alkyl-carbonyloxy-$C_{1-8}$alkoxy, amino, $C_{1-8}$alkyl-amino, amino-$C_{1-8}$alkyl, $C_{1-8}$alkyl-amino-$C_{1-8}$alkyl, amino-$C_{1-8}$alkoxy, $C_{1-8}$alkyl-amino-$C_{1-8}$alkoxy, $C_{1-8}$alkoxy-$C_{1-8}$alkyl-amino-$C_{1-8}$alkoxy, amino-$C_{1-8}$alkyl-amino-$C_{1-8}$alkoxy, $C_{1-8}$alkyl-amino-$C_{1-8}$alkyl-amino-$C_{1-8}$alkoxy, $C_{1-8}$alkoxy-carbonyl-amino, carboxyl-amino, amino-carbonyl, amino-carbonyl-amino, $C_{1-8}$alkyl-amino-carbonyl-amino, $C_{1-8}$alkylthio, $C_{1-8}$alkyl-sulfinyl, $C_{1-8}$alkyl-sulfonyl, $C_{1-8}$alkyl-sulfonyl-amino, $C_{3-14}$cycloalkyl, $C_{3-14}$cycloalkyl-$C_{1-8}$alkyl, $C_{3-14}$cycloalkyl-$C_{1-8}$alkoxy, $C_{3-14}$cycloalkyloxy, aryl, aryl-$C_{1-8}$alkyl, aryl-$C_{1-8}$alkoxy, aryloxy, aryl-carbonyl-amino, heteroaryl, heteroaryl-$C_{1-8}$alkyl, heteroaryl-$C_{1-8}$alkoxy, heteroaryloxy, heterocyclyl, heterocyclyl-$C_{1-8}$alkyl, heterocyclyl-$C_{1-8}$alkoxy, heterocyclyloxy or heterocyclyl-carbonyloxy, wherein each instance of $C_{3-14}$cycloalkyl, aryl, heteroaryl and heterocyclyl is optionally substituted with one, two, three or four substituents each selected from halogen, cyano, $C_{1-8}$alkyl, $C_{1-8}$alkoxy, $C_{1-8}$alkoxy-$C_{1-8}$alkyl, amino, $C_{1-8}$alkyl-amino, amino-$C_{1-8}$alkyl or $C_{1-8}$alkyl-amino-$C_{1-8}$alkyl;

$R_3$ is hydrogen or $C_{1-8}$alkyl, optionally substituted on $C_{1-8}$alkyl with one or more substituents each selected from halogen, hydroxy, cyano, $C_{1-8}$alkoxy, amino or $C_{1-8}$alkyl-amino;

$R_4$ is $C_{1-8}$alkyl, halo-$C_{1-8}$alkyl, $C_{1-8}$alkoxy, halo-$C_{1-8}$alkoxy, $C_{3-14}$cycloalkyl, $C_{3-14}$cycloalkyl-$C_{1-8}$alkyl, aryl, aryl-$C_{1-8}$alkyl, heteroaryl, heteroaryl-$C_{1-8}$alkyl, heterocyclyl or heterocyclyl-$C_{1-8}$alkyl, wherein each instance of aryl, heteroaryl, heterocyclyl and $C_{3-14}$cycloalkyl is optionally substituted with one or two substituents each selected from halogen, $C_{1-8}$alkyl, halo-$C_{1-8}$alkyl, $C_{1-8}$alkoxy, halo-$C_{1-8}$alkoxy, amino or $C_{1-8}$alkyl-amino;

$R_5$ is hydrogen;

$R_6$ is hydrogen, $C_{1-8}$alkyl, hydroxy-$C_{1-8}$alkyl, halo-$C_{1-8}$alkyl, cyano-$C_{1-8}$alkyl, $C_{1-8}$alkoxy-$C_{1-8}$alkyl, amino-$C_{1-8}$alkyl, $C_{1-8}$alkyl-amino-$C_{1-8}$alkyl, $C_{1-8}$alkyl-carbonyl, $C_{1-8}$alkoxy-carbonyl, $C_{3-14}$cycloalkyl, $C_{3-14}$cycloalkyl-$C_{1-8}$alkyl, aryl, aryl-$C_{1-8}$alkyl, heteroaryl, heteroaryl-$C_{1-8}$alkyl, heterocyclyl or heterocyclyl-$C_{1-8}$alkyl, wherein each instance of aryl, heteroaryl, heterocyclyl and $C_{3-14}$cycloalkyl is optionally substituted with one or two substituents each selected from halogen, $C_{1-8}$alkyl, halo-$C_{1-8}$alkyl, $C_{1-8}$alkoxy, halo-$C_{1-8}$alkoxy, amino or $C_{1-8}$alkyl-amino; and and a HCV protease inhibitor or a free acid, free base, salt, isotopologue, racemate, enantiomer, diastereomer or stereoisomer form thereof selected from:

tert-butyl 1-((2S)-1-(1-amino-1,2-dioxohexan-3-ylamino)-4-methyl-1-oxopentan-2-ylamino)-3,3-dimethyl-1-oxobutan-2-ylcarbamate, (S)-2-acetamido-N-((S)-1-((S)-5-guanidino-1-oxopentan-2-ylamino)-4-methyl-1-oxopentan-2-yl)-4-methylpentanamide, tert-butyl (1S)-2-((2S)-2-(4-amino-1-cyclopropyl-3,4-dioxobutan-2-ylcarbamoyl)indolin-1-yl)-1-cyclohexyl-2-oxoethylcarbamate, (3S,18S)-N-[(3S)-1-amino-1,2-dioxohexan-3-yl]-18-cyclohexyl-16,19-dioxo-3,4-dihydro-1H-7,2-(eboxyheptanoiminoethano)isoguinoline-3-carboxamide, tert-butyl (3S)-1-((2S)-1-(4-amino-1-cyclopropyl-3,4-dioxobutan-2-ylamino)-4-methyl-1-oxopentan-2-yl)-2-oxoazonan-3-ylcarbamate, (2S)-isopropyl 2-(3-((3S)-1-((2S)-1-(4-amino-1-cyclobutyl-3,4-dioxobutan-2-ylamino)-4-methyl-1-oxopentan-2-yl)-2-oxoazonan-3-yl)ureido)-3,3-dimethylbutanoate, tert-butyl (1S)-2-((1S,3aR,6aS)-1-(4-amino-1-cyclopropyl-3,4-dioxobutan-2-ylcarbamoyl)hexahydrocyclopenta[c]pyrrol-2(1H)-yl)-1-cyclohexyl-2-oxoethylcarbamate, tert-butyl (S)-2-((1R,2S,5S)-2-((S)-4-amino-1-cyclopropyl-3,4-dioxobutan-2-ylcarbamoyl)-6,6,7,7-tetramethyl-3-azabicyclo[3.2.0]heptan-3-yl)-1-cyclohexyl-2-oxoethylcarbamate, (2S)-N-(4-amino-1-cyclobutyl-3,4-dioxobutan-2-yl)-3-((S)-2-(3-cyclohexylureido)-3,3-dimethylbutanoyl)-6,6-dimethyl-3-azabicyclo[3.1.0]hexane-2-carboxamide, (1R,2S,5S)-N-(4-amino-1-cyclobutyl-3,4-dioxobutan-2-yl)-3-((S)-2-(3-tert-butylureido)-3,3-dimethylbutanoyl)-6,6-dimethyl-3-azabicyclo[3.1.0]hexane-2-carboxamide, (1R,2S,5S)-N-((S)-4-amino-1-cyclobutyl-3,4-dioxobutan-2-yl)-3-((S)-2-(3-tert-butylureido)-3,3-dimethylbutanoyl)-6,6-dimethyl-3-azabicyclo[3.1.0]hexane-2-carboxamide, (1R,2S,5S)-N-((R)-4-amino-1-cyclobutyl-3,4-dioxobutan-2-yl)-3-((S)-2-(3-tert-butylureido)-3,3-dimethylbutanoyl)-6,6-dimethyl-3-azabicyclo[3.1.0]hexane-2-carboxamide, (1R,2S,5S)-3-((S)-2-(3-(1-(tert-butylsulfonylmethyl)cyclohexyl)ureido)-3,3-dimethylbutanoyl)-N-((S)-1-(cyclopropylamino)-1,2-dioxohexan-3-yl)-6,6-dimethyl-3-azabicyclo[3.1.0]hexane-2-carboxamide, (1R,2S,5S)-3-((S)-2-(3-(1-(tert-butylsulfonylmethyl)cyclohexyl)ureido)-3,3-dimethylbutanoyl)-N-((S)-1-(cyclopropylamino)-1,2-dioxoheptan-3-yl)-6,6-dimethyl-3-azabicyclo[3.1.0]hexane-2-carboxamide, (1R,2S,5S)-3-((S)-2-(3-(1-(tert-butylsulfonylmethyl)cyclohexyl)ureido)-3,3-dimethylbutanoyl)-N-((R)-1-(cyclopropylamino)-1,2-dioxoheptan-3-yl)-6,6-dimethyl-3-azabicyclo[3.1.0]hexane-2-carboxamide, (1R,2S,5S)-3-((S)-2-(3-(1-(tert-butylsulfonylmethyl)cyclohexyl)ureido)-3,3-dimethylbutanoyl)-N-((S)-5-cyclopropyl-1-(cyclopropylamino)-1,2-dioxopentan-3-yl)-6,6-dimethyl-3-azabicyclo[3.1.0]hexane-2-carboxamide, (1R,2S,5S)-3-((S)-2-(3-(1-(tert-butylsulfonylmethyl)cyclohexyl)ureido)-3,3-dimethylbutanoyl)-N-((R)-5-cyclopropyl-1-(cyclopropylamino)-1,2-dioxopentan-3-yl)-6,6-dimethyl-3-azabicyclo[3.1.0]hexane-2-carboxamide, (1R,2S,5S)-N-((S)-1-(allylamino)-5-cyclopropyl-1,2-dioxopentan-3-yl)-3-((S)-2-(3-(1-(tert-butylsulfonylmethyl)cyclohexyl)ureido)-3,3-dimethylbutanoyl)-6,6-dimethyl-3-azabicyclo[3.1.0]hexane-2-carboxamide, (1R,2S,5S)-N-((S)-4-(allylamino)-1-cyclopropyl-3,4-dioxobutan-2-yl)-3-((S)-2-(3-(1-(tert-butylsulfonylmethyl)cyclohexyl)ureido)-3,3-dimethylbutanoyl)-6,6-dimethyl-3-azabicyclo[3.1.0]hexane-2-carboxamide, (1R,2S,5S)-N-((S)-4-(allylamino)-1-cyclopropyl-3,4-dioxobutan-2-yl)-3-((S)-2-(3-(1-(tert-butylsulfonylmethyl)cyclohexyl)ureido)-2-(1-methylcyclohexyl)acetyl)-6,6-dimethyl-3-azabicyclo[3.1.0]hexane-2-carboxamide, (1R,2S,5S)-3-((S)-2-(3-(1-(tert-butylsulfonylmethyl)cyclohexyl)ureido)-2-(1-methylcyclohexyl)acetyl)-N-((S)-5-cyclopropyl-1-(cyclopropylamino)-1,2-dioxopentan-3-yl)-6,6-dimethyl-3-azabicyclo[3.1.0]hexane-2-carboxamide, (1R,2S,5S)-3-((S)-2-(3-(1-(tert-butylsulfonylmethyl)cyclohexyl)ureido)-2-(1-methylcyclohexyl)acetyl)-N-((S)-1-(cyclopropylamino)-1,2-dioxoheptan-3-yl)-6,6-dimethyl-3-azabicyclo[3.1.0]hexane-2-carboxamide, (1R,2S,5S)-N-((S)-1-(cyclopropylamino)-1,2-dioxoheptan-3-yl)-3-((S)-3,3-dimethyl-2-(3-(1-((4-methyltetrahydro-2H-pyran-4-ylsulfonyl)methyl)cyclohexyl)ureido)butanoyl)-6,6-dimethyl-3-azabicyclo[3.1.0]hexane-2-carboxamide, (1R,2S,5S)-3-[N-({1-[(2S)-3,3-dioxido-1,3-oxathiolan-2-yl]cyclohexyl}carbamoyl)-3-methyl-L-valyl]-N-[(3S)-1,2-dioxo-1-(prop-2-en-1-ylamino)heptan-3-yl]-6,6-dimethyl-3-azabicyclo[3.1.0]hexane-2-carboxamide, (1R,2S,5S)- N-[(3S)-1-(cyclopropylamino)-1,2-dioxoheptan-3-yl]-3-[N-({1-[(2R)-1,1-dioxidotetrahydrothiophen-2-yl]cyclohexyl}carbamoyl)-3-methyl-L-valyl]-6,6-dimethyl-3-azabicyclo[3.1.0]hexane-2-carboxamide, (1R,2S,5S)-3-[N-({1-[(2R)-1,1-dioxidotetrahydrothiophen-2-yl]cyclohexyl}carbamoyl)-3-methyl-L-valyl]-N-[(3S)-1,2-dioxo-1-(prop-2-en-1-ylamino)heptan-3-yl]-6,6-dimethyl-3-azabicyclo[3.1.0]hexane-2-carboxamide, (1R,2S,5S)-N-[(2S)-1-cyclopropyl-3,4-dioxo-4-(prop-2-en-1-ylamino)butan-2-yl]-3-[N-({1-[(2S)-1,1-dioxidotetrahydro-2H-thiopyran-2-yl]cyclohexyl}carbamoyl)-3-methyl-L-valyl]-6,6-dimethyl-3-azabicyclo[3.1.0]hexane-2-carboxamide, or (1R,2S,5S)-3-[N-({1-[(3R)-4,4-dioxido-1,4-oxathian-3-yl]cyclohexyl}carbamoyl)-3-methyl-L-valyl]-N-[(3S)-1,2-dioxo-1-(prop-2-en-1-ylamino)heptan-3-yl]-6,6-dimethyl-3-azabicyclo[3.1.0]hexane-2-carboxamide.

2. The product of claim 1, wherein the HCV inhibitor is selected from:

6-[3-cyano-6-(difluoromethoxy)-1-(propan-2-yl)-1H-indol-2-yl]-N-(propan-2-yl)pyridine-3-sulfonamide, 6-[3-cyano-6-(difluoromethoxy)-1-(propan-2-yl)-1H-indol-2-yl]-N-cyclobutylpyridine-3-sulfonamide, 6-[3-cyano-6-(difluoromethoxy)-1-propyl-1H-indol-2-yl]-N-(propan-2-yl)pyridine-3-sulfonamide, 5-[3-cyano-1-cyclobutyl-6-(cyclobutyloxy)-1H-indol-2-yl]-N-(propan-2-yl)pyridine-2-sulfonamide, 6-(3-cyano-1-cyclobutyl-5-fluoro-1H-indol-2-yl)-N-(propan-2-yl)pyridine-3-sulfonamide, 6-[3-cyano-1-(cyclopropylmethyl)-5-fluoro-1H-indol-2-yl]-N-(propan-2-yl)pyridine-3-sulfonamide, 6-(3-cyano-1-cyclobutyl-6-cyclopropyl-1H-indol-2-yl)-N-(propan-2-yl)pyridine-3-sulfonamide, 6-(3-cyano-1-cyclobutyl-5-cyclopropyl-1H-indol-2-yl)-N-(propan-2-yl)pyridine-3-sulfonamide, N-tert-butyl-6-(3-cyano-1-cyclobutyl-5-fluoro-1H-indol-2-yl)pyridine-3-sulfonamide, 6-[3-cyano-1-cyclobutyl-6-(trifluoromethoxy)-1H-indol-2-yl]-N-(propan-2-yl)pyridine-3-sulfonamide, 6-[3-cyano-1-(cyclopropylmethyl)-6-(trifluoromethoxy)-1H-indol-2-yl]-N-(propan-2-yl)pyridine-3-sulfonamide, 6-[3-cyano-1-(propan-2-yl)-6-(trifluoromethoxy)-1H-indol-2-yl]-N-(propan-2-yl)pyridine-3-sulfonamide, 6-[3-cyano-1-(cyclopropylmethyl)-6-(difluoromethoxy)-1H-indol-2-yl]-N-(propan-2-yl)pyridine-3-sulfonamide, 6-(5-chloro-3-cyano-1-cyclobutyl-1H-indol-2-yl)-N-(propan-2-yl)pyridine-3-sulfonamide, N-tert-butyl-6-(5-chloro-3-cyano-1-cyclobutyl-1H-indol-2-yl)pyridine-3-sulfonamide, 6-[3-cyano-1-cyclobutyl-6-(propan-2-ylsulfanyl)-1H-indol-2-yl]-N-(propan-2-yl)pyridine-3-sulfonamide, 6-[3-cyano-1-cyclopentyl-6-(trifluoromethoxy)-1H-indol-2-yl]-N-(propan-2-yl)pyridine-3-sulfonamide, N-tert-butyl-6-[3-cyano-1-cyclopentyl-6-(trifluoromethoxy)-1H-indol-2-yl]pyridine-3-sulfonamide, 6-[3-cyano-1-cyclobutyl-5-(difluoromethoxy)-1H-indol-2-yl]-N-(propan-2-yl)pyridine-3-sulfonamide, N-tert-butyl-6-[3-cyano-1-cyclobutyl-5-(difluoromethoxy)-1H-indol-2-yl]pyridine-3-sulfonamide, 6-[3-cyano-1-cyclopentyl-5-(difluoromethoxy)-1H-indol-2-yl]-N-(propan-2-yl)pyridine-3-sulfonamide, 6-[3-cyano-1-cyclobutyl-5-(trifluoromethoxy)-1H-indol-2-yl]-N-(propan-2-yl)pyridine-3-sulfonamide, 6-[3-cyano-1-cyclobutyl-6-(trifluoromethoxy)-1H-indol-2-yl]-N-(1,3-difluoropropan-2-yl)pyridine-3-sulfonamide,
6-[3-cyano-1-cyclobutyl-5-(trifluoromethoxy)-1H-indol-2-yl]-N-(1,3-difluoropropan-2-yl)pyridine-3-sulfonamide,
5-[3-cyano-1-cyclobutyl-6-(trifluoromethoxy)-1H-indol-2-yl]-N-(propan-2-yl)pyridine-2-sulfonamide,
5-(3-cyano-1-cyclobutyl-6-cyclopropyl-1H-indol-2-yl)-N-(propan-2-yl)pyridine-2-sulfonamide,
5-(5-chloro-3-cyano-1-cyclobutyl-1H-indol-2-yl)-N-(propan-2-yl)pyridine-2-sulfonamide,
6-(3-cyano-1-cyclobutyl-5-fluoro-1H-indol-2-yl)-N-(1,3-difluoropropan-2-yl)pyridine-3-sulfonamide,
6-(5-chloro-3-cyano-1-cyclobutyl-1H-indol-2-yl)-N-(1,3-difluoropropan-2-yl)pyridine-3-sulfonamide,
6-[3-cyano-1-cyclobutyl-6-(difluoromethoxy)-1H-indol-2-yl]-N-(1,3-difluoropropan-2-yl)pyridine-3-sulfonamide,
6-[3-cyano-1-cyclobutyl-5-(difluoromethoxy)-1H-indol-2-yl]-N-(1,3-difluoropropan-2-yl)pyridine-3-sulfonamide,
6-[3-cyano-1-cyclopentyl-5-(difluoromethoxy)-1H-indol-2-yl]-N-(1,3-difluoropropan-2-yl)pyridine-3-sulfonamide,
6-[3-cyano-1-cyclopentyl-5-(trifluoromethoxy)-1H-indol-2-yl]-N-(1,3-difluoropropan-2-yl)pyridine-3-sulfonamide,
6-(3-cyano-1-cyclobutyl-6-cyclopropyl-1H-indol-2-yl)-N-(1,3-difluoropropan-2-yl)pyridine-3-sulfonamide,
6-[3-cyano-6-(difluoromethoxy)-1-(propan-2-yl)-1H-indol-2-yl]-N-(1,3-difluoropropan-2-yl)pyridine-3-sulfonamide,
6-(6-chloro-3-cyano-1-cyclobutyl-1H-indol-2-yl)-N-(1,3-difluoropropan-2-yl)pyridine-3-sulfonamide,
6-(3-cyano-1-cyclopentyl-5-fluoro-1H-indol-2-yl)-N-(1,3-difluoropropan-2-yl)pyridine-3-sulfonamide,
5-[3-cyano-1-cyclopropyl-6-(difluoromethoxy)-1H-indol-2-yl]-N-(propan-2-yl)pyridine-2-sulfonamide,
5-[3-cyano-1-(cyclopropylmethyl)-6-(difluoromethoxy)-1H-indol-2-yl]-N-(propan-2-yl)pyridine-2-sulfonamide,
6-[3-cyano-1-(cyclopropylmethyl)-6-(difluoromethoxy)-1H-indol-2-yl]-N-(1,3-difluoropropan-2-yl)pyridine-3-sulfonamide,
6-[3-cyano-1-cyclopropyl-6-(difluoromethoxy)-1H-indol-2-yl]-N-(1,3-difluoropropan-2-yl)pyridine-3-sulfonamide,
6-[3-cyano-1-cyclobutyl-6-(propan-2-yl)-1H-indol-2-yl]-N-(1,3-difluoropropan-2-yl)pyridine-3-sulfonamide,
6-(3-cyano-1-cyclopentyl-6-methyl-1H-indol-2-yl)-N-(1,3-difluoropropan-2-yl)pyridine-3-sulfonamide,
6-[3-cyano-6-(difluoromethoxy)-1-propyl-1H-indol-2-yl]-N-(1,3-difluoropropan-2-yl)pyridine-3-sulfonamide,
6-[3-cyano-5-fluoro-1-(tetrahydrofuran-3-yl)-1H-indol-2-yl]-N-(1,3-difluoropropan-2-yl)pyridine-3-sulfonamide,
6-[3-cyano-5-fluoro-1-(tetrahydrofuran-3-yl)-1H-indol-2-yl]-N-(propan-2-yl)pyridine-3-sulfonamide,
6-(3-cyano-1-cyclobutyl-6-ethyl-1H-indol-2-yl)-N-(1,3-difluoropropan-2-yl)pyridine-3-sulfonamide,
6-[3-cyano-1-cyclopentyl-6-(difluoromethoxy)-1H-indol-2-yl]-N-(1,3-difluoropropan-2-yl)pyridine-3-sulfonamide,
6-(6-chloro-3-cyano-1-cyclobutyl-5-fluoro-1H-indol-2-yl)-N-(1,3-difluoropropan-2-yl)pyridine-3-sulfonamide,
6-[3-cyano-1-cyclobutyl-6-(difluoromethoxy)-1H-indol-2-yl]-N-(propan-2-yl)pyridine-3-sulfonamide,
6-[3-cyano-1-cyclopentyl-6-(difluoromethoxy)-1H-indol-2-yl]-N-(propan-2-yl)pyridine-3-sulfonamide,
6-[3-cyano-1-cyclopentyl-6-(difluoromethoxy)-1H-indol-2-yl]-N-(1,1,1-trifluoropropan-2-yl)pyridine-3-sulfonamide,
6-{3-cyano-6-methyl-1-[(3R)-tetrahydrofuran-3-yl]-1H-indol-2-yl}-N-(1,3-difluoropropan-2-yl)pyridine-3-sulfonamide,
6-{3-cyano-6-methyl-1-[(3R)-tetrahydrofuran-3-yl]-1H-indol-2-yl}-N-(propan-2-yl)pyridine-3-sulfonamide,
6-(3-cyano-1-cyclobutyl-6-fluoro-1H-indol-2-yl)-N-(1,3-difluoropropan-2-yl)pyridine-3-sulfonamide,
6-[3-cyano-1-(cyclopropylmethyl)-6-fluoro-1H-indol-2-yl]-N-(1,3-difluoropropan-2-Apyridine-3-sulfonamide,
6-[3-cyano-1-(cyclopropylmethyl)-5-fluoro-1H-indol-2-yl]-N-(1,3-difluoropropan-2-Apyridine-3-sulfonamide,
6-[3-cyano-1-cyclobutyl-6-(2,2-difluoroethoxy)-1H-indol-2-yl]-N-(propan-2-yl)pyridine-3-sulfonamide,
6-[3-cyano-5-fluoro-1-(propan-2-yl)-1H-indol-2-yl]-N-(1,3-difluoropropan-2-yl)pyridine-3-sulfonamide,
6-[3-cyano-6-fluoro-1-(propan-2-yl)-1H-indol-2-yl]-N-(1,3-difluoropropan-2-yl)pyridine-3-sulfonamide,
6-[6-chloro-3-cyano-1-(cyclopropylmethyl)-1H-indol-2-yl]-N-(1,3-difluoropropan-2-yl)pyridine-3-sulfonamide,
6-[6-chloro-3-cyano-1-(propan-2-yl)-1H-indol-2-yl]-N-(1,3-difluoropropan-2-yl)pyridine-3-sulfonamide,
6-(6-chloro-3-cyano-1-cyclopentyl-1H-indol-2-yl)-N-(1,3-difluoropropan-2-yl)pyridine-3-sulfonamide,
6-[5-chloro-3-cyano-1-(propan-2-yl)-1H-indol-2-yl]-N-(1,3-difluoropropan-2-yl)pyridine-3-sulfonamide,
6-(3-cyano-1-cyclopentyl-7-fluoro-1H-indol-2-yl)-N-(propan-2-yl)pyridine-3-sulfonamide,
6-[3-cyano-1-cyclopentyl-6-(difluoromethoxy)-1H-indol-2-yl]-N-(1-fluoro-2-methylpropan-2-yl)pyridine-3-sulfonamide,
6-[3-cyano-1-(cyclopropylmethyl)-6-(trifluoromethoxy)-1H-indol-2-yl]-N-(1,3-difluoropropan-2-yl)pyridine-3-sulfonamide,
6-[3-cyano-1-(propan-2-yl)-6-(trifluoromethoxy)-1H-indol-2-yl]-N-(1,3-difluoropropan-2-yl)pyridine-3-sulfonamide,
6-[3-cyano-1-cyclopentyl-6-(trifluoromethoxy)-1H-indol-2-yl]-N-(1,3-difluoropropan-2-yl)pyridine-3-sulfonamide,
2-(3-cyano-1-cyclobutyl-6-cyclopropyl-1H-indol-2-yl)-N-(propan-2-yl)pyrimidine-5-sulfonamide,
6-(5-chloro-3-cyano-1-cyclopentyl-1H-indol-2-yl)-N-(1,3-difluoropropan-2-yl)pyridine-3-sulfonamide,
6-[5-chloro-3-cyano-1-(cyclopropylmethyl)-1H-indol-2-yl]-N-(1,3-difluoropropan-2-yl)pyridine-3-sulfonamide,
2-(3-cyano-1-cyclopentyl-6-methyl-1H-indol-2-yl)-N-(propan-2-yl)pyrimidine-5-sulfonamide,
6-[3-cyano-6-ethyl-1-(propan-2-yl)-1H-indol-2-yl]-N-(propan-2yl)pyridine-3-sulfonamide,
6-[3-cyano-1-cyclobutyl-6-(difluoromethoxy)-1H-indol-2-yl]-N-(1-fluoro-2-methylpropan-2-yl)pyridine-3-sulfonamide,
6-[3-cyano-1-cyclobutyl-6-(difluoromethoxy)-1H-indol-2-yl]-N-(1,1,1-trifluoropropan-2-yl)pyridine-3-sulfonamide, 6-(5-chloro-3-cyano-1-cyclohexyl-1H-indol-2-yl)-N-(1,3-difluoropropan-2-yl)pyridine-3-sulfonamide,
6-[3-cyano-6-methyl-1-(propan-2-yl)-1H-indol-2-yl]-N-(1,3-difluoropropan-2-yl)pyridine-3-sulfonamide,
6-[3-cyano-1-(cyclopropylmethyl)-6-methyl-1H-indol-2-yl]-N-(1,3-difluoropropan-2-yl)pyridine-3-sulfonamide,
6-(3-cyano-1-cyclobutyl-6-methyl-1H-indol-2-yl)-N-(1,3-difluoropropan-2-yl)pyridine-3-sulfonamide,
6-[3-cyano-6-cyclopropyl-1-(propan-2-yl)-1H-indol-2-yl]-N-(1,3-difluoropropan-2-yl)pyridine-3-sulfonamide,
6-[3-cyano-6-cyclopropyl-1-(cyclopropylmethyl)-1H-indol-2-yl]-N-(1,3-difluoropropan-2-yl)pyridine-3-sulfonamide,
6-(3-cyano-1-cyclopentyl-6-cyclopropyl-1H-indol-2-yl)-N-(1,3-difluoropropan-2-yl)pyridine-3-sulfonamide,
6-(3-cyano-1-cyclopentyl-6-cyclopropyl-1H-indol-2-yl)-N-(1,1,1-trifluoropropan-2-yl)pyridine-3-sulfonamide,
6-(3-cyano-1-cyclopentyl-7-fluoro-1H-indol-2-yl)-N-(1,3-difluoropropan-2-yl)pyridine-3-sulfonamide,
6-(7-chloro-3-cyano-1-cyclopentyl-1H-indol-2-yl)-N-(1,3-difluoropropan-2-yl)pyridine-3-sulfonamide,
6-(6-chloro-3-cyano-1-cyclohexyl-1H-indol-2-yl)-N-(1,3-difluoropropan-2-yl)pyridine-3-sulfonamide,
6-(3-cyano-1-cyclobutyl-6-cyclopropyl-1H-indol-2-yl)pyridine-3-sulfonamide,
6-(3-cyano-1-cyclohexyl-6-cyclopropyl-1H-indol-2-yl)-N-(1,3-difluoropropan-2-yl)pyridine-3-sulfonamide,
6-[3-cyano-1-cyclobutyl-6-(difluoromethoxy)-1H-indol-2-yl]-N-[1-(trifluoromethyl)cyclopropyl]pyridine-3-sulfonamide,
6-[3-cyano-1-cyclopentyl-6-(difluoromethoxy)-1H-indol-2-yl]-N-[1-(trifluoromethyl)cyclopropyl]pyridine-3-sulfonamide,
6-(3-cyano-6-cyclopropyl-1-phenyl-1H-indol-2-yl)-N-(1,3-difluoropropan-2-yl)pyridine-3-sulfonamide,
6-[3-cyano-5-fluoro-1-(pyridin-2-yl)-1H-indol-2-yl]-N-(1,3-difluoropropan-2-yl)pyridine-3-sulfonamide,
2-(5-chloro-3-cyano-1-cyclohexyl-1H-indol-2-yl)-N-(propan-2-yl)pyrimidine-5-sulfonamide,
2-(3-cyano-1-cyclohexyl-6-methyl-1H-indol-2-yl)-N-(propan-2-yl)pyrimidine-5-sulfonamide,
6-[3-cyano-1-cyclohexyl-6-(difluoromethoxy)-1H-indol-2-yl]-N-(propan-2-yl)pyridine-3-sulfonamide,
6-[3-cyano-1-cyclohexyl-6-(difluoromethoxy)-1H-indol-2-yl]-N-(1,3-difluoropropan-2-yl)pyridine-3-sulfonamide,
6-(3-cyano-1-cyclobutyl-5-fluoro-6-methoxy-1H-indol-2-yl)-N-(propan-2-yl)pyridine-3-sulfonamide,
6-(3-cyano-1-cyclobutyl-5-fluoro-6-methoxy-1H-indol-2-yl)-N-(1,3-difluoropropan-2-yl)pyridine-3-sulfonamide,
6-[3-cyano-1-cyclobutyl-6-(2,2-difluoroethenyl)-1H-indol-2-yl]-N-(1,3-difluoropropan-2-yl)pyridine-3-sulfonamide,
6-(3-cyano-1-cyclohexyl-5-fluoro-1H-indol-2-yl)-N-(1,3-difluoropropan-2-yl)pyridine-3-sulfonamide,
6-[3-cyano-1-cyclohexyl-6-(trifluoromethoxy)-1H-indol-2-yl]-N-(1,3-difluoropropan-2-yl)pyridine-3-sulfonamide,
6-[3-cyano-1-cyclobutyl-6-(difluoromethoxy)-1H-indol-2-yl]-N-[1-(trifluoromethyl)cyclobutyl]pyridine-3-sulfonamide,
6-(3-cyano-1-cyclobutyl-6-cyclopropyl-5-fluoro-1H-indol-2-yl)-N-(1,3-difluoropropan-2-yl)pyridine-3-sulfonamide,
6-(3-cyano-1-cyclobutyl-5-fluoro-6-methyl-1H-indol-2-yl)-N-(1,3-difluoropropan-2-yl)pyridine-3-sulfonamide,
6-(3-cyano-1,6-dicyclopropyl-1H-indol-2-yl)-N-(propan-2-yl)pyridine-3-sulfonamide,
6-[6-chloro-3-cyano-1-(cyclopropylmethyl)-5-fluoro-1H-indol-2-yl]-N-(1,3-difluoropropan-2-yl)pyridine-3-sulfonamide,
6-(3-cyano-6-methyl-1-phenyl-1H-indol-2-yl)-N-(1,3-difluoropropan-2-yl)pyridine-3-sulfonamide,
6-(5-chloro-3-cyano-1-phenyl-1H-indol-2-yl)-N-(1,3-difluoropropan-2-yl)pyridine-3-sulfonamide,
6-(3-cyano-5-fluoro-1-phenyl-1H-indol-2-yl)-N-(1,3-difluoropropan-2-yl)pyridine-3-sulfonamide,
2-(5-chloro-3-cyano-1-cyclobutyl-1H-indol-2-yl)-N-(propan-2-yl)pyrimidine-5-sulfonamide,
2-(6-chloro-3-cyano-1-cyclobutyl-1H-indol-2-yl)-N-(propan-2-yl)pyrimidine-5-sulfonamide,
2-[3-cyano-1-cyclobutyl-6-(trifluoromethoxy)-1H-indol-2-yl]-N-(propan-2-yl)pyrimidine-5-sulfonamide,
2-[3-cyano-1-cyclopentyl-6-(trifluoromethoxy)-1H-indol-2-yl]-N-(propan-2-yl)pyrimidine-5-sulfonamide,
6-(5-chloro-3-cyano-1-cyclopentyl-1H-indol-2-yl)-N-[(1S)-1-cyclopropylethyl]pyridine-3-sulfonamide,
6-(5-chloro-3-cyano-1-cyclobutyl-1H-indol-2-yl)-N-[(1S)-1-cyclopropylethyl]pyridine-3-sulfonamide,
2-[5-chloro-3-cyano-1-(propan-2-yl)-1H-indol-2-yl]-N-(propan-2-yl)pyrimidine-5-sulfonamide,
2-(3-cyano-1-cyclobutyl-5-methyl-1H-indol-2-yl)-N-(propan-2-yl)pyrimidine-5-sulfonamide,
2-(3-cyano-1-cyclobutyl-5-methyl-1H-indol-2-yl)-N-(1,3-difluoropropan-2-yl)pyrimidine-5-sulfonamide,
2-[3-cyano-5-fluoro-1-(propan-2-yl)-1H-indol-2-yl]-N-(propan-2-yl)pyrimidine-5-sulfonamide,
2-[3-cyano-6-cyclopropyl-1-(cyclopropylmethyl)-1H-indol-2-yl]-N-(propan-2-yl)pyrimidine-5-sulfonamide,
2-(3-cyano-1-cyclopentyl-6-cyclopropyl-1H-indol-2-yl)-N-(propan-2-yl)pyrimidine-5-sulfonamide,
2-(3-cyano-1-cyclobutyl-6-cyclopropyl-1H-indol-2-yl)-N-(1,3-difluoropropan-2-yl)pyrimidine-5-sulfonamide,
2-[3-cyano-1-cyclobutyl-6-(difluoromethoxy)-1H-indol-2-yl]-N-(propan-2-yl)pyrimidine-5-sulfonamide,
2-[3-cyano-1-cyclobutyl-6-(difluoromethoxy)-1H-indol-2-yl]-N-(1,1,1-trifluoropropan-2-yl)pyrimidine-5-sulfonamide,
2-[3-cyano-1-cyclobutyl-6-(difluoromethoxy)-1H-indol-2-yl]-N-(1,3-difluoropropan-2-yl)pyrimidine-5-sulfonamide,
2-[3-cyano-1-cyclobutyl-6-(difluoromethoxy)-1H-indol-2-yl]-N-[(1S)-1-cyclopropylethyl]pyrimidine-5-sulfonamide,
2-(3-cyano-1-cyclobutyl-6-cyclopropyl-1H-indol-2-yl)-N-[(1S)-1-cyclopropylethyl]pyrimidine-5-sulfonamide,
2-(3-cyano-1-cyclobutyl-6-methyl-1H-indol-2-yl)-N-(1,3-difluoropropan-2-yl)pyrimidine-5-sulfonamide,
2-[3-cyano-1-(cyclopropylmethyl)-6-methyl-1H-indol-2-yl]-N-(1,3-difluoropropan-2-yl)pyrimidine-5-sulfonamide,
2-[3-cyano-6-methyl-1-(propan-2-yl)-1H-indol-2-yl]-N-(1,3-difluoropropan-2-yl)pyrimidine-5-sulfonamide,
2-(3-cyano-1-cyclopentyl-6-methyl-1H-indol-2-yl)-N-(1,3-difluoropropan-2-yl)pyrimidine-5-sulfonamide,
2-[3-cyano-1-(cyclopropylmethyl)-6-(difluoromethoxy)-1H-indol-2-yl]-N-(1,3-difluoropropan-2-yl)pyrimidine-5-sulfonamide, 2-[3-cyano-6-(difluoromethoxy)-1-(propan-2-yl)-1H-indol-2-yl]-N-(1,3-difluoropropan-2-yl)pyrimidine-5-sulfonamide,
2-(3-cyano-1-cyclobutyl-6-fluoro-1H-indol-2-yl)-N-(propan-2-yl)pyrimidine-5-sulfonamide,
2-[3-cyano-1-(cyclopropylmethyl)-6-fluoro-1H-indol-2-yl]-N-(propan-2-yl)pyrimidine-5-sulfonamide,
2-[3-cyano-6-fluoro-1-(propan-2-yl)-1H-indol-2-yl]-N-(propan-2-yl)pyrimidine-5-sulfonamide,
2-(3-cyano-1-cyclopentyl-6-fluoro-1H-indol-2-yl)-N-(propan-2-yl)pyrimidine-5-sulfonamide,
6-(3-cyano-1-cyclobutyl-5-fluoro-1H-indol-2-yl)-N-[(1S)-1-cyclopropylethyl]pyridine-3-sulfonamide,
6-(3-cyano-1-cyclopentyl-5-fluoro-1H-indol-2-yl)-N-[(1S)-1-cyclopropylethyl]pyridine-3-sulfonamide,
6-(3-cyano-1-cyclobutyl-6-fluoro-1H-indol-2-yl)-N-[(1S)-1-cyclopropylethyl]pyridine-3-sulfonamide,
2-(3-cyano-1-cyclobutyl-6-cyclopropyl-5-fluoro-1H-indol-2-yl)-N-(1,3-difluoropropan-2-yl)pyrimidine-5-sulfonamide,
2-(3-cyano-1-cyclobutyl-5-fluoro-6-methyl-1H-indol-2-yl)-N-(1,3-difluoropropan-2-yl)pyrimidine-5-sulfonamide,
6-(3-cyano-1,6-dicyclopropyl-1H-indol-2-yl)-N-(1,3-difluoropropan-2-yl)pyridine-3-sulfonamide,
2-(3-cyano-1,6-dicyclopropyl-1H-indol-2-yl)-N-(1,3-difluoropropan-2-yl)pyrimidine-5-sulfonamide,
2-(6-chloro-3-cyano-1-cyclobutyl-5-fluoro-1H-indol-2-yl)-N-(1,3-difluoropropan-2-yl)pyrimidine-5-sulfonamide,
2-(3-cyano-1-cyclobutyl-5-fluoro-6-methoxy-1H-indol-2-yl)-N-(1,3-difluoropropan-2-yl)pyrimidine-5-sulfonamide,
6-[3-cyano-1-cyclobutyl-6-(difluoromethoxy)-1H-indol-2-yl]-N-[(1S)-1-cyclopropylethyl]pyridine-3-sulfonamide,
6-[3-cyano-1-cyclobutyl-6-(trifluoromethoxy)-1H-indol-2-yl]-N-[(1S)-1-cyclopropylethyl]pyridine-3-sulfonamide,
6-(3-cyano-1-cyclobutyl-6-cyclopropyl-1H-indol-2-yl)-N-[1-(trifluoromethyl)cyclopropyl]pyridine-3-sulfonamide,
6-(6-chloro-3-cyano-1-cyclobutyl-1H-indol-2-yl)-N-[(1S)-1-cyclopropylethyl]pyridine-3-sulfonamide,
6-(6-chloro-3-cyano-1-cyclopentyl-1H-indol-2-yl)-N-[(1S)-1-cyclopropylethyl]pyridine-3-sulfonamide,
2-[6-chloro-3-cyano-1-(propan-2-yl)-1H-indol-2-yl]-N-(propan-2-yl)pyrimidine-5-sulfonamide,
2-(6-chloro-3-cyano-1-cyclopentyl-1H-indol-2-yl)-N-(1,3-difluoropropan-2-yl)pyrimidine-5-sulfonamide,
6-(3-cyano-1-cyclopentyl-5-methyl-1H-indol-2-yl)-N-(1,3-difluoropropan-2-yl)pyridine-3-sulfonamide,
2-(3-cyano-1-cyclopentyl-5-methyl-1H-indol-2-yl)-N-(propan-2-yl)pyrimidine-5-sulfonamide,
2-(3-cyano-1-cyclopentyl-5-methyl-1H-indol-2-yl)-N-(1,3-difluoropropan-2-yl)pyrimidine-5-sulfonamide,
6-[3-cyano-1-cyclobutyl-6-(methylsulfanyl)-1H-indol-2-yl]-N-(1,3-difluoropropan-2-yl)pyridine-3-sulfonamide,
2-[3-cyano-1-cyclobutyl-6-(methylsulfanyl)-1H-indol-2-yl]-N-(1,3-difluoropropan-2-yl)pyrimidine-5-sulfonamide,
2-(3-cyano-1-cyclobutyl-6-fluoro-1H-indol-2-yl)-N-(1,3-difluoropropan-2-yl)pyrimidine-5-sulfonamide,
2-[3-cyano-1-(cyclopropylmethyl)-6-fluoro-1H-indol-2-yl]-N-(1,3-difluoropropan-2-yl)pyrimidine-5-sulfonamide,
2-[3-cyano-6-fluoro-1-(propan-2-yl)-1H-indol-2-yl]-N-(1,3-difluoropropan-2-yl)pyrimidine-5-sulfonamide,
2-(3-cyano-1-cyclopentyl-6-fluoro-1H-indol-2-yl)-N-(1,3-difluoropropan-2-yl)pyrimidine-5-sulfonamide,
2-[3-cyano-6-methyl-1-(propan-2-yl)-1H-indol-2-yl]-N-(propan-2-yl)pyrimidine-5-sulfonamide,
2-[3-cyano-1-(cyclopropylmethyl)-6-methyl-1H-indol-2-yl]-N-(propan-2-yl)pyrimidine-5-sulfonamide,
2-(3-cyano-1-cyclobutyl-6-methyl-1H-indol-2-yl)-N-(propan-2-yl)pyrimidine-5-sulfonamide,
2-[3-cyano-1-(cyclopropylmethyl)-6-(difluoromethoxy)-1H-indol-2-yl]-N-(propan-2-yl)pyrimidine-5-sulfonamide,
2-[3-cyano-6-(difluoromethoxy)-1-(propan-2-yl)-1H-indol-2-yl]-N-(propan-2-yl)pyrimidine-5-sulfonamide,
2-(3-cyano-1-cyclobutyl-6-methoxy-1H-indol-2-yl)-N-(propan-2-yl)pyrimidine-5-sulfonamide,
2-(3-cyano-1-cyclopentyl-6-cyclopropyl-1H-indol-2-yl)-N-(1,3-difluoropropan-2-yl)pyrimidine-5-sulfonamide,
6-[3-cyano-1-cyclopentyl-6-(difluoromethoxy)-1H-indol-2-yl]-N-[(1S)-1-cyclopropylethyl]pyridine-3-sulfonamide,
2-(5-chloro-3-cyano-1-cyclobutyl-1H-indol-2-yl)-N-(1,3-difluoropropan-2-yl)pyrimidine-5-sulfonamide,
2-(6-chloro-3-cyano-1-cyclobutyl-1H-indol-2-yl)-N-(1,3-difluoropropan-2-yl)pyrimidine-5-sulfonamide,
2-[3-cyano-1-cyclobutyl-6-(trifluoromethoxy)-1H-indol-2-yl]-N-(1,3-difluoropropan-2-yl)pyrimidine-5-sulfonamide,
2-[3-cyano-1-cyclopentyl-6-(trifluoromethoxy)-1H-indol-2-yl]-N-(1,3-difluoropropan-2-yl)pyrimidine-5-sulfonamide,
2-[3-cyano-1-cyclohexyl-6-(difluoromethoxy)-1H-indol-2-yl]-N-(1,3-difluoropropan-2-yl)pyrimidine-5-sulfonamide,
2-(3-cyano-1-cyclobutyl-6-cyclopropyl-1H-indol-2-yl)-N-[(2R)-1,1,1-trifluoropropan-2-yl]pyrimidine-5-sulfonamide,
2-(3-cyano-1-cyclobutyl-6-methyl-1H-indol-2-yl)-N-[(2R)-1,1,1-trifluoropropan-2-yl]pyrimidine-5-sulfonamide,
2-(3-cyano-1-cyclopentyl-6-methyl-1H-indol-2-yl)-N-[(2R)-1,1,1-trifluoropropan-2-yl]pyrimidine-5-sulfonamide,
2-(3-cyano-1-cyclobutyl-6-methoxy-1H-indol-2-yl)-N-[(2R)-1,1,1-trifluoropropan-2-yl]pyrimidine-5-sulfonamide,
2-[3-cyano-1-cyclobutyl-6-(difluoromethoxy)-1H-indol-2-yl]-N-[(2R)-1,1,1-trifluoropropan-2-yl]pyrimidine-5-sulfonamide,
2-[3-cyano-1-cyclobutyl-6-(propan-2-yl)-1H-indol-2-yl]-N-(propan-2-yl)pyrimidine-5-sulfonamide,
2-[3-cyano-1-cyclobutyl-6-(propan-2-yl)-1H-indol-2-yl]-N-(1,3-difluoropropan-2-yl)pyrimidine-5-sulfonamide,
2-[5-chloro-3-cyano-1-(propan-2-yl)-1H-indol-2-yl]-N-(1,3-difluoropropan-2-yl)pyrimidine-5-sulfonamide,
2-(5-chloro-3-cyano-1-cyclopentyl-1H-indol-2-yl)-N-(1,3-difluoropropan-2-yl)pyrimidine-5-sulfonamide,
2-(6-chloro-3-cyano-1-cyclopentyl-1H-indol-2-yl)-N-(propan-2-yl)pyrimidine-5-sulfonamide,
6-(3-cyano-1-cyclopentyl-6-methyl-1H-indol-2-yl)-N-[1-(trifluoromethyl)cyclopropyl]pyridine-3-sulfonamide,
6-[3-cyano-1-cyclobutyl-6-(trifluoromethoxy)-1H-indol-2-yl]-N-[(2R)-1,1,1-trifluoropropan-2-yl]pyridine-3-sulfonamide, 6-(3-cyano-1-cyclobutyl-6-methyl-1H-indol-2-yl)-N-[(2R)-1,1,1-trifluoropropan-2-yl]pyridine-3-sulfonamide, 2-(3-cyano-1-cyclohexyl-6-cyclopropyl-1H-indol-2-yl)-N-(1,3-difluoropropan-2-yl)pyrimidine-5-sulfonamide, 6-[3-cyano-6-(difluoromethoxy)-1-(propan-2-yl)-1H-indol-2-yl]-N-[(2R)-1,1,1-trifluoropropan-2-yl]pyridine-3-sulfonamide, 6-[3-cyano-1-cyclohexyl-6-(difluoromethoxy)-1H-indol-2-yl]-N-[(2R)-1,1,1-trifluoropropan-2-yl]pyridine-3-sulfonamide, 6-[3-cyano-1-cyclobutyl-6-(difluoromethoxy)-1H-indol-2-yl]-N-[(2R)-1,1,1-trifluoropropan-2-yl]pyridine-3-sulfonamide, 6-[3-cyano-1-(cyclopropylmethyl)-6-methyl-1H-indol-2-yl]-N-[(2R)-1,1,1-trifluoropropan-2-yl]pyridine-3-sulfonamide, 2-(3-cyano-1-cyclohexyl-5-methyl-1H-indol-2-yl)-N-(1,3-difluoropropan-2-yl)pyrimidine-5-sulfonamide, 6-(3-cyano-1-cyclohexyl-5-methyl-1H-indol-2-yl)-N-(1,3-difluoropropan-2-yl)pyridine-3-sulfonamide, 2-(3-cyano-1-cyclohexyl-5-methyl-1H-indol-2-yl)-N-(propan-2-yl)pyrimidine-5-sulfonamide, 6-(3-cyano-1-cyclobutyl-5-methyl-1H-indol-2-yl)-N-[(1S)-1-cyclopropylethyl]pyridine-3-sulfonamide, 2-(3-cyano-1-cyclobutyl-6-methyl-1H-indol-2-yl)-N-[(1S)-1-cyclopropylethyl]pyrimidine-5-sulfonamide, 2-[3-cyano-1-(cyclopropylmethyl)-6-methyl-1H-indol-2-yl]-N-[(1S)-1-cyclopropylethyl]pyrimidine-5-sulfonamide, 2-(3-cyano-1-cyclopentyl-6-methyl-1H-indol-2-yl)-N-[(1S)-1-cyclopropylethyl]pyrimidine-5-sulfonamide, 2-(3-cyano-1-cyclobutyl-6-methoxy-1H-indol-2-yl)-N-[(1S)-1-cyclopropylethyl]pyrimidine-5-sulfonamide, 2-(3-cyano-1-cyclopentyl-6-methoxy-1H-indol-2-yl)-N-[(1S)-1-cyclopropylethyl]pyrimidine-5-sulfonamide, 2-[3-cyano-6-(difluoromethoxy)-1-(propan-2-yl)-1H-indol-2-yl]-N-[(1S)-1-cyclopropylethyl]pyrimidine-5-sulfonamide, 2-[3-cyano-6-(difluoromethoxy)-1-propyl-1H-indol-2-yl]-N-[(1S)-1-cyclopropylethyl]pyrimidine-5-sulfonamide, 2-[3-cyano-1-cyclopentyl-6-(difluoromethoxy)-1H-indol-2-yl]-N-[(1S)-1-cyclopropylethyl]pyrimidine-5-sulfonamide, 6-[3-cyano-6-methyl-1-(propan-2-yl)-1H-indol-2-yl]-N-[(2R)-1,1,1-trifluoropropan-2-yl]pyridine-3-sulfonamide, 6-(3-cyano-1-cyclopentyl-6-cyclopropyl-1H-indol-2-yl)-N-[(2R)-1,1,1-trifluoropropan-2-yl]pyridine-3-sulfonamide, 6-(3-cyano-1-cyclobutyl-6-cyclopropyl-1H-indol-2-yl)-N-[(2R)-1,1,1-trifluoropropan-2-yl]pyridine-3-sulfonamide, 6-(3-cyano-1-cyclohexyl-6-methyl-1H-indol-2-yl)-N-[(2R)-1,1,1-trifluoropropan-2-yl]pyridine-3-sulfonamide, 6-(3-cyano-1-cyclopentyl-6-methyl-1H-indol-2-yl)-N-[(2R)-1,1,1-trifluoropropan-2-yl]pyridine-3-sulfonamide, 6-(3-cyano-1-cyclobutyl-6-fluoro-1H-indol-2-yl)-N-[(2R)-1,1,1-trifluoropropan-2-yl]pyridine-3-sulfonamide, 6-[3-cyano-1-(cyclopropylmethyl)-6-fluoro-1H-indol-2-yl]-N-[(2R)-1,1,1-trifluoropropan-2-yl]pyridine-3-sulfonamide, 6-(3-cyano-6-fluoro-1-propyl-1H-indol-2-yl)-N-[(2R)-1,1,1-trifluoropropan-2-yl]pyridine-3-sulfonamide, 6-(3-cyano-1-cyclopentyl-6-fluoro-1H-indol-2-yl)-N-[(2R)-1,1,1-trifluoropropan-2-yl]pyridine-3-sulfonamide, 6-(3-cyano-1-cyclobutyl-5-fluoro-1H-indol-2-yl)-N-[(2R)-1,1,1-trifluoropropan-2-yl]pyridine-3-sulfonamide, 6-(3-cyano-1-cyclopentyl-5-fluoro-1H-indol-2-yl)-N-[(2R)-1,1,1-trifluoropropan-2-yl]pyridine-3-sulfonamide, 2-[5-chloro-3-cyano-1-(cyclopropylmethyl)-1H-indol-2-yl]-N-(1,3-difluoropropan-2-yl)pyrimidine-5-sulfonamide, 6-(6-chloro-3-cyano-1-cyclobutyl-1H-indol-2-yl)-N-[(2R)-1,1,1-trifluoropropan-2-yl]pyridine-3-sulfonamide, 6-(6-chloro-3-cyano-1-cyclopentyl-1H-indol-2-yl)-N-[(2R)-1,1,1-trifluoropropan-2-yl]pyridine-3-sulfonamide, 6-(5-chloro-3-cyano-1-cyclopentyl-1H-indol-2-yl)-N-[(2R)-1,1,1-trifluoropropan-2-yl]pyridine-3-sulfonamide, 6-[3-cyano-1-(cyclopropylmethyl)-5-fluoro-6-methoxy-1H-indol-2-yl]-N-(1,3-difluoropropan-2-yl)pyridine-3-sulfonamide, 6-[3-cyano-6-(difluoromethoxy)-1-phenyl-1H-indol-2-yl]-N-(1,3-difluoropropan-2-yl)pyridine-3-sulfonamide, 6-[3-cyano-6-(difluoromethoxy)-1-(2-fluorophenyl)-1H-indol-2-yl]-N-(1,3-difluoropropan-2-yl)pyridine-3-sulfonamide, 6-[3-cyano-6-(difluoromethoxy)-1-(4-fluorophenyl)-1H-indol-2-yl]-N-(1,3-difluoropropan-2-yl)pyridine-3-sulfonamide, 6-(3-cyano-1-cyclobutyl-6-methoxy-1H-indol-2-yl)-N-(1,3-difluoropropan-2-yl)pyridine-3-sulfonamide, 2-(3-cyano-1-cyclobutyl-6-methoxy-1H-indol-2-yl)-N-(1,3-difluoropropan-2-yl)pyrimidine-5-sulfonamide, 2-(3-cyano-1-cyclopentyl-6-methoxy-1H-indol-2-yl)-N-(1,3-difluoropropan-2-yl)pyrimidine-5-sulfonamide, 2-[3-cyano-6-(difluoromethoxy)-1-propyl-1H-indol-2-yl]-N-(1,3-difluoropropan-2-yl)pyrimidine-5-sulfonamide, 2-[3-cyano-1-cyclopentyl-6-(difluoromethoxy)-1H-indol-2-yl]-N-(1,3-difluoropropan-2-yl)pyrimidine-5-sulfonamide, 6-(3-cyano-1-cyclohexyl-6-fluoro-1H-indol-2-yl)-N-(1,3-difluoropropan-2-yl)pyridine-3-sulfonamide, 2-(3-cyano-1-cyclohexyl-6-fluoro-1H-indol-2-yl)-N-(1,3-difluoropropan-2-yl)pyrimidine-5-sulfonamide, 6-(3-cyano-1-cyclobutyl-6-cyclopropyl-1H-indol-2-yl)-N-[(1S)-1-cyclopropylethyl]pyridine-3-sulfonamide, 6-[3-cyano-1-(cyclopropylmethyl)-6-methyl-1H-indol-2-yl]-N-[(1S)-1-cyclopropylethyl]pyridine-3-sulfonamide, 6-(3-cyano-1-cyclobutyl-6-methyl-1H-indol-2-yl)-N-[(1S)-1-cyclopropylethyl]pyridine-3-sulfonamide, 6-[3-cyano-1-cyclobutyl-6-(difluoromethoxy)-1H-indol-2-yl]-N-(1,3-dihydroxypropan-2-yl)pyridine-3-sulfonamide, 2-(3-cyano-1-cyclopentyl-5-fluoro-1H-indol-2-yl)-N-(1,3-difluoropropan-2-yl)pyrimidine-5-sulfonamide, 2-(3-cyano-1-cyclohexyl-6-methyl-1H-indol-2-yl)-N-(1,3-difluoropropan-2-yl)pyrimidine-5-sulfonamide, 2-[3-cyano-5-(difluoromethoxy)-1-ethyl-1H-indol-2-yl]-N-(propan-2-yl)pyrimidine-5-sulfonamide, 6-(5-chloro-3-cyano-1-cyclobutyl-1H-indol-2-yl)-N-(3,3-difluorocyclobutyl)pyridine-3-sulfonamide,
6-(6-chloro-3-cyano-1-cyclobutyl-1H-indol-2-yl)-N-(3,3-difluorocyclobutyl)pyridine-3-sulfonamide,
6-(3-cyano-1-cyclobutyl-6-methyl-1H-indol-2-yl)-N-(3,3-difluorocyclobutyl)pyridine-3-sulfonamide,
6-(3-cyano-1-cyclopentyl-6-methoxy-1H-indol-2-yl)-N-(3,3-difluorocyclobutyl)pyridine-3-sulfonamide,
6-(3-cyano-1-cyclobutyl-6-cyclopropyl-1H-indol-2-yl)-N-(3,3-difluorocyclobutyl)pyridine-3-sulfonamide,
6-[3-cyano-6-methyl-1-(pyridin-2-yl)-1H-indol-2-yl]-N-(1,3-difluoropropan-2-yl)pyridine-3-sulfonamide,
6-[3-cyano-6-(difluoromethoxy)-1-(pyridin-2-yl)-1H-indol-2-yl]-N-(1,3-difluoropropan-2-yl)pyridine-3-sulfonamide,
6-(3-cyano-1-cyclohexyl-5-fluoro-1H-indol-2-yl)-N-[(1S)-1-cyclopropylethyl]pyridine-3-sulfonamide,
2-(3-cyano-1-cyclohexyl-6-fluoro-1H-indol-2-yl)-N-(propan-2-yl)pyrimidine-5-sulfonamide,
6-(3-cyano-1-cyclohexyl-6-fluoro-1H-indol-2-yl)-N-[(2R)-1,1,1-trifluoropropan-2-yl]pyridine-3-sulfonamide,
6-(3-cyano-1-cyclopentyl-6-methyl-1H-indol-2-yl)-N-[1-(trifluoromethyl)cyclobutyl]pyridine-3-sulfonamide,
2-(3-cyano-1-cyclopentyl-6-cyclopropyl-1H-indol-2-yl)-N-[(1S)-1-cyclopropylethyl]pyrimidine-5-sulfonamide,
6-[3-cyano-1-(cyclopropylmethyl)-6-methyl-1H-indol-2-yl]-N-[1-(trifluoromethyl)cyclopropyl]pyridine-3-sulfonamide,
6-(3-cyano-1-cyclobutyl-6-methyl-1H-indol-2-yl)-N-[1-(trifluoromethyl)cyclopropyl]pyridine-3-sulfonamide,
2-[6-chloro-3-cyano-1-(propan-2-yl)-1H-indol-2-yl]-N-(1,3-difluoropropan-2-yl)pyrimidine-5-sulfonamide,
6-(3-cyano-1-cyclobutyl-5-ethyl-1H-indol-2-yl)-N-(1,3-difluoropropan-2-yl)pyridine-3-sulfonamide,
6-[3-cyano-5-fluoro-1-(pyridin-4-yl)-1H-indol-2-yl]-N-(1,3-difluoropropan-2-yl)pyridine-3-sulfonamide,
2-(3-cyano-6-methyl-1-phenyl-1H-indol-2-yl)-N-(1,3-difluoropropan-2-yl)pyrimidine-5-sulfonamide,
6-(3-cyano-1-cyclohexyl-5-fluoro-1H-indol-2-yl)-N-[(2R)-1,1,1-trifluoropropan-2-yl]pyridine-3-sulfonamide,
6-(3-cyano-1-cyclohexyl-6-fluoro-1H-indol-2-yl)-N-[(1S)-1-cyclopropylethyl]pyridine-3-sulfonamide,
6-(3-cyano-1,6-dicyclobutyl-1H-indol-2-yl)-N-[(1S)-1-cyclopropylethyl]pyridine-3-sulfonamide,
2-(3-cyano-1,6-dicyclobutyl-1H-indol-2-yl)-N-(1,3-difluoropropan-2-yl)pyrimidine-5-sulfonamide,
2-(3-cyano-1,6-dicyclobutyl-1H-indol-2-yl)-N-(propan-2-yl)pyrimidine-5-sulfonamide,
6-(3-cyano-1,6-dicyclobutyl-1H-indol-2-yl)-N-(propan-2-yl)pyridine-3-sulfonamide,
6-[3-cyano-1-cyclobutyl-6-(2,2-difluoroethyl)-1H-indol-2-yl]-N-(1,3-difluoropropan-2-yl)pyridine-3-sulfonamide,
6-[3-cyano-1-cyclobutyl-6-(difluoromethoxy)-1H-indol-2-yl]-N-[(2S)-1,1,1-trifluoropropan-2-yl]pyridine-3-sulfonamide,
6-[3-cyano-1-cyclobutyl-6-(difluoromethoxy)-1H-indol-2-yl]-N-(1-cyanoethyl)pyridine-3-sulfonamide,
2-[3-cyano-1-(cyclopropylmethyl)-5-fluoro-1H-indol-2-yl]-N-(1,3-difluoropropan-2-yl)pyrimidine-5-sulfonamide,
2-[3-cyano-1-(cyclopropylmethyl)-5-fluoro-1H-indol-2-yl]-N-(propan-2-yl)pyrimidine-5-sulfonamide,
6-[3-cyano-1-cyclohexyl-6-(trifluoromethoxy)-1H-indol-2-yl]-N-[(2R)-1,1,1-trifluoropropan-2-yl]pyridine-3-sulfonamide,
6-[3-cyano-1-cyclohexyl-6-(trifluoromethoxy)-1H-indol-2-yl]-N-[(1S)-1-cyclopropylethyl]pyridine-3-sulfonamide,
2-[3-cyano-1-cyclohexyl-6-(trifluoromethoxy)-1H-indol-2-yl]-N-(1,3-difluoropropan-2-yl)pyrimidine-5-sulfonamide,
6-(3-cyano-1-cyclopentyl-6-fluoro-1H-indol-2-yl)-N-(1,3-difluoropropan-2-yl)pyridine-3-sulfonamide,
6-[3-cyano-1-(propan-2-yl)-6-(trifluoromethoxy)-1H-indol-2-yl]-N-[(1S)-1-cyclopropylethyl]pyridine-3-sulfonamide,
6-[3-cyano-1-(cyclopropylmethyl)-6-(trifluoromethoxy)-1H-indol-2-yl]-N-[(1S)-1-cyclopropylethyl]pyridine-3-sulfonamide,
6-(3-cyano-1-cyclopentyl-6-ethyl-1H-indol-2-yl)-N-(1,3-difluoropropan-2-yl)pyridine-3-sulfonamide,
6-(3-cyano-1-cyclopentyl-6-ethyl-1H-indol-2-yl)-N-[(2R)-1,1,1-trifluoropropan-2-yl]pyridine-3-sulfonamide,
6-(3-cyano-1-cyclopentyl-6-ethyl-1H-indol-2-yl)-N-[(1S)-1-cyclopropylethyl]pyridine-3-sulfonamide,
6-(3-cyano-1-cyclopentyl-5-methyl-1H-indol-2-yl)-N-[1-(trifluoromethyl)cyclopropyl]pyridine-3-sulfonamide,
2-(5-chloro-3-cyano-1-cyclopentyl-1H-indol-2-yl)-N-(propan-2-yl)pyrimidine-5-sulfonamide,
2-[3-cyano-1-cyclobutyl-6-(fluoromethyl)-1H-indol-2-yl]-N-(propan-2-yl)pyrimidine-5-sulfonamide,
6-(5-chloro-3-cyano-1-cyclobutyl-1H-indol-2-yl)-N-[(2R)-1,1,1-trifluoropropan-2-yl]pyridine-3-sulfonamide,
6-[3-cyano-1-cyclobutyl-6-(fluoromethyl)-1H-indol-2-yl]-N-[(1S)-1-cyclopropylethyl]pyridine-3-sulfonamide,
6-[3-cyano-1-cyclobutyl-6-(fluoromethyl)-1H-indol-2-yl]-N-(1,3-difluoropropan-2-yl)pyridine-3-sulfonamide,
6-[3-cyano-1-cyclobutyl-6-(fluoromethyl)-1H-indol-2-yl]-N-[(2R)-1,1,1-trifluoropropan-2-yl]pyridine-3-sulfonamide,
6-[3-cyano-1-cyclopentyl-6-(trifluoromethoxy)-1H-indol-2-yl]-N-[(1S)-1-cyclopropylethyl]pyridine-3-sulfonamide,
2-[3-cyano-1-cyclobutyl-6-(morpholin-4-yl)-1H-indol-2-yl]-N-(1,3-difluoropropan-2-yl)pyrimidine-5-sulfonamide,
6-[3-cyano-1-cyclobutyl-6-(morpholin-4-yl)-1H-indol-2-yl]-N-(1,3-difluoropropan-2-yl)pyridine-3-sulfonamide,
2-[3-cyano-1-cyclobutyl-6-(difluoromethoxy)-1H-indol-2-yl]-N-[(2S)-1,1,1-trifluoropropan-2-yl]pyrimidine-5-sulfonamide,
2-(3-cyano-1-cyclobutyl-6-cyclopropyl-1H-indol-2-yl)-N-[(2S)-1,1,1-trifluoropropan-2-yl]pyrimidine-5-sulfonamide,
2-(3-cyano-1-cyclobutyl-6-methyl-1H-indol-2-yl)-N-[(2S)-1,1,1-trifluoropropan-2-yl]pyrimidine-5-sulfonamide,
2-[3-cyano-1-cyclopentyl-6-(difluoromethoxy)-1H-indol-2-yl]-N-[(2S)-1,1,1-trifluoropropan-2-yl]pyrimidine-5-sulfonamide,
6-(3-cyano-1-cyclopentyl-5-fluoro-1H-indol-2-yl)-N-[1-(trifluoromethyl)cyclopropyl]pyridine-3-sulfonamide,
6-(3-cyano-1-cyclobutyl-5-methyl-1H-indol-2-yl)-N-[1-(trifluoromethyl)cyclopropyl]pyridine-3-sulfonamide, 6-(3-cyano-1-cyclobutyl-5-fluoro-1H-indol-2-yl)-N-[1-(trifluoromethyl)cyclopropyl]pyridine-3-sulfonamide,
2-[3-cyano-1-cyclobutyl-6-(difluoromethyl)-1H-indol-2-yl]-N-(1,3-difluoropropan-2-yl)pyrimidine-5-sulfonamide,
6-[3-cyano-1-cyclobutyl-6-(difluoromethyl)-1H-indol-2-yl]-N-(1,3-difluoropropan-2-yl)pyridine-3-sulfonamide,
2-[3-cyano-1-cyclobutyl-6-(difluoromethyl)-1H-indol-2-yl]-N-(propan-2-yl)pyrimidine-5-sulfonamide,
6-[3-cyano-1-cyclobutyl-6-(difluoromethyl)-1H-indol-2-yl]-N-(propan-2-yl)pyridine-3-sulfonamide,
6-[3-cyano-1-cyclobutyl-6-(difluoromethyl)-1H-indol-2-yl]-N-[(2R)-1,1,1-trifluoropropan-2-yl]pyridine-3-sulfonamide,
6-[3-cyano-1-cyclobutyl-6-(difluoromethyl)-1H-indol-2-yl]-N-[(1S)-1-cyclopropylethyl]pyridine-3-sulfonamide,
6-[3-cyano-5-fluoro-1-(4-methoxyphenyl)-1H-indol-2-yl]-N-(1,3-difluoropropan-2-yl)pyridine-3-sulfonamide,
2-[3-cyano-5-fluoro-1-(4-methoxyphenyl)-1H-indol-2-yl]-N-(1,3-difluoropropan-2-yl)pyrimidine-5-sulfonamide,
6-(3-cyano-1-cyclobutyl-6-ethyl-1H-indol-2-yl)-N-[(2S)-1,1,1-trifluoropropan-2-yl]pyridine-3-sulfonamide,
6-(3-cyano-1-cyclobutyl-5-ethyl-1H-indol-2-yl)-N-[(2S)-1,1,1-trifluoropropan-2-yl]pyridine-3-sulfonamide,
6-(3-cyano-1-cyclobutyl-5-fluoro-6-methyl-1H-indol-2-yl)-N-[(2S)-1,1,1-trifluoropropan-2-yl]pyridine-3-sulfonamide,
6-[3-cyano-1-cyclohexyl-6-(difluoromethoxy)-1H-indol-2-yl]-N-[(2S)-1,1,1-trifluoropropan-2-yl]pyridine-3-sulfonamide,
6-(3-cyano-1,6-dicyclobutyl-1H-indol-2-yl)-N-(1,3-difluoropropan-2-yl)pyridine-3-sulfonamide,
6-(3-cyano-6-cyclobutyl-1-cyclopentyl-1H-indol-2-yl)-N-[(2R)-1,1,1-trifluoropropan-2-yl]pyridine-3-sulfonamide,
2-[3-cyano-6-cyclopropyl-1-(cyclopropylmethyl)-1H-indol-2-yl]-N-(1,3-difluoropropan-2-yl)pyrimidine-5-sulfonamide,
6-(3-cyano-1-cyclopentyl-5-methyl-1H-indol-2-yl)-N-[(2S)-1,1,1-trifluoropropan-2-yl]pyridine-3-sulfonamide,
6-(3,5-dicyano-1-cyclopentyl-1H-indol-2-yl)-N-[(2S)-1,1,1-trifluoropropan-2-yl]pyridine-3-sulfonamide,
6-[3,6-dicyano-1-(cyclopropylmethyl)-1H-indol-2-yl]-N-(1,3-difluoropropan-2-yl)pyridine-3-sulfonamide,
6-[3,6-dicyano-1-(cyclopropylmethyl)-1H-indol-2-yl]-N-(propan-2-yl)pyridine-3-sulfonamide,
6-[3,6-dicyano-1-(cyclopropylmethyl)-1H-indol-2-yl]-N-[(2S)-1,1,1-trifluoropropan-2-yl]pyridine-3-sulfonamide,
N-[(1S)-1-cyclopropylethyl]-6-[3,6-dicyano-1-(cyclopropylmethyl)-1H-indol-2-yl]pyridine-3-sulfonamide,
6-(3-cyano-1-cyclobutyl-6-methyl-1H-indol-2-yl)-N-[(2S)-1,1,1-trifluoropropan-2-yl]pyridine-3-sulfonamide,
6-(3-cyano-1-cyclopentyl-6-methyl-1H-indol-2-yl)-N-[(2S)-1,1,1-trifluoropropan-2-yl]pyridine-3-sulfonamide,
6-[3-cyano-1-(cyclopropylmethyl)-6-methyl-1H-indol-2-yl]-N-[(2S)-1,1,1-trifluoropropan-2-yl]pyridine-3-sulfonamide,
6-(3-cyano-1-cyclohexyl-6-methyl-1H-indol-2-yl)-N-[(2S)-1,1,1-trifluoropropan-2-yl]pyridine-3-sulfonamide,
6-[3-cyano-6-methyl-1-(propan-2-yl)-1H-indol-2-yl]-N-[(2S)-1,1,1-trifluoropropan-2-yl]pyridine-3-sulfonamide,
6-[3-cyano-5-fluoro-1-(4-methylphenyl)-1H-indol-2-yl]-N-(1,3-difluoropropan-2-yl)pyridine-3-sulfonamide,
2-[3-cyano-5-fluoro-1-(4-methylphenyl)-1H-indol-2-yl]-N-(propan-2-yl)pyrimidine-5-sulfonamide,
6-[3-cyano-1-cyclopentyl-6-(trifluoromethoxy)-1H-indol-2-yl]-N-[(2S)-1,1,1-trifluoropropan-2-yl]pyridine-3-sulfonamide,
6-[3-cyano-6-(difluoromethoxy)-1-(propan-2-yl)-1H-indol-2-yl]-N-[(2S)-1,1,1-trifluoropropan-2-yl]pyridine-3-sulfonamide,
6-(6-chloro-3-cyano-1-cyclobutyl-5-fluoro-1H-indol-2-yl)-N-[(2S)-1,1,1-trifluoropropan-2-yl]pyridine-3-sulfonamide,
2-[3-cyano-1-cyclobutyl-6-(fluoromethyl)-1H-indol-2-yl]-N-(1,3-difluoropropan-2-yl)pyrimidine-5-sulfonamide,
6-[3-cyano-1-cyclobutyl-6-(fluoromethyl)-1H-indol-2-yl]-N-[(2S)-1,1,1-trifluoropropan-2-yl]pyridine-3-sulfonamide,
6-[3-cyano-1-cyclobutyl-6-(difluoromethyl)-1H-indol-2-yl]-N-[(2S)-1,1,1-trifluoropropan-2-yl]pyridine-3-sulfonamide,
6-(6-chloro-3-cyano-1-cyclopentyl-1H-indol-2-yl)-N-[(2S)-1,1,1-trifluoropropan-2-yl]pyridine-3-sulfonamide,
6-(5-chloro-3-cyano-1-cyclopentyl-1H-indol-2-yl)-N-[(2S)-1,1,1-trifluoropropan-2-yl]pyridine-3-sulfonamide,
N-[(1S)-1-cyclopropylethyl]-2-(3,5-dicyano-1-cyclopentyl-1H-indol-2-yl)pyrimidine-5-sulfonamide,
6-[3-cyano-6-(difluoromethoxy)-1-(4-fluorophenyl)-1H-indol-2-yl]-N-[(2S)-1,1,1-trifluoropropan-2-yl]pyridine-3-sulfonamide,
6-(3-cyano-1-cyclobutyl-6-cyclopropyl-1H-indol-2-yl)-N-[(2S)-1,1,1-trifluoropropan-2-yl]pyridine-3-sulfonamide,
6-[3-cyano-1-cyclobutyl-6-(trifluoromethoxy)-1H-indol-2-yl]-N-[(2S)-1,1,1-trifluoropropan-2-yl]pyridine-3-sulfonamide,
6-(3-cyano-1-cyclopentyl-6-methyl-1H-indol-2-yl)-N-(1,1,1-trifluoro-2-methylpropan-2-yl)pyridine-3-sulfonamide,
6-[3-cyano-1-(cyclopropylmethyl)-5-methyl-1H-indol-2-yl]-N-[(2S)-1,1,1-trifluoropropan-2-yl]pyridine-3-sulfonamide,
6-[3-cyano-1-(cyclopropylmethyl)-5-methyl-1H-indol-2-yl]-N-(1,3-difluoropropan-2-yl)pyridine-3-sulfonamide,
6-(3-cyano-1-cyclopentyl-5-ethyl-1H-indol-2-yl)-N-[(2S)-1,1,1-trifluoropropan-2-yl]pyridine-3-sulfonamide,
6-(6-chloro-3-cyano-1-cyclobutyl-1H-indol-2-yl)-N-[(2S)-1,1,1-trifluoropropan-2-yl]pyridine-3-sulfonamide,
6-(5-chloro-3-cyano-1-cyclobutyl-1H-indol-2-yl)-N-[(2S)-1,1,1-trifluoropropan-2-yl]pyridine-3-sulfonamide,
2-[3-cyano-1-cyclobutyl-5-(fluoromethyl)-1H-indol-2-yl]-N-(1,3-difluoropropan-2-yl)pyrimidine-5-sulfonamide, 6-[3-cyano-1-cyclobutyl-5-(difluoromethyl)-1H-indol-2-yl]-N-(1,3-difluoropropan-2-yl)pyridine-3-sulfonamide, 2-[3-cyano-1-cyclobutyl-5-(difluoromethyl)-1H-indol-2-yl]-N-(1,3-difluoropropan-2-yl)pyrimidine-5-sulfonamide, 2-[3-cyano-1-cyclobutyl-5-(difluoromethyl)-1H-indol-2-yl]-N-[(2S)-1,1,1-trifluoropropan-2-yl]pyrimidine-5-sulfonamide, 6-(3-cyano-1-cyclopentyl-5-ethyl-1H-indol-2-yl)-N-(1,3-difluoropropan-2-yl)pyridine-3-sulfonamide, 6-[3-cyano-1-cyclopentyl-6-(difluoromethoxy)-1H-indol-2-yl]-N-(1,1,1-trifluoro-2-methylpropan-2-yl)pyridine-3-sulfonamide, 6-(3-cyano-1-cyclopentyl-6-cyclopropyl-1H-indol-2-yl)-N-[(2S)-1,1,1-trifluoropropan-2-yl]pyridine-3-sulfonamide, 6-[3-cyano-1-cyclobutyl-6-(2,2-difluoroethyl)-1H-indol-2-yl]-N-[(2S)-1,1,1-trifluoropropan-2-yl]pyridine-3-sulfonamide, 2-[3-cyano-1-cyclobutyl-6-(2,2-difluoroethyl)-1H-indol-2-yl]-N-[(2S)-1,1,1-trifluoropropan-2-yl]pyrimidine-5-sulfonamide, 6-[3-cyano-5-fluoro-1-(pyridin-2-yl)-1H-indol-2-yl]-N-[(2S)-1,1,1-trifluoropropan-2-yl]pyridine-3-sulfonamide, 6-[3-cyano-6-(difluoromethoxy)-1-(pyridin-2-yl)-1H-indol-2-yl]-N-[(2S)-1,1,1-trifluoropropan-2-yl]pyridine-3-sulfonamide, 2-[3-cyano-1-(cyclopropylmethyl)-5-methyl-1H-indol-2-yl]-N-(propan-2-yl)pyrimidine-5-sulfonamide, 2-[3-cyano-1-(cyclopropylmethyl)-5-methyl-1H-indol-2-yl]-N-[(2S)-1,1,1-trifluoropropan-2-yl]pyrimidine-5-sulfonamide, 2-(3-cyano-1-cyclohexyl-5-methyl-1H-indol-2-yl)-N-[(2S)-1,1,1-trifluoropropan-2-yl]pyrimidine-5-sulfonamide, 2-(3-cyano-1-cyclopentyl-5-methyl-1H-indol-2-yl)-N-[(2S)-1,1,1-trifluoropropan-2-yl]pyrimidine-5-sulfonamide, 2-(3,5-dicyano-1-cyclopentyl-1H-indol-2-yl)-N-[(2S)-1,1,1-trifluoropropan-2-yl]pyrimidine-5-sulfonamide, 2-(3-cyano-1-cyclohexyl-5-fluoro-1H-indol-2-yl)-N-[(2S)-1,1,1-trifluoropropan-2-yl]pyrimidine-5-sulfonamide, 6-(3-cyano-1-cyclohexyl-6-fluoro-1H-indol-2-yl)-N-[(2S)-1,1,1-trifluoropropan-2-yl]pyridine-3-sulfonamide, 6-(3-cyano-1-cyclobutyl-6-fluoro-1H-indol-2-yl)-N-[(2S)-1,1,1-trifluoropropan-2-yl]pyridine-3-sulfonamide, 6-(3-cyano-1-cyclopentyl-6-fluoro-1H-indol-2-yl)-N-[(2S)-1,1,1-trifluoropropan-2-yl]pyridine-3-sulfonamide, 6-[3-cyano-1-(cyclopropylmethyl)-6-fluoro-1H-indol-2-yl]-N-[(2S)-1,1,1-trifluoropropan-2-yl]pyridine-3-sulfonamide, 2-[3-cyano-1-(cyclopropylmethyl)-6-(difluoromethoxy)-1H-indol-2-yl]-N-[(2S)-1,1,1-trifluoropropan-2-yl]pyrimidine-5-sulfonamide, 2-[3-cyano-6-(difluoromethoxy)-1-(propan-2-yl)-1H-indol-2-yl]-N-[(2S)-1,1,1-trifluoropropan-2-yl]pyrimidine-5-sulfonamide, 2-[3-cyano-6-(difluoromethoxy)-1-propyl-1H-indol-2-yl]-N-[(2S)-1,1,1-trifluoropropan-2-yl]pyrimidine-5-sulfonamide, 2-(3-cyano-1-cyclopentyl-6-cyclopropyl-1H-indol-2-yl)-N-[(2S)-1,1,1-trifluoropropan-2-yl]pyrimidine-5-sulfonamide, 2-[3-cyano-1-(cyclopropylmethyl)-6-methyl-1H-indol-2-yl]-N-[(2S)-1,1,1-trifluoropropan-2-yl]pyrimidine-5-sulfonamide, 2-[3-cyano-6-methyl-1-(propan-2-yl)-1H-indol-2-yl]-N-[(2S)-1,1,1-trifluoropropan-2-yl]pyrimidine-5-sulfonamide, 2-(3-cyano-1-cyclopentyl-6-methyl-1H-indol-2-yl)-N-[(2S)-1,1,1-trifluoropropan-2-yl]pyrimidine-5-sulfonamide, 2-(3-cyano-1-cyclobutyl-6-methoxy-1H-indol-2-yl)-N-[(2S)-1,1,1-trifluoropropan-2-yl]pyrimidine-5-sulfonamide, 2-(3-cyano-1-cyclopentyl-6-methoxy-1H-indol-2-yl)-N-[(2S)-1,1,1-trifluoropropan-2-yl]pyrimidine-5-sulfonamide, 6-(3-cyano-1-cyclopentyl-5-fluoro-6-methyl-1H-indol-2-yl)-N-(1,3-difluoropropan-2-yl)pyridine-3-sulfonamide, 6-(3-cyano-1-cyclopentyl-5-fluoro-6-methyl-1H-indol-2-yl)-N-[(2S)-1,1,1-trifluoropropan-2-yl]pyridine-3-sulfonamide, 6-(3-cyano-1-cyclopentyl-5-fluoro-6-methyl-1H-indol-2-yl)-N-[(2R)-1,1,1-trifluoropropan-2-yl]pyridine-3-sulfonamide, 6-(3-cyano-1-cyclohexyl-5-fluoro-1H-indol-2-yl)-N-[(2S)-1,1,1-trifluoropropan-2-yl]pyridine-3-sulfonamide, 2-(3-cyano-1-cyclohexyl-6-fluoro-1H-indol-2-yl)-N-[(2S)-1,1,1-trifluoropropan-2-yl]pyrimidine-5-sulfonamide, 6-[3-cyano-1-(cyclohex-2-en-1-yl)-5-fluoro-1H-indol-2-yl]-N-[(2R)-1,1,1-trifluoropropan-2-yl]pyridine-3-sulfonamide, 6-[3-cyano-1-(cyclohex-2-en-1-yl)-5-fluoro-1H-indol-2-yl]-N-[(2S)-1,1,1-trifluoropropan-2-yl]pyridine-3-sulfonamide, 2-(3-cyano-1-cyclobutyl-5-methyl-1H-indol-2-yl)-N-[(2S)-1,1,1-trifluoropropan-2-yl]pyrimidine-5-sulfonamide, 2-[6-chloro-3-cyano-1-(cyclopropylmethyl)-1H-indol-2-yl]-N-[(2S)-1,1,1-trifluoropropan-2-yl]pyrimidine-5-sulfonamide, 2-(3-cyano-1-cyclobutyl-5-fluoro-1H-indol-2-yl)-N-(propan-2-yl)pyrimidine-5-sulfonamide, 2-(6-chloro-3-cyano-1-cyclopentyl-1H-indol-2-yl)-N-[(2S)-1,1,1-trifluoropropan-2-yl]pyrimidine-5-sulfonamide, 2-[6-chloro-3-cyano-1-(propan-2-yl)-1H-indol-2-yl]-N-[(2S)-1,1,1-trifluoropropan-2-yl]pyrimidine-5-sulfonamide, 2-(5-chloro-3-cyano-1-cyclopentyl-1H-indol-2-yl)-N-[(2S)-1,1,1-trifluoropropan-2-yl]pyrimidine-5-sulfonamide, 2-[5-chloro-3-cyano-1-(propan-2-yl)-1H-indol-2-yl]-N-[(2S)-1,1,1-trifluoropropan-2-yl]pyrimidine-5-sulfonamide, 6-(3-cyano-1-cyclobutyl-7-fluoro-6-methyl-1H-indol-2-yl)-N-[(2S)-1,1,1-trifluoropropan-2-yl]pyridine-3-sulfonamide, 6-(3-cyano-1-cyclobutyl-7-fluoro-6-methyl-1H-indol-2-yl)-N-(1,3-difluoropropan-2-yl)pyridine-3-sulfonamide, 6-(3-cyano-1-cyclopentyl-7-fluoro-6-methyl-1H-indol-2-yl)-N-(1,3-difluoropropan-2-yl)pyridine-3-sulfonamide,
6-(3-cyano-1-cyclopentyl-7-fluoro-6-methyl-1H-indol-2-yl)-N-[(2S)-1,1,1-trifluoropropan-2-yl]pyridine-3-sulfonamide,
6-[3-cyano-6-methyl-1-(propan-2-yl)-1H-indol-2-yl]-N-[(1S)-1-cyclopropylethyl]pyridine-3-sulfonamide,
6-(3-cyano-1-cyclopentyl-6-methyl-1H-indol-2-yl)-N-[(1S)-1-cyclopropylethyl]pyridine-3-sulfonamide,
6-(3-cyano-1-cyclobutyl-6-methoxy-1H-indol-2-yl)-N-[(2S)-1,1,1-trifluoropropan-2-yl]pyridine-3-sulfonamide,
6-(3-cyano-1-cyclobutyl-6-methoxy-1H-indol-2-yl)-N-[(2R)-1,1,1-trifluoropropan-2-yl]pyridine-3-sulfonamide,
6-(3-cyano-1-cyclobutyl-6-methoxy-1H-indol-2-yl)-N-[(1S)-1-cyclopropylethyl]pyridine-3-sulfonamide,
6-(3-cyano-1-cyclopentyl-6-methoxy-1H-indol-2-yl)-N-[(2S)-1,1,1-trifluoropropan-2-yl]pyridine-3-sulfonamide,
6-(3-cyano-1-cyclopentyl-6-methoxy-1H-indol-2-yl)-N-[(2R)-1,1,1-trifluoropropan-2-yl]pyridine-3-sulfonamide,
6-(3-cyano-1-cyclopentyl-6-methoxy-1H-indol-2-yl)-N-[(1S)-1-cyclopropylethyl]pyridine-3-sulfonamide,
6-(3-cyano-1-cyclopentyl-6-cyclopropyl-1H-indol-2-yl)-N-[(1S)-1-cyclopropylethyl]pyridine-3-sulfonamide,
6-(3-cyano-1-cyclobutyl-5-fluoro-1H-indol-2-yl)-N-[(2S)-1,1,1-trifluoropropan-2-yl]pyridine-3-sulfonamide,
6-(3-cyano-1-cyclopentyl-5-fluoro-1H-indol-2-yl)-N-[(2S)-1,1,1-trifluoropropan-2-yl]pyridine-3-sulfonamide,
6-[3-cyano-1-(cyclopropylmethyl)-5-fluoro-1H-indol-2-yl]-N-[(2S)-1,1,1-trifluoropropan-2-yl]pyridine-3-sulfonamide,
6-[6-chloro-3-cyano-1-(pyridin-2-yl)-1H-indol-2-yl]-N-[(2S)-1,1,1-trifluoropropan-2-yl]pyridine-3-sulfonamide,
6-[6-chloro-3-cyano-1-(pyridin-2-yl)-1H-indol-2-yl]-N-(1,3-difluoropropan-2-yl)pyridine-3-sulfonamide,
6-[3-cyano-5-fluoro-1-(pyridin-2-yl)-1H-indol-2-yl]-N-(propan-2-yl)pyridine-3-sulfonamide,
6-(3-cyano-6-methyl-1-phenyl-1H-indol-2-yl)-N-[(2S)-1,1,1-trifluoropropan-2-yl]pyridine-3-sulfonamide,
6-(5-chloro-3-cyano-1-phenyl-1H-indol-2-yl)-N-[(2S)-1,1,1-trifluoropropan-2-yl]pyridine-3-sulfonamide,
6-[5-chloro-3-cyano-1-(pyridin-2-yl)-1H-indol-2-yl]-N-[(2S)-1,1,1-trifluoropropan-2-yl]pyridine-3-sulfonamide,
6-[5-chloro-3-cyano-1-(pyridin-2-yl)-1H-indol-2-yl]-N-(1,3-difluoropropan-2-yl)pyridine-3-sulfonamide,
6-(5-chloro-3-cyano-1-cyclobutyl-6-methyl-1H-indol-2-yl)-N-(1,3-difluoropropan-2-yl)pyridine-3-sulfonamide,
6-(5-chloro-3-cyano-1-cyclobutyl-6-methyl-1H-indol-2-yl)-N-[(2R)-1,1,1-trifluoropropan-2-yl]pyridine-3-sulfonamide,
6-(5-chloro-3-cyano-1-cyclobutyl-6-methyl-1H-indol-2-yl)-N-[(2S)-1,1,1-trifluoropropan-2-yl]pyridine-3-sulfonamide,
2-(5-chloro-3-cyano-1-cyclobutyl-6-methyl-1H-indol-2-yl)-N-(1,3-difluoropropan-2-yl)pyrimidine-5-sulfonamide,
2-(5-chloro-3-cyano-1-cyclobutyl-6-methyl-1H-indol-2-yl)-N-[(2S)-1,1,1-trifluoropropan-2-yl]pyrimidine-5-sulfonamide,
2-[6-chloro-3-cyano-1-(pyridin-2-yl)-1H-indol-2-yl]-N-[(2S)-1,1,1-trifluoropropan-2-yl]pyrimidine-5-sulfonamide,
2-[6-chloro-3-cyano-1-(pyridin-2-yl)-1H-indol-2-yl]-N-(1,3-difluoropropan-2-yl)pyrimidine-5-sulfonamide,
2-(3-cyano-1-cyclobutyl-5-fluoro-1H-indol-2-yl)-N-[(2S)-1,1,1-trifluoropropan-2-yl]pyrimidine-5-sulfonamide,
2-(3-cyano-1-cyclobutyl-5-fluoro-1H-indol-2-yl)-N-(1,3-difluoropropan-2-yl)pyrimidine-5-sulfonamide,
6-(3-cyano-1-cyclobutyl-5-methoxy-1H-indol-2-yl)-N-[(2S)-1,1,1-trifluoropropan-2-yl]pyridine-3-sulfonamide,
2-(5-chloro-3-cyano-1-cyclobutyl-1H-indol-2-yl)-N-[(2S)-1,1,1-trifluoropropan-2-yl]pyrimidine-5-sulfonamide,
2-[3-cyano-1-cyclobutyl-6-(propan-2-yl)-1H-indol-2-yl]-N-[(2S)-1,1,1-trifluoropropan-2-yl]pyrimidine-5-sulfonamide,
6-[3-cyano-1,6-di(propan-2-yl)-1H-indol-2-yl]-N-(1,3-difluoropropan-2-yl)pyridine-3-sulfonamide,
6-[3-cyano-1-cyclopentyl-6-(propan-2-yl)-1H-indol-2-yl]-N-(1,3-difluoropropan-2-yl)pyridine-3-sulfonamide,
6-[3-cyano-1-(cyclopropylmethyl)-5-methyl-1H-indol-2-yl]-N-[(2R)-1,1,1-trifluoropropan-2-yl]pyridine-3-sulfonamide,
6-[3-cyano-1-cyclohexyl-6-(trifluoromethoxy)-1H-indol-2-yl]-N-[(2S)-1,1,1-trifluoropropan-2-yl]pyridine-3-sulfonamide,
6-[3-cyano-1-(cyclopropylmethyl)-6-(propan-2-yl)-1H-indol-2-yl]-N-(1,3-difluoropropan-2-yl)pyridine-3-sulfonamide,
6-(5-chloro-3-cyano-1-cyclohexyl-1H-indol-2-yl)-N-[(2R)-1,1,1-trifluoropropan-2-yl]pyridine-3-sulfonamide,
6-(5-chloro-3-cyano-1-cyclohexyl-1H-indol-2-yl)-N-[(2S)-1,1,1-trifluoropropan-2-yl]pyridine-3-sulfonamide,
2-(5-chloro-3-cyano-1-cyclohexyl-1H-indol-2-yl)-N-(1,3-difluoropropan-2-yl)pyrimidine-5-sulfonamide,
2-(5-chloro-3-cyano-1-cyclohexyl-1H-indol-2-yl)-N-[(2S)-1,1,1-trifluoropropan-2-yl]pyrimidine-5-sulfonamide,
6-(3,6-dicyano-1-cyclobutyl-1H-indol-2-yl)-N-(1,3-difluoropropan-2-yl)pyridine-3-sulfonamide,
2-(3,6-dicyano-1-cyclobutyl-1H-indol-2-yl)-N-(1,3-difluoropropan-2-yl)pyrimidine-5-sulfonamide,
6-(3,6-dicyano-1-cyclobutyl-1H-indol-2-yl)-N-[(2S)-1,1,1-trifluoropropan-2-yl]pyridine-3-sulfonamide,
6-(3,6-dicyano-1-cyclopentyl-1H-indol-2-yl)-N-(1,3-difluoropropan-2-yl)pyridine-3-sulfonamide,
2-(3,6-dicyano-1-cyclopentyl-1H-indol-2-yl)-N-(1,3-difluoropropan-2-yl)pyrimidine-5-sulfonamide,
6-(3,6-dicyano-1-cyclopentyl-1H-indol-2-yl)-N-[(2S)-1,1,1-trifluoropropan-2-yl]pyridine-3-sulfonamide,
2-[3-cyano-1-cyclohexyl-6-(difluoromethoxy)-1H-indol-2-yl]-N-[(1S)-1-cyclopropylethyl]pyrimidine-5-sulfonamide,
2-[3-cyano-1-cyclohexyl-6-(difluoromethoxy)-1H-indol-2-yl]-N-[(2S)-1,1,1-trifluoropropan-2-yl]pyrimidine-5-sulfonamide,
2-[3-cyano-1-cyclohexyl-6-(difluoromethoxy)-1H-indol-2-yl]-N-(propan-2-yl)pyrimidine-5-sulfonamide, 2-[3-cyano-5-fluoro-1-(pyridin-2-yl)-1H-indol-2-yl]-N-[(2S)-1,1,1-trifluoropropan-2-yl]pyrimidine-5-sulfonamide, 2-[3-cyano-6-methyl-1-(pyridin-2-yl)-1H-indol-2-yl]-N-[(2S)-1,1,1-trifluoropropan-2-yl]pyrimidine-5-sulfonamide, 6-[3-cyano-6-methyl-1-(pyridin-2-yl)-1H-indol-2-yl]-N-[(2S)-1,1,1-trifluoropropan-2-yl]pyridine-3-sulfonamide, 2-[3-cyano-6-(difluoromethoxy)-1-(4-fluorophenyl)-1H-indol-2-yl]-N-(1,3-difluoropropan-2-yl)pyrimidine-5-sulfonamide, 6-(3-cyano-1-cyclobutyl-6-methyl-1H-indol-2-yl)-N-(1,1,1-trifluoro-2-methylpropan-2-yl)pyridine-3-sulfonamide, 6-[3-cyano-1-cyclobutyl-6-(difluoromethoxy)-1H-indol-2-yl]-N-(1,1,1-trifluoro-2-methylpropan-2-yl)pyridine-3-sulfonamide, 6-(3-cyano-1-cyclobutyl-5-methyl-1H-indol-2-yl)-N-(1,1,1-trifluoro-2-methylpropan-2-yl)pyridine-3-sulfonamide, 6-(3-cyano-1-cyclobutyl-6-ethyl-1H-indol-2-yl)-N-(1,1,1-trifluoro-2-methylpropan-2-yl)pyridine-3-sulfonamide, 6-(3-cyano-1-cyclopentyl-6-fluoro-5-methyl-1H-indol-2-yl)-N-(1,3-difluoropropan-2-yl)pyridine-3-sulfonamide, 6-(3-cyano-1-cyclopentyl-6-fluoro-5-methyl-1H-indol-2-yl)-N-[(2S)-1,1,1-trifluoropropan-2-yl]pyridine-3-sulfonamide, 6-(3-cyano-1-cyclobutyl-5-methyl-1H-indol-2-yl)-N-[(2R)-1,1,1-trifluoropropan-2-yl]pyridine-3-sulfonamide, 6-[3-cyano-5-methyl-1-(propan-2-yl)-1H-indol-2-yl]-N-[(2R)-1,1,1-trifluoropropan-2-yl]pyridine-3-sulfonamide, 6-(3-cyano-1-cyclopentyl-5-methyl-1H-indol-2-yl)-N-[(2R)-1,1,1-trifluoropropan-2-yl]pyridine-3-sulfonamide, 6-(3-cyano-1-cyclohexyl-5-methyl-1H-indol-2-yl)-N-[(2R)-1,1,1-trifluoropropan-2-yl]pyridine-3-sulfonamide, 6-[6-chloro-3-cyano-1-(pyridin-2-yl)-1H-indol-2-yl]-N-[(1S)-1-cyclopropylethyl]pyridine-3-sulfonamide, 6-[6-chloro-3-cyano-1-(pyridin-2-yl)-1H-indol-2-yl]-N-[(2R)-1,1,1-trifluoropropan-2-yl]pyridine-3-sulfonamide, 6-[5-chloro-3-cyano-1-(pyridin-2-yl)-1H-indol-2-yl]-N-[(1S)-1-cyclopropylethyl]pyridine-3-sulfonamide, 6-[5-chloro-3-cyano-1-(pyridin-2-yl)-1H-indol-2-yl]-N-[(2R)-1,1,1-trifluoropropan-2-yl]pyridine-3-sulfonamide, 6-(3-cyano-1-cyclobutyl-6-fluoro-5-methyl-1H-indol-2-yl)-N-[(2S)-1,1,1-trifluoropropan-2-yl]pyridine-3-sulfonamide, 6-(3-cyano-1-cyclobutyl-6-fluoro-5-methyl-1H-indol-2-yl)-N-(1,3-difluoropropan-2-yl)pyridine-3-sulfonamide, 2-(3-cyano-1-cyclobutyl-6-fluoro-1H-indol-2-yl)-N-[(2S)-1,1,1-trifluoropropan-2-yl]pyrimidine-5-sulfonamide, 2-(3-cyano-1-cyclopentyl-6-fluoro-1H-indol-2-yl)-N-[(2S)-1,1,1-trifluoropropan-2-yl]pyrimidine-5-sulfonamide, 2-(3-cyano-1-cyclobutyl-6-fluoro-1H-indol-2-yl)-N-[(1S)-1-cyclopropylethyl]pyrimidine-5-sulfonamide, 2-(3-cyano-1-cyclopentyl-6-fluoro-1H-indol-2-yl)-N-[(1S)-1-cyclopropylethyl]pyrimidine-5-sulfonamide, 2-[3-cyano-1-(cyclopropylmethyl)-6-fluoro-1H-indol-2-yl]-N-[(1S)-1-cyclopropylethyl]pyrimidine-5-sulfonamide, 2-(3-cyano-1-cyclohexyl-6-fluoro-1H-indol-2-yl)-N-[(1S)-1-cyclopropylethyl]pyrimidine-5-sulfonamide, 6-(3-cyano-1-cyclobutyl-5-methoxy-1H-indol-2-yl)-N-[(2R)-1,1,1-trifluoropropan-2-yl]pyridine-3-sulfonamide, 6-[3-cyano-6-cyclopropyl-1-(pyridin-2-yl)-1H-indol-2-yl]-N-(1,3-difluoropropan-2-yl)pyridine-3-sulfonamide, 6-[3-cyano-6-cyclopropyl-1-(pyridin-2-yl)-1H-indol-2-yl]-N-[(2S)-1,1,1-trifluoropropan-2-yl]pyridine-3-sulfonamide, 6-[3-cyano-5-methyl-1-(pyridin-2-yl)-1H-indol-2-yl]-N-[(2S)-1,1,1-trifluoropropan-2-yl]pyridine-3-sulfonamide, 6-[3-cyano-5-methyl-1-(pyridin-2-yl)-1H-indol-2-yl]-N-(1,3-difluoropropan-2-yl)pyridine-3-sulfonamide, 6-(6-chloro-3-cyano-1-cyclobutyl-5-methyl-1H-indol-2-yl)-N-(1,3-difluoropropan-2-yl)pyridine-3-sulfonamide, 6-(6-chloro-3-cyano-1-cyclobutyl-5-methyl-1H-indol-2-yl)-N-[(2S)-1,1,1-trifluoropropan-2-yl]pyridine-3-sulfonamide, 2-(6-chloro-3-cyano-1-cyclobutyl-5-methyl-1H-indol-2-yl)-N-(propan-2-yl)pyrimidine-5-sulfonamide, 6-(3-cyano-1-cyclopentyl-5,7-difluoro-6-methyl-1H-indol-2-yl)-N-[(2S)-1,1,1-trifluoropropan-2-yl]pyridine-3-sulfonamide, 6-(3-cyano-1-cyclopentyl-5,7-difluoro-6-methyl-1H-indol-2-yl)-N-(1,3-difluoropropan-2-yl)pyridine-3-sulfonamide, 6-(6-chloro-3-cyano-1-cyclobutyl-5-methyl-1H-indol-2-yl)-N-[(2R)-1,1,1-trifluoropropan-2-yl]pyridine-3-sulfonamide, 6-(1-cyclobutyl-6-methyl-1H-indol-2-yl)-N-(1,3-difluoropropan-2-yl)pyridine-3-sulfonamide, 6-[3-cyano-6-(difluoromethoxy)-1-(pyrimidin-2-yl)-1H-indol-2-yl]-N-[(2S)-1,1,1-trifluoropropan-2-yl]pyridine-3-sulfonamide, 6-(3-cyano-1-cyclohexyl-6-methyl-1H-indol-2-yl)-N-(1,3-difluoropropan-2-yl)pyridine-3-sulfonamide, 6-(6-chloro-3-cyano-1-cyclohexyl-1H-indol-2-yl)-N-[(2R)-1,1,1-trifluoropropan-2-yl]pyridine-3-sulfonamide, 6-(6-chloro-3-cyano-1-cyclohexyl-1H-indol-2-yl)-N-[(2S)-1,1,1-trifluoropropan-2-yl]pyridine-3-sulfonamide, 2-(6-chloro-3-cyano-1-cyclohexyl-1H-indol-2-yl)-N-[(2S)-1,1,1-trifluoropropan-2-yl]pyrimidine-5-sulfonamide, 2-(6-chloro-3-cyano-1-cyclohexyl-1H-indol-2-yl)-N-(1,3-difluoropropan-2-yl)pyrimidine-5-sulfonamide, 6-(3-cyano-1-cyclohexyl-6-methoxy-1H-indol-2-yl)-N-[(2R)-1,1,1-trifluoropropan-2-yl]pyridine-3-sulfonamide, 6-(3-cyano-1-cyclohexyl-6-methoxy-1H-indol-2-yl)-N-[(2S)-1,1,1-trifluoropropan-2-yl]pyridine-3-sulfonamide, 2-(3-cyano-1-cyclohexyl-6-methoxy-1H-indol-2-yl)-N-(1,3-difluoropropan-2-yl)pyrimidine-5-sulfonamide, 6-(6-chloro-3-cyano-1-cyclopentyl-5-methyl-1H-indol-2-yl)-N-(1,3-difluoropropan-2-yl)pyridine-3-sulfonamide, 6-(6-chloro-3-cyano-1-cyclopentyl-5-methyl-1H-indol-2-yl)-N-[(2S)-1,1,1-trifluoropropan-2-yl]pyridine-3-sulfonamide,
2-(6-chloro-3-cyano-1-cyclopentyl-5-methyl-1H-indol-2-yl)-N-(propan-2-yl)pyrimidine-5-sulfonamide,
2-[3-cyano-1-(cyclopropylmethyl)-5-methyl-1H-indol-2-yl]-N-(1,3-difluoropropan-2-yl)pyrimidine-5-sulfonamide,
6-[3-cyano-1-(cyclopropylmethyl)-5-methyl-1H-indol-2-yl]-N-[(1S)-1-cyclopropylethyl]pyridine-3-sulfonamide,
2-(3-cyano-1-cyclohexyl-5-fluoro-1H-indol-2-yl)-N-(propan-2-yl)pyrimidine-5-sulfonamide,
2-(3-cyano-1-cyclohexyl-5-fluoro-1H-indol-2-yl)-N-(1,3-difluoropropan-2-yl)pyrimidine-5-sulfonamide,
2-(3-cyano-1-cyclohexyl-5-fluoro-1H-indol-2-yl)-N-[(1S)-1-cyclopropylethyl]pyrimidine-5-sulfonamide,
2-[3-cyano-5-fluoro-1-(propan-2-yl)-1H-indol-2-yl]-N-[(1S)-1-cyclopropylethyl]pyrimidine-5-sulfonamide,
2-(3-cyano-1-cyclopentyl-5-fluoro-1H-indol-2-yl)-N-[(1S)-1-cyclopropylethyl]pyrimidine-5-sulfonamide,
2-[3-cyano-1-(cyclopropylmethyl)-5-fluoro-1H-indol-2-yl]-N-[(1S)-1-cyclopropylethyl]pyrimidine-5-sulfonamide,
6-(3-cyano-1-cyclobutyl-5,7-difluoro-6-methyl-1H-indol-2-yl)-N-[(2S)-1,1,1-trifluoropropan-2-yl]pyridine-3-sulfonamide,
6-(3-cyano-1-cyclobutyl-5,7-difluoro-6-methyl-1H-indol-2-yl)-N-(1,3-difluoropropan-2-yl)pyridine-3-sulfonamide,
6-[3-cyano-6-(difluoromethoxy)-1-(pyridin-2-yl)-1H-indol-2-yl]-N-[(2R)-1,1,1-trifluoropropan-2-yl]pyridine-3-sulfonamide,
6-[3-cyano-1-cyclopentyl-5-(difluoromethyl)-1H-indol-2-yl]-N-(1,3-difluoropropan-2-yl)pyridine-3-sulfonamide,
2-[3-cyano-1-cyclopentyl-5-(difluoromethyl)-1H-indol-2-yl]-N-(1,3-difluoropropan-2-yl)pyrimidine-5-sulfonamide,
6-[3-cyano-1-cyclopentyl-5-(difluoromethyl)-1H-indol-2-yl]-N-[(2S)-1,1,1-trifluoropropan-2-yl]pyridine-3-sulfonamide,
6-[3-cyano-1-cyclopentyl-5-(difluoromethyl)-1H-indol-2-yl]-N-[(2R)-1,1,1-trifluoropropan-2-yl]pyridine-3-sulfonamide,
6-(3-cyano-1-cyclobutyl-5-fluoro-6-methyl-1H-indol-2-yl)-N-(1,1,1-trifluoro-2-methylpropan-2-yl)pyridine-3-sulfonamide,
6-[3-cyano-5-fluoro-6-methyl-1-(pyridin-2-yl)-1H-indol-2-yl]-N-(1,3-difluoropropan-2-yl)pyridine-3-sulfonamide,
6-[3-cyano-5-fluoro-6-methyl-1-(pyridin-2-yl)-1H-indol-2-yl]-N-[(2S)-1,1,1-trifluoropropan-2-yl]pyridine-3-sulfonamide,
6-[3-cyano-1-cyclobutyl-6-(difluoromethoxy)-5-fluoro-1H-indol-2-yl]-N-(1,3-difluoropropan-2-yl)pyridine-3-sulfonamide,
N-tert-butyl-6-[3-cyano-1-cyclobutyl-6-(difluoromethoxy)-1H-indol-2-yl]pyridine-3-sulfonamide,
2-(3-cyano-1-cyclobutyl-5-fluoro-1H-indol-2-yl)-N-[(1S)-1-cyclopropylethyl]pyrimidine-5-sulfonamide,
2-(3-cyano-1-cyclobutyl-5-methyl-1H-indol-2-yl)-N-[(1S)-1-cyclopropylethyl]pyrimidine-5-sulfonamide,
2-[3-cyano-5-fluoro-1-(propan-2-yl)-1H-indol-2-yl]-N-[(2S)-1,1,1-trifluoropropan-2-yl]pyrimidine-5-sulfonamide,
2-(3-cyano-1-cyclopentyl-5-fluoro-1H-indol-2-yl)-N-[(2S)-1,1,1-trifluoropropan-2-yl]pyrimidine-5-sulfonamide,
2-[3-cyano-1-(cyclopropylmethyl)-5-fluoro-1H-indol-2-yl]-N-[(2S)-1,1,1-trifluoropropan-2-yl]pyrimidine-5-sulfonamide,
6-[3-cyano-1-cyclobutyl-6-(difluoromethoxy)-5-fluoro-1H-indol-2-yl]-N-[(2S)-1,1,1-trifluoropropan-2-yl]pyridine-3-sulfonamide,
6-(3-cyano-1-cyclobutyl-5-methoxy-1H-indol-2-yl)-N-(1,3-difluoropropan-2-yl)pyridine-3-sulfonamide,
2-(3-cyano-1-cyclobutyl-5-methoxy-1H-indol-2-yl)-N-(1,3-difluoropropan-2-yl)pyrimidine-5-sulfonamide,
6-[3-cyano-1-cyclobutyl-6-(difluoromethoxy)-1H-indol-2-yl]pyridine-3-sulfonamide,
6-[3-cyano-6-(difluoromethoxy)-1-phenyl-1H-indol-2-yl]-N-[(2S)-1,1,1-trifluoropropan-2-yl]pyridine-3-sulfonamide,
6-[3-cyano-6-(difluoromethoxy)-1-phenyl-1H-indol-2-yl]-N-[(2R)-1,1,1-trifluoropropan-2-yl]pyridine-3-sulfonamide,
6-(3-cyano-1-cyclobutyl-4,6-difluoro-5-methyl-1H-indol-2-yl)-N-[(2S)-1,1,1-trifluoropropan-2-yl]pyridine-3-sulfonamide,
6-(3-cyano-1-cyclobutyl-4,6-difluoro-5-methyl-1H-indol-2-yl)-N-(1,3-difluoropropan-2-yl)pyridine-3-sulfonamide,
2-(3-cyano-1-cyclobutyl-7-fluoro-6-methyl-1H-indol-2-yl)-N-(1,3-difluoropropan-2-yl)pyrimidine-5-sulfonamide,
6-(3-cyano-1-cyclopentyl-4,6-difluoro-5-methyl-1H-indol-2-yl)-N-(1,3-difluoropropan-2-yl)pyridine-3-sulfonamide,
6-(3-cyano-1-cyclopentyl-4,6-difluoro-5-methyl-1H-indol-2-yl)-N-[(2S)-1,1,1-trifluoropropan-2-yl]pyridine-3-sulfonamide,
6-(3-cyano-1-cyclohexyl-5-methyl-1H-indol-2-yl)-N-[(2S)-1,1,1-trifluoropropan-2-yl]pyridine-3-sulfonamide,
2-[3-cyano-1-(cyclopropylmethyl)-5-methyl-1H-indol-2-yl]-N-[(1S)-1-cyclopropylethyl]pyrimidine-5-sulfonamide,
2-(3-cyano-1-cyclopentyl-5-methyl-1H-indol-2-yl)-N-[(1S)-1-cyclopropylethyl]pyrimidine-5-sulfonamide,
2-[3-cyano-5-methyl-1-(propan-2-yl)-1H-indol-2-yl]-N-[(1S)-1-cyclopropylethyl]pyrimidine-5-sulfonamide,
6-[3-cyano-5-methyl-1-(propan-2-yl)-1H-indol-2-yl]-N-[(1S)-1-cyclopropylethyl]pyridine-3-sulfonamide,
2-[3-cyano-5-methyl-1-(propan-2-yl)-1H-indol-2-yl]-N-(propan-2-yl)pyrimidine-5-sulfonamide,
2-[3-cyano-5-methyl-1-(propan-2-yl)-1H-indol-2-yl]-N-[(2S)-1,1,1-trifluoropropan-2-yl]pyrimidine-5-sulfonamide,
2-[3-cyano-5-methyl-1-(propan-2-yl)-1H-indol-2-yl]-N-(1,3-difluoropropan-2-yl)pyrimidine-5-sulfonamide,
1-cyclobutyl-6-(difluoromethoxy)-2-(5-sulfamoylpyridin-2-yl)-1H-indole-3-carboxamide,
2-(3-cyano-1-cyclobutyl-5-methoxy-1H-indol-2-yl)-N-[(2S)-1,1,1-trifluoropropan-2-yl]pyrimidine-5-sulfonamide,
2-(3-cyano-1-cyclobutyl-5-methoxy-1H-indol-2-yl)-N-[(1S)-1-cyclopropylethyl]pyrimidine-5-sulfonamide,
6-(3-cyano-1-cyclopentyl-5-methoxy-1H-indol-2-yl)-N-(1,3-difluoropropan-2-yl)pyridine-3-sulfonamide,
2-(3-cyano-1-cyclopentyl-5-methoxy-1H-indol-2-yl)-N-(1,3-difluoropropan-2-yl)pyrimidine-5-sulfonamide, 6-[3-cyano-1-cyclopentyl-6-(difluoromethoxy)-5-fluoro-1H-indol-2-yl]-N-(1,3-difluoropropan-2-yl)pyridine-3-sulfonamide, 6-[3-cyano-1-cyclopentyl-6-(difluoromethoxy)-5-fluoro-1H-indol-2-yl]-N-[(2S)-1,1,1-trifluoropropan-2-yl]pyridine-3-sulfonamide, 6-(3-cyano-1-cyclopentyl-5-fluoro-6-hydroxy-1H-indol-2-yl)-N-(1,3-difluoropropan-2-yl)pyridine-3-sulfonamide, 6-(3-cyano-1-cyclopentyl-5-fluoro-6-hydroxy-1H-indol-2-yl)-N-[(2S)-1,1,1-trifluoropropan-2-yl]pyridine-3-sulfonamide, 6-(3-cyano-1-cyclobutyl-5,7-difluoro-6-methyl-1H-indol-2-yl)-N-(1,1,1-trifluoro-2-methylpropan-2-yl)pyridine-3-sulfonamide, 6-(3-cyano-1-cyclobutyl-7-fluoro-6-methyl-1H-indol-2-yl)-N-(1,1,1-trifluoro-2-methylpropan-2-yl)pyridine-3-sulfonamide, 6-(3-cyano-1-cyclopentyl-7-fluoro-6-methyl-1H-indol-2-yl)-N-(1,1,1-trifluoro-2-methylpropan-2-yl)pyridine-3-sulfonamide, 6-(3-cyano-1-cyclopentyl-5,7-difluoro-6-methyl-1H-indol-2-yl)-N-(1,1,1-trifluoro-2-methylpropan-2-yl)pyridine-3-sulfonamide, 1-cyclobutyl-6-(difluoromethoxy)-2-{5-[(1,3-difluoropropan-2-yl)sulfamoyl]pyridin-2-yl}-1H-indole-3-carboxamide, 1-cyclobutyl-6-cyclopropyl-2-{5-[(1,3-difluoropropan-2-yl)sulfamoyl]pyridin-2-yl}-1H-indole-3-carboxamide, 6-[3-cyano-6-(difluoromethoxy)-1-(pyridin-2-yl)-1H-indol-2-yl]-N-(1,1,1-trifluoro-2-methylpropan-2-yl)pyridine-3-sulfonamide, 6-[3-cyano-6-cyclopropyl-1-(pyridin-2-yl)-1H-indol-2-yl]-N-(1,1,1-trifluoro-2-methylpropan-2-yl)pyridine-3-sulfonamide, 6-(3-cyano-6-methyl-1-phenyl-1H-indol-2-yl)-N-(1,1,1-trifluoro-2-methylpropan-2-yl)pyridine-3-sulfonamide, 2-(3-cyano-1-cyclopentyl-7-fluoro-6-methyl-1H-indol-2-yl)-N-(1,3-difluoropropan-2-yl)pyrimidine-5-sulfonamide, 6-(3-cyano-1-cyclobutyl-6-methyl-1H-indol-2-yl)-N-[1-(trifluoromethyl)cyclobutyl]pyridine-3-sulfonamide, 6-[3-cyano-1-cyclopentyl-6-(difluoromethoxy)-1H-indol-2-yl]-N-[1-(trifluoromethyl)cyclobutyl]pyridine-3-sulfonamide, 6-[3-cyano-1-cyclopentyl-6-(difluoromethoxy)-1H-indol-2-yl]-N-[(2S)-1,1,1-trifluoropropan-2-yl]pyridine-3-sulfonamide, 6-[3-cyano-1-cyclobutyl-6-(2,2-difluoroethyl)-1H-indol-2-yl]-N-[(1S)-1-cyclopropylethyl]pyridine-3-sulfonamide, 2-[3-cyano-1-cyclobutyl-6-(2,2-difluoroethyl)-1H-indol-2-yl]-N-(1,3-difluoropropan-2-yl)pyrimidine-5-sulfonamide, 2-[3-cyano-1-cyclobutyl-6-(2,2-difluoroethyl)-1H-indol-2-yl]-N-[(1S)-1-cyclopropylethyl]pyrimidine-5-sulfonamide, 6-[3-cyano-1-cyclopentyl-6-(2,2-difluoroethyl)-1H-indol-2-yl]-N-(1,3-difluoropropan-2-yl)pyridine-3-sulfonamide, 6-[3-cyano-1-cyclopentyl-6-(2,2-difluoroethyl)-1H-indol-2-yl]-N-[(1S)-1-cyclopropylethyl]pyridine-3-sulfonamide, 6-[3-cyano-1-cyclopentyl-6-(2,2-difluoroethyl)-1H-indol-2-yl]-N-[(2S)-1,1,1-trifluoropropan-2-yl]pyridine-3-sulfonamide, 6-[3-cyano-1-cyclopentyl-6-(2,2-difluoroethyl)-1H-indol-2-yl]-N-(1,1,1-trifluoro-2-methylpropan-2-yl)pyridine-3-sulfonamide, 2-[3-cyano-1-cyclopentyl-6-(2,2-difluoroethyl)-1H-indol-2-yl]-N-[(1S)-1-cyclopropylethyl]pyrimidine-5-sulfonamide, 2-[3-cyano-1-cyclopentyl-6-(2,2-difluoroethyl)-1H-indol-2-yl]-N-(propan-2-yl)pyrimidine-5-sulfonamide, 2-[3-cyano-1-cyclopentyl-6-(2,2-difluoroethyl)-1H-indol-2-yl]-N-(1,3-difluoropropan-2-yl)pyrimidine-5-sulfonamide, 2-[3-cyano-1-cyclopentyl-6-(2,2-difluoroethyl)-1H-indol-2-yl]-N-[(2S)-1,1,1-trifluoropropan-2-yl]pyrimidine-5-sulfonamide, 6-[3-cyano-5-fluoro-1-(pyrimidin-2-yl)-1H-indol-2-yl]-N-[(2S)-1,1,1-trifluoropropan-2-yl]pyridine-3-sulfonamide, 6-[3-cyano-5-fluoro-1-(pyrimidin-2-yl)-1H-indol-2-yl]-N-(1,1,1-trifluoro-2-methylpropan-2-yl)pyridine-3-sulfonamide, 2-(3-cyano-1-cyclopentyl-5-fluoro-1H-indol-2-yl)-N-(propan-2-yl)pyrimidine-5-sulfonamide, 6-[3-cyano-5-fluoro-1-(propan-2-yl)-1H-indol-2-yl]-N-[(1S)-1-cyclopropylethyl]pyridine-3-sulfonamide, 2-(3-cyano-1-cyclohexyl-6-methyl-1H-indol-2-yl)-N-[(2S)-1,1,1-trifluoropropan-2-yl]pyrimidine-5-sulfonamide, 6-(3-cyano-1-cyclohexyl-5-methyl-1H-indol-2-yl)-N-[(1S)-1-cyclopropylethyl]pyridine-3-sulfonamide, 6-(3-cyano-1-cyclopentyl-5-methyl-1H-indol-2-yl)-N-(1,1,1-trifluoro-2-methylpropan-2-yl)pyridine-3-sulfonamide, 6-[3-cyano-5-fluoro-1-(pyrimidin-2-yl)-1H-indol-2-yl]-N-(1,3-difluoropropan-2-yl)pyridine-3-sulfonamide, 6-(3-cyano-1-cyclobutyl-5-fluoro-6-methyl-1H-indol-2-yl)-N-[(2R)-1,1,1-trifluoropropan-2-yl]pyridine-3-sulfonamide, 2-[3-cyano-6-(difluoromethoxy)-1-phenyl-1H-indol-2-yl]-N-(1,3-difluoropropan-2-yl)pyrimidine-5-sulfonamide, 2-[3-cyano-6-(difluoromethoxy)-1-phenyl-1H-indol-2-yl]-N-[(2S)-1,1,1-trifluoropropan-2-yl]pyrimidine-5-sulfonamide, 6-[3-cyano-6-(difluoromethoxy)-1-phenyl-1H-indol-2-yl]-N-(1,1,1-trifluoro-2-methylpropan-2-yl)pyridine-3-sulfonamide, 6-(3-cyano-1-cyclobutyl-5-fluoro-6-methyl-1H-indol-2-yl)-N-[1-(trifluoromethyl)cyclopropyl]pyridine-3-sulfonamide, 6-(3-cyano-1-cyclopentyl-4-fluoro-5-methyl-1H-indol-2-yl)-N-(1,1,1-trifluoro-2-methylpropan-2-yl)pyridine-3-sulfonamide, 6-(3-cyano-1-cyclopentyl-4-fluoro-5-methyl-1H-indol-2-yl)-N-[(2S)-1,1,1-trifluoropropan-2-yl]pyridine-3-sulfonamide, 6-[3-cyano-1-(cyclopropylmethyl)-6-(2,2-difluoroethyl)-1H-indol-2-yl]-N-(1,3-difluoropropan-2-yl)pyridine-3-sulfonamide, 6-[3-cyano-1-(cyclopropylmethyl)-6-(2,2-difluoroethyl)-1H-indol-2-yl]-N-[(1S)-1-cyclopropylethyl]pyridine-3-sulfonamide, 6-[3-cyano-1-(cyclopropylmethyl)-6-(2,2-difluoroethyl)-1H-indol-2-yl]-N-[(2S)-1,1,1-trifluoropropan-2-yl]pyridine-3-sulfonamide, 2-[3-cyano-1-(cyclopropylmethyl)-6-(2,2-difluoroethyl)-1H-indol-2-yl]-N-[(1S)-1-cyclopropylethyl]pyrimidine-5-sulfonamide, 2-[3-cyano-1-(cyclopropylmethyl)-6-(2,2-difluoroethyl)-1H-indol-2-yl]-N-(propan-2-yl)pyrimidine-5-sulfonamide, 2-[3-cyano-1-(cyclopropylmethyl)-6-(2,2-difluoroethyl)-1H-indol-2-yl]-N-(1,3-difluoropropan-2-yl)pyrimidine-5-sulfonamide, 2-[3-cyano-1-(cyclopropylmethyl)-6-(2,2-difluoroethyl)-1H-indol-2-yl]-N-[(2S)-1,1,1-trifluoropropan-2-yl]pyrimidine-5-sulfonamide, 6-[3-cyano-6-(difluoromethoxy)-1-(pyridin-2-yl)-1H-indol-2-yl]-N-[1-(trifluoromethyl)cyclopropyl]pyridine-3-sulfonamide, N-tert-butyl-6-[3-cyano-6-(difluoromethoxy)-1-phenyl-1H-indol-2-yl]pyridine-3-sulfonamide, 6-(3-cyano-1-cyclopentyl-4-fluoro-6-methyl-1H-indol-2-yl)-N-[(2S)-1,1,1-trifluoropropan-2-yl]pyridine-3-sulfonamide, 6-(3-cyano-1-cyclopentyl-4-fluoro-6-methyl-1H-indol-2-yl)-N-(1,1,1-trifluoro-2-methylpropan-2-yl)pyridine-3-sulfonamide, 6-(3-cyano-1-cyclobutyl-4-fluoro-6-methyl-1H-indol-2-yl)-N-[(2S)-1,1,1-trifluoropropan-2-yl]pyridine-3-sulfonamide, 6-(3-cyano-1-cyclopentyl-4-fluoro-6-methyl-1H-indol-2-yl)-N-[1-(trifluoromethyl)cyclopropyl]pyridine-3-sulfonamide, 6-(3-cyano-1-cyclobutyl-4-fluoro-6-methyl-1H-indol-2-yl)-N-[1-(trifluoromethyl)cyclopropyl]pyridine-3-sulfonamide, 6-(3-cyano-1-cyclobutyl-6-cyclopropyl-5-fluoro-1H-indol-2-yl)-N-[(2S)-1,1,1-trifluoropropan-2-yl]pyridine-3-sulfonamide, 6-(3-cyano-1-cyclobutyl-6-cyclopropyl-5-fluoro-1H-indol-2-yl)-N-[(2R)-1,1,1-trifluoropropan-2-yl]pyridine-3-sulfonamide, 6-(3-cyano-1-cyclopentyl-6-ethyl-5-fluoro-1H-indol-2-yl)-N-[(2R)-1,1,1-trifluoropropan-2-yl]pyridine-3-sulfonamide, 6-(3-cyano-1-cyclopentyl-6-ethyl-5-fluoro-1H-indol-2-yl)-N-[(2S)-1,1,1-trifluoropropan-2-yl]pyridine-3-sulfonamide, 6-[3-cyano-5-fluoro-6-methyl-1-(pyrimidin-2-yl)-1H-indol-2-yl]-N-[(2S)-1,1,1-trifluoropropan-2-yl]pyridine-3-sulfonamide, 6-[3-cyano-6-(difluoromethoxy)-1-(pyrimidin-2-yl)-1H-indol-2-yl]-N-(1,3-difluoropropan-2-yl)pyridine-3-sulfonamide, 6-[5-chloro-3-cyano-1-cyclobutyl-6-(difluoromethoxy)-1H-indol-2-yl]-N-[(2S)-1,1,1-trifluoropropan-2-yl]pyridine-3-sulfonamide, 6-(3-cyano-1-cyclopentyl-6-ethyl-5-fluoro-1H-indol-2-yl)-N-[1-(trifluoromethyl)cyclopropyl]pyridine-3-sulfonamide, 2-(3-cyano-1-cyclopentyl-6-ethyl-5-fluoro-1H-indol-2-yl)-N-(1,3-difluoropropan-2-yl)pyrimidine-5-sulfonamide, 6-(3-cyano-1-cyclopentyl-6-ethyl-5-fluoro-1H-indol-2-yl)-N-(1,3-difluoropropan-2-yl)pyridine-3-sulfonamide, 6-(3-cyano-1-cyclobutyl-6-ethyl-5-fluoro-1H-indol-2-yl)-N-[(2S)-1,1,1-trifluoropropan-2-yl]pyridine-3-sulfonamide, 6-(3-cyano-1-cyclobutyl-6-ethyl-5-fluoro-1H-indol-2-yl)-N-[(2R)-1,1,1-trifluoropropan-2-yl]pyridine-3-sulfonamide, 6-(3-cyano-1-cyclobutyl-6-ethyl-5-fluoro-1H-indol-2-yl)-N-[1-(trifluoromethyl)cyclopropyl]pyridine-3-sulfonamide, N-tert-butyl-6-(3-cyano-1-cyclopentyl-5-fluoro-6-methyl-1H-indol-2-yl)pyridine-3-sulfonamide, 6-(3-cyano-1-cyclopentyl-5-fluoro-6-methyl-1H-indol-2-yl)-N-[1-(trifluoromethyl)cyclopropyl]pyridine-3-sulfonamide, 6-(3-cyano-1-cyclopentyl-5-fluoro-6-methyl-1H-indol-2-yl)-N-(1-methylcyclopropyl)pyridine-3-sulfonamide, 6-[1-cyclobutyl-6-(difluoromethoxy)-5-methyl-1H-indol-2-yl]-N-[(2S)-1,1,1-trifluoropropan-2-yl]pyridine-3-sulfonamide, 6-[3-cyano-1-cyclobutyl-6-(difluoromethoxy)-5-ethyl-1H-indol-2-yl]-N-[(2S)-1,1,1-trifluoropropan-2-yl]pyridine-3-sulfonamide, 6-[3-cyano-1-cyclobutyl-6-(difluoromethoxy)-5-fluoro-1H-indol-2-yl]-N-[(2R)-1,1,1-trifluoropropan-2-yl]pyridine-3-sulfonamide, 6-[3-cyano-6-(difluoromethoxy)-1-(4-fluorophenyl)-1H-indol-2-yl]-N-[(2R)-1,1,1-trifluoropropan-2-yl]pyridine-3-sulfonamide, 6-[3-cyano-6-cyclopropyl-1-(pyrimidin-2-yl)-1H-indol-2-yl]-N-[(2S)-1,1,1-trifluoropropan-2-yl]pyridine-3-sulfonamide, N-tert-butyl-6-(3-cyano-1-cyclobutyl-5-fluoro-6-methyl-1H-indol-2-yl)pyridine-3-sulfonamide, 6-(3-cyano-1-cyclobutyl-5-fluoro-6-methyl-1H-indol-2-yl)-N-cyclopropylpyridine-3-sulfonamide, 6-(3-cyano-1-cyclopentyl-5,7-difluoro-6-methyl-1H-indol-2-yl)-N-[(2R)-1,1,1-trifluoropropan-2-yl]pyridine-3-sulfonamide, 6-(3-cyano-1-cyclopentyl-5,7-difluoro-6-methyl-1H-indol-2-yl)-N-[1-(trifluoromethyl)cyclopropyl]pyridine-3-sulfonamide, 6-(3-cyano-1-cyclobutyl-5-fluoro-6-methyl-1H-indol-2-yl)-N-(propan-2-yl)pyridine-3-sulfonamide, 2-(3-cyano-1-cyclopentyl-5,7-difluoro-6-methyl-1H-indol-2-yl)-N-(1,3-difluoropropan-2-yl)pyrimidine-5-sulfonamide, 6-[3-cyano-6-(difluoromethoxy)-5-fluoro-1-(pyridine-2-yl)-1H-indol-2-yl]-N-[(2S)-1,1,1-trifluoropropan-2-yl]pyridine-3-sulfonamide, 6-[5-chloro-3-cyano-1-cyclobutyl-6-(difluoromethoxy)-1H-indol-2-yl]-N-(1-methylcyclopropyl)pyridine-3-sulfonamide, 2-[5-chloro-3-cyano-1-cyclobutyl-6-(difluoromethoxy)-1H-indol-2-yl]-N-(1,3-difluoropropan-2-yl)pyrimidine-5-sulfonamide, 6-[3-cyano-1-cyclobutyl-6-(difluoromethoxy)-5-methyl-1H-indol-2-yl]-N-[(2S)-1,1,1-trifluoropropan-2-yl]pyridine-3-sulfonamide, 6-(3-cyano-1-cyclopentyl-6-cyclopropyl-5-fluoro-1H-indol-2-yl)-N-[(2S)-1,1,1-trifluoropropan-2-yl]pyridine-3-sulfonamide, 6-(3-cyano-1-cyclopentyl-6-cyclopropyl-5-fluoro-1H-indol-2-yl)-N-[(2R)-1,1,1-trifluoropropan-2-yl]pyridine-3-sulfonamide, 6-[3-cyano-6-(difluoromethoxy)-1-(pyrimidin-2-yl)-1H-indol-2-yl]-N-(1,1,1-trifluoro-2-methylpropan-2-yl)pyridine-3-sulfonamide, 6-[3-cyano-6-(difluoromethoxy)-1-(4-fluorophenyl)-1H-indol-2-yl]-N-[1-(trifluoromethyl)cyclopropyl]pyridine-3-sulfonamide, 6-[3-cyano-1-cyclobutyl-6-(difluoromethoxy)-5-methyl-1H-indol-2-yl]-N-[(2R)-1,1,1-trifluoropropan-2-yl]pyridine-3-sulfonamide, 6-(3-cyano-1-cyclobutyl-6-ethyl-5-fluoro-1H-indol-2-yl)-N-[1-(trifluoromethyl)cyclopropyl]pyridine-3-sulfonamide, 6-(3-cyano-1-cyclobutyl-5,7-difluoro-6-methyl-1H-indol-2-yl)-N-[(2R)-1,1,1-trifluoropropan-2-yl]pyridine-3-sulfonamide, 6-(3-cyano-1-cyclobutyl-5,7-difluoro-6-methyl-1H-indol-2-yl)-N-[1-(trifluoromethyl)cyclopropyl]pyridine-3-sulfonamide, 2-(3-cyano-1-cyclobutyl-5,7-difluoro-6-methyl-1H-indol-2-yl)-N-(1,3-difluoropropan-2-yl)pyrimidine-5-sulfonamide, 6-(3-cyano-1-cyclopentyl-5-methoxy-6-methyl-1H-indol-2-yl)-N-[(2S)-1,1,1-trifluoropropan-2-yl]pyridine-3-sulfonamide, 6-[3-cyano-6-(difluoromethoxy)-5-fluoro-1-(pyridin-2-yl)-1H-indol-2-yl]-N-[(2R)-1,1,1-trifluoropropan-2-yl]pyridine-3-sulfonamide, 6-[3-cyano-6-methyl-1-(pyridin-2-yl)-1H-indol-2-yl]-N-[(2R)-1,1,1-trifluoropropan-2-yl]pyridine-3-sulfonamide, 6-(3-cyano-1-cyclopentyl-6-ethyl-5-fluoro-1H-indol-2-yl)-N-(1,1,1-trifluoro-2-methylpropan-2-yl)pyridine-3-sulfonamide, 6-[3-cyano-5-fluoro-1-(pyrimidin-2-yl)-1H-indol-2-yl]-N-[(2R)-1,1,1-trifluoropropan-2-yl]pyridine-3-sulfonamide, 6-[3-cyano-1-cyclobutyl-6-(difluoromethoxy)-5-hydroxy-1H-indol-2-yl]-N-[(2S)-1,1,1-trifluoropropan-2-yl]pyridine-3-sulfonamide, 6-(5-bromo-3-cyano-1-cyclopentyl-6-methyl-1H-indol-2-yl)-N-[(2S)-1,1,1-trifluoropropan-2-yl]pyridine-3-sulfonamide, 6-[3-cyano-1-cyclobutyl-6-(difluoromethoxy)-5-fluoro-1H-indol-2-yl]-N-(1,1,1-trifluoro-2-methylpropan-2-yl)pyridine-3-sulfonamide, 6-[3-cyano-6-methyl-1-(pyrimidin-2-yl)-1H-indol-2-yl]-N-[(2S)-1,1,1-trifluoropropan-2-yl]pyridine-3-sulfonamide, 6-(3-cyano-1-cyclohexyl-5-fluoro-6-methyl-1H-indol-2-yl)-N-[(2S)-1,1,1-trifluoropropan-2-yl]pyridine-3-sulfonamide, 2-(3-cyano-1-cyclohexyl-5-fluoro-6-methyl-1H-indol-2-yl)-N-[(2S)-1,1,1-trifluoropropan-2-yl]pyrimidine-5-sulfonamide, 6-(3-cyano-1-cyclohexyl-5-fluoro-6-methyl-1H-indol-2-yl)-N-[(2R)-1,1,1-trifluoropropan-2-yl]pyridine-3-sulfonamide, 6-(3-cyano-1-cyclopentyl-5-fluoro-6-methyl-1H-indol-2-yl)-N-(1,1,1-trifluoro-2-methylpropan-2-yl)pyridine-3-sulfonamide, 6-[3-cyano-6-(difluoromethoxy)-5-fluoro-1-(pyrimidin-2-yl)-1H-indol-2-yl]-N-[(2S)-1,1,1-trifluoropropan-2-yl]pyridine-3-sulfonamide, 2-[5-(tert-butylsulfamoyl)pyridin-2-yl]-1-cyclopentyl-5-fluoro-6-methyl-1H-indole-3-carboxamide, 6-(5-bromo-3-cyano-1-cyclobutyl-6-hydroxy-1H-indol-2-yl)-N-[(2S)-1,1,1-trifluoropropan-2-yl]pyridine-3-sulfonamide, 6-[3-cyano-1-cyclobutyl-6-(difluoromethoxy)-5-(methylsulfanyl)-1H-indol-2-yl]-N-[(2S)-1,1,1-trifluoropropan-2-yl]pyridine-3-sulfonamide, 6-[3-cyano-6-methyl-1-(pyridin-2-yl)-1H-indol-2-yl]-N-(1,1,1-trifluoro-2-methylpropan-2-yl)pyridine-3-sulfonamide, 6-[3-cyano-6-(difluoromethoxy)-1-(4-fluorophenyl)-1H-indol-2-yl]-N-(1,1,1-trifluoro-2-methylpropan-2-yl)pyridine-3-sulfonamide, 6-[3-cyano-6-methyl-1-(pyrimidin-2-yl)-1H-indol-2-yl]-N-[(2R)-1,1,1-trifluoropropan-2-yl]pyridine-3-sulfonamide, 6-[3-cyano-6-methyl-1-(pyrimidin-2-yl)-1H-indol-2-yl]-N-(1,1,1-trifluoro-2-methylpropan-2-yl)pyridine-3-sulfonamide, 6-[3-cyano-6-(difluoromethoxy)-1-(pyrimidin-2-yl)-1H-indol-2-yl]-N-[1-(trifluoromethyl)cyclopropyl]pyridine-3-sulfonamide, 6-(3-cyano-1-cyclopentyl-5-hydroxy-6-methyl-1H-indol-2-yl)-N-[(2S)-1,1,1-trifluoropropan-2-yl]pyridine-3-sulfonamide, 6-(5-bromo-3-cyano-1-cyclopentyl-6-methyl-1H-indol-2-yl)-N-[(2R)-1,1,1-trifluoropropan-2-yl]pyridine-3-sulfonamide, 6-(3-cyano-1-cyclopentyl-5-hydroxy-6-methyl-1H-indol-2-yl)-N-[(2R)-1,1,1-trifluoropropan-2-yl]pyridine-3-sulfonamide, 6-(3-cyano-1-cyclopentyl-5-methoxy-6-methyl-1H-indol-2-yl)-N-[(2R)-1,1,1-trifluoropropan-2-yl]pyridine-3-sulfonamide, 6-[3-cyano-5-fluoro-6-methyl-1-(pyrimidin-2-yl)-1H-indol-2-yl]-N-[(2R)-1,1,1-trifluoropropan-2-yl]pyridine-3-sulfonamide, 6-[3-cyano-1-cyclobutyl-5-(2,2-difluoroethyl)-1H-indol-2-yl]-N-(1-methylcyclopropyl)pyridine-3-sulfonamide, 6-[3-cyano-1-cyclobutyl-6-(2,2-difluoroethyl)-5-fluoro-1H-indol-2-yl]-N-[(2S)-1,1,1-trifluoropropan-2-yl]pyridine-3-sulfonamide, 6-[3-cyano-5-fluoro-6-methyl-1-(pyridin-2-yl)-1H-indol-2-yl]-N-[(2R)-1,1,1-trifluoropropan-2-yl]pyridine-3-sulfonamide, 1-cyclopentyl-5-fluoro-6-methyl-2-(5-{[(2R)-1,1,1-trifluoropropan-2-yl]sulfamoyl}pyridin-2-yl)-1H-indole-3-carboxamide, 1-cyclopentyl-5-fluoro-6-methyl-2-(5-{[(2S)-1,1,1-trifluoropropan-2-yl]sulfamoyl}pyridin-2-yl)-1H-indole-3-carboxamide, 1-cyclopentyl-5-fluoro-6-methyl-2-{5-[(1,1,1-trifluoro-2-methylpropan-2-yl)sulfamoyl]pyridin-2-yl}-1H-indole-3-carboxamide, 6-[3-cyano-1-cyclobutyl-5-(2,2-difluoroethyl)-1H-indol-2-yl]-N-[(2S)-1,1,1-trifluoropropan-2-yl]pyridine-3-sulfonamide, 1-cyclobutyl-6-(difluoromethoxy)-5-fluoro-2-(5-{[(2S)-1,1,1-trifluoropropan-2-yl]sulfamoyl}pyridin-2-yl)-1H-indole-3-carboxamide, 6-[3-cyano-6-ethyl-5-fluoro-1-(pyridin-2-yl)-1H-indol-2-yl]-N-[(2S)-1,1,1-trifluoropropan-2-yl]pyridine-3-sulfonamide, 6-(3-cyano-1-cyclohexyl-5-fluoro-6-methyl-1H-indol-2-yl)-N-(1,1,1-trifluoro-2-methylpropan-2-yl)pyridine-3-sulfonamide, 1-cyclohexyl-5-fluoro-6-methyl-2-(5-{[(2S)-1,1,1-trifluoropropan-2-yl]sulfamoyl}pyridin-2-yl)-1H-indole-3-carboxamide, 1-cyclohexyl-5-fluoro-6-methyl-2-(5-{[(2S)-1,1,1-trifluoropropan-2-yl]sulfamoyl}pyrimidin-2-yl)-1H-indole-3-carboxamide, 6-[5-chloro-3-cyano-1-(pyrimidin-2-yl)-1H-indol-2-yl]-N-[(2S)-1,1,1-trifluoropropan-2-yl]pyridine-3-sulfonamide, N-tert-butyl-6-(3-cyano-1-cyclohexyl-5-fluoro-6-methyl-1H-indol-2-yl)pyridine-3-sulfonamide, 6-(3-cyano-1-cyclobutyl-5-fluoro-6-hydroxy-1H-indol-2-yl)-N-[(2S)-1,1,1-trifluoropropan-2-yl]pyridine-3-sulfonamide, 6-[3-cyano-1-cyclopentyl-6-(difluoromethoxy)-5-fluoro-1H-indol-2-yl]-N-[(2R)-1,1,1-trifluoropropan-2-yl]pyridine-3-sulfonamide, 1-cyclohexyl-5-fluoro-6-methyl-2-{5-[(1,1,1-trifluoro-2-methylpropan-2-yl)sulfamoyl]pyridin-2-yl}-1H-indole-3-carboxamide, 1-cyclohexyl-5-fluoro-6-methyl-2-(5-sulfamoylpyridin-2-yl)-1H-indole-3-carboxamide, 1-cyclohexyl-5-fluoro-6-methyl-2-(5-{[(2R)-1,1,1-trifluoropropan-2-yl]sulfamoyl}pyridin-2-yl)-1H-indole-3-carboxamide methyl 1-cyclohexyl-5-fluoro-2-(5-{[(2S)-1,1,1-trifluoropropan-2-yl]sulfamoyl}pyridin-2-yl)-1H-indole-3-carboxylate 1-cyclopentyl-6-(difluoromethoxy)-5-fluoro-2-(5-{[(2R)-1,1,1-trifluoropropan-2-yl]sulfamoyl}pyridin-2-yl)-1H-indole-3-carboxamide N-tert-butyl-6-(3-cyano-1-cyclobutyl-5-fluoro-6-hydroxy-1H-indol-2-yl)pyridine-3-sulfonamide 6-[3-cyano-1-cyclobutyl-6-(difluoromethoxy)-5-fluoro-1H-indol-2-yl]pyridine-3-sulfonamide 2-[5-(tert-butylsulfamoyl)pyridin-2-yl]-1-cyclobutyl-6-(difluoromethoxy)-5-fluoro-1H-indole-3-carboxamide 6-{3-cyano-5-fluoro-1-[5-(trifluoromethyl)pyridin-2-yl]-1H-indol-2-yl}-N-[(2S)-1,1,1-trifluoropropan-2-yl]pyridine-3-sulfonamide 6-(3-cyano-1-cyclobutyl-5-fluoro-6-methoxy-1H-indol-2-yl)-N-[(2S)-1,1,1-trifluoropropan-2-yl]pyridine-3-sulfonamide 6-(3-cyano-1-cyclobutyl-6-ethoxy-5-fluoro-1H-indol-2-yl)-N-[(2S)-1,1,1-trifluoropropan-2-yl]pyridine-3-sulfonamide 6-[1-cyclobutyl-6-(difluoromethoxy)-5-fluoro-1H-indol-2-yl]-N-[(2S)-1,1,1-trifluoropropan-2-yl]pyridine-3-sulfonamide 6-(1-cyclobutyl-5-fluoro-6-hydroxy-1H-indol-2-yl)-N-[(2S)-1,1,1-trifluoropropan-2-yl]pyridine-3-sulfonamide, 1-cyclobutyl-6-(difluoromethoxy)-5-fluoro-2-{5-[(1,1,1-trifluoro-2-methylpropan-2-yl)sulfamoyl]pyridin-2-yl}-1H-indole-3-carboxamide, 1-cyclopentyl-5-fluoro-6-methyl-2-(5-{[1-(trifluoromethyl)cyclopropyl]sulfamoyl}pyridin-2-yl)-1H-indole-3-carboxamide, 1-cyclobutyl-6-cyclopropyl-5-fluoro-2-(5-{[(2S)-1,1,1-trifluoropropan-2-yl]sulfamoyl}pyridin-2-yl)-1H-indole-3-carboxamide, 1-cyclobutyl-5-fluoro-6-methyl-2-(5-{[(2R)-1,1,1-trifluoropropan-2-yl]sulfamoyl}pyridin-2-yl)-1H-indole-3-carboxamide, 5-chloro-1-cyclobutyl-6-methyl-2-(5-{[(2S)-1,1,1-trifluoropropan-2-yl]sulfamoyl}pyrimidin-2-yl)-1H-indole-3-carboxamide, 5-chloro-1-cyclobutyl-6-methyl-2-(5-{[(2S)-1,1,1-trifluoropropan-2-yl]sulfamoyl}pyridin-2-yl)-1H-indole-3-carboxamide, 5-chloro-1-cyclobutyl-6-methyl-2-(5-{[(2R)-1,1,1-trifluoropropan-2-yl]sulfamoyl}pyridin-2-yl)-1H-indole-3-carboxamide, 6-chloro-1-cyclobutyl-5-fluoro-2-(5-{[(2S)-1,1,1-trifluoropropan-2-yl]sulfamoyl}pyridin-2-yl)-1H-indole-3-carboxamide, 1-cyclobutyl-5-fluoro-6-methyl-2-(5-{[(2S)-1,1,1-trifluoropropan-2-yl]sulfamoyl}pyridin-2-yl)-1H-indole-3-carboxamide, 6-[3-cyano-1-cyclobutyl-6-(difluoromethoxy)-5-fluoro-1H-indol-2-yl]-N-[(2S)-1,1,1-trifluorobutan-2-yl]pyridine-3-sulfonamide, 6-[3-cyano-5-fluoro-6-methyl-1-(3-methylpyridin-2-yl)-1H-indol-2-yl]-N-[(2S)-1,1,1-trifluoropropan-2-yl]pyridine-3-sulfonamide, 6-{3-cyano-5-fluoro-6-methyl-1-[5-(trifluoromethyl)pyridin-2-yl]-1H-indol-2-yl}-N-[(2S)-1,1,1-trifluoropropan-2-yl]pyridine-3-sulfonamide, 1-cyclohexyl-5-fluoro-2-(5-{[(2S)-1,1,1-trifluoropropan-2-yl]sulfamoyl}pyridin-2-yl)-1H-indole-3-carboxylic acid, 6-[3-cyano-5-fluoro-1-(5-fluoropyridin-2-yl)-6-methyl-1H-indol-2-yl]-N-[(2S)-1,1,1-trifluoropropan-2-yl]pyridine-3-sulfonamide, 6-[3-cyano-1-(5-cyanopyridin-2-yl)-5-fluoro-6-methyl-1H-indol-2-yl]-N-[(2S)-1,1,1-trifluoropropan-2-yl]pyridine-3-sulfonamide, 6-[3-cyano-5-fluoro-6-methyl-1-(5-nitropyridin-2-yl)-1H-indol-2-yl]-N-[(2S)-1,1,1-trifluoropropan-2-yl]pyridine-3-sulfonamide, 5-chloro-1-cyclobutyl-2-[5-(propan-2-ylsulfamoyl)pyrimidin-2-yl]-1H-indole-3-carboxamide, 1-cyclohexyl-6-(difluoromethoxy)-2-(5-{[(2S)-1,1,1-trifluoropropan-2-yl]sulfamoyl}pyrimidin-2-yl)-1H-indole-3-carboxamide, 1-cyclohexyl-6-(difluoromethoxy)-2-[5-(propan-2-ylsulfamoyl)pyrimidin-2-yl]-1H-indole-3-carboxamide, 5-fluoro-1-(pyridin-2-yl)-2-(5-{[(2S)-1,1,1-trifluoropropan-2-yl]sulfamoyl}pyridin-2-yl)-1H-indole-3-carboxamide, 6-[3-cyano-5-fluoro-6-methyl-1-(tetrahydro-2H-pyran-4-yl)-1H-indol-2-yl]-N-[(2R)-1,1,1-trifluoropropan-2-yl]pyridine-3-sulfonamide, 6-[3-cyano-5-fluoro-6-methyl-1-(tetrahydro-2H-pyran-4-yl)-1H-indol-2-yl]-N-(1,1,1-trifluoro-2-methylpropan-2-yl)pyridine-3-sulfonamide, 6-[3-cyano-5-fluoro-6-methyl-1-(tetrahydro-2H-pyran-4-yl)-1H-indol-2-yl]-N-[(2S)-1,1,1-trifluoropropan-2-yl]pyridine-3-sulfonamide, N-tert-butyl-6-[3-cyano-5-fluoro-6-methyl-1-(tetrahydro-2H-pyran-4-yl)-1H-indol-2-yl]pyridine-3-sulfonamide, 2-[3-cyano-5-fluoro-6-methyl-1-(tetrahydro-2H-pyran-4-yl)-1H-indol-2-yl]-N-[(2S)-1,1,1-trifluoropropan-2-yl]pyrimidine-5-sulfonamide, methyl 1-cyclopentyl-5-fluoro-6-methyl-2-{5-[(1,1,1-trifluoro-2-methylpropan-2-yl)sulfamoyl]pyridin-2-yl}-1H-indole-3-carboxylate, methyl 2-[5-(tert-butylsulfamoyl)pyridin-2-yl]-1-cyclopentyl-5-fluoro-6-methyl-1H-indole-3-carboxylate, methyl 1-cyclopentyl-5-fluoro-6-methyl-2-(5-{[(2S)-1,1,1-trifluoropropan-2-yl]sulfamoyl}pyridin-2-yl)-1H-indole-3-carboxylate, 6-(3-cyano-1-cyclobutyl-5-methoxy-6-methyl-1H-indol-2-yl)-N-[(2S)-1,1,1-trifluoropropan-2-yl]pyridine-3-sulfonamide, 1-cyclopentyl-5-fluoro-6-methyl-2-(5-{[(2S)-1,1,1-trifluoropropan-2-yl]sulfamoyl}pyridin-2-yl)-1H-indole-3-carboxylic acid, 6-(1-cyclopentyl-5-fluoro-6-methyl-1H-indol-2-yl)-N-[(2S)-1,1,1-trifluoropropan-2-yl]pyridine-3-sulfonamide, 1-cyclopentyl-5-fluoro-N,6-dimethyl-2-(5-{[(2S)-1,1,1-trifluoropropan-2-yl]sulfamoyl}pyridin-2-yl)-1H-indole-3-carboxamide,
1-cyclopentyl-N-ethyl-5-fluoro-6-methyl-2-(5-{[(2S)-1,1,1-trifluoropropan-2-yl]sulfamoyl}pyridin-2-yl)-1H-indole-3-carboxamide,
1-cyclopentyl-5-fluoro-6-methyl-N-(propan-2-yl)-2-(5-{[(2S)-1,1,1-trifluoropropan-2-yl]sulfamoyl}pyridin-2-yl)-1H-indole-3-carboxamide,
N-tert-butyl-6-(3-cyano-1-cyclobutyl-6-ethyl-5-fluoro-1H-indol-2-yl)pyridine-3-sulfonamide,
1-cyclopentyl-5-fluoro-6-methyl-2-{5-[(1,1,1-trifluoro-2-methylpropan-2-yl)sulfamoyl]pyridin-2-yl}-1H-indole-3-carboxylic acid,
2-[5-(tert-butylsulfamoyl)pyridin-2-yl]-1-cyclopentyl-5-fluoro-6-methyl-1H-indole-3-carboxylic acid
5-fluoro-6-methyl-1-(tetrahydro-2H-pyran-4-yl)-2-(5-{[(2R)-1,1,1-trifluoropropan-2-yl]sulfamoyl}pyridin-2-yl)-1H-indole-3-carboxamide,
5-fluoro-6-methyl-1-(tetrahydro-2H-pyran-4-yl)-2-{5-[(1,1,1-trifluoro-2-methylpropan-2-yl)sulfamoyl]pyridin-2-yl}-1H-indole-3-carboxamide,
5-fluoro-6-methyl-1-(tetrahydro-2H-pyran-4-yl)-2-(5-{[(2S)-1,1,1-trifluoropropan-2-yl]sulfamoyl}pyridin-2-yl)-1H-indole-3-carboxamide,
methyl 2-[5-(tert-butylsulfamoyl)pyridin-2-yl]-1-cyclobutyl-5-fluoro-6-methyl-1H-indole-3-carboxylate,
methyl 1-cyclobutyl-5-fluoro-6-methyl-2-(5-{[(2S)-1,1,1-trifluoropropan-2-yl]sulfamoyl}pyridin-2-yl)-1H-indole-3-carboxylate,
6-[3-cyano-1-cyclobutyl-5-fluoro-6-(methylsulfanyl)-1H-indol-2-yl]-N-[(2S)-1,1,1-trifluoropropan-2-yl]pyridine-3-sulfonamide,
6-[3-cyano-1-(cyclopropylmethyl)-6-(difluoromethoxy)-4-fluoro-1H-indol-2-yl]-N-[(2S)-1,1,1-trifluoropropan-2-yl]pyridine-3-sulfonamide,
methyl 1-cyclobutyl-5-fluoro-6-methyl-2-(5-{[(2S)-1,1,1-trifluoropropan-2-yl]sulfamoyl}pyrimidin-2-yl)-1H-indole-3-carboxylate,
1-cyclobutyl-5-fluoro-6-methyl-2-(5-{[(2S)-1,1,1-trifluoropropan-2-yl]sulfamoyl}pyrimidin-2-yl)-1H-indole-3-carboxylic acid,
2-[5-(tert-butylsulfamoyl)pyridin-2-yl]-1-cyclobutyl-5-fluoro-6-methyl-1H-indole-3-carboxylic acid,
6-[3-cyano-6-ethyl-5-fluoro-1-(5-fluoropyridin-2-yl)-1H-indol-2-yl]-N-[(2S)-1,1,1-trifluoropropan-2-yl]pyridine-3-sulfonamide,
6-[3-cyano-6-ethyl-5-fluoro-1-(pyridin-2-yl)-1H-indol-2-yl]-N-[(2S)-1,1,1-trifluoropropan-2-yl]pyridine-3-sulfonamide,
6-chloro-1-cyclobutyl-2-[5-(propan-2-ylsulfamoyl)pyrimidin-2-yl]-1H-indole-3-carboxamide,
1-cyclobutyl-2-[5-(propan-2-ylsulfamoyl)pyrimidin-2-yl]-6-(trifluoromethoxy)-1H-indole-3-carboxamide,
1-cyclopentyl-2-[5-(propan-2-ylsulfamoyl)pyrimidin-2-yl]-6-(trifluoromethoxy)-1H-indole-3-carboxamide,
1-cyclopentyl-5-fluoro-N,N,6-trimethyl-2-(5-{[(2S)-1,1,1-trifluoropropan-2-yl]sulfamoyl}pyridin-2-yl)-1H-indole-3-carboxamide,
6-[3-cyano-6-(difluoromethoxy)-4-fluoro-1-(propan-2-yl)-1H-indol-2-yl]-N-[(2S)-1,1,1-trifluoropropan-2-yl]pyridine-3-sulfonamide,
6-[5-chloro-3-cyano-6-methyl-1-(pyrimidin-2-yl)-1H-indol-2-yl]-N-[(2S)-1,1,1-trifluoropropan-2-yl]pyridine-3-sulfonamide,
6-[3-cyano-6-(difluoromethoxy)-5-fluoro-1-propyl-1H-indol-2-yl]-N-[(2S)-1,1,1-trifluoropropan-2-yl]pyridine-3-sulfonamide,
6-[3-cyano-1-(cyclopropylmethyl)-6-(difluoromethoxy)-5-fluoro-1H-indol-2-yl]-N-[(2S)-1,1,1-trifluoropropan-2-yl]pyridine-3-sulfonamide,
6-[3-cyano-6-(difluoromethoxy)-5-fluoro-1-propyl-1H-indol-2-yl]-N-[(2R)-1,1,1-trifluoropropan-2-yl]pyridine-3-sulfonamide,
6-[3-cyano-1-(cyclopropylmethyl)-6-(difluoromethoxy)-5-fluoro-1H-indol-2-yl]-N-[(2R)-1,1,1-trifluoropropan-2-yl]pyridine-3-sulfonamide,
6-[3-cyano-1-cyclobutyl-6-(difluoromethoxy)-5-fluoro-1H-indol-2-yl]-N-(1,1,1-trifluorobutan-2-yl)pyridine-3-sulfonamide,
6-[3-cyano-1-cyclobutyl-6-(difluoromethoxy)-5-fluoro-1H-indol-2-yl]-N-phenylpyridine-3-sulfonamide,
1-cyclobutyl-5-fluoro-6-methyl-2-(5-{[(2S)-1,1,1-trifluoropropan-2-yl]sulfamoyl}pyridin-2-yl)-1H-indole-3-carboxylic acid,
2-[5-(tert-butylsulfamoyl)pyrimidin-2-yl]-1-cyclobutyl-5-fluoro-6-methyl-1H-indole-3-carboxylic acid,
2-[5-(tert-butylsulfamoyl)pyridin-2-yl]-1-cyclobutyl-5-fluoro-N,6-dimethyl-1H-indole-3-carboxamide,
6-(3-cyano-1-cyclobutyl-5-hydroxy-6-methyl-1H-indol-2-yl)-N-[(2S)-1,1,1-trifluoropropan-2-yl]pyridine-3-sulfonamide,
6-[3-cyano-1-cyclobutyl-6-(difluoromethoxy)-4-fluoro-1H-indol-2-yl]-N-[(2S)-1,1,1-trifluoropropan-2-yl]pyridine-3-sulfonamide,
2-[5-(tert-butylsulfamoyl)pyridin-2-yl]-1-cyclopentyl-5-fluoro-N,6-dimethyl-1H-indole-3-carboxamide,
2-[5-(tert-butylsulfamoyl)pyridin-2-yl]-1-cyclobutyl-5-fluoro-6-methyl-1H-indole-3-carboxamide,
1-cyclobutyl-5-fluoro-N,6-dimethyl-2-(5-{[(2S)-1,1,1-trifluoropropan-2-yl]sulfamoyl}pyridin-2-yl)-1H-indole-3-carboxamide,
2-[5-(tert-butylsulfamoyl)pyrimidin-2-yl]-1-cyclobutyl-5-fluoro-N,6-dimethyl-1H-indole-3-carboxamide,
6-[5-chloro-3-cyano-6-methyl-1-(pyridin-2-yl)-1H-indol-2-yl]-N-[(2S)-1,1,1-trifluoropropan-2-yl]pyridine-3-sulfonamide,
6-[5-chloro-3-cyano-1-(5-fluoropyridin-2-yl)-6-methyl-1H-indol-2-yl]-N-[(2S)-1,1,1-trifluoropropan-2-yl]pyridine-3-sulfonamide,
N-tert-butyl-6-(3-cyano-1-cyclobutyl-5-hydroxy-6-methyl-1H-indol-2-yl)pyridine-3-sulfonamide,
1-cyclopentyl-6-(difluoromethoxy)-5-fluoro-2-(5-{[(2S)-1,1,1-trifluoropropan-2-yl]sulfamoyl}pyridin-2-yl)-1H-indole-3-carboxamide,
6-(3-cyano-1-cyclobutyl-5-hydroxy-6-methyl-1H-indol-2-yl)-N-[(2R)-1,1,1-trifluoropropan-2-yl]pyridine-3-sulfonamide,
6-[3-cyano-1-cyclobutyl-6-(difluoromethoxy)-5-fluoro-1H-indol-2-yl]-N-[1-(trifluoromethyl)cyclopropyl]pyridine-3-sulfonamide,
1-cyclobutyl-6-(difluoromethoxy)-5-fluoro-2-(5-{[1-(trifluoromethyl)cyclopropyl]sulfamoyl}pyridin-2-yl)-1H-indole-3-carboxamide,
6-[3-cyano-1-cyclobutyl-6-(difluoromethoxy)-5-fluoro-4-methyl-1H-indol-2-yl]-N-[(2S)-1,1,1-trifluoropropan-2-yl]pyridine-3-sulfonamide,
6-[3-cyano-1-cyclobutyl-6-(difluoromethoxy)-5-fluoro-7-methyl-1H-indol-2-yl]-N-[(2S)-1,1,1-trifluoropropan-2-yl]pyridine-3-sulfonamide,
6-[3-cyano-1-(cyclopropylmethyl)-6-(difluoromethoxy)-5-fluoro-1H-indol-2-yl]pyridine-3-sulfonamide, 6-(3-cyano-1-cyclobutyl-5-fluoro-6-hydroxy-1H-indol-2-yl)-N-[1-(trifluoromethyl)cyclopropyl]pyridine-3-sulfonamide, 6-[3-cyano-5-fluoro-1-(3-fluoropyridin-2-yl)-6-methyl-1H-indol-2-yl]-N-[(2S)-1,1,1-trifluoropropan-2-yl]pyridine-3-sulfonamide, 6-[3-cyano-5-fluoro-1-(6-fluoropyridin-2-yl)-6-methyl-1H-indol-2-yl]-N-[(2S)-1,1,1-trifluoropropan-2-yl]pyridine-3-sulfonamide, 6-[3-cyano-5-fluoro-1-(4-methoxypyridin-2-yl)-6-methyl-1H-indol-2-yl]-N-[(2S)-1,1,1-trifluoropropan-2-yl]pyridine-3-sulfonamide, 6-[3-cyano-5-fluoro-6-methyl-1-(pyrazin-2-yl)-1H-indol-2-yl]-N-[(2S)-1,1,1-trifluoropropan-2-yl]pyridine-3-sulfonamide, 6-[3-cyano-6-cyclopropyl-5-fluoro-1-(5-fluoropyridin-2-yl)-1H-indol-2-yl]-N-[(2S)-1,1,1-trifluoropropan-2-yl]pyridine-3-sulfonamide, 6-[3-cyano-6-cyclopropyl-5-fluoro-1-(pyridin-2-yl)-1H-indol-2-yl]-N-[(2S)-1,1,1-trifluoropropan-2-yl]pyridine-3-sulfonamide, 6-[3-cyano-6-cyclopropyl-5-fluoro-1-(pyrimidin-2-yl)-1H-indol-2-yl]-N-[(2S)-1,1,1-trifluoropropan-2-yl]pyridine-3-sulfonamide, 6-(3-cyano-1-cyclopentyl-5-fluoro-6-methyl-1H-indol-2-yl)-N-[(2S)-1,1,1-trifluorobutan-2-yl]pyridine-3-sulfonamide, 6-[3-cyano-1-cyclobutyl-6-(difluoromethoxy)-5-fluoro-1H-indol-2-yl]-4-methyl-N-[(2S)-1,1,1-trifluoropropan-2-yl]pyridine-3-sulfonamide, N-tert-butyl-6-[3-cyano-5-fluoro-1-(pyrimidin-2-yl)-1H-indol-2-yl]pyridine-3-sulfonamide, N-tert-butyl-6-[3-cyano-5-fluoro-6-methyl-1-(pyrimidin-2-yl)-1H-indol-2-yl]pyridine-3-sulfonamide, 1-cyclobutyl-6-(difluoromethoxy)-4-fluoro-2-(5-{[(2S)-1,1,1-trifluoropropan-2-yl]sulfamoyl}pyridin-2-yl)-1H-indole-3-carboxamide, 6-(3-cyano-1-cyclobutyl-5-fluoro-6-methyl-1H-indol-2-yl)-N-[(2S)-1,1,1-trifluorobutan-2-yl]pyridine-3-sulfonamide, 6-[3-cyano-1-cyclobutyl-6-(difluoromethoxy)-5-fluoro-1H-indol-2-yl]-5-methyl-N-[(2S)-1,1,1-trifluoropropan-2-yl]pyridine-3-sulfonamide, 2-[5-(tert-butylsulfamoyl)pyridin-2-yl]-1-cyclobutyl-5-hydroxy-6-methyl-1H-indole-3-carboxamide, 1-cyclopentyl-6-cyclopropyl-5-fluoro-2-(5-{[(2R)-1,1,1-trifluoropropan-2-yl]sulfamoyl}pyridin-2-yl)-1H-indole-3-carboxamide, 1-cyclopentyl-6-ethyl-5-fluoro-2-(5-{[(2S)-1,1,1-trifluoropropan-2-yl]sulfamoyl}pyridin-2-yl)-1H-indole-3-carboxamide, 6-(3-cyano-1-cyclopentyl-6-cyclopropyl-5-fluoro-1H-indol-2-yl)-N-(1,1,1-trifluoro-2-methylpropan-2-yl)pyridine-3-sulfonamide, N-tert-butyl-6-(3-cyano-1-cyclopentyl-6-cyclopropyl-5-fluoro-1H-indol-2-yl)pyridine-3-sulfonamide, 1-cyclobutyl-5-hydroxy-6-methyl-2-(5-{[(2S)-1,1,1-trifluoropropan-2-yl]sulfamoyl}pyridin-2-yl)-1H-indole-3-carboxamide, 1-cyclopentyl-5-methoxy-6-methyl-2-(5-{[(2R)-1,1,1-trifluoropropan-2-yl]sulfamoyl}pyridin-2-yl)-1H-indole-3-carboxamide, 1-cyclohexyl-5-fluoro-6-methyl-2-(5-{[1-(trifluoromethyl)cyclopropyl]sulfamoyl}pyridin-2-yl)-1H-indole-3-carboxylic acid, 6-(3-cyano-1-cyclopentyl-5-fluoro-6-methyl-1H-indol-2-yl)-5-methyl-N-[(2S)-1,1,1-trifluoropropan-2-yl]pyridine-3-sulfonamide, 1-cyclopentyl-6-cyclopropyl-5-fluoro-2-(5-{[(2S)-1,1,1-trifluoropropan-2-yl]sulfamoyl}pyridin-2-yl)-1H-indole-3-carboxamide, 6-(difluoromethoxy)-4-fluoro-1-(propan-2-yl)-2-(5-{[(2S)-1,1,1-trifluoropropan-2-yl]sulfamoyl}pyridin-2-yl)-1H-indole-3-carboxamide, 1-(cyclopropylmethyl)-6-(difluoromethoxy)-4-fluoro-2-(5-{[(2S)-1,1,1-trifluoropropan-2-yl]sulfamoyl}pyridin-2-yl)-1H-indole-3-carboxamide, 1-cyclopentyl-5-hydroxy-6-methyl-2-(5-{[(2S)-1,1,1-trifluoropropan-2-yl]sulfamoyl}pyridin-2-yl)-1H-indole-3-carboxamide, 6-(3-cyano-1-cyclopentyl-5-fluoro-6-methyl-1H-indol-2-yl)-4-methyl-N-[(2S)-1,1,1-trifluoropropan-2-yl]pyridine-3-sulfonamide, 6-[3-cyano-5-methyl-1-(pyrimidin-2-yl)-1H-indol-2-yl]-N-[(2S)-1,1,1-trifluoropropan-2-yl]pyridine-3-sulfonamide, 6-[3-cyano-1-(3-fluoropyridin-2-yl)-5-methyl-1H-indol-2-yl]-N-[(2S)-1,1,1-trifluoropropan-2-yl]pyridine-3-sulfonamide, 6-[3-cyano-5-methyl-1-(pyrazin-2-yl)-1H-indol-2-yl]-N-[(2S)-1,1,1-trifluoropropan-2-yl]pyridine-3-sulfonamide, 5-methyl-1-(pyrimidin-2-yl)-2-(5-{[(2S)-1,1,1-trifluoropropan-2-yl]sulfamoyl}pyridin-2-yl)-1H-indole-3-carboxamide, 6-[3-cyano-5-fluoro-1-(pyridin-2-yl)-1H-indol-2-yl]-4-methyl-N-[(2S)-1,1,1-trifluoropropan-2-yl]pyridine-3-sulfonamide, 6-[3-cyano-5-fluoro-1-(pyrimidin-2-yl)-1H-indol-2-yl]-4-methyl-N-[(2S)-1,1,1-trifluoropropan-2-yl]pyridine-3-sulfonamide, 6-ethyl-5-fluoro-1-(pyrimidin-2-yl)-2-(5-{[(2S)-1,1,1-trifluoropropan-2-yl]sulfamoyl}pyridin-2-yl)-1H-indole-3-carboxamide, 1-cyclopentyl-6-cyclopropyl-5-fluoro-2-{5-[(1,1,1-trifluoro-2-methylpropan-2-yl)sulfamoyl]pyridin-2-yl}-1H-indole-3-carboxamide, 6-[3-cyano-6-ethyl-5-fluoro-1-(pyrimidin-2-yl)-1H-indol-2-yl]-4-methyl-N-[(2S)-1,1,1-trifluoropropan-2-yl]pyridine-3-sulfonamide, 6-[3-cyano-6-ethyl-5-fluoro-1-(pyridin-2-yl)-1H-indol-2-yl]-4-methyl-N-[(2S)-1,1,1-trifluoropropan-2-yl]pyridine-3-sulfonamide, 6-[3-cyano-5-fluoro-6-methyl-1-(pyrimidin-2-yl)-1H-indol-2-yl]-4-methyl-N-[(2S)-1,1,1-trifluoropropan-2-yl]pyridine-3-sulfonamide, 6-[3-cyano-5-fluoro-6-methyl-1-(pyridin-2-yl)-1H-indol-2-yl]-4-methyl-N-[(2S)-1,1,1-trifluoropropan-2-yl]pyridine-3-sulfonamide, N-tert-butyl-6-[3-cyano-6-ethyl-5-fluoro-1-(pyrimidin-2-yl)-1H-indol-2-yl]pyridine-3-sulfonamide, 6-(3-cyano-1-cyclohexyl-5-fluoro-6-methyl-1H-indol-2-yl)-N-[1-(trifluoromethyl)cyclopropyl]pyridine-3-sulfonamide, 1-cyclohexyl-5-fluoro-6-methyl-2-(5-{[1-(trifluoromethyl)cyclopropyl]sulfamoyl}pyridin-2-yl)-1H-indole-3-carboxamide, 6-(3-cyano-1-cyclobutyl-6-ethyl-4-methoxy-1H-indol-2-yl)-N-[(2S)-1,1,1-trifluoropropan-2-yl]pyridine-3-sulfonamide, 6-[3-cyano-6-ethyl-5-fluoro-1-(pyrimidin-2-yl)-1H-indol-2-yl]-N-(1,1,1-trifluoro-2-methylpropan-2-yl)pyridine-3-sulfonamide, 6-[3-cyano-6-ethyl-5-fluoro-1-(pyrimidin-2-yl)-1H-indol-2-yl]-N-(1-methylcyclopropyl)pyridine-3-sulfonamide, 6-[3-cyano-1-cyclopentyl-6-(difluoromethoxy)-5-fluoro-1H-indol-2-yl]-N-(1,1,1-trifluoro-2-methylpropan-2-yl)pyridine-3-sulfonamide, 1-cyclopentyl-6-(difluoromethoxy)-5-fluoro-2-{5-[(1,1,1-trifluoro-2-methylpropan-2-yl)sulfamoyl]pyridin-2-yl}-1H-indole-3-carboxamide 6-[3-cyano-6-ethyl-5-fluoro-1-(pyrimidin-2-yl)-1H-indol-2-yl]-N-[1-(trifluoromethyl)cyclopropyl]pyridine-3-sulfonamide 6-[3-cyano-5-fluoro-6-methyl-1-(5-methylpyrazin-2-yl)-1H-indol-2-yl]-N-[(2S)-1,1,1-trifluoropropan-2-yl]pyridine-3-sulfonamide 6-[3-cyano-5-fluoro-1-(4-methoxypyrimidin-2-yl)-6-methyl-1H-indol-2-yl]-N-[(2S)-1,1,1-trifluoropropan-2-yl]pyridine-3-sulfonamide 6-[3-cyano-6-ethyl-5-fluoro-1-(pyrimidin-2-yl)-1H-indol-2-yl]-5-methyl-N-[(2S)-1,1,1-trifluoropropan-2-yl]pyridine-3-sulfonamide 6-(3-cyano-1-cyclopentyl-5-fluoro-6-methyl-1H-indol-2-yl)-2-methyl-N-[(2S)-1,1,1-trifluoropropan-2-yl]pyridine-3-sulfonamide N-tert-butyl-6-[6-ethyl-5-fluoro-3-(methylsulfonyl)-1-(pyrimidin-2-yl)-1H-indol-2-yl]pyridine-3-sulfonamide 6-[3-cyano-6-ethyl-5-fluoro-1-(pyridin-2-yl)-1H-indol-2-yl]-5-methyl-N-[(2S)-1,1,1-trifluoropropan-2-yl]pyridine-3-sulfonamide, 1-cyclopentyl-6-ethyl-5-fluoro-2-{5-[(1,1,1-trifluoro-2-methylpropan-2-yl)sulfamoyl]pyridin-2-yl}-1H-indole-3-carboxamide, 1-cyclopentyl-6-ethyl-5-fluoro-2-(5-{[1-(trifluoromethyl)cyclopropyl]sulfamoyl}pyridin-2-yl)-1H-indole-3-carboxamide, 6-[3-cyano-5-fluoro-6-methyl-1-(4-methylpyrimidin-2-yl)-1H-indol-2-yl]-N-[(2S)-1,1,1-trifluoropropan-2-yl]pyridine-3-sulfonamide, 5-fluoro-6-methyl-1-(pyridin-2-yl)-2-(5-{[(2S)-1,1,1-trifluoropropan-2-yl]sulfamoyl}pyridin-2-yl)-1H-indole-3-carboxamide, 5-fluoro-6-methyl-1-(pyrazin-2-yl)-2-(5-{[(2S)-1,1,1-trifluoropropan-2-yl]sulfamoyl}pyridin-2-yl)-1H-indole-3-carboxamide, 5-fluoro-1-(5-fluoropyridin-2-yl)-6-methyl-2-(5-{[(2S)-1,1,1-trifluoropropan-2-yl]sulfamoyl}pyridin-2-yl)-1H-indole-3-carboxamide, 5-fluoro-1-(6-fluoropyridin-2-yl)-6-methyl-2-(5-{[(2S)-1,1,1-trifluoropropan-2-yl]sulfamoyl}pyridin-2-yl)-1H-indole-3-carboxamide, 6-[3-cyano-6-ethyl-5-fluoro-1-(pyrimidin-2-yl)-1H-indol-2-yl]-N-[(2R)-1,1,1-trifluoropropan-2-yl]pyridine-3-sulfonamide, 6-[3-cyano-6-ethyl-5-fluoro-1-(pyrimidin-2-yl)-1H-indol-2-yl]-N-[(2R)-1,1,1-trifluoropropan-2-yl]pyridine-3-sulfonamide, 6-[3-cyano-6-ethyl-5-fluoro-1-(5-fluoropyridin-2-yl)-1H-indol-2-yl]-N-[(2R)-1,1,1-trifluoropropan-2-yl]pyridine-3-sulfonamide 6-[3-cyano-6-ethyl-5-fluoro-1-(pyrimidin-2-yl)-1H-indol-2-yl]-2-methyl-N-[(2S)-1,1,1-trifluoropropan-2-yl]pyridine-3-sulfonamide, N-tert-butyl-6-[3-cyano-6-ethyl-5-fluoro-1-(pyridin-2-yl)-1H-indol-2-yl]pyridine-3-sulfonamide, 2-[5-(tert-butylsulfamoyl)pyridin-2-yl]-6-ethyl-5-fluoro-1-(pyridin-2-yl)-1H-indole-3-carboxamide, N-tert-butyl-6-(3-cyano-6-ethyl-5-fluoro-1-phenyl-1H-indol-2-yl)pyridine-3-sulfonamide, 6-[3-cyano-5-fluoro-6-methyl-1-(5-methylpyridin-2-yl)-1H-indol-2-yl]-N-[(2S)-1,1,1-trifluoropropan-2-yl]pyridine-3-sulfonamide, 6-[3-cyano-5-fluoro-6-methyl-1-(4-methylpyridin-2-yl)-1H-indol-2-yl]-N-[(2S)-1,1,1-trifluoropropan-2-yl]pyridine-3-sulfonamide, 6-[3-cyano-6-ethyl-5-fluoro-1-(pyridin-2-yl)-1H-indol-2-yl]-2-methyl-N-[(2S)-1,1,1-trifluoropropan-2-yl]pyridine-3-sulfonamide, 6-[3-cyano-5-fluoro-6-methyl-1-(pyrimidin-2-yl)-1H-indol-2-yl]-5-methyl-N-[(2S)-1,1,1-trifluoropropan-2-yl]pyridine-3-sulfonamide, 6-[3-cyano-5-fluoro-6-methyl-1-(pyridin-2-yl)-1H-indol-2-yl]-5-methyl-N-[(2S)-1,1,1-trifluoropropan-2-yl]pyridine-3-sulfonamide, 6-[3-cyano-6-ethyl-5-fluoro-1-(pyrimidin-2-yl)-1H-indol-2-yl]-4-methyl-N-[(2R)-1,1,1-trifluoropropan-2-yl]pyridine-3-sulfonamide, 6-[3-cyano-6-ethyl-5-fluoro-1-(pyridin-2-yl)-1H-indol-2-yl]-4-methyl-N-[(2R)-1,1,1-trifluoropropan-2-yl]pyridine-3-sulfonamide, 6-[3-cyano-5-fluoro-6-methyl-1-(pyridazin-3-yl)-1H-indol-2-yl]-N-[(2S)-1,1,1-trifluoropropan-2-yl]pyridine-3-sulfonamide, 6-[3-cyano-5-fluoro-6-methyl-1-(pyridin-3-yl)-1H-indol-2-yl]-N-[(2S)-1,1,1-trifluoropropan-2-yl]pyridine-3-sulfonamide, 6-[3-cyano-5-fluoro-6-methyl-1-(pyrimidin-5-yl)-1H-indol-2-yl]-N-[(2S)-1,1,1-trifluoropropan-2-yl]pyridine-3-sulfonamide, 6-[6-bromo-3-cyano-5-fluoro-1-(pyrimidin-2-yl)-1H-indol-2-yl]-N-[(2S)-1,1,1-trifluoropropan-2-yl]pyridine-3-sulfonamide, 6-[3-cyano-5-fluoro-6-methyl-1-(pyrimidin-4-yl)-1H-indol-2-yl]-N-[(2S)-1,1,1-trifluoropropan-2-yl]pyridine-3-sulfonamide, 6-[3-cyano-1-(pyrazin-2-yl)-5-(trifluoromethyl)-1H-indol-2-yl]-N-[(2S)-1,1,1-trifluoropropan-2-yl]pyridine-3-sulfonamide, 6-[3-cyano-1-(pyrazin-2-yl)-5-(trifluoromethoxy)-1H-indol-2-yl]-N-[(2S)-1,1,1-trifluoropropan-2-yl]pyridine-3-sulfonamide, N-tert-butyl-6-[3-cyano-6-ethyl-5-fluoro-1-(pyrazin-2-yl)-1H-indol-2-yl]pyridine-3-sulfonamide, N-tert-butyl-6-[3-cyano-6-ethyl-5-fluoro-1-(3-fluoropyridin-2-yl)-1H-indol-2-yl]pyridine-3-sulfonamide, 6-[3-cyano-6-fluoro-5-methyl-1-(pyrimidin-2-yl)-1H-indol-2-yl]-N-[(2S)-1,1,1-trifluoropropan-2-yl]pyridine-3-sulfonamide, 5-fluoro-1-(3-fluoropyridin-2-yl)-6-methyl-2-(5-{[(2S)-1,1,1-trifluoropropan-2-yl]sulfamoyl}pyridin-2-yl)-1H-indole-3-carboxamide, 6-[5-fluoro-6-methyl-1-(1,3-thiazol-2-yl)-1H-indol-2-yl]-N-[(2S)-1,1,1-trifluoropropan-2-yl]pyridine-3-sulfonamide, 5-fluoro-6-methyl-1-(5-methylpyrazin-2-yl)-2-(5-{[(2S)-1,1,1-trifluoropropan-2-yl]sulfamoyl}pyridin-2-yl)-1H-indole-3-carboxamide, 5-fluoro-6-methyl-1-(4-methylpyrimidin-2-yl)-2-(5-{[(2S)-1,1,1-trifluoropropan-2-yl]sulfamoyl}pyridin-2-yl)-1H-indole-3-carboxamide 5-fluoro-1-(4-methoxypyrimidin-2-yl)-6-methyl-2-(5-{[(2S)-1,1,1-trifluoropropan-2-yl]sulfamoyl}pyridin-2-yl)-1H-indole-3-carboxamide
6-[6-acetyl-3-cyano-5-fluoro-1-(pyrimidin-2-yl)-1H-indol-2-yl]-N-[(2S)-1,1,1-trifluoropropan-2-yl]pyridine-3-sulfonamide
6-[3-cyano-6-ethenyl-5-fluoro-1-(pyrimidin-2-yl)-1H-indol-2-yl]-N-[(2S)-1,1,1-trifluoropropan-2-yl]pyridine-3-sulfonamide
6-ethyl-5-fluoro-1-(pyridin-2-yl)-2-(5-{[(2S)-1,1,1-trifluoropropan-2-yl]sulfamoyl}pyridin-2-yl)-1H-indole-3-carboxamide
6-(3-cyano-1-cyclopropyl-6-ethyl-5-fluoro-1H-indol-2-yl)-N-[(2S)-1,1,1-trifluoropropan-2-yl]pyridine-3-sulfonamide
6-[3-cyano-5-fluoro-6-(1-hydroxyethyl)-1-(pyrimidin-2-yl)-1H-indol-2-yl]-N-[(2S)-1,1,1-trifluoropropan-2-yl]pyridine-3-sulfonamide
5-fluoro-6-methyl-1-(pyridazin-3-yl)-2-(5-{[(2S)-1,1,1-trifluoropropan-2-yl]sulfamoyl}pyridin-2-yl)-1H-indole-3-carboxamide
5-fluoro-6-methyl-1-(pyridin-3-yl)-2-(5-{[(2S)-1,1,1-trifluoropropan-2-yl]sulfamoyl}pyridin-2-yl)-1H-indole-3-carboxamide
6-[1-(5-chloropyrimidin-2-yl)-3-cyano-5-fluoro-6-methyl-1H-indol-2-yl]-N-[(2S)-1,1,1-trifluoropropan-2-yl]pyridine-3-sulfonamide,
6-[3-cyano-5-fluoro-6-methyl-1-(6-methylpyrazin-2-yl)-1H-indol-2-yl]-N-[(2S)-1,1,1-trifluoropropan-2-yl]pyridine-3-sulfonamide,
5-methyl-1-(pyrazin-2-yl)-2-(5-{[(2S)-1,1,1-trifluoropropan-2-yl]sulfamoyl}pyridin-2-yl)-1H-indole-3-carboxamide,
6-[3-cyano-6-fluoro-5-methyl-1-(pyridin-2-yl)-1H-indol-2-yl]-N-[(2S)-1,1,1-trifluoropropan-2-yl]pyridine-3-sulfonamide,
6-fluoro-5-methyl-1-(pyrimidin-2-yl)-2-(5-{[(2S)-1,1,1-trifluoropropan-2-yl]sulfamoyl}pyridin-2-yl)-1H-indole-3-carboxamide,
6-[3-cyano-6-fluoro-5-methyl-1-(pyrazin-2-yl)-1H-indol-2-yl]-N-[(2S)-1,1,1-trifluoropropan-2-yl]pyridine-3-sulfonamide,
6-[3-cyano-1-(4-fluorophenyl)-5-methyl-1H-indol-2-yl]-N-[(2S)-1,1,1-trifluoropropan-2-yl]pyridine-3-sulfonamide,
6-(3-cyano-5-methyl-1-phenyl-1H-indol-2-yl)-N-[(2S)-1,1,1-trifluoropropan-2-yl]pyridine-3-sulfonamide,
6-[3-cyano-1-(pyrimidin-2-yl)-5-(trifluoromethyl)-1H-indol-2-yl]-N-[(2S)-1,1,1-trifluoropropan-2-yl]pyridine-3-sulfonamide,
6-[3-cyano-5-fluoro-6-methyl-1-(6-methylpyridin-2-yl)-1H-indol-2-yl]-N-[(2S)-1,1,1-trifluoropropan-2-yl]pyridine-3-sulfonamide,
6-[3-cyano-5-fluoro-1-(5-fluoropyrimidin-2-yl)-6-methyl-1H-indol-2-yl]-N-[(2S)-1,1,1-trifluoropropan-2-yl]pyridine-3-sulfonamide,
6-[3-cyano-5-fluoro-6-methyl-1-(5-methylpyrimidin-2-yl)-1H-indol-2-yl]-N-[(2S)-1,1,1-trifluoropropan-2-yl]pyridine-3-sulfonamide,
6-[3-cyano-5-fluoro-1-(4-fluoropyridin-2-yl)-6-methyl-1H-indol-2-yl]-N-[(2S)-1,1,1-trifluoropropan-2-yl]pyridine-3-sulfonamide,
6-[3-cyano-5-fluoro-6-(2-methyl-1,3-dioxolan-2-yl)-1-(pyrimidin-2-yl)-1H-indol-2-yl]-N-[(2S)-1,1,1-trifluoropropan-2-yl]pyridine-3-sulfonamide,
1-cyclohexyl-6-(difluoromethoxy)-5-fluoro-2-{5-[(1,1,1-trifluoro-2-methylpropan-2-yl)sulfamoyl]pyridin-2-yl}-1H-indole-3-carboxylic acid,
6-[3-cyano-6-ethyl-5-fluoro-1-(pyrazin-2-yl)-1H-indol-2-yl]-N-[(2S)-1,1,1-trifluoropropan-2-yl]pyridine-3-sulfonamide,
6-[3-cyano-6-ethyl-5-fluoro-1-(6-fluoropyridin-2-yl)-1H-indol-2-yl]-N-[(2S)-1,1,1-trifluoropropan-2-yl]pyridine-3-sulfonamide,
6-[3-cyano-6-ethyl-5-fluoro-1-(5-methylpyridin-2-yl)-1H-indol-2-yl]-N-[(2S)-1,1,1-trifluoropropan-2-yl]pyridine-3-sulfonamide,
6-[3-cyano-6-ethyl-5-fluoro-1-(4-methylpyridin-2-yl)-1H-indol-2-yl]-N-[(2S)-1,1,1-trifluoropropan-2-yl]pyridine-3-sulfonamide,
6-[3-cyano-5-fluoro-6-methyl-1-(pyridin-4-yl)-1H-indol-2-yl]-N-[(2S)-1,1,1-trifluoropropan-2-yl]pyridine-3-sulfonamide,
6-[3-cyano-5-fluoro-6-methyl-1-(1,3-thiazol-2-yl)-1H-indol-2-yl]-N-[(2S)-1,1,1-trifluoropropan-2-yl]pyridine-3-sulfonamide,
6-[3-cyano-6-ethyl-5-fluoro-1-(1,3-thiazol-2-yl)-1H-indol-2-yl]-N-[(2S)-1,1,1-trifluoropropan-2-yl]pyridine-3-sulfonamide,
6-[3-cyano-6-(difluoromethoxy)-5-fluoro-1-(propan-2-yl)-1H-indol-2-yl]-N-[(2S)-1,1,1-trifluoropropan-2-yl]pyridine-3-sulfonamide,
6-[3-cyano-6-(difluoromethoxy)-5-fluoro-1-(2-methylpropyl)-1H-indol-2-yl]-N-[(2S)-1,1,1-trifluoropropan-2-yl]pyridine-3-sulfonamide,
6-[6-bromo-3-cyano-5-fluoro-1-(pyrimidin-2-yl)-1H-indol-2-yl]-N-tert-butylpyridine-3-sulfonamide,
N-tert-butyl-6-[3,6-diacetyl-5-fluoro-1-(pyrimidin-2-yl)-1H-indol-2-yl]pyridine-3-sulfonamide,
6-[3-cyano-6-(difluoromethoxy)-5-fluoro-1-(2-hydroxyethyl)-1H-indol-2-yl]-N-[(2S)-1,1,1-trifluoropropan-2-yl]pyridine-3-sulfonamide,
6-[3-cyano-1-(1,6-dihydropyrimidin-2-yl)-6-ethyl-5-fluoro-1H-indol-2-yl]-N-[(2S)-1,1,1-trifluoropropan-2-yl]pyridine-3-sulfonamide,
6-[1-(5-chloropyrimidin-2-yl)-3-cyano-6-ethyl-5-fluoro-1H-indol-2-yl]-N-[(2S)-1,1,1-trifluoropropan-2-yl]pyridine-3-sulfonamide,
6-[3-cyano-6-ethyl-5-fluoro-1-(2-methylpyrimidin-4-yl)-1H-indol-2-yl]-N-[(2S)-1,1,1-trifluoropropan-2-yl]pyridine-3-sulfonamide,
6-[5-fluoro-1-(2-fluoropyridin-4-yl)-6-methyl-1H-indol-2-yl]-N-[(2S)-1,1,1-trifluoropropan-2-yl]pyridine-3-sulfonamide,
6-[3-cyano-5-fluoro-1-(5-fluoropyridin-3-yl)-6-methyl-1H-indol-2-yl]-N-[(2S)-1,1,1-trifluoropropan-2-yl]pyridine-3-sulfonamide,
6-[3-cyano-6-ethyl-5-fluoro-1-(5-fluoropyrimidin-2-yl)-1H-indol-2-yl]-N-[(2S)-1,1,1-trifluoropropan-2-yl]pyridine-3-sulfonamide,
6-[3-chloro-6-cyclopropyl-5-fluoro-1-(pyrimidin-2-yl)-1H-indol-2-yl]-N-[(2S)-1,1,1-trifluoropropan-2-yl]pyridine-3-sulfonamide,
6-[3-cyano-1-(5-fluoropyrimidin-2-yl)-5-methyl-1H-indol-2-yl]-N-[(2S)-1,1,1-trifluoropropan-2-yl]pyridine-3-sulfonamide,
6-[3-cyano-6-fluoro-1-(5-fluoropyrimidin-2-yl)-5-methyl-1H-indol-2-yl]-N-[(2S)-1,1,1-trifluoropropan-2-yl]pyridine-3-sulfonamide,
6-[3-cyano-1-(pyrimidin-2-yl)-6-(trifluoromethyl)-1H-indol-2-yl]-N-[(2S)-1,1,1-trifluoropropan-2-yl]pyridine-3-sulfonamide, 6-[3-cyano-1-(pyrazin-2-yl)-6-(trifluoromethyl)-1H-indol-2-yl]-N-[(2S)-1,1,1-trifluoropropan-2-yl]pyridine-3-sulfonamide, 6-[3-cyano-1-(pyridin-2-yl)-6-(trifluoromethyl)-1H-indol-2-yl]-N-[(2S)-1,1,1-trifluoropropan-2-yl]pyridine-3-sulfonamide, 6-[3-cyano-6-ethyl-5-fluoro-1-(pyrimidin-2-yl)-1H-indol-2-yl]-N-(cyclobutylmethyl)pyridine-3-sulfonamide, 6-[3-cyano-6-ethyl-5-fluoro-1-(pyridin-3-yl)-1H-indol-2-yl]-N-[(2S)-1,1,1-trifluoropropan-2-yl]pyridine-3-sulfonamide, 6-[3-cyano-6-ethyl-5-fluoro-1-(4-methoxypyridin-2-yl)-1H-indol-2-yl]-N-[(2S)-1,1,1-trifluoropropan-2-yl]pyridine-3-sulfonamide, 6-[3-cyano-6-ethyl-5-fluoro-1-(pyrimidin-2-yl)-1H-indol-2-yl]-N-[(2S)-1,1,1-trifluoro(2-deuterium)propan-2-yl]pyridine-3-sulfonamide, 13

6-[5-fluoro-6-methyl-1-(1,3-thiazol-4-yl)-1H-indol-2-yl]-N-[(2S)-1,1,1-trifluoropropan-2-yl]pyridine-3-sulfonamide, 6-[5-fluoro-6-methyl-1-(1,3,4-thiadiazol-2-yl)-1H-indol-2-yl]-N-[(2S)-1,1,1-trifluoropropan-2-yl]pyridine-3-sulfonamide, 6-[5-fluoro-6-methyl-1-(1,3-thiazol-5-yl)-1H-indol-2-yl]-N-[(2S)-1,1,1-trifluoropropan-2-yl]pyridine-3-sulfonamide, 6-[3-cyano-5-fluoro-6-methyl-1-(1,3-thiazol-4-yl)-1H-indol-2-yl]-N-[(2S)-1,1,1-trifluoropropan-2-yl]pyridine-3-sulfonamide, 6-[3-cyano-5-fluoro-1-(5-fluoro-6-methylpyridin-2-yl)-6-methyl-1H-indol-2-yl]-N-[(2S)-1,1,1-trifluoropropan-2-yl]pyridine-3-sulfonamide, 6-[1-(6-chloropyridin-2-yl)-3-cyano-5-fluoro-6-methyl-1H-indol-2-yl]-N-[(2S)-1,1,1-trifluoropropan-2-yl]pyridine-3-sulfonamide, 6-[3-cyano-6-ethyl-5-fluoro-1-(pyrimidin-5-yl)-1H-indol-2-yl]-N-[(2S)-1,1,1-trifluoropropan-2-yl]pyridine-3-sulfonamide, 6-[3-cyano-6-ethyl-5-fluoro-1-(pyrimidin-4-yl)-1H-indol-2-yl]-N-[(2S)-1,1,1-trifluoropropan-2-yl]pyridine-3-sulfonamide, 6-[1-(3-chloropyridin-2-yl)-3-cyano-6-ethyl-5-fluoro-1H-indol-2-yl]-N-[(2S)-1,1,1-trifluoropropan-2-yl]pyridine-3-sulfonamide, 6-[1-(5-chloropyridin-2-yl)-3-cyano-6-ethyl-5-fluoro-1H-indol-2-yl]-N-[(2S)-1,1,1-trifluoropropan-2-yl]pyridine-3-sulfonamide, 6-[3-cyano-5-fluoro-6-(prop-2-en-1-yl)-1-(pyrimidin-2-yl)-1H-indol-2-yl]-N-[(2S)-1,1,1-trifluoropropan-2-yl]pyridine-3-sulfonamide, 6-[3-chloro-5-fluoro-6-(prop-2-en-1-yl)-1-(pyrimidin-2-yl)-1H-indol-2-yl]-N-[(2S)-1,1,1-trifluoropropan-2-yl]pyridine-3-sulfonamide, 6-[5-fluoro-6-(prop-2-en-1-yl)-1-(pyrimidin-2-yl)-1H-indol-2-yl]-N-[(2S)-1,1,1-trifluoropropan-2-yl]pyridine-3-sulfonamide, 6-[3-cyano-5-fluoro-6-(2-hydroxyethyl)-1-(pyrimidin-2-yl)-1H-indol-2-yl]-N-[(2S)-1,1,1-trifluoropropan-2-yl]pyridine-3-sulfonamide, 6-[1-(3-chloropyridin-2-yl)-3-cyano-5-fluoro-6-methyl-1H-indol-2-yl]-N-[(2S)-1,1,1-trifluoropropan-2-yl]pyridine-3-sulfonamide, 6-[3-chloro-5-fluoro-6-methyl-1-(1,3,4-thiadiazol-2-yl)-1H-indol-2-yl]-N-[(2S)-1,1,1-trifluoropropan-2-yl]pyridine-3-sulfonamide, 6-[3-cyano-5-fluoro-6-methyl-1-(1,3-thiazol-5-yl)-1H-indol-2-yl]-N-[(2S)-1,1,1-trifluoropropan-2-yl]pyridine-3-sulfonamide, 6-[3-cyano-6-ethyl-5-fluoro-1-(pyridin-4-yl)-1H-indol-2-yl]-N-[(2S)-1,1,1-trifluoropropan-2-yl]pyridine-3-sulfonamide, 6-[3-cyano-6-ethyl-5-fluoro-1-(pyridazin-3-yl)-1H-indol-2-yl]-N-[(2S)-1,1,1-trifluoropropan-2-yl]pyridine-3-sulfonamide, 6-[3-cyano-6-ethyl-5-fluoro-1-(5-methylpyrimidin-2-yl)-1H-indol-2-yl]-N-[(2S)-1,1,1-trifluoropropan-2-yl]pyridine-3-sulfonamide, 6-[3-cyano-5-fluoro-6-methyl-1-(1,3,4-thiadiazol-2-yl)-1H-indol-2-yl]-N-[(2S)-1,1,1-trifluoropropan-2-yl]pyridine-3-sulfonamide, 6-ethyl-5-fluoro-1-(pyrimidin-2-yl)-2-{5-[(1,1,1-trifluoro-2-methylpropan-2-yl)sulfamoyl]pyridin-2-yl}-1H-indole-3-carboxamide, 6-ethyl-5-fluoro-1-(pyrimidin-2-yl)-2-(5-{[1-(trifluoromethyl)cyclopropyl]sulfamoyl}pyridin-2-yl)-1H-indole-3-carboxamide, 6-ethyl-5-fluoro-1-(4-methylpyridin-2-yl)-2-(5-{[(2S)-1,1,1-trifluoropropan-2-yl]sulfamoyl}pyridin-2-yl)-1H-indole-3-carboxamide, 6-ethyl-5-fluoro-1-(5-fluoropyridin-2-yl)-2-(5-{[(2S)-1,1,1-trifluoropropan-2-yl]sulfamoyl}pyridin-2-yl)-1H-indole-3-carboxamide, 6-ethyl-5-fluoro-1-(2-methylpyrimidin-4-yl)-2-(5-{[(2S)-1,1,1-trifluoropropan-2-yl]sulfamoyl}pyridin-2-yl)-1H-indole-3-carboxamide, 6-[1-(5-chloropyridin-3-yl)-3-cyano-6-ethyl-5-fluoro-1H-indol-2-yl]-N-[(2S)-1,1,1-trifluoropropan-2-yl]pyridine-3-sulfonamide, 6-{3-cyano-5-fluoro-1-[5-(hydroxymethyl)-1,3-thiazol-2-yl]-6-methyl-1H-indol-2-yl}-N-[(2S)-1,1,1-trifluoropropan-2-yl]pyridine-3-sulfonamide, methyl 2-[3-cyano-5-fluoro-6-methyl-2-(5-{[(2S)-1,1,1-trifluoropropan-2-yl]sulfamoyl}pyridin-2-yl)-1H-indol-1-yl]-1,3-thiazole-5-carboxylate, methyl 2-[3-cyano-5-fluoro-6-methyl-2-(5-{[(2S)-1,1,1-trifluoropropan-2-yl]sulfamoyl}pyridin-2-yl)-1H-indol-1-yl]-1,3-thiazole-4-carboxylate, 6-[5-fluoro-6-methyl-1-(thiophen-3-yl)-1H-indol-2-yl]-N-[(2S)-1,1,1-trifluoropropan-2-yl]pyridine-3-sulfonamide, 6-[5-fluoro-1-(furan-3-yl)-6-methyl-1H-indol-2-yl]-N-[(2S)-1,1,1-trifluoropropan-2-yl]pyridine-3-sulfonamide, 6-[5-fluoro-6-methyl-1-(thiophen-2-yl)-1H-indol-2-yl]-N-[(2S)-1,1,1-trifluoropropan-2-yl]pyridine-3-sulfonamide, 6-[3-cyano-5-fluoro-6-methyl-1-(thiophen-2-yl)-1H-indol-2-yl]-N-[(2S)-1,1,1-trifluoropropan-2-yl]pyridine-3-sulfonamide, 6-[3-cyano-5-fluoro-1-(furan-3-yl)-6-methyl-1H-indol-2-yl]-N-[(2S)-1,1,1-trifluoropropan-2-yl]pyridine-3-sulfonamide 6-[3-cyano-5-fluoro-6-methyl-1-(thiophen-3-yl)-1H-indol-2-yl]-N-[(2S)-1,1,1-trifluoropropan-2-yl]pyridine-3-sulfonamide, 6-[1-(4-chloropyridin-2-yl)-3-cyano-6-ethyl-5-fluoro-1H-indol-2-yl]-N-[(2S)-1,1,1-trifluoropropan-2-yl]pyridine-3-sulfonamide, 6-ethyl-5-fluoro-1-(pyrazin-2-yl)-2-(5-{[(2S)-1,1,1-trifluoropropan-2-yl]sulfamoyl}pyridin-2-yl)-1H-indole-3-carboxamide, 6-ethyl-5-fluoro-1-(6-fluoropyridin-2-yl)-2-(5-{[(2S)-1,1,1-trifluoropropan-2-yl]sulfamoyl}pyridin-2-yl)-1H-indole-3-carboxamide, 5-chloro-1-cyclobutyl-2-(5-{[(2S)-1,1,1-trifluoropropan-2-yl]sulfamoyl}pyridin-2-yl)-1H-indole-3-carboxamide, 1-cyclobutyl-5-fluoro-2-(5-{[(2S)-1,1,1-trifluoropropan-2-yl]sulfamoyl}pyridin-2-yl)-1H-indole-3-carboxamide, 6-[3-cyano-5-fluoro-6-methyl-1-(3-methylthiophen-2-yl)-1H-indol-2-yl]-N-[(2S)-1,1,1-trifluoropropan-2-yl]pyridine-3-sulfonamide, 6-[3-cyano-1-(4,6-difluoropyridin-2-yl)-5-fluoro-6-methyl-1H-indol-2-yl]-N-[(2S)-1,1,1-trifluoropropan-2-yl]pyridine-3-sulfonamide, 6-[3-cyano-6-ethyl-5-fluoro-1-(4-fluorophenyl)-1H-indol-2-yl]-N-[(2S)-1,1,1-trifluoropropan-2-yl]pyridine-3-sulfonamide, 6-[1-(4-chlorophenyl)-3-cyano-6-ethyl-5-fluoro-1H-indol-2-yl]-N-[(2S)-1,1,1-trifluoropropan-2-yl]pyridine-3-sulfonamide, 6-[3-cyano-6-ethyl-5-fluoro-1-(4-methylphenyl)-1H-indol-2-yl]-N-[(2S)-1,1,1-trifluoropropan-2-yl]pyridine-3-sulfonamide, 6-[3-cyano-6-ethyl-5-fluoro-1-(4-methoxyphenyl)-1H-indol-2-yl]-N-[(2S)-1,1,1-trifluoropropan-2-yl]pyridine-3-sulfonamide, 6-{3-cyano-6-ethyl-5-fluoro-1-[4-(trifluoromethyl)phenyl]-1H-indol-2-yl}-N-[(2S)-1,1,1-trifluoropropan-2-yl]pyridine-3-sulfonamide, 6-[3-cyano-1-(4-cyanophenyl)-6-ethyl-5-fluoro-1H-indol-2-yl]-N-[(2S)-1,1,1-trifluoropropan-2-yl]pyridine-3-sulfonamide, 6-[3-cyano-6-ethyl-5-fluoro-1-(3-fluorophenyl)-1H-indol-2-yl]-N-[(2S)-1,1,1-trifluoropropan-2-yl]pyridine-3-sulfonamide, 6-[3-cyano-6-ethyl-5-fluoro-1-(3-methylphenyl)-1H-indol-2-yl]-N-[(2S)-1,1,1-trifluoropropan-2-yl]pyridine-3-sulfonamide, 6-[3-cyano-6-ethyl-5-fluoro-1-(3-methoxyphenyl)-1H-indol-2-yl]-N-[(2S)-1,1,1-trifluoropropan-2-yl]pyridine-3-sulfonamide, 6-{3-cyano-6-ethyl-5-fluoro-1-[3-(trifluoromethyl)phenyl]-1H-indol-2-yl}-N-[(2S)-1,1,1-trifluoropropan-2-yl]pyridine-3-sulfonamide, 6-[3-cyano-1-(3-cyanophenyl)-6-ethyl-5-fluoro-1H-indol-2-yl]-N-[(2S)-1,1,1-trifluoropropan-2-yl]pyridine-3-sulfonamide, 6-[3-cyano-5-fluoro-1-(2-fluoropyridin-4-yl)-6-methyl-1H-indol-2-yl]-N-[(2S)-1,1,1-trifluoropropan-2-yl]pyridine-3-sulfonamide, 6-[3-cyano-5-fluoro-1-(3-fluoropyridin-4-yl)-6-methyl-1H-indol-2-yl]-N-[(2S)-1,1,1-trifluoropropan-2-yl]pyridine-3-sulfonamide, 6-[3-cyano-5-fluoro-1-(6-fluoropyridin-3-yl)-6-methyl-1H-indol-2-yl]-N-[(2S)-1,1,1-trifluoropropan-2-yl]pyridine-3-sulfonamide, 6-[3-cyano-5-fluoro-6-methyl-1-(1-methyl-1H-pyrazol-4-yl)-1H-indol-2-yl]-N-[(2S)-1,1,1-trifluoropropan-2-yl]pyridine-3-sulfonamide, 6-[3-cyano-5-fluoro-6-methyl-1-(5-methyl-1,3-thiazol-2-yl)-1H-indol-2-yl]-N-[(2S)-1,1,1-trifluoropropan-2-yl]pyridine-3-sulfonamide, 6-[1-(3-chlorophenyl)-3-cyano-6-ethyl-5-fluoro-1H-indol-2-yl]-N-[(2S)-1,1,1-trifluoropropan-2-yl]pyridine-3-sulfonamide, 6-ethyl-5-fluoro-1-(4-fluorophenyl)-2-(5-{[(2S)-1,1,1-trifluoropropan-2-yl]sulfamoyl}pyridin-2-yl)-1H-indole-3-carboxamide, 1-(4-chlorophenyl)-6-ethyl-5-fluoro-2-(5-{[(2S)-1,1,1-trifluoropropan-2-yl]sulfamoyl}pyridin-2-yl)-1H-indole-3-carboxamide, 6-ethyl-5-fluoro-1-(4-methylphenyl)-2-(5-{[(2S)-1,1,1-trifluoropropan-2-yl]sulfamoyl}pyridin-2-yl)-1H-indole-3-carboxamide, 6-ethyl-5-fluoro-1-[4-(trifluoromethyl)phenyl]-2-(5-{[(2S)-1,1,1-trifluoropropan-2-yl]sulfamoyl}pyridin-2-yl)-1H-indole-3-carboxamide, 6-ethyl-5-fluoro-1-(3-fluorophenyl)-2-(5-{[(2S)-1,1,1-trifluoropropan-2-yl]sulfamoyl}pyridin-2-yl)-1H-indole-3-carboxamide, 6-ethyl-5-fluoro-1-(3-methylphenyl)-2-(5-{[(2S)-1,1,1-trifluoropropan-2-yl]sulfamoyl}pyridin-2-yl)-1H-indole-3-carboxamide, 6-ethyl-5-fluoro-1-(3-methoxyphenyl)-2-(5-{[(2S)-1,1,1-trifluoropropan-2-yl]sulfamoyl}pyridin-2-yl)-1H-indole-3-carboxamide, 6-ethyl-5-fluoro-1-[3-(trifluoromethyl)phenyl]-2-(5-{[(2S)-1,1,1-trifluoropropan-2-yl]sulfamoyl}pyridin-2-yl)-1H-indole-3-carboxamide, 1-(3-chlorophenyl)-6-ethyl-5-fluoro-2-(5-{[(2S)-1,1,1-trifluoropropan-2-yl]sulfamoyl}pyridin-2-yl)-1H-indole-3-carboxamide, 6-[3-cyano-5-fluoro-6-methyl-1-(3-methyl-1H-pyrazol-4-yl)-1H-indol-2-yl]-N-[(2S)-1,1,1-trifluoropropan-2-yl]pyridine-3-sulfonamide, 6-[3-cyano-5-fluoro-6-methyl-1-(5-methylthiophen-2-yl)-1H-indol-2-yl]-N-[(2S)-1,1,1-trifluoropropan-2-yl]pyridine-3-sulfonamide, 6-[1-(5-chlorothiophen-2-yl)-3-cyano-5-fluoro-6-methyl-1H-indol-2-yl]-N-[(2S)-1,1,1-trifluoropropan-2-yl]pyridine-3-sulfonamide, 6-[3-cyano-1-(5-cyanothiophen-2-yl)-5-fluoro-6-methyl-1H-indol-2-yl]-N-[(2S)-1,1,1-trifluoropropan-2-yl]pyridine-3-sulfonamide, 6-[3-cyano-5-fluoro-6-methyl-1-(5-sulfamoylthiophen-2-yl)-1H-indol-2-yl]-N-[(2S)-1,1,1-trifluoropropan-2-yl]pyridine-3-sulfonamide, 6-[1-(5-acetylthiophen-2-yl)-3-cyano-5-fluoro-6-methyl-1H-indol-2-yl]-N-[(2S)-1,1,1-trifluoropropan-2-yl]pyridine-3-sulfonamide, 6-[3-cyano-5-fluoro-6-methyl-1-(4-methyl-1,3-thiazol-2-yl)-1H-indol-2-yl]-N-[(2S)-1,1,1-trifluoropropan-2-yl]pyridine-3-sulfonamide, 6-ethyl-5-fluoro-1-(5-methylpyridin-2-yl)-2-(5-{[(2S)-1,1,1-trifluoropropan-2-yl]sulfamoyl}pyridin-2-yl)-1H-indole-3-carboxamide, 6-ethyl-5-fluoro-1-(pyridin-3-yl)-2-(5-{[(2S)-1,1,1-trifluoropropan-2-yl]sulfamoyl}pyridin-2-yl)-1H-indole-3-carboxamide, 6-ethyl-5-fluoro-1-(pyrimidin-4-yl)-2-(5-{[(2S)-1,1,1-trifluoropropan-2-yl]sulfamoyl}pyridin-2-yl)-1H-indole-3-carboxamide, 1-(3-chloropyridin-2-yl)-6-ethyl-5-fluoro-2-(5-{[(2S)-1,1,1-trifluoropropan-2-yl]sulfamoyl}pyridin-2-yl)-1H-indole-3-carboxamide, 1-(5-chloropyridin-2-yl)-6-ethyl-5-fluoro-2-(5-{[(2S)-1,1,1-trifluoropropan-2-yl]sulfamoyl}pyridin-2-yl)-1H-indole-3-carboxamide, 1-(5-chloropyridin-3-yl)-6-ethyl-5-fluoro-2-(5-{[(2S)-1,1,1-trifluoropropan-2-yl]sulfamoyl}pyridin-2-yl)-1H-indole-3-carboxamide 6-ethyl-5-fluoro-1-(pyridin-4-yl)-2-(5-{[(2S)-1,1,1-trifluoropropan-2-yl]sulfamoyl}pyridin-2-yl)-1H-indole-3-carboxamide,
6-ethyl-5-fluoro-1-(pyridazin-3-yl)-2-(5-{[(2S)-1,1,1-trifluoropropan-2-yl]sulfamoyl}pyridin-2-yl)-1H-indole-3-carboxamide,
6-ethyl-5-fluoro-1-(5-methylpyrimidin-2-yl)-2-(5-{[(2S)-1,1,1-trifluoropropan-2-yl]sulfamoyl}pyridin-2-yl)-1H-indole-3-carboxamide,
1-(4-chloropyridin-2-yl)-6-ethyl-5-fluoro-2-(5-{[(2S)-1,1,1-trifluoropropan-2-yl]sulfamoyl}pyridin-2-yl)-1H-indole-3-carboxamide,
6-[1-(2-acetylthiophen-3-yl)-3-cyano-5-fluoro-6-methyl-1H-indol-2-yl]-N-[(2S)-1,1,1-trifluoropropan-2-yl]pyridine-3-sulfonamide,
6-[3-cyano-5-fluoro-6-methyl-1-(4-methylthiophen-3-yl)-1H-indol-2-yl]-N-[(2S)-1,1,1-trifluoropropan-2-yl]pyridine-3-sulfonamide,
6-[1-(2-chlorothiophen-3-yl)-3-cyano-5-fluoro-6-methyl-1H-indol-2-yl]-N-[(2S)-1,1,1-trifluoropropan-2-yl]pyridine-3-sulfonamide,
6-[3-cyano-5-fluoro-6-methyl-1-(5-methylthiophen-3-yl)-1H-indol-2-yl]-N-[(2S)-1,1,1-trifluoropropan-2-yl]pyridine-3-sulfonamide,
6-[5-fluoro-6-methyl-1-(1,3-oxazol-2-yl)-1H-indol-2-yl]-N-[(2S)-1,1,1-trifluoropropan-2-yl]pyridine-3-sulfonamide,
6-[1-(5-cyanofuran-2-yl)-5-fluoro-6-methyl-1H-indol-2-yl]-N-[(2S)-1,1,1-trifluoropropan-2-yl]pyridine-3-sulfonamide,
6-[3-cyano-1-(3,4-difluorophenyl)-6-ethyl-5-fluoro-1H-indol-2-yl]-N-[(2S)-1,1,1-trifluoropropan-2-yl]pyridine-3-sulfonamide,
6-[1-(3-chloro-4-fluorophenyl)-3-cyano-6-ethyl-5-fluoro-1H-indol-2-yl]-N-[(2S)-1,1,1-trifluoropropan-2-yl]pyridine-3-sulfonamide,
6-[3-cyano-1-(3-cyanofuran-2-yl)-5-fluoro-6-methyl-1H-indol-2-yl]-N-[(2S)-1,1,1-trifluoropropan-2-yl]pyridine-3-sulfonamide,
6-[3-cyano-5-fluoro-6-methyl-1-(1,3-oxazol-2-yl)-1H-indol-2-yl]-N-[(2S)-1,1,1-trifluoropropan-2-yl]pyridine-3-sulfonamide,
6-[3-cyano-1-(4-cyano-1,3-oxazol-2-yl)-5-fluoro-6-methyl-1H-indol-2-yl]-N-[(2S)-1,1,1-trifluoropropan-2-yl]pyridine-3-sulfonamide,
6-[3-cyano-6-ethyl-5-fluoro-1-(2-fluorophenyl)-1H-indol-2-yl]-N-[(2S)-1,1,1-trifluoropropan-2-yl]pyridine-3-sulfonamide,
6-{3-cyano-6-[(1,1-dideuterium)ethyl]-5-fluoro-1-(pyrimidin-2-yl)-1H-indol-2-yl}-N-[(2S)-1,1,1-trifluoropropan-2-yl]pyridine-3-sulfonamide,
6-{3-cyano-6-[(1,1-dideuterium)ethyl]-5-fluoro-1-(pyrimidin-2-yl)-1H-indol-2-yl}-N-[(2S)-1,1,1-trifluoro(2-deuterium)propan-2-yl]pyridine-3-sulfonamide,
6-[3-cyano-6-cyclopropyl-4-fluoro-1-(pyrimidin-2-yl)-1H-indol-2-yl]-N-(1,1,1-trifluoro-2-methylpropan-2-yl)pyridine-3-sulfonamide,
6-[3-cyano-5-fluoro-6-(1,1,1-trideuterium)methyl-1-(pyrimidin-2-yl)-1H-indol-2-yl]-N-[(2S)-1,1,1-trifluoro(2-deuterium)propan-2-yl]pyridine-3-sulfonamide,
N-tert-butyl-6-(3-cyano-5-fluoro-6-methyl-1-phenyl-1H-indol-2-yl)pyridine-3-sulfonamide,
2-[5-(tert-butylsulfamoyl)pyridin-2-yl]-6-ethyl-5-fluoro-1-phenyl-1H-indole-3-carboxamide,
6-(3-cyano-1-cyclobutyl-5-fluoro-6-methyl-1H-indol-2-yl)-N-[(2-deuterium)propan-2-yl]pyridine-3-sulfonamide,
6-(3-cyano-1-cyclobutyl-5-fluoro-6-methyl-1H-indol-2-yl)-N-[(2S)-1,1,1-trifluoro(2-deuterium)propan-2-yl]pyridine-3-sulfonamide,
6-[3-cyano-1-cyclobutyl-5-fluoro-6-(1,1,1-trideuterium)methyl-1H-indol-2-yl]-N-[(2S)-1,1,1-trifluoro(2-deuterium)propan-2-yl]pyridine-3-sulfonamide,
2-[5-(tert-butylsulfamoyl)pyridin-2-yl]-1-cyclohexyl-5-fluoro-6-methyl-1H-indole-3-carboxamide,
2-[5-(tert-butylsulfamoyl)pyridin-2-yl]-5-fluoro-6-methyl-1-phenyl-1H-indole-3-carboxamide,
N-tert-butyl-6-(3-cyano-6-cyclopropyl-5-fluoro-1-phenyl-1H-indol-2-yl)pyridine-3-sulfonamide or
6-[3-cyano-1-(cyclopropylmethyl)-5-fluoro-6-(1,1,1-trideuterium)methyl-1H-indol-2-yl]-N-[(2-deuterium)propan-2-yl]pyridine-3-sulfonamide.

3. The product of claim 2, wherein the HCV inhibitor is selected from:
6-(3-cyano-1-cyclobutyl-6-cyclopropyl-1H-indol-2-yl)-N-(propan-2-yl)pyridine-3-sulfonamide,
6-[3-cyano-1-cyclobutyl-6-(difluoromethoxy)-1H-indol-2-yl]-N-(1,3-difluoropropan-2-yl)pyridine-3-sulfonamide,
6-(3-cyano-1-cyclobutyl-6-cyclopropyl-1H-indol-2-yl)-N-(1,3-difluoropropan-2-yl)pyridine-3-sulfonamide,
6-(3-cyano-1-cyclopentyl-6-methyl-1H-indol-2-yl)-N-(1,3-difluoropropan-2-yl)pyridine-3-sulfonamide,
6-[3-cyano-1-cyclobutyl-6-(difluoromethoxy)-1H-indol-2-yl]-N-(propan-2-yl)pyridine-3-sulfonamide,
6-(3-cyano-1-cyclobutyl-6-cyclopropyl-5-fluoro-1H-indol-2-yl)-N-(1,3-difluoropropan-2-yl)pyridine-3-sulfonamide,
6-(3-cyano-1-cyclobutyl-5-fluoro-6-methyl-1H-indol-2-yl)-N-(1,3-difluoropropan-2-yl)pyridine-3-sulfonamide,
6-(3-cyano-1-cyclopentyl-6-methyl-1H-indol-2-yl)-N-[1-(trifluoromethyl)cyclopropyl]pyridine-3-sulfonamide,
6-[3-cyano-1-cyclobutyl-6-(difluoromethoxy)-1H-indol-2-yl]-N-[(2S)-1,1,1-trifluoropropan-2-yl]pyridine-3-sulfonamide,
6-(3-cyano-1-cyclopentyl-6-methyl-1H-indol-2-yl)-N-(1,1,1-trifluoro-2-methylpropan-2-yl)pyridine-3-sulfonamide,
6-[3-cyano-6-(difluoromethoxy)-1-(pyridin-2-yl)-1H-indol-2-yl]-N-[(2S)-1,1,1-trifluoropropan-2-yl]pyridine-3-sulfonamide,
6-(3-cyano-1-cyclopentyl-5-fluoro-6-methyl-1H-indol-2-yl)-N-(1,3-difluoropropan-2-yl)pyridine-3-sulfonamide,
6-(3-cyano-1-cyclopentyl-5-fluoro-6-methyl-1H-indol-2-yl)-N-[(2S)-1,1,1-trifluoropropan-2-yl]pyridine-3-sulfonamide,
6-(3-cyano-1-cyclopentyl-5-fluoro-6-methyl-1H-indol-2-yl)-N-[(2R)-1,1,1-trifluoropropan-2-yl]pyridine-3-sulfonamide,
6-(3-cyano-1-cyclobutyl-7-fluoro-6-methyl-1H-indol-2-yl)-N-[(2S)-1,1,1-trifluoropropan-2-yl]pyridine-3-sulfonamide,
6-[3-cyano-6-(difluoromethoxy)-1-(pyrimidin-2-yl)-1H-indol-2-yl]-N-[(2S)-1,1,1-trifluoropropan-2-yl]pyridine-3-sulfonamide,
6-(3-cyano-1-cyclobutyl-5,7-difluoro-6-methyl-1H-indol-2-yl)-N-[(2S)-1,1,1-trifluoropropan-2-yl]pyridine-3-sulfonamide,
6-[3-cyano-5-fluoro-6-methyl-1-(pyridin-2-yl)-1H-indol-2-yl]-N-[(2S)-1,1,1-trifluoropropan-2-yl]pyridine-3-sulfonamide, 6-[3-cyano-1-cyclobutyl-6-(difluoromethoxy)-5-fluoro-1H-indol-2-yl]-N-[(2S)-1,1,1-trifluoropropan-2-yl]pyridine-3-sulfonamide, 6-[3-cyano-5-fluoro-1-(pyrimidin-2-yl)-1H-indol-2-yl]-N-[(2S)-1,1,1-trifluoropropan-2-yl]pyridine-3-sulfonamide, 6-[3-cyano-5-fluoro-6-methyl-1-(pyrimidin-2-yl)-1H-indol-2-yl]-N-[(2S)-1,1,1-trifluoropropan-2-yl]pyridine-3-sulfonamide, 6-(3-cyano-1-cyclobutyl-6-ethyl-5-fluoro-1H-indol-2-yl)-N-[(2S)-1,1,1-trifluoropropan-2-yl]pyridine-3-sulfonamide, 6-[3-cyano-6-cyclopropyl-1-(pyrimidin-2-yl)-1H-indol-2-yl]-N-[(2S)-1,1,1-trifluoropropan-2-yl]pyridine-3-sulfonamide, 6-[3-cyano-6-(difluoromethoxy)-5-fluoro-1-(pyridine-2-yl)-1H-indol-2-yl]-N-[(2S)-1,1,1-trifluoropropan-2-yl]pyridine-3-sulfonamide, 6-[3-cyano-6-(difluoromethoxy)-5-fluoro-1-(pyrimidin-2-yl)-1H-indol-2-yl]-N-[(2S)-1,1,1-trifluoropropan-2-yl]pyridine-3-sulfonamide, 2-[5-(tert-butylsulfamoyl)pyridin-2-yl]-1-cyclopentyl-5-fluoro-6-methyl-1H-indole-3-carboxamide, 6-[3-cyano-6-ethyl-5-fluoro-1-(pyrimidin-2-yl)-1H-indol-2-yl]-N-[(2S)-1,1,1-trifluoropropan-2-yl]pyridine-3-sulfonamide, 1-cyclohexyl-5-fluoro-6-methyl-2-(5-{[(2R)-1,1,1-trifluoropropan-2-yl]sulfamoyl}pyridin-2-yl)-1H-indole-3-carboxamide, 6-[3-cyano-5-fluoro-6-methyl-1-(tetrahydro-2H-pyran-4-yl)-1H-indol-2-yl]-N-[(2R)-1,1,1-trifluoropropan-2-yl]pyridine-3-sulfonamide, 6-[3-cyano-1-cyclobutyl-6-(difluoromethoxy)-5-fluoro-4-methyl-1H-indol-2-yl]-N-[(2S)-1,1,1-trifluoropropan-2-yl]pyridine-3-sulfonamide, 6-[3-cyano-6-cyclopropyl-5-fluoro-1-(pyrimidin-2-yl)-1H-indol-2-yl]-N-[(2S)-1,1,1-trifluoropropan-2-yl]pyridine-3-sulfonamide, 6-(3-cyano-1-cyclopentyl-5-fluoro-6-methyl-1H-indol-2-yl)-N-[(2S)-1,1,1-trifluorobutan-2-yl]pyridine-3-sulfonamide, 6-ethyl-5-fluoro-1-(pyrimidin-2-yl)-2-(5-{[(2S)-1,1,1-trifluoropropan-2-yl]sulfamoyl}pyridin-2-yl)-1H-indole-3-carboxamide, 6-[3-cyano-6-(difluoromethoxy)-5-fluoro-1-(2-methylpropyl)-1H-indol-2-yl]-N-[(2S)-1,1,1-trifluoropropan-2-yl]pyridine-3-sulfonamide, 6-[3-cyano-5-fluoro-6-methyl-1-(1,3-thiazol-4-yl)-1H-indol-2-yl]-N-[(2S)-1,1,1-trifluoropropan-2-yl]pyridine-3-sulfonamide or 6-[3-cyano-5-fluoro-6-methyl-1-(1,3,4-thiadiazol-2-yl)-1H-indol-2-yl]-N-[(2S)-1,1,1-trifluoropropan-2-yl]pyridine-3-sulfonamide.

4. The product of claim 3, wherein the HCV inhibitor is selected from:

6-[3-cyano-1-cyclobutyl-6-(difluoromethoxy)-1H-indol-2-yl]-N-[(2S)-1,1,1-trifluoropropan-2-yl]pyridine-3-sulfonamide, 6-[3-cyano-6-(difluoromethoxy)-1-(pyridin-2-yl)-1H-indol-2-yl]-N-[(2S)-1,1,1-trifluoropropan-2-yl]pyridine-3-sulfonamide, 6-(3-cyano-1-cyclopentyl-5-fluoro-6-methyl-1H-indol-2-yl)-N-[(2R)-1,1,1-trifluoropropan-2-yl]pyridine-3-sulfonamide, 6-[3-cyano-6-(difluoromethoxy)-1-(pyrimidin-2-yl)-1H-indol-2-yl]-N-[(2S)-1,1,1-trifluoropropan-2-yl]pyridine-3-sulfonamide, 6-[3-cyano-5-fluoro-6-methyl-1-(pyridin-2-yl)-1H-indol-2-yl]-N-[(2S)-1,1,1-trifluoropropan-2-yl]pyridine-3-sulfonamide, 6-[3-cyano-1-cyclobutyl-6-(difluoromethoxy)-5-fluoro-1H-indol-2-yl]-N-[(2S)-1,1,1-trifluoropropan-2-yl]pyridine-3-sulfonamide, 6-[3-cyano-5-fluoro-1-(pyrimidin-2-yl)-1H-indol-2-yl]-N-[(2S)-1,1,1-trifluoropropan-2-yl]pyridine-3-sulfonamide, 6-[3-cyano-5-fluoro-6-methyl-1-(pyrimidin-2-yl)-1H-indol-2-yl]-N-[(2S)-1,1,1-trifluoropropan-2-yl]pyridine-3-sulfonamide, 6-[3-cyano-6-cyclopropyl-1-(pyrimidin-2-yl)-1H-indol-2-yl]-N-[(2S)-1,1,1-trifluoropropan-2-yl]pyridine-3-sulfonamide, 6-[3-cyano-6-(difluoromethoxy)-5-fluoro-1-(pyrimidin-2-yl)-1H-indol-2yl]-N-[(2S)-1,1,1-trifluoropropan-2-yl]pyridine-3-sulfonamide, 6-[3-cyano-6-ethyl-5-fluoro-1-(pyrimidin-2-yl)-1H-indol-2-yl]-N-[(2S)-1,1,1-trifluoropropan-2-yl]pyridine-3-sulfonamide, 6-[3-cyano-6-cyclopropyl-5-fluoro-1-(pyrimidin-2-yl)-1H-indol-2-yl]-N-[(2S)-1,1,1-trifluoropropan-2-yl]pyridine-3-sulfonamide, 6-ethyl-5-fluoro-1-(pyrimidin-2-yl)-2-(5-{[(2S)-1,1,1-trifluoropropan-2-yl]sulfamoyl}pyridin-2-yl)-1H-indole-3-carboxamide or 6-[3-cyano-5-fluoro-6-methyl-1-(1,3-thiazol-4-yl)-1H-indol-2-yl]-N-[(2S)-1,1,1-trifluoropropan-2-yl]pyridine-3-sulfonamide.

5. The product of claim 1, wherein the HCV protease inhibitor is selected from:

(1R,2S,5S)-N-(4-amino-1-cyclobutyl-3,4-dioxobutan-2-yl)-3-((S)-2-(3-tert-butylureido)-3,3-dimethylbutanoyl)-6,6-dimethyl-3-azabicyclo[3.1.0]hexane-2-carboxamide, (1R,2S,5S)-N-((S)-4-amino-1-cyclobutyl-3,4-dioxobutan-2-yl)-3-((S)-2-(3-tert-butylureido)-3,3-dimethylbutanoyl)-6,6-dimethyl-3-azabicyclo[3.1.0]hexane-2-carboxamide, (1R,2S,5S)-N-((R)-4-amino-1-cyclobutyl-3,4-dioxobutan-2-yl)-3-((S)-2-(3-tert-butylureido)-3,3-dimethylbutanoyl)-6,6-dimethyl-3-azabicyclo[3.1.0]hexane-2-carboxamide, (1R,2S,5S)-3-((S)-2-(3-(1-(tert-butylsulfonylmethyl)cyclohexyl)ureido)-3,3-dimethylbutanoyl)-N-((S)-1-(cyclopropylamino)-1,2-dioxohexan-3-yl)-6,6-dimethyl-3-azabicyclo[3.1.0]hexane-2-carboxamide, (1R,2S,5S)-3-((S)-2-(3-(1-(tert-butylsulfonylmethyl)cyclohexyl)ureido)-3,3-dimethylbutanoyl)-N-((S)-1-(cyclopropylamino)-1,2-dioxoheptan-3-yl)-6,6-dimethyl-3-azabicyclo[3.1.0]hexane-2-carboxamide, (1R,2S,5S)-3-((S)-2-(3-(1-(tert-butylsulfonylmethyl)cyclohexyl)ureido)-3,3-dimethylbutanoyl)-N-((S)-5-cyclopropyl-1-(cyclopropylamino)-1,2-dioxopentan-3-yl)-6,6-dimethyl-3-azabicyclo[3.1.0]hexane-2-carboxamide, (1R,2S,5S)-3-((S)-2-(3-(1-(tert-butylsulfonylmethyl)cyclohexyl)ureido)-2-(1-methylcyclohexyl)acetyl)-N-((S)-5-cyclopropyl-1-(cyclopropylamino)-1,2-dioxopentan-3-yl)-6,6-dimethyl-3-azabicyclo[3.1.0]hexane-2-carboxamide, or (1R,2S,5S)-3-[N-({1-[(3R)-4,4-dioxido-1,4-oxathian-3-yl]cyclohexyl}carbamoyl)-3-methyl-L-valyl]-N-[(3S)-1,2-dioxo-1-(prop-2-en-1-ylamino)heptan-3-yl]-6,6-dimethyl-3-azabicyclo[3.1.0]hexane-2-carboxamide.

6. The product of claim 1, wherein the effective amount of each of the HCV inhibitor and the HCV protease inhibitor is in a range of from about 0.1 µg to about 4.5 g per day.

7. A method for treating or ameliorating HCV infection or disorders or symptoms associated therewith in a subject in need thereof comprising administering an effective amount of the combination product of claim 1 to the subject.

8. The method of claim 7, wherein the effective amount of each of the HCV inhibitor and the HCV protease inhibitor is in a range of from about 0.1 µg to about 4.5 g per day.

* * * * *